US012767709B2

(12) United States Patent
Lu et al.

(10) Patent No.: US 12,767,709 B2
(45) Date of Patent: Oct. 20, 2026

(54) CONFORMATION-SPECIFIC ANTIBODIES THAT BIND TAU PROTEIN AND USES THEREOF

(71) Applicant: Beth Israel Deaconess Medical Center, Inc., Boston, MA (US)

(72) Inventors: Kun Ping Lu, Newton, MA (US); Xiao Zhen Zhou, Newton, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 868 days.

(21) Appl. No.: 18/021,912

(22) PCT Filed: Sep. 2, 2021

(86) PCT No.: PCT/US2021/048859

§ 371 (c)(1),
(2) Date: Feb. 17, 2023

(87) PCT Pub. No.: WO2022/051489

PCT Pub. Date: Mar. 10, 2022

(65) Prior Publication Data

US 2023/0348578 A1 Nov. 2, 2023

Related U.S. Application Data

(60) Provisional application No. 63/074,725, filed on Sep. 4, 2020.

(51) Int. Cl.
*C07K 16/18* (2006.01)
*A61P 25/28* (2006.01)
*A61K 39/00* (2006.01)

(52) U.S. Cl.
CPC .............. *C07K 16/18* (2013.01); *A61P 25/28* (2018.01); *A61K 2039/505* (2013.01); *C07K 2317/24* (2013.01); *C07K 2317/30* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 4,489,078 A 12/1984 Temple, Jr.
4,591,588 A 5/1986 Wade
4,734,413 A 3/1988 Wade
4,816,567 A 3/1989 Cabilly et al.
5,530,101 A 6/1996 Queen et al.
5,627,153 A 5/1997 Little, II et al.
5,639,600 A 6/1997 McGrath et al.
5,654,010 A 8/1997 Johnson et al.
5,821,337 A 10/1998 Carter et al.
5,952,467 A 9/1999 Hunter et al.
5,972,697 A 10/1999 Hunter et al.
6,054,297 A 4/2000 Carter et al.
6,093,550 A 7/2000 Chang et al.
6,165,464 A 12/2000 Hudziak et al.
6,299,863 B1 10/2001 Aberg et al.
6,365,157 B2 4/2002 Rockwell et al.
6,462,173 B1 10/2002 Lu et al.
6,495,376 B1 12/2002 Lu et al.
6,555,583 B2 4/2003 Nieman et al.
6,562,363 B1 5/2003 Mantelle et al.
6,569,839 B1 5/2003 McKay
6,596,848 B1 7/2003 Hunter et al.
6,696,248 B1 2/2004 Knappik et al.
6,706,484 B1 3/2004 Knappik et al.
6,828,422 B1 12/2004 Achim et al.
6,830,745 B1 12/2004 Budny et al.
6,864,275 B1 3/2005 Camden et al.
6,869,974 B1 3/2005 Del Soldato
6,894,033 B2 5/2005 Cruz et al.
6,984,654 B2 1/2006 Camden
7,056,917 B2 6/2006 Nakayama et al.
7,087,648 B1 8/2006 McGrath
7,112,578 B2 9/2006 Levin
7,125,677 B2 10/2006 Hunter et al.
7,125,842 B2 10/2006 Kawabe et al.
7,125,955 B2 10/2006 Hunter et al.
7,148,003 B2 12/2006 Hunter et al.
7,161,060 B1 1/2007 Duff et al.
7,164,012 B2 1/2007 Hunter et al.
(Continued)

FOREIGN PATENT DOCUMENTS

WO WO-83/00229 A1 1/1983
WO WO-9607399 A1 3/1996
(Continued)

OTHER PUBLICATIONS

Schroeder et al. (J Allergy Clin Immunol 2010, 125:S41-S52).*
Lloyd et al. Protein Engineering, Design & Selection 2009, 22:159-168.*
Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*
(Continued)

*Primary Examiner* — Sharon X Wen
(74) *Attorney, Agent, or Firm* — Clark & Elbing LLP

(57) ABSTRACT

The present disclosure provides antibodies or antigen-binding fragments thereof that specifically bind to the cis conformation of phosphorylated-Threonine231-Proline (pThr231-Pro) of tau protein. This disclosure also provides methods for treating a subject having or at risk of developing a neurological disorder. This disclosure includes related pharmaceutical compositions, polynucleotides, vectors, host cells, methods of production, methods of treatment, diagnostic methods, and kits.

13 Claims, 156 Drawing Sheets

Specification includes a Sequence Listing.

(56) References Cited

U.S. PATENT DOCUMENTS

| | | | |
|---|---|---|---|
| 7,199,119 | B2 | 4/2007 | Burkitt et al. |
| 7,202,259 | B2 | 4/2007 | Chen |
| 7,217,737 | B2 | 5/2007 | Chen et al. |
| 7,264,963 | B1 | 9/2007 | Knappik et al. |
| 8,129,131 | B2 | 3/2012 | Lu et al. |
| 8,258,099 | B2 | 9/2012 | Lu et al. |
| 8,771,693 | B2 | 7/2014 | Lu et al. |
| 9,688,747 | B2 | 6/2017 | Lu et al. |
| 9,796,784 | B2 | 10/2017 | Lu et al. |
| 10,487,114 | B2 | 11/2019 | Lu et al. |
| 2002/0025521 | A1 | 2/2002 | Lu et al. |
| 2002/0168684 | A1 | 11/2002 | Comb et al. |
| 2004/0171019 | A1 | 9/2004 | Matthews et al. |
| 2005/0147608 | A1 | 7/2005 | Ryo et al. |
| 2005/0221391 | A1 | 10/2005 | Davies |
| 2005/0239095 | A1 | 10/2005 | Lu et al. |
| 2006/0074222 | A1 | 4/2006 | Lu et al. |
| 2006/0258564 | A1 | 11/2006 | Pluschke et al. |
| 2007/0172496 | A1 | 7/2007 | Olesen |
| 2008/0058276 | A1 | 3/2008 | Lu et al. |
| 2008/0118505 | A1 | 5/2008 | Tedder |
| 2008/0131438 | A1 | 6/2008 | Barden et al. |
| 2008/0214470 | A1 | 9/2008 | Lu et al. |
| 2008/0248043 | A1 | 10/2008 | Babcook et al. |
| 2009/0258352 | A1 | 10/2009 | Lu et al. |
| 2010/0028357 | A1 | 2/2010 | Matsubara et al. |
| 2010/0233205 | A1 | 9/2010 | Pizza et al. |
| 2010/0260783 | A1 | 10/2010 | Matsubara et al. |
| 2010/0278832 | A1 | 11/2010 | Kamogawa et al. |
| 2010/0297664 | A1 | 11/2010 | Wadhwa et al. |
| 2011/0104756 | A1 | 5/2011 | Rodriguez et al. |
| 2012/0183560 | A1 | 7/2012 | Akassoglou |
| 2013/0028900 | A1 | 1/2013 | Lu et al. |
| 2014/0086909 | A1 | 3/2014 | Lu et al. |
| 2014/0242100 | A1 | 8/2014 | Lu et al. |
| 2017/0112792 | A1 | 4/2017 | Lu et al. |
| 2018/0072814 | A1 | 3/2018 | Lu et al. |
| 2022/0087977 | A1 | 3/2022 | Panigrahy et al. |
| 2022/0348645 | A1 | 11/2022 | Lu et al. |

FOREIGN PATENT DOCUMENTS

| | | | | |
|---|---|---|---|---|
| WO | WO-96/40072 A2 | 12/1996 | | |
| WO | WO-97/03692 A1 | 2/1997 | | |
| WO | WO-97/17986 A1 | 5/1997 | | |
| WO | WO-99/09969 A1 | 3/1999 | | |
| WO | WO-02/065091 A2 | 8/2002 | | |
| WO | WO-02/092765 A2 | 11/2002 | | |
| WO | WO-2004/016751 A2 | 2/2004 | | |
| WO | WO-2004/101745 A2 | 11/2004 | | |
| WO | WO-2005/027727 A2 | 3/2005 | | |
| WO | WO-2006/074397 A2 | 7/2006 | | |
| WO | WO-2008/006087 A2 | 1/2008 | | |
| WO | WO-2009/146218 A2 | 12/2009 | | |
| WO | WO-2011/056561 A1 | 5/2011 | | |
| WO | WO-2012/082647 A2 | 6/2012 | | |
| WO | WO-2012/149334 A2 | 11/2012 | | |
| WO | WO-2012/162698 A1 | 11/2012 | | |
| WO | WO-2013/138118 A1 | 9/2013 | | |
| WO | WO-2013/185055 A1 | 12/2013 | | |
| WO | WO-2014/152157 A2 | 9/2014 | | |
| WO | WO-2019/040319 A1 | 2/2019 | | |
| WO | WO-2019094595 A2 * | 5/2019 | .............. | A61P 25/28 |
| WO | WO-2022/051489 A1 | 3/2022 | | |

OTHER PUBLICATIONS

Hwang et al., "Synthesis and structure-activity relationship studies of urea-containing pyrazoles as dual inhibitors of cyclooxygenase-2 and soluble epoxide hydrolase," J Med Chem. 54(8):3037-50 (Epub Apr. 2011).

U.S. Appl. No. 61/968,862, Lu et al.

An et al., "Retention of the cis proline conformation in tripeptide fragments of bovine pancreatic ribonuclease A containing a non-natural proline analogue, 5,5-dimethylproline," J Am Chem Soc. 121(49):11558-66 (1999).

Asuni et al., "Immunotherapy targeting pathological tau conformers in a tangle mouse model reduces brain pathology with associated functional improvements," J Neurosci. 27(34):9115-29 (2007).

Bayry et al., "Intravenous immunoglobulin for infectious diseases: back to the pre-antibiotic and passive prophylaxis era?," Trends Pharmacol Sci. 25(6):306-10 (2004).

Boimel et al., "Efficacy and safety of immunization with phosphorylated tau against neurofibrillary tangles in mice," Exp Neurol. 224(2):472-85 (2010).

Boutajangout et al., "Immunotherapy targeting pathological tau prevents cognitive decline in a new tangle mouse model," J Neurosci. 30(49):16559-66 (2010).

Campbell, General properties and applications of monoclonal antibodies. *Monoclonal Antibody Technology: The Production and Characterization of Rodent and Human Hybridomas*. Elsevier Science, 1-32 (1984) (19 pages).

Casadevall et al., "Passive antibody therapy for infectious diseases," Nat Rev Microbiol. 2(9):695-703 (2004) (10 pages).

Channappanavar et al., "Pathogenic human coronavirus infections: causes and consequences of cytokine storm and immunopathology," Semin Immunopathol. 39(5):529-539 (2017).

Citron, "Alzheimer's disease: strategies for disease modification," Nat Rev Drug Discov. 9(5):387-98 (2010).

Clackson et al., "Making antibody fragments using phage display libraries," Nature. 352(6336):624-8 (1991).

Dunman et al., "Passive immunization as prophylaxis: when and where will this work?," Curr Opin Pharmacol. 3(5):486-96 (2003).

Edwards et al., "The remarkable flexibility of the human antibody repertoire; isolation of over one thousand different antibodies to a single protein, BLyS," J Mol Biol. 334(1):103-18 (2003).

Enever et al., "Next generation immunotherapeutics—honing the magic bullet," Curr Opin Biotechnol. 20(4):405-11 (2009).

Esnault et al., "Pin1 modulates the type 1 immune response," PLoS One. 2(2):e226 (2007) (9 pages).

Extended European Search Report for European Application No. 14768309.8, mailed Oct. 27, 2016 (11 pages).

Gartung et al., "Growth by a Dual COX-2/sEH Inhibitor," The FASEB Journal. 32(1_supplement):1-3 (2018).

Gartung et al., "Suppression of chemotherapy-induced cytokine/lipid mediator surge and ovarian cancer by a dual COX-2/sEH inhibitor," Proc Natl Acad Sci U S A. 116(5):1698-1703 (2019).

Harlow et al., Immunizations. *Antibodies: a Laboratory Manual*. Cold Spring Harbor Laboratory Press, 76 (1988) (3 pages).

Huse et al., "Generation of a large combinatorial library of the immunoglobulin repertoire in phage lambda," Science. 246(4935):1275-81 (1989).

Hwang et al., "Rationally designed multitarget agents against inflammation and pain," available in PMC Jul. 28, 2014, published in final edited form as: Curr Med Chem. 20(13):1783-99 (2013).

International Preliminary Report on Patentability for International Application No. PCT/US2014/027017, issued Sep. 15, 2015 (13 pages).

International Preliminary Report on Patentability for International Application No. PCT/US2020/053851 dated Apr. 5, 2022.

International Preliminary Report on Patentability for International Patent Application No. PCT/US2020/013149, mailed Jul. 22, 2021 (8 pages).

(56) References Cited

OTHER PUBLICATIONS

International Search Report and Written Opinion for International Application No. PCT/US14/27017, mailed Oct. 28, 2014 (19 pages).
International Search Report and Written Opinion for International Application No. PCT/US14/27017, mailed Oct. 28, 2014 (30 pages).
International Search Report and Written Opinion for International Application No. PCT/US20/13149, mailed May 27, 2020 (14 pages).
International Search Report and Written Opinion for International Patent Application No. PCT/US2020/053851, mailed Mar. 26, 2021 (20 pages).
International Search Report and Written Opinion for International Patent Application No. PCT/US21/48859, mailed Feb. 4, 2022 (21 pages).
International Search Report for International Application No. PCT/US10/54077, mailed Feb. 15, 2011 (5 pages).
International Search Report for International Application No. PCT/US12/35473, mailed Dec. 10, 2012 (5 pages).
International Search Report for International Application No. PCT/US2012/039850, mailed Oct. 3, 2012 (3 pages).
Invitation to Pay Additional Fees for International Application No. PCT/US20/13149, mailed Mar. 30, 2020 (3 pages).
Jeong et al., "Novel role of Pin1 induction in type II collagen-mediated rheumatoid arthritis," J Immunol. 183(10):6689-97 (2009) (10 pages).
Jicha et al., "A conformation- and phosphorylation-dependent antibody recognizing the paired helical filaments of Alzheimer's disease," J Neurochem. 69(5):2087-95 (1997).
Jones et al., "Replacing the complementarity-determining regions in a human antibody with those from a mouse," Nature. 321(6069):522-5 (1986).
Kayed et al., "Prefilament tau species as potential targets for immunotherapy for Alzheimer disease and related disorders," Curr Opin Immunol. 21(3):359-63 (2009).
Kondo et al., "cis p-tau: early driver of brain injury and tauopathy blocked by antibody," available in PMC Jan. 23, 2016, published in final edited form as: Nature. 523(7561):431-6 (2015) (37 pages).
Köhler et al., "Continuous cultures of fused cells secreting antibody of predefined specificity," Nature. 256(5517):495-7 (1975).
Köhler et al., "Derivation of specific antibody-producing tissue culture and tumor lines by cell fusion," Eur J Immunol. 6(7): 511-519 (1976).
Lemere, "Immunotherapy for Alzheimer's disease: hoops and hurdles," Mol Neurodegener. 8:36 (2013) (6 pages).
Lim et al., "Pinning down phosphorylated tau and tauopathies," Biochim Biophys Acta. 1739(2-3):311-322 (2005).
Liu et al., "Inhibition of soluble epoxide hydrolase enhances the anti-inflammatory effects of aspirin and 5-lipoxygenase activation protein inhibitor in a murine model," available in PMC Feb. 23, 2012, published in final edited form as: Biochem Pharmacol. 79(6):880-7 (2010).
Lu et al., "Pinning down proline-directed phosphorylation signaling," Trends Cell Biol. 12(4):164-72 (2002).
Lu et al., "Prolyl cis-trans isomerization as a molecular timer," Nat Chem Biol. 3(10):619-629 (2007) (11 pages).
Lu et al., "Role of Tau Conformations in Vascular Contribution to Cognitive Impairment and Dementia," National Institute of Health. Jul. 21, 2017, <https://grantome.com/grant/NIH/R01-AG055559-01>, retrieved on May 27, 2022 (Abstract only) (3 pages).
Lu et al., "Targeting carcinogenesis: a role for the prolyl isomerase Pin1?" Mol Carcinog. 45(6):397-402 (2006).
Lu et al., "The prolyl isomerase PIN1: a pivotal new twist in phosphorylation signalling and disease," Nat Rev Mol Cell Biol. 8(11):904-16 (2007).
Lu, "Pinning down cell signaling, cancer and Alzheimer's disease," Trends Biochem Sci. 29(4):200-9 (2004).
Lummis et al., "Cis-trans isomerization at a proline opens the pore of a neurotransmitter-gated ion channel," Nature. 438(7065):248-52 (2005).
Ma et al., "Antibody catalysis of peptidyl-prolyl cis-trans isomerization in the folding of RNase T1," Proc Natl Acad Sci USA. 95(13):7251-6 (1998).
Marks et al., "By-passing immunization. Human antibodies from V-gene libraries displayed on phage," J Mol Biol. 222(3):581-97 (1991).
Nakamura et al., "Proline isomer-specific antibodies reveal the early pathogenic tau conformation in Alzheimer's disease" Cell. 149(1):232-44 (2012).
Office Action for U.S. Appl. No. 14/113,991, mailed Sep. 2, 2015 (27 pages).
Office Action for U.S. Appl. No. 14/325,013, mailed Sep. 2, 2015 (45 pages).
Padlan et al., "Structure of an antibody-antigen complex: crystal structure of the HyHEL-10 Fab-lysozyme complex," Proc Natl Acad Sci USA. 86(15):5938-5942 (1989).
Pastorino et al., "Phosphorylation of the amyloid precursor protein (APP): is this a mechanism in favor or against Alzheimer's disease," Neurosci Res Commun. 35(3):213-31 (2004).
Paul, Chapter 9: Structure and Function of Immunoglobulins, *Fundamental Immunology, Third Edition*. Raven Press Ltd., 292-295 (1993) (6 pages).
Presta, "Antibody engineering," Curr Opin Struct Biol. 2:593-596 (1992).
Rafii et al., "Recent developments in Alzheimer's disease therapeutics," BMC Med. 7:7 (2009) (4 pages).
Riechmann et al., "Reshaping human antibodies for therapy," Nature. 332(6162):323-7 (1988).
Rudikoff et al., "Single amino acid substitution altering antigen-binding specificity," Proc Natl Acad Sci U S A. 79(6):1979-83 (1982).
Schmelzer et al., "Enhancement of antinociception by coadministration of nonsteroidal anti-inflammatory drugs and soluble epoxide hydrolase inhibitors," Proc Natl Acad Sci U S A. 130(37):13646-13651 (2006).
Tabira, "Immunization therapy for Alzheimer disease: a comprehensive review of active immunization strategies," Tohoku J Exp Med. 220(2):95-106 (2010).
Third Party Observation mailed May 12, 2021 for International Patent Application No. PCT/US2020/013149, Panigrahy et al., "Methods for the prevention or treatment of cytokine storm, and for preventing diseases or conditions caused by cytokine storm," filed Jan. 10, 2020 (7 pages).
Tisoncik et al., "Into the eye of the cytokine storm," Microbiol Mol Biol Rev. 76(1):16-32 (2012).
Ubhi et al., "Recent advances in the development of immunotherapies for tauopathies," available in PMC Aug. 1, 2012, published in final edited form as: Exp Neurol. 230(2):157-61 (2011) (12 pages).
Wang et al., "Serine-cis-proline and serine-trans-proline isosteres: stereoselective synthesis of (Z)- and (E)-alkene mimics by Still-Wittig and Ireland-Claisen rearrangements," J Org Chem. 68(6):2343-9 (2003).
Wisniewski et al., "Vaccination as a therapeutic approach to Alzheimer's disease," Mt Sinai J Med. 77(1):17-31 (2010).
Wittelsberger et al., "Pseudoprolines: Targeting a cis Conformation in a Mimetic of the gp120 V3 Loop of HIV-1," Angew Chem Int Ed Engl. 39(6):1111-5 (2000).
Wolfe, "The role of tau in neurodegenerative diseases and its potential as a therapeutic target," Scientifica 2012:796024 (2012) (20 pages).
Written Opinion of the International Search Authority for International Application No. PCT/US12/35473, mailed Dec. 10, 2012 (7 pages).
Written Opinion of the International Searching Authority for International Application No. PCT/US2012/039850, mailed Oct. 3, 2012 (5 pages).
Wulf et al., "Phosphorylation-specific prolyl isomerization: is there an underlying theme?" Nat Cell Biol. 7(5):435-41 (2005).

* cited by examiner

FIG. 1D

| | FW region 1 (1–23) | CDR-L1 (24–39) | FW region 2 (40–54) | CDR-L2 (55–60) | |
|---|---|---|---|---|---|
| Light Chain of C113 and HT13 (SEQ ID NO: 15) | DVVMTQTPLSLPVSLGDQASISC | RSSQSLVHSDGNTYLH | WYLQKPGQSPKLLIY | KVSNRF | 60 |
| Light Chain of HT1, HT2, HT3, HT4 (SEQ ID NO: 16) | DVVMTQSPLSLPVTLGQPASISC | RSSQSLVHSDGNTYLH | WYLQKPGQSPQLLIY | KVSNRF | 60 |
| Light Chain of HT14, HT15, HT16, HT17 (SEQ ID NO: 17) | DVVMTQSPLSLPVTLGQPASISC | RSSQSLVHSDGNTYLN | WYLQKPGQSPQLLIY | KVSNRF | 60 |
| Light Chain of HT5, HT6, HT7, HT8 (SEQ ID NO: 18) | DVVMTQSPLSLPVTLGQPASISC | RSSQSLVHSDGNTYLH | WYLQKPGQSPQLLIY | KVSNRD | 60 |
| Light Chain of HT9, HT10, HT11, HT12 (SEQ ID NO: 19) | DVVMTQSPLSLPVTLGQPASISC | RSSQSLVHSDGNTYLH | WYLQKPGQSPQLLIY | KVSNRF | 60 |
| Light Chain of HT18 (SEQ ID NO: 20) | DIQMTQSPSTLSASVGDRVTITC | RSSQSLVHSDGNTYLH | WYQQKPGKAPKLLIY | KVSNRF | 60 |
| Light Chain of humanized cis-mAb (SEQ ID NO: 21) | DIVMTQSPLSLPVTPGEPASISC | RSSQSLVHSDGNTYLH | WYLQKPGQSPKLLIY | KVSNRF | 60 |
| Light Chain of humanized cis-mAb (SEQ ID NO: 22) | DIVMTQSPLSLPVTPGEPASISC | RSSQSLVHSDGNTYLH | WYLQKPGQSPKLLIY | KVSNRF | 60 |
| Light Chain of humanized cis-mAb (SEQ ID NO: 23) | DIQMTQSPSTLSASVGDRVTITC | RSSQSLVHSDGNTYLH | WYLQKPGKAPKLLIY | KVSNRF | 60 |

| | CDR-L2 (61) | FW region 3 (62–93) | CDR-L3 (94–100) | FW region 4 (101–112) | |
|---|---|---|---|---|---|
| Light Chain of C113 and HT13 (SEQ ID NO: 15) | S | GVPDRFSGSGSGTDFTLKISRLEAEDLGVYFC | SQSTHVP | WTFGGGTKLEIK | 112 |
| Light Chain of HT1, HT2, HT3, HT4 (SEQ ID NO: 16) | S | GVPDRFSGSGSGTDFTLKISRVEAEDVGVYFC | SQSTHVP | WTFGGGTKVEIK | 112 |
| Light Chain of HT14, HT15, HT16, HT17 (SEQ ID NO: 17) | S | GVPDRFSGSGSGTDFTLKISRVEAEDVGVYFC | SQSTHVP | WTFGGGTKVEIK | 112 |
| Light Chain of HT5, HT6, HT7, HT8 (SEQ ID NO: 18) | S | GVPDRFSGSGSGTDFTLKISRVEAEDVGVYFC | SQSTHVP | WTFGGGTKVEIK | 112 |
| Light Chain of HT9, HT10, HT11, HT12 (SEQ ID NO: 19) | S | GVPDRFSGSGSGTDFTLKISRVEAEDVGVYYC | SQSTHVP | WTFGGGTKVEIK | 112 |
| Light Chain of HT18 (SEQ ID NO: 20) | S | GVPSRFSGSGSGTEFTLTISSLQPDDFATYYC | SQSTHVP | WTFGQGTKLEIK | 112 |
| Light Chain of humanized cis-mAb (SEQ ID NO: 21) | S | GVPDRFSGSGSGTDFTLKISRLEAEDVGVYYC | SQSTHVP | WTFGQGTKLEIK | 112 |
| Light Chain of humanized cis-mAb (SEQ ID NO: 22) | S | GVPDRFSGSGSGTDFTLKISRVEAEDVGVYYC | SQSTHVP | WTFGQGTKLEIK | 112 |
| Light Chain of humanized cis-mAb (SEQ ID NO: 23) | S | GVPSRFSGSGSGTEFTLTISSLQPDDFATYYC | SQSTHVP | WTFGQGTKLEIK | 112 |

AT8 (early tangle) + DAPI

Control VaD

AT100 (late tangle) + DAPI

Control VaD

ThioS + Haematoxylin

Control VaD

FIG. 13B
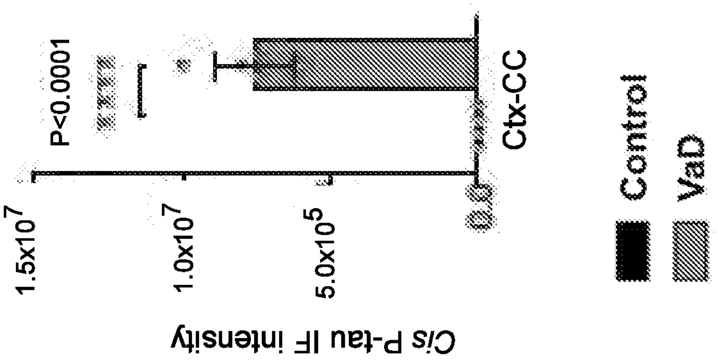
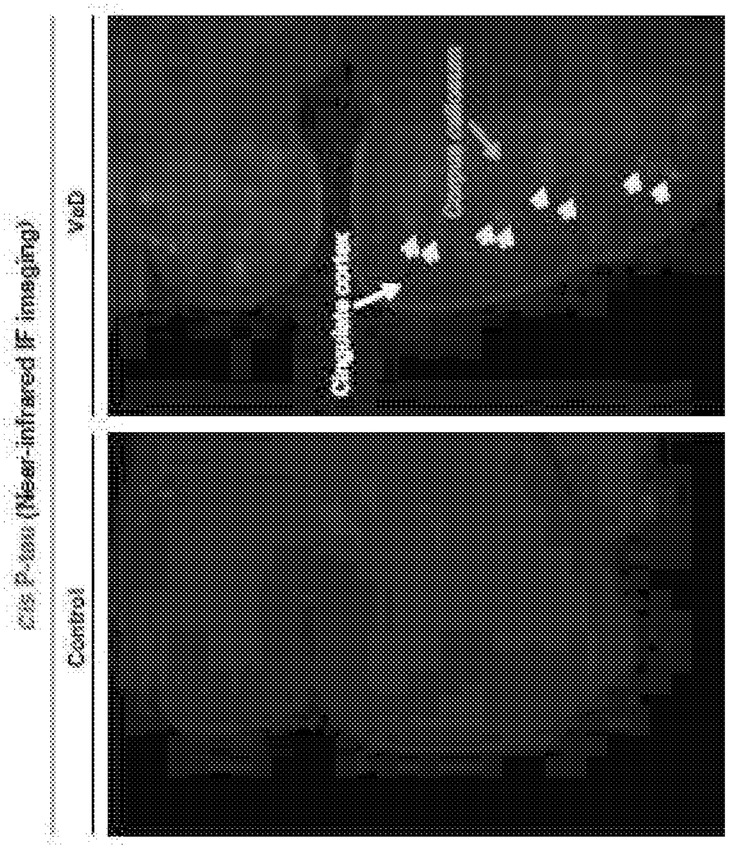
FIG. 13A

FIG. 32A
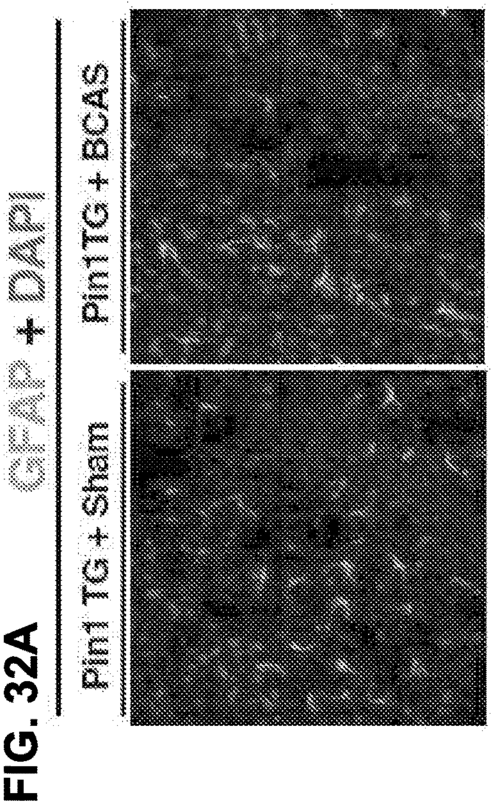
FIG. 32B
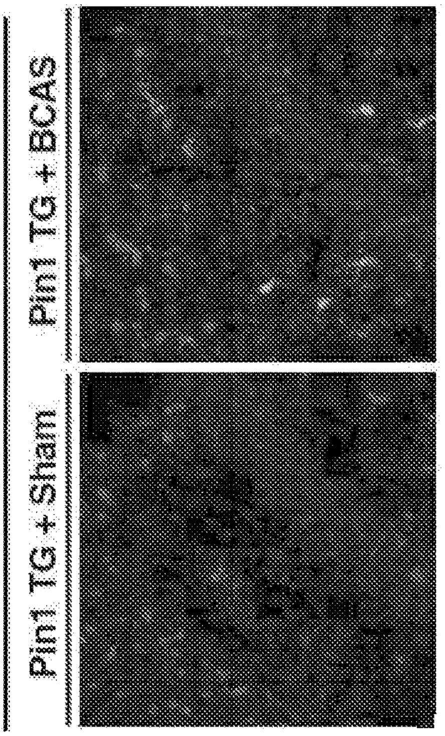
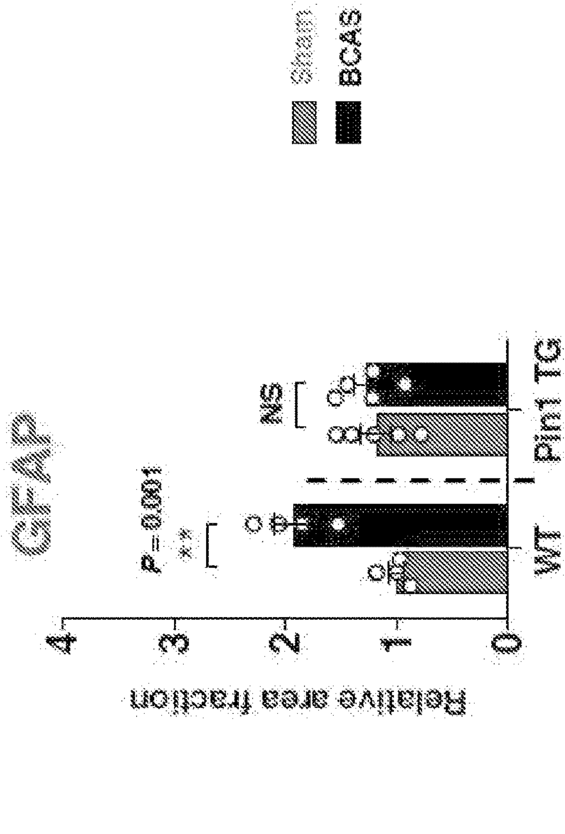
FIG. 32C
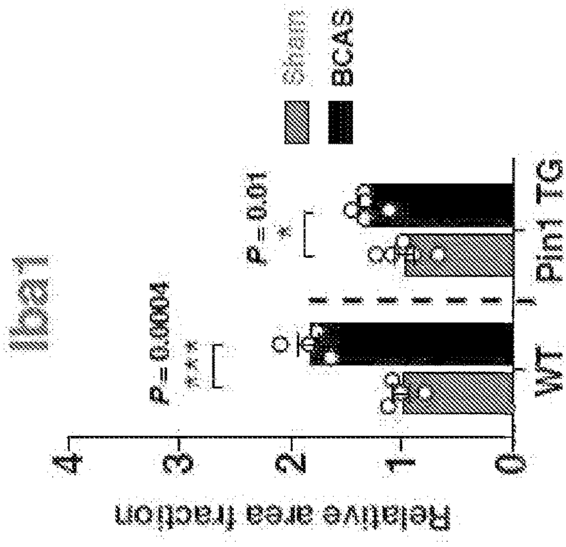
FIG. 32D htau mice
Cis mAb or IgG
(first four months weekly and continued biweekly)
0
3M
7M
11M Escape latency (s)
100
80
60
40
20
0
1
2
3
4
***
**

Morris water maze
Probe trial
WT+veh
htau+IgG
htau+cis mAb
WT + veh
htau + IgG
htau + cis mAb
Time in target quad (s)
40
30
20
10
0
P<0.006
P<0.03
**
*
Probe
WT + veh
htau + IgG
htau + cis mAb

SEQUENCE LISTING

```
<160> NUMBER OF SEQ ID NOS: 54

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: Xaa is His or Asn

<400> SEQUENCE: 1

Arg Ser Ser Gln Ser Leu Val His Ser Asp Gly Asn Thr Tyr Leu Xaa
1               5                   10                  15


<210> SEQ ID NO 2
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa is Phe or Asp

<400> SEQUENCE: 2

Lys Val Ser Asn Arg Xaa Ser
1               5


<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Ser Gln Ser Thr His Val Pro
1               5


<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Ser Tyr Trp Ile His
1               5


<210> SEQ ID NO 5
<211> LENGTH: 17
<212> TYPE: PRT
<213> ORGANISM: Artificial Sequence
```

<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: Xaa is Lys or Gln

<400> SEQUENCE: 5

Val Ile Asp Pro Ser Asp Ser Tyr Thr Arg Tyr Asn Gln Lys Phe Xaa
1 5 10 15

Gly

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Trp Glu Val Asp Tyr
1 5

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Arg Ser Ser Gln Ser Leu Val His Ser Asp Gly Asn Thr Tyr Leu His
1 5 10 15

<210> SEQ ID NO 8
<211> LENGTH: 16
<212> TYPE: PRT
<213> ORGANISM: Artificial Sequence
<220> FEATURE:
<223> OTHER INFORMATION: Synthetic Construct

<400> SEQUENCE: 8

Arg Ser Ser Gln Ser Leu Val His Ser Asp Gly Asn Thr Tyr Leu Asn
1 5 10 15

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Lys Val Ser Asn Arg Phe Ser
1 5

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Lys Val Ser Asn Arg Asp Ser
1 5

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Val Ile Asp Pro Ser Asp Ser Tyr Thr Arg Tyr Asn Gln Lys Phe Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Val Ile Asp Pro Ser Asp Ser Tyr Thr Arg Tyr Asn Gln Lys Phe Gln
1               5                   10                  15

Gly

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Thr Trp Glu Val Asp Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Thr Thr Trp Glu Val Asp Tyr
1               5

<210> SEQ ID NO 15
<211> LENGTH: 112
<212> TYPE: PRT
<213> ORGANISM: Artificial Sequence
<220> FEATURE:
<223> OTHER INFORMATION: Synthetic Construct

<400> SEQUENCE: 15

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

```
65                  70                  75                  80

Ser Arg Leu Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110


<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Val Glu Ile Lys
            100                 105                 110


<210> SEQ ID NO 17
<211> LENGTH: 112
<212> TYPE: PRT
<213> ORGANISM: Artificial Sequence
<220> FEATURE:
<223> OTHER INFORMATION: Synthetic Construct

<400> SEQUENCE: 17

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Val Glu Ile Lys
            100                 105                 110


<210> SEQ ID NO 18
<211> LENGTH: 112
<212> TYPE: PRT
<213> ORGANISM: Artificial Sequence
<220> FEATURE:
<223> OTHER INFORMATION: Synthetic Construct

<400> SEQUENCE: 18
```

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val His Ser
20 25 30

Asp Gly Asn Thr Tyr Leu His Trp Tyr Leu Gln Lys Pro Gly Gln Ser
35 40 45

Pro Gln Leu Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Ser Gln Ser
85 90 95

Thr His Val Pro Trp Thr Phe Gly Gly Gly Thr Lys Val Glu Ile Lys
100 105 110

<210> SEQ ID NO 19
<211> LENGTH: 112
<212> TYPE: PRT
<213> ORGANISM: Artificial Sequence
<220> FEATURE:
<223> OTHER INFORMATION: Synthetic Construct

<400> SEQUENCE: 19

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val His Ser
20 25 30

Asp Gly Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Trp Thr Phe Gly Gly Gly Thr Lys Val Glu Ile Lys
100 105 110

<210> SEQ ID NO 20
<211> LENGTH: 112
<212> TYPE: PRT
<213> ORGANISM: Artificial Sequence
<220> FEATURE:
<223> OTHER INFORMATION: Synthetic Construct

<400> SEQUENCE: 20

Asp Ile Gln Met Thr Gln Ser Pro Ser Thr Leu Ser Ala Ser Val Gly
1 5 10 15

Asp Arg Val Thr Ile Thr Cys Arg Ser Ser Gln Ser Leu Val His Ser
20 25 30

Asp Gly Asn Thr Tyr Leu His Trp Tyr Gln Gln Lys Pro Gly Lys Ala
35 40 45

Pro Lys Leu Leu Ile Tyr Lys Val Ser Asn Arg Phe Ser Gly Val Pro
50 55 60

Ser Arg Phe Ser Gly Ser Gly Ser Gly Thr Glu Phe Thr Leu Thr Ile
65 70 75 80

Ser Ser Leu Gln Pro Asp Asp Phe Ala Thr Tyr Tyr Cys Ser Gln Ser

```
                85                  90                  95

Thr His Val Pro Trp Thr Phe Gly Gln Gly Thr Lys Leu Glu Ile Lys
            100                 105                 110


<210> SEQ ID NO 21
<211> LENGTH: 112
<212> TYPE: PRT
<213> ORGANISM: Artificial Sequence
<220> FEATURE:
<223> OTHER INFORMATION: Synthetic Construct

<400> SEQUENCE: 21

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
            100                 105                 110


<210> SEQ ID NO 22
<211> LENGTH: 112
<212> TYPE: PRT
<213> ORGANISM: Artificial Sequence
<220> FEATURE:
<223> OTHER INFORMATION: Synthetic Construct

<400> SEQUENCE: 22

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
            100                 105                 110


<210> SEQ ID NO 23
<211> LENGTH: 112
<212> TYPE: PRT
<213> ORGANISM: Artificial Sequence
<220> FEATURE:
<223> OTHER INFORMATION: Synthetic Construct

<400> SEQUENCE: 23

Asp Ile Gln Met Thr Gln Ser Pro Ser Thr Leu Ser Ala Ser Val Gly
1               5                   10                  15
```

```
Asp Arg Val Thr Ile Thr Cys Arg Ser Ser Gln Ser Leu Val His Ser
            20                  25                  30

Asp Gly Asn Thr Tyr Leu His Trp Tyr Leu Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Ser Gln Ser
                85                  90                  95

Thr His Val Pro Trp Thr Phe Gly Gln Gly Thr Lys Leu Glu Ile Lys
            100                 105                 110


<210> SEQ ID NO 24
<211> LENGTH: 114
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Ser Tyr Thr Arg Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Thr Trp Glu Val Asp Tyr Trp Gly Gln Gly Thr Thr Leu Thr Val
            100                 105                 110

Ser Ser


<210> SEQ ID NO 25
<211> LENGTH: 114
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Leu Lys Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Ser Tyr Thr Arg Tyr Asn Gln Lys Phe
    50                  55                  60

Lys Gly Arg Ala Thr Leu Thr Val Asp Thr Ser Ala Ser Thr Ala Tyr
65                  70                  75                  80

Met Gln Leu Ser Ser Leu Thr Ser Glu Asp Ser Ala Val Tyr Tyr Cys
                85                  90                  95
```

```
Thr Thr Trp Glu Val Asp Tyr Trp Gly Gln Gly Thr Thr Val Thr Val
            100                 105                 110

Ser Ser


<210> SEQ ID NO 26
<211> LENGTH: 114
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Ser Tyr Thr Arg Tyr Asn Gln Lys Phe
    50                  55                  60

Lys Gly Arg Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Thr Trp Glu Val Asp Tyr Trp Gly Gln Gly Thr Leu Val Thr Val
            100                 105                 110

Ser Ser


<210> SEQ ID NO 27
<211> LENGTH: 114
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Arg Pro Gly Gln Gly Leu Glu Trp Ile
        35                  40                  45

Gly Val Ile Asp Pro Ser Asp Ser Tyr Thr Arg Tyr Asn Gln Lys Phe
    50                  55                  60

Lys Gly Arg Val Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Thr Trp Glu Val Asp Tyr Trp Gly Gln Gly Thr Leu Val Thr Val
            100                 105                 110

Ser Ser


<210> SEQ ID NO 28
<211> LENGTH: 114
<212> TYPE: PRT
<213> ORGANISM: Artificial Sequence
<220> FEATURE:
<223> OTHER INFORMATION: Synthetic Construct
```

<400> SEQUENCE: 28

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Ile His Trp Val Arg Gln Arg Pro Gly Gln Gly Leu Glu Trp Ile
35 40 45

Gly Val Ile Asp Pro Ser Asp Ser Tyr Thr Arg Tyr Asn Gln Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Thr Thr Trp Glu Val Asp Tyr Trp Gly Gln Gly Thr Leu Val Thr Val
100 105 110

Ser Ser

<210> SEQ ID NO 29
<211> LENGTH: 114
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile His Trp Val Arg Gln Ala Pro Gly Gln Gly Leu Glu Trp Met
35 40 45

Gly Val Ile Asp Pro Ser Asp Ser Tyr Thr Arg Tyr Asn Gln Lys Phe
50 55 60

Lys Gly Arg Val Thr Ile Thr Arg Asp Thr Ser Met Ser Thr Ala Tyr
65 70 75 80

Thr Glu Leu Ser Ser Leu Arg Ser Glu Asp Thr Ala Val Tyr Tyr Cys
85 90 95

Thr Thr Trp Glu Val Asp Tyr Trp Gly Gln Gly Thr Leu Val Thr Val
100 105 110

Ser Ser

<210> SEQ ID NO 30
<211> LENGTH: 114
<212> TYPE: PRT
<213> ORGANISM: Artificial Sequence
<220> FEATURE:
<223> OTHER INFORMATION: Synthetic Construct

<400> SEQUENCE: 30

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile His Trp Val Arg Gln Ala Pro Gly Gln Gly Leu Glu Trp Met
35 40 45

Gly Val Ile Asp Pro Ser Asp Ser Tyr Thr Arg Tyr Asn Gln Lys Phe

```
    50                  55                  60

Lys Gly Arg Val Thr Ile Thr Arg Asp Thr Ser Met Ser Thr Ala Tyr
65                  70                  75                  80

Thr Glu Leu Ser Ser Leu Arg Ser Glu Asp Ser Ala Val Tyr Tyr Cys
                85                  90                  95

Thr Thr Trp Glu Val Asp Tyr Trp Gly Gln Gly Thr Leu Val Thr Val
            100                 105                 110

Ser Ser


<210> SEQ ID NO 31
<211> LENGTH: 114
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Val Ile Asp Pro Ser Asp Ser Tyr Thr Arg Tyr Asn Gln Lys Phe
    50                  55                  60

Lys Gly Arg Val Thr Ile Thr Arg Asp Thr Ser Met Ser Thr Ala Tyr
65                  70                  75                  80

Thr Glu Leu Ser Ser Leu Arg Ser Glu Asp Thr Ala Val Tyr Tyr Cys
                85                  90                  95

Ala Thr Trp Glu Val Asp Tyr Trp Gly Gln Gly Thr Leu Val Thr Val
            100                 105                 110

Ser Ser


<210> SEQ ID NO 32
<211> LENGTH: 114
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Val Ile Asp Pro Ser Asp Ser Tyr Thr Arg Tyr Asn Gln Lys Phe
    50                  55                  60

Lys Gly Arg Val Thr Ile Thr Arg Asp Thr Ser Met Ser Thr Ala Tyr
65                  70                  75                  80

Thr Glu Leu Ser Ser Leu Arg Ser Glu Asp Ser Ala Val Tyr Tyr Cys
                85                  90                  95

Thr Thr Trp Glu Val Asp Tyr Trp Gly Gln Gly Thr Leu Val Thr Val
            100                 105                 110

Ser Ser
```

<210> SEQ ID NO 33
<211> LENGTH: 114
<212> TYPE: PRT
<213> ORGANISM: Artificial Sequence
<220> FEATURE:
<223> OTHER INFORMATION: Synthetic Construct

<400> SEQUENCE: 33

Gln Asp Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile His Trp Val Arg Gln Ala Pro Gly Gln Gly Leu Glu Trp Met
35 40 45

Gly Val Ile Asp Pro Ser Asp Ser Tyr Thr Arg Tyr Asn Gln Lys Phe
50 55 60

Gln Gly Arg Val Thr Ile Thr Arg Asp Thr Ser Met Ser Thr Ala Tyr
65 70 75 80

Thr Glu Leu Ser Ser Leu Arg Ser Glu Asp Thr Ala Val Tyr Tyr Cys
85 90 95

Ala Arg Trp Glu Val Asp Tyr Trp Gly Gln Gly Thr Leu Val Thr Val
100 105 110

Ser Ser

<210> SEQ ID NO 34
<211> LENGTH: 114
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Leu Ser
1 5 10 15

Ser Val Lys Val Ser Cys Lys Ala Ser Gly Tyr Thr Phe Thr Ser Tyr
20 25 30

Trp Ile His Trp Val Arg Gln Ala Pro Gly Gln Gly Leu Glu Trp Met
35 40 45

Gly Val Ile Asp Pro Ser Asp Ser Tyr Thr Arg Tyr Asn Gln Lys Phe
50 55 60

Gln Gly Arg Val Thr Ile Thr Arg Asp Thr Ser Met Ser Thr Ala Tyr
65 70 75 80

Thr Glu Leu Ser Ser Leu Arg Ser Glu Asp Thr Ala Val Tyr Tyr Cys
85 90 95

Ala Arg Trp Glu Val Asp Tyr Trp Gly Gln Gly Thr Leu Val Thr Val
100 105 110

Ser Ser

<210> SEQ ID NO 35
<211> LENGTH: 114
<212> TYPE: PRT
<213> ORGANISM: Artificial Sequence
<220> FEATURE:
<223> OTHER INFORMATION: Synthetic Construct

<400> SEQUENCE: 35

Gln Val Gln Leu Val Gln Ser Gly Ala Glu Val Lys Lys Pro Gly Ser
1 5 10 15

```
Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Val Ile Asp Pro Ser Asp Ser Tyr Thr Arg Tyr Asn Gln Lys Phe
    50                  55                  60

Gln Gly Arg Val Thr Ile Thr Arg Asp Thr Ser Met Ser Thr Ala Tyr
65                  70                  75                  80

Thr Glu Leu Ser Ser Leu Arg Ser Glu Asp Thr Ala Val Tyr Tyr Cys
                85                  90                  95

Ala Arg Trp Glu Val Asp Tyr Trp Gly Gln Gly Thr Leu Val Thr Val
            100                 105                 110

Ser Ser


<210> SEQ ID NO 36
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa is Ser or Leu
<220> FEATURE:
<221> NAME/KEY: misc_feature
<222> LOCATION: (4)..(4)
<223> OTHER INFORMATION: Xaa is Ser or Thr
<220> FEATURE:
<221> NAME/KEY: misc_feature
<222> LOCATION: (6)..(6)
<223> OTHER INFORMATION: Xaa is Ser or Pro
<220> FEATURE:
<221> NAME/KEY: misc_feature
<222> LOCATION: (7)..(7)
<223> OTHER INFORMATION: Xaa is Val or Ala
<220> FEATURE:
<221> NAME/KEY: misc_feature
<222> LOCATION: (8)..(8)
<223> OTHER INFORMATION: Xaa is Ser or Thr
<220> FEATURE:
<221> NAME/KEY: misc_feature
<222> LOCATION: (9)..(9)
<223> OTHER INFORMATION: Xaa is Leu or Val
<220> FEATURE:
<221> NAME/KEY: misc_feature
<222> LOCATION: (11)..(11)
<223> OTHER INFORMATION: Xaa is Asp or Gln
<220> FEATURE:
<221> NAME/KEY: misc_feature
<222> LOCATION: (12)..(12)
<223> OTHER INFORMATION: Xaa is Arg or Pro
<220> FEATURE:
<221> NAME/KEY: misc_feature
<222> LOCATION: (13)..(13)
<223> OTHER INFORMATION: Xaa is Val or Ala
<220> FEATURE:
<221> NAME/KEY: misc_feature
<222> LOCATION: (14)..(14)
<223> OTHER INFORMATION: Xaa is Ser or Thr
<220> FEATURE:
<221> NAME/KEY: misc_feature
<222> LOCATION: (16)..(16)
<223> OTHER INFORMATION: Xaa is Ser or Thr

<400> SEQUENCE: 36

Ser Pro Xaa Xaa Leu Xaa Xaa Xaa Xaa Gly Xaa Xaa Xaa Xaa Ile Xaa
1               5                   10                  15

Cys
```

<210> SEQ ID NO 37
<211> LENGTH: 17
<212> TYPE: PRT
<213> ORGANISM: Artificial Sequence
<220> FEATURE:
<223> OTHER INFORMATION: Synthetic Construct

<400> SEQUENCE: 37

Ser Pro Leu Ser Leu Pro Val Thr Leu Gly Gln Pro Ala Ser Ile Ser
1 5 10 15

Cys

<210> SEQ ID NO 38
<211> LENGTH: 17
<212> TYPE: PRT
<213> ORGANISM: Artificial Sequence
<220> FEATURE:
<223> OTHER INFORMATION: Synthetic Construct

<400> SEQUENCE: 38

Ser Pro Ser Thr Leu Ser Ala Ser Val Gly Asp Arg Val Thr Ile Thr
1 5 10 15

Cys

<210> SEQ ID NO 39
<211> LENGTH: 15
<212> TYPE: PRT
<213> ORGANISM: Artificial Sequence
<220> FEATURE:
<223> OTHER INFORMATION: Synthetic Construct

<400> SEQUENCE: 39

Trp Tyr Leu Gln Lys Pro Gly Gln Ser Pro Gln Leu Leu Ile Tyr
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

Trp Tyr Gln Gln Lys Pro Gly Lys Ala Pro Lys Leu Leu Ile Tyr
1 5 10 15

<210> SEQ ID NO 41
<211> LENGTH: 32
<212> TYPE: PRT
<213> ORGANISM: Artificial Sequence
<220> FEATURE:
<223> OTHER INFORMATION: Synthetic Construct

<400> SEQUENCE: 41

Gly Val Pro Asp Arg Phe Ser Gly Ser Gly Ser Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 43
<211> LENGTH: 15
<212> TYPE: PRT
<213> ORGANISM: Artificial Sequence
<220> FEATURE:
<223> OTHER INFORMATION: Synthetic Construct

<400> SEQUENCE: 43

Trp Tyr Leu Gln Lys Pro Gly Gln Ser Pro Gln Leu Leu Ile Tyr
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

Trp Tyr Gln Gln Lys Pro Gly Lys Ala Pro Lys Leu Leu Ile Tyr
1 5 10 15

<210> SEQ ID NO 45
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa is Val or Leu
<220> FEATURE:
<221> NAME/KEY: misc_feature
<222> LOCATION: (12)..(12)
<223> OTHER INFORMATION: Xaa is Ser or Ala
<220> FEATURE:
<221> NAME/KEY: misc_feature
<222> LOCATION: (16)..(16)
<223> OTHER INFORMATION: Xaa is Val or Met

<400> SEQUENCE: 45

Val Gln Ser Gly Ala Glu Xaa Lys Lys Pro Gly Xaa Ser Val Lys Xaa
1 5 10 15

Ser Cys Lys Ala Ser Gly Tyr Thr Phe Thr
20 25

<210> SEQ ID NO 46
<211> LENGTH: 26
<212> TYPE: PRT
<213> ORGANISM: Artificial Sequence
<220> FEATURE:
<223> OTHER INFORMATION: Synthetic Construct

<400> SEQUENCE: 46

Val Gln Ser Gly Ala Glu Val Lys Lys Pro Gly Ala Ser Val Lys Met
1 5 10 15

Ser Cys Lys Ala Ser Gly Tyr Thr Phe Thr
20 25

<210> SEQ ID NO 47
<211> LENGTH: 26
<212> TYPE: PRT
<213> ORGANISM: Artificial Sequence
<220> FEATURE:
<223> OTHER INFORMATION: Synthetic Construct

<400> SEQUENCE: 47

```
Val Gln Ser Gly Ala Glu Val Lys Lys Pro Gly Ser Ser Val Lys Val
1               5                   10                  15

Ser Cys Lys Ala Ser Gly Tyr Thr Phe Thr
            20                  25
```

<210> SEQ ID NO 48
<211> LENGTH: 14
<212> TYPE: PRT
<213> ORGANISM: Artificial Sequence
<220> FEATURE:
<223> OTHER INFORMATION: Synthetic Construct

<400> SEQUENCE: 48

```
Trp Val Lys Gln Arg Pro Gly Gln Gly Leu Glu Trp Ile Gly
1               5                   10
```

<210> SEQ ID NO 49
<211> LENGTH: 14
<212> TYPE: PRT
<213> ORGANISM: Artificial Sequence
<220> FEATURE:
<223> OTHER INFORMATION: Synthetic Construct

<400> SEQUENCE: 49

```
Trp Val Arg Gln Ala Pro Gly Gln Gly Leu Glu Trp Met Gly
1               5                   10
```

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

```
Arg Ala Thr Leu Thr Val Asp Thr Ser Ala Ser Thr Ala Tyr Met Glu
1               5                   10                  15

Leu Ser Ser Leu Arg Ser Glu Asp Thr Ala Val Tyr Tyr Cys Thr Thr
            20                  25                  30
```

<210> SEQ ID NO 51
<211> LENGTH: 32
<212> TYPE: PRT
<213> ORGANISM: Artificial Sequence
<220> FEATURE:
<223> OTHER INFORMATION: Synthetic Construct

<400> SEQUENCE: 51

```
Arg Val Thr Ile Thr Arg Asp Thr Ser Met Ser Thr Ala Tyr Thr Glu
1               5                   10                  15

Leu Ser Ser Leu Arg Ser Glu Asp Thr Ala Val Tyr Tyr Cys Thr Thr
            20                  25                  30
```

<210> SEQ ID NO 52
<211> LENGTH: 11
<212> TYPE: PRT
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa is Leu or Thr

<400> SEQUENCE: 52

Trp Gly Gln Gly Thr Xaa Val Thr Val Ser Ser
1               5                   10


<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Trp Gly Gln Gly Thr Leu Val Thr Val Ser Ser
1               5                   10


<210> SEQ ID NO 54
<211> LENGTH: 11
<212> TYPE: PRT
<213> ORGANISM: Artificial Sequence
<220> FEATURE:
<223> OTHER INFORMATION: Synthetic Construct

<400> SEQUENCE: 54

Trp Gly Gln Gly Thr Leu Val Thr Val Ser Ser
1               5                   10
```

CONFORMATION-SPECIFIC ANTIBODIES THAT BIND TAU PROTEIN AND USES THEREOF

STATEMENT AS TO FEDERALLY SPONSORED RESEARCH

This invention was made with government support under grant numbers AG039405, CA167677, and CA122434 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Aug. 31, 2021, is named 01948-277WO2_Sequence Listing_8_31_21_ST25 and is 32,671 bytes in size.

BACKGROUND OF THE DISCLOSURE

Tau is a microtubule-associated protein, predominantly expressed in neurons, that plays a critical role in promoting axonal microtubule assembly and stability. Tau's role as a microtubule stabilizing protein depends on its phosphorylation state. Non-phosphorylated tau, commonly referred to as T-tau, is more effective than phosphorylated tau, commonly referred to as P-tau, in polymerizing microtubules. Furthermore, P-tau, when phosphorylated at the Thr231-Pro motif, is normally converted from cis to trans conformation by a unique phosphorylation-specific proline isomerase Pin1. The loss of function of Pin1 has been linked to the formation of abnormal levels of cis P-tau and to the eventual development of neurodegeneration. Moreover, hyperphosphorylation of tau, especially on serine and/or threonine residues preceding proline (pSer/Thr-Pro), is a neuropathological hallmark of neurological disorders such as Alzheimer's Disease (AD), chronic traumatic encephalopathy (CTE), and others. Hyperphosphorylated tau disrupts microtubule assembly and stability, it leads to axonopathy including impaired axonal microtubules and intracellular transport, compromised neuronal and synaptic function and to an increased propensity for tau oligomerization, aggregation and to the eventual formation of neurofibrillary tangles (NFTs). There is a need to understand how physiologic tau becomes pathogenic at early stages of neurological disease and to develop new therapeutics that specifically target only the pathogenic form of tau protein without affecting physiologic tau for the treatment of neurological disease.

SUMMARY OF THE DISCLOSURE

The present disclosure provides conformation-specific antibodies or antigen-binding fragments that bind specifically to the cis conformation of the phosphorylated-Threonine231-Proline motif of tau protein. The disclosure also provides methods for treating a subject with elevated levels of soluble cis P-tau by reducing the levels of cis P-tau with therapeutic antibodies. Some aspects of the present disclosure are based, at least in part, on the surprising discovery that levels of soluble cis P-tau are elevated in the brain in response to ischemia or hypoxia and that elevated levels of soluble cis P-tau can occur in advance of the onset of symptoms associated with a neurological disorder. Also included in the disclosure are related pharmaceutical compositions, polynucleotides, vectors, host cells, methods of production, methods of treatment, diagnostic methods, and kits.

In a first aspect, the disclosure provides an isolated antibody or an antigen-binding fragment thereof including a complementarity-determining region (CDR) light chain 1 (CDR-L1) having the amino acid sequence of SEQ ID NO: 1 or a variant thereof; a complementarity-determining region (CDR) light chain 2 (CDR-L2) having the amino acid sequence of SEQ ID NO: 2 or a variant thereof; and/or a complementarity-determining region (CDR) light chain 3 (CDR-L3) having the amino acid sequence of SEQ ID NO: 3 or a variant thereof; and/or a complementarity-determining region (CDR) heavy chain 1 (CDR-H1) having the amino acid sequence of SEQ ID NO: 4 or a variant thereof; a complementarity-determining region (CDR) heavy chain 2 (CDR-H2) having the amino acid sequence of SEQ ID NO: 5 or a variant thereof; and/or a complementarity-determining region (CDR) heavy chain 3 (CDR-H3) having the amino acid sequence of SEQ ID NO: 6 or a variant thereof. Variant CDRs for CDR-L1-L3 and for CDRH1-H3 are also envisioned, which may include one, two, three, four, or five amino acid substitutions, deletions, or additions relative to the recited sequence (e.g., one or more of SEQ ID NOs: 1-6). In some embodiments, the isolated antibody or an antigen-binding fragment thereof is a humanized antibody. In some embodiments, the light chain variable domain includes a serine residue seventeen amino acid residues N-terminal to the CDR-L1. In some embodiments, the heavy chain variable domain includes (i) a valine residue twenty-six amino acid residues N-terminal to the CDR-H1; (ii) a serine residue twenty-four amino acid residues N-terminal to the CDR-H1; (iii) a lysine residue nineteen amino acid residues N-terminal to the CDR-H1; (iv) an arginine residue at the amino acid residue directly C-terminal to CDR-H2; and/or (v) a valine residue seven amino residues C-terminal to CDR-H3.

In some embodiments, the light chain variable domain comprises a serine residue seventeen amino acid residues N-terminal to the CDR-L1 (e.g., in the framework region of the light chain variable domain that is N-terminal to CDR-L1).

In some embodiments, the heavy chain variable domain comprises a valine residue twenty-six amino acid residues N-terminal to the CDR-H1 (e.g., in the framework region of the heavy chain variable domain that is N-terminal to CDR-H1). In some embodiments, the heavy chain variable domain comprises a serine residue twenty-four amino acid residues N-terminal to the CDR-H1 (e.g., in the framework region of the heavy chain variable domain that is N-terminal to CDR-H1). In some embodiments, the heavy chain variable domain comprises a lysine residue nineteen amino acid residues N-terminal to the CDR-H1 (e.g., in the framework region of the heavy chain variable domain that is N-terminal to CDR-H1). In some embodiments, the heavy chain variable domain comprises an arginine residue at the amino acid residue directly C-terminal to CDR-H2 (e.g., in the framework region of the heavy chain variable domain that is between CDR-H2 and CDR-H3). In some embodiments, the heavy chain variable domain comprises a valine residue seven amino residues C-terminal to CDR-H3 (e.g., in the framework region of the heavy chain variable domain that is C-terminal to CDR-H1).

In some embodiments, the framework region of the heavy chain variable domain that is N-terminal to CDR-H1 includes a valine residue twenty-six amino acid residues N-terminal to the CDR-H1; a serine residue twenty-four amino acid residues N-terminal to the CDR-H1; and a lysine residue nineteen amino acid residues N-terminal to the CDR-H1.

In some embodiments, the antibody or antigen-binding fragment thereof includes a complementarity-determining region (CDR) light chain 1 (CDR-L1) having the amino acid sequence of SEQ ID NO: 7, SEQ ID NO: 8, or a variant thereof (e.g., a variant with one, two, three, four, or five amino acid substitutions, deletions, or additions relative to the recited sequences).

In some embodiments, the antibody or antigen-binding fragment thereof includes a complementarity-determining region (CDR) light chain 2 (CDR-L2) having the amino acid sequence of SEQ ID NO: 9, SEQ ID NO: 10, or a variant thereof (e.g., a variant with one, two, three, four, or five amino acid substitutions, deletions, or additions relative to the recited sequences).

In some embodiments, the antibody or antigen-binding fragment thereof includes a complementarity-determining region (CDR) heavy chain 2 (CDR-H2) having the amino acid sequence of SEQ ID NO: 11, SEQ ID NO: 12, or a variant thereof (e.g., a variant with one, two, three, four, or five amino acid substitutions, deletions, or additions relative to the recited sequences).

In some embodiments, the antibody or antigen-binding fragment thereof includes a threonine residue directly N-terminal to CDR-H3, wherein, optionally, CDR-H3 and the amino acid residue directly N-terminal to CDR-H3 together include the amino acid sequence of SEQ ID NO: 13. In some embodiments, the antibody or antigen-binding fragment thereof includes two threonine residues directly N-terminal to CDR-H3, wherein, optionally, CDR-H3 and the two amino acid residues directly N-terminal to CDR-H3 together include the amino acid sequence of SEQ ID NO: 14.

In some embodiments, the antibody or antigen-binding fragment thereof includes a framework region of the light chain variable domain that is N-terminal to CDR-L1 and which includes an amino acid sequence with at least 90%, 91%, 92%, 93%, 94%, 95%, 96%, 97%, 98%, 99% or 100% sequence identity to the sequence of SEQ ID NO: 36.

In some embodiments, the antibody or antigen-binding fragment thereof includes a framework region that is N-terminal to CDR-L1 of the light chain variable domain and which includes an amino acid sequence with at least 90%, 91%, 92%, 93%, 94%, 95%, 96%, 97%, 98%, 99% or 100% sequence identity to the amino acid sequence of SEQ ID NO: 37 or SEQ ID NO: 38.

In some embodiments, the antibody or antigen-binding fragment thereof includes a framework region that is between CDR-L1 and CDR-L2 of the light chain variable domain and which includes an amino acid sequence with at least 90%, 91%, 92%, 93%, 94%, 95%, 96%, 97%, 98%, 99% or 100% sequence identity to the amino acid sequence of SEQ ID NO: 39 or SEQ ID NO: 40.

In some embodiments, the antibody or antigen-binding fragment thereof includes a framework region that is between CDR-L2 and CDR-L3 of the light chain variable domain and which includes an amino acid sequence with at least 90%, 91%, 92%, 93%, 94%, 95%, 96%, 97%, 98%, 99% or 100% sequence identity to the amino acid sequence of SEQ ID NO: 41 or SEQ ID NO: 42.

In some embodiments, the antibody or antigen-binding fragment thereof includes a framework region that is C-terminal to CDR-L3 of the light chain variable domain and which includes an amino acid sequence with at least 90%, 91%, 92%, 93%, 94%, 95%, 96%, 97%, 98%, 99% or 100% sequence identity to the amino acid sequence of SEQ ID NO: 43 or SEQ ID NO: 44.

In some embodiments, the antibody or antigen-binding fragment thereof includes a framework region of the heavy chain variable domain that is N-terminal to CDR-H1 and which includes an amino acid sequence with at least 90%, 91%, 92%, 93%, 94%, 95%, 96%, 97%, 98%, 99% or 100% sequence identity to the sequence of SEQ ID NO: 45.

In some embodiments, the antibody or antigen-binding fragment thereof includes a framework region that is N-terminal to CDR-H1 of the heavy chain variable domain and which includes an amino acid sequence with at least 90%, 91%, 92%, 93%, 94%, 95%, 96%, 97%, 98%, 99% or 100% sequence identity to the amino acid sequence of SEQ ID NO: 46 or SEQ ID NO: 47.

In some embodiments, the antibody or antigen-binding fragment thereof includes a framework region that is between CDR-H1 and CDR-H2 of the heavy chain variable domain and which includes an amino acid sequence with at least 90%, 91%, 92%, 93%, 94%, 95%, 96%, 97%, 98%, 99% or 100% sequence identity to the amino acid sequence of SEQ ID NO: 48 or SEQ ID NO: 49.

In some embodiments, the antibody or antigen-binding fragment thereof includes a framework region that is between CDR-H2 and CDR-H3 of the heavy chain variable domain and which includes an amino acid sequence with at least 90%, 91%, 92%, 93%, 94%, 95%, 96%, 97%, 98%, 99% or 100% sequence identity to the amino acid sequence of SEQ ID NO: 50 or SEQ ID NO: 51.

In some embodiments, the antibody or antigen-binding fragment thereof includes a framework region that is C-terminal to CDR-H3 of the heavy chain variable domain and which includes an amino acid sequence with at least 90%, 91%, 92%, 93%, 94%, 95%, 96%, 97%, 98%, 99% or 100% sequence identity to the amino acid sequence of SEQ ID NO: 52.

20 In some embodiments, the antibody or antigen-binding fragment thereof includes a framework region that is C-terminal to CDR-H3 of the heavy chain variable domain and which includes an amino acid sequence with at least 90%, 91%, 92%, 93%, 94%, 95%, 96%, 97%, 98%, 99% or 100% sequence identity to the amino acid sequence of SEQ ID NO: 53 or SEQ ID NO: 54.

In some embodiments, the antibody or antigen-binding fragment thereof includes a light chain variable domain including an amino acid sequence with at least 70%, 75%, 80%, 85%, 90%, 95%, 97%, or 99% sequence identity to the amino acid sequence of any one of SEQ ID NOs: 16-23. In some embodiments, the antibody or antigen-binding fragment thereof includes a light chain variable domain having the amino acid sequence of any one of SEQ ID NOs: 16-23.

In some embodiments, the antibody or antigen-binding fragment thereof includes a heavy chain variable domain including an amino acid sequence with at least 70%, 75%, 80%, 85%, 90%, 95%, 97%, or 99% sequence identity to the amino acid sequence of any one of SEQ ID NOs: 25-35. In some embodiments, the antibody or antigen-binding fragment thereof includes a heavy chain variable domain having the amino acid sequence of any one of SEQ ID NOs: 25-35.

In another aspect, the disclosure provides a polynucleotide encoding an antibody or antigen-binding fragment thereof described herein.

In another aspect, the disclosure provides a vector including a polynucleotide encoding an antibody or antigen-binding fragment thereof described herein. In some embodiments, the vector is an expression vector (e.g., a eukaryotic expression vector or a viral vector). In some embodiments, wherein the expression vector is a viral vector, the viral vector is selected from the group consisting of adenovirus (Ad), retrovirus, poxvirus, adeno-associated virus, baculovirus, herpes simplex virus, and vaccinia virus.

In another aspect, the disclosure provides a host cell including (e.g. transformed with) a vector including a polynucleotide encoding an antibody or antigen-binding fragment thereof described herein. In some embodiments, the host cell is a prokaryotic cell or a eukaryotic cell (e.g., a mammalian cell, such as a human cell).

In another aspect, the disclosure provides a pharmaceutical composition including an antibody or antigen-binding fragment thereof described herein, a polynucleotide described herein, a vector described herein, or a host cell described herein, and a pharmaceutically acceptable carrier or excipient. In some embodiments, the antibody or antigen-binding fragment thereof is present in the pharmaceutical composition, e.g., in an amount of from about 0.001 mg/ml to about 200 mg/ml.

In another aspect, the disclosure provides a kit including an agent selected from any antibody or antigen-binding fragment thereof, any polynucleotide, any vector, any host cell, or any pharmaceutical composition described herein. In some embodiments, the kit includes any one of the antibodies or antigen-binding fragments thereof described herein (e.g., an antibody or antigen-binding fragment thereof that specifically binds an epitope including the cis conformation of pThr231-Pro of the tau protein). In some embodiments, the kit further includes an additional therapeutic agent. In some embodiments, the kit further includes instructions for transfecting the vector into a host cell. In some embodiments, the kit further includes instructions for expressing the antibody, antigen-binding fragment thereof, or construct in the host cell. In some embodiments, the kit further includes a reagent that can be used to express the antibody, antigen-binding fragment thereof, or construct in the host cell. In some embodiments, the kit further includes instructions for administering the agent to a subject (e.g., a human subject).

In another aspect, the disclosure provides a method of treating a subject having or at risk of developing a disorder, wherein the method includes administering to the subject an antibody or antigen-binding fragment thereof described herein, a polynucleotide described herein, a vector described herein, a host cell described herein, or a pharmaceutical composition described herein. In some embodiments, the disorder is associated with pathogenic accumulation of tau protein. In some embodiments, the disorder is associated with an increased level of cis-pThr231-tau as compared to a reference value of cis-pThr231-tau (e.g., a reference value indicative of a subject not having or not at risk of developing the disorder). In particular embodiments, the reference value for a subject not having or not at risk of developing the disorder is a level of cis-pThr231 tau that is below the threshold limit for detection (e.g., a subject not having or not at risk of developing the disorder has no detectable cis-pThr231-tau, for example, in a cerebrospinal fluid (CSF) or blood sample from the subject). Accordingly, a subject having or at risk of developing a disorder for treatment may have a detectable level of soluble cis-pThr231-tau, as determined from a sample (e.g., blood or CSF) from the subject. A subject with a disorder for treatment may exhibit an increase in the level of cis-pThr231-Pro tau of 10%, 20%, 30%, 40%, 50%, 60%, 70%, 80%, 90%, or more, which is measured, for example, in a sample from the subject (e.g., blood or CSF). In some embodiments, the disorder is associated with an increased ratio of cis-pThr231-tau to trans-pThr231-tau as compared to a reference ratio of cis-pThr231-tau to trans-pThr231-tau (e.g., a reference ratio indicative of a subject not having or not at risk of developing the disorder). A subject with a disorder for treatment may exhibit an increased ratio of cis:trans of pThr231-Pro tau of 10%, 20%, 30%, 40%, 50%, 60%, 70%, 80%, 90%, or more, which is measured, for example, in a sample from the subject (e.g., blood or CSF). In some embodiments, the disorder is a neurological disorder (e.g., a neurological disorder associated with the pathogenic accumulation of tau protein). In some embodiments, the neurological disorder is selected from traumatic brain injury (TBI), chronic traumatic encephalopathy (CTE), mild cognitive impairment, Alzheimer's disease, Parkinson's disease, multiple sclerosis, muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalitis, epilepsy, vascular dementia, age-related dementia, stroke, transient ischemic attacks (TIA, also commonly referred to as mini strokes), neurofibromatosis, Lewy body disease, amyotrophic lateral sclerosis (ALS), a peripheral neuropathy, diabetic neuropathy, macular degeneration, ischemia-related retinopathy, and diabetic retinopathy. In particular embodiments, the neurological disorder is a vascular disease of the central nervous system (CNS), e.g., a vascular disease of the CNS selected from vascular dementia, ischemia-related retinopathy, diabetic retinopathy, age-related macular degeneration, diabetic neuropathy, stroke, and transient ischemic attacks (TIAs).

For diagnoses based on levels of substrate in a particular conformation (e.g., a cis-pTau substrate in the cis conformation), a subject with a disorder will show an alteration (e.g., an increase of 10%, 20%, 30%, 40%, 50%, 60%, 70%, 80%, 90%, or more) in the amount of the substrate in, for example, the cis conformation. A subject with a disorder may be diagnosed on the basis of an increased ratio of cis:trans of pThr231-Pro tau, for example as measured in PBMCs (e.g., an increase of 10%, 20%, 30%, 40%, 50%, 60%, 70%, 80%, 90%, or more). A normal reference sample can be, for example, a prior sample taken from the same subject prior to the development of the disorder or of symptoms suggestive of the disorder, a sample from a subject not having the disorder, a sample from a subject not having symptoms of the disorder, or a sample of a purified reference polypeptide in a given conformation at a known normal concentration (i.e., not indicative of the disorder).

In another aspect, the disclosure provides a method of producing an antibody or antigen-binding fragment thereof described herein, the method including expressing a polynucleotide encoding the antibody or antigen-binding fragment thereof in a host cell and recovering the antibody or antigen-binding fragment thereof from host cell medium.

In another aspect, the disclosure provides a method of determining the level of cis-phosphorylated-Threonine231-tau protein (cis-pThr231-tau) in a sample from a subject (e.g., a human subject), the method including: (i) contacting the sample with an antibody or antigen-binding fragment thereof described herein; and (ii) detecting the level of cis-pThr231-tau in the sample (i) by determining the level of the antibody or antigen-binding fragment thereof bound to the cis-pThr231-tau. In some embodiments, the method further includes: (iii) comparing the level of cis-pThr231-tau detected in (ii) to a reference value of cis-pThr231-tau (e.g., a reference value that is the average level of cis-pThr231-tau in a population of subjects having a neurological disorder). In some embodiments, a level of cis-pThr231-tau in the sample that is greater than the reference value of cis-pThr231-tau indicates that the subject has or is at risk of developing a neurological disorder. In some embodiments, the method further includes administering a therapeutically effective amount of an antibody or antigen-binding fragment thereof described herein, a polynucleotide described herein, a vector described herein, a host cell described herein, or a pharmaceutical composition described herein to the subject determined based on the level of cis-pThr231-tau in the sample to have or to be at risk of developing the neurological disorder.

In another aspect, the disclosure provides a method of determining the level of cis-phosphorylated-Threonine231-tau protein (cis-pThr231-tau) in a sample from a subject, the method including: (i) contacting the sample with an antibody or antigen-binding fragment thereof described herein; and (ii) detecting the level of cis-pThr231-tau in the sample (i) by determining the level of the antibody or antigen-binding fragment thereof bound to the cis-pThr231-tau. In some embodiments, the method further includes: (iii) determining the level of trans-pThr231-tau in the sample; and/or (iv) determining the ratio of cis-pThr231-tau to trans-pThr231-tau. In some embodiments, the method further includes: (v) comparing the ratio of cis-pThr231-tau to trans-pThr231-tau determined in (iv) to a reference value of the ratio of cis-pThr231-tau to trans-p231Thr-tau (e.g., a reference value that is the average ratio of cis-pThr231-tau to trans-pThr231-tau in a population of subjects having a neurological disorder). In some embodiments, the ratio of cis-pThr231-tau to trans-pThr231-tau of greater than the reference ratio of cis-pThr231-tau to trans-pThr231-tau indicates that the subject has or is at risk of developing a neurological disorder. In some embodiments, the method further includes administering a therapeutically effective amount of an antibody or antigen-binding fragment thereof described herein, a polynucleotide described herein, a vector described herein, a host cell described herein, or a pharmaceutical composition described herein to the subject determined based on the ratio of cis-pThr231-tau to trans-pThr231-tau in the sample to have or to be at risk of developing the neurological disorder.

In another aspect, the disclosure provides a method of treating a subject having or at risk of developing a neurological disorder, the method including administering to the subject an isolated conformation-specific antibody or an antigen-binding fragment thereof that binds specifically to a cis conformation of a phosphorylated-Threonine231-Proline (pThr231-Pro) motif of phosphorylated-Threonine231-tau protein (pThr231-tau), wherein the subject is characterized as lacking any detectable neurofibrillary tangles (NFTs) and as having at least one of: (i) a detectable level of cis-pThr231-tau in the cerebrospinal fluid (CSF) or blood; and (ii) demyelination and/or neuroinflammation of neurons of the central nervous system. An elevated level of glial fibrillary acidic protein (GFAP) may be utilized as a marker for neuroinflammation (e.g., elevated relative to a healthy subject or a reference value indicating a healthy subject).

In another aspect, the disclosure provides a method of treating a subject having or at risk of developing a neurological disorder, the method including administering to the subject an isolated conformation-specific antibody or an antigen-binding fragment thereof that binds specifically to a cis conformation of a phosphorylated-Threonine231-Proline (pThr231-Pro) motif of phosphorylated-Threonine231-tau protein (pThr231-tau), wherein the subject has been determined to have: (i) increased expression of one or more genes selected from Meg3, Mme, Lrrc17, Hsd3b2, Phkg1, Grin 2a, Grin 2b, and EphA7 (e.g., an increase of 10%, 20%, 30%, 40%, 50%, 60%, 70%, 80%, 90%, 100% or more relative to a reference value); and/or (ii) decreased expression of one or more genes selected from GluI, Slc1a2, Actb, Actg1, Atp6v1 b2, Mbp, Nsf, Ywhag, Kif5a, Actb, Actg1, Pafah1 b1 and Pak1 (e.g., a decrease of 10%, 20%, 30%, 40%, 50%, 60%, 70%, 80%, 90%, 100% or more relative to a reference value).

In another aspect, the disclosure provides a method of treating a subject having or at risk of developing a neurological disorder, the method including administering to the subject an isolated conformation-specific antibody or an antigen-binding fragment thereof that binds specifically to the cis conformation of a phosphorylated-Threonine231-Proline (pThr231-Pro) motif of phosphorylated-Threonine231-tau protein (pThr231-tau), wherein the subject has an increased risk of developing the neurological disorders based on the subject's genetic pre-disposition or medical history.

In some embodiments, the antibody or an antigen-binding fragment thereof is administered to the subject when the subject is pre-symptomatic or asymptomatic. In some embodiments, the subject has one or more relatives (e.g., one or more first, second, and/or third degree family members) that have been diagnosed with the neurological disorder. In some embodiments, the subject has previously experienced a head injury.

In some embodiments, the disorder is associated with pathogenic accumulation of tau protein. In some embodiments, the disorder is associated with an increased level of cis-pThr231-tau as compared to a reference value of cis-pThr231-tau (e.g., a reference value indicative of a subject not having or not at risk of developing the disorder). In some embodiments, the disorder is associated with an increased ratio of cis-pThr231-tau to trans-pThr231-tau as compared to a reference ratio of cis-pThr231-tau to trans-pThr231-tau (e.g., a reference ratio indicative of a subject not having or not at risk of developing the disorder). In some embodiments, the disorder is a neurological disorder (e.g., a neurological disorder associated with the pathogenic accumulation of tau protein). In some embodiments, the neurological disorder is selected from traumatic brain injury (TBI), chronic traumatic encephalopathy (CTE), mild cognitive impairment, Alzheimer's disease, Parkinson's disease, multiple sclerosis, muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalitis, epilepsy, vascular dementia, age-related dementia, stroke, transient ischemic attacks (TIA), neurofibromatosis, Lewy body disease, amyotrophic lateral sclerosis (ALS), a peripheral neuropathy, diabetic neuropathy, macular degeneration, ischemia-related retinopathy, and diabetic retinopathy. In particular embodiments, the neurological disorder is a vascular disease of the central nervous system (CNS), e.g., a vascular disease of the CNS selected from vascular dementia, ischemia-related retinopathy, diabetic retinopathy, age-related macular degeneration, diabetic neuropathy, stroke, and transient ischemic attacks (TIA).

In another aspect, the disclosure provides a method of treating a subject having or at risk of developing traumatic brain injury, the method including administering to the subject an isolated conformation-specific antibody or an antigen-binding fragment thereof that binds specifically to the cis conformation of a phosphorylated-Threonine231-Proline (pThr231-Pro) motif of phosphorylated-Threonine231-tau protein (pThr231-tau), wherein the antibody or an antigen-binding fragment thereof is administered to the subject within 2 weeks, within 1 week, within 48 hours, within 24 hours, or within 12 hours of a head injury.

In another aspect, the disclosure features a method of testing a subject for responsiveness to treatment with a conformation-specific antibody or an antigen-binding fragment thereof that specifically binds to a cis conformation of a phosphorylated-Threonine231-Proline (pThr231-Pro) motif of phosphorylated-Threonine231-tau protein (pThr231-tau), the method including detecting an elevated level of cis-pThr231-tau in a sample of blood or cerebrospinal fluid (CSF) from the subject. In some embodiments, the level of cis-pThr231-tau in the sample is determined by an immunoassay, e.g., an immunoassay in which an antibody or antigen-binding fragment thereof described herein binds to cis-pThr231-tau in the sample. In some embodiments the immunoassay is ELISA or immunoprecipitation. In some embodiments, the subject is at risk of developing a neurological disorder. In some embodiments, the subject has suffered a head injury, a stroke, or a vascular injury. In some embodiments, elevated level of cis-pThr231-tau is any level of cis-pThr231-tau that is above the limit of detection. In some embodiments, the subject is treated with a conformation-specific antibody or an antigen-binding fragment thereof that specifically binds to a cis conformation of a phosphorylated-Threonine231-Proline (pThr231-Pro) motif of phosphorylated-Threonine231-tau protein (pThr231-tau). In some embodiments, the subject is treated with any antibody or antigen-binding fragment thereof described herein.

In another aspect, the disclosure features a method of monitoring responsiveness to treatment with a conformation-specific antibody or an antigen-binding fragment thereof that specifically binds to a cis conformation of a phosphorylated-Threonine231-Proline (pThr231-Pro) motif of phosphorylated-Threonine231-tau protein (pThr231-tau), the method including determining a level of cis-pThr231-tau in a sample of blood or cerebrospinal fluid (CSF) from the subject prior to treatment with the antibody or an antigen-binding fragment thereof and determining a level of cis-pThr231-tau in a sample of blood or CSF from the subject after to treatment with the antibody or an antigen-binding fragment thereof. In some embodiments, the level of cis-pThr231-tau in the sample is determined by an immunoassay, e.g., an immunoassay in which an antibody or antigen-binding fragment thereof described herein binds to cis-pThr231-tau in the sample. In some embodiments the immunoassay is ELISA or immunoprecipitation. In some embodiments, the method further includes comparing the level of cis-pThr231-tau prior to treatment with the level of cis-pThr231-tau after treatment. In some embodiments, a decrease in the level of cis-pThr231-tau after treatment as compared to the level of cis-pThr231-tau prior to treatment is indicative of responsiveness to treatment. In some embodiments, the subject is at risk of developing a neurological disorder. In some embodiments, the subject has suffered a head injury, a stroke, or a vascular injury.

In some embodiments, the antibody or antigen-binding fragment thereof binds specifically to a cis conformation of a phosphorylated-Threonine231-Proline (pThr231-Pro) motif of phosphorylated-Threonine231-tau protein (pThr231-tau). In some embodiments, the antibody or antigen-binding fragment thereof binds to a cis conformation of the pThr231-Pro motif with at least 10-fold, 20-fold, 30-fold, 40-fold, 50-fold, 60-fold, 70-fold, 80-fold, 90-fold, 100-fold, 200-fold, or 500-fold greater affinity than to a trans conformation of the pThr231-Pro motif.

In some embodiments, the antibody or antigen-binding fragment thereof is selected from the group consisting of a monoclonal antibody or antigen-binding fragment thereof, a polyclonal antibody or antigen-binding fragment thereof, a human antibody or antigen-binding fragment thereof, a humanized antibody or antigen-binding fragment thereof, a primatized antibody or antigen-binding fragment thereof, a bispecific antibody or antigen-binding fragment thereof, a multi-specific antibody or antigen-binding fragment thereof, a dual-variable immunoglobulin domain, a monovalent antibody or antigen-binding fragment thereof, a chimeric antibody or antigen-binding fragment thereof, a single-chain Fv molecule (scFv), a diabody, a triabody, a nanobody, an antibody-like protein scaffold, a domain antibody, a Fv fragment, a Fab fragment, a F(ab')2 molecule, and a tandem scFv (taFv). In some embodiments, the antibody or antigen-binding fragment thereof is a human, humanized, or chimeric antibody or antigen-binding fragment thereof.

Numbered Embodiments

[1] An isolated antibody or an antigen-binding fragment thereof comprising:

a complementarity-determining region (CDR) light chain 1 (CDR-L1) having the amino acid sequence of SEQ ID NO: 1 or a variant thereof; a complementarity-determining region (CDR) light chain 2 (CDR-L2) having the amino acid sequence of SEQ ID NO: 2 or a variant thereof; and/or a complementarity-determining region (CDR) light chain 3 (CDR-L3) having the amino acid sequence of SEQ ID NO: 3 or a variant thereof; and/or a complementarity-determining region (CDR) heavy chain 1 (CDR-H1) having the amino acid sequence of SEQ ID NO: 4 or a variant thereof; a complementarity-determining region (CDR) heavy chain 2 (CDR-H2) having the amino acid sequence of SEQ ID NO: 5 or a variant thereof; and/or a complementarity-determining region (CDR) heavy chain 3 (CDR-H3) having the amino acid sequence of SEQ ID NO: 6 or a variant thereof, wherein a variant of a CDR comprises between 1 and 5 of any combination of amino acid substitutions, deletions, or additions;

wherein the antibody or antigen-binding fragment thereof is a humanized antibody or antigen binding fragment thereof;

and wherein (A) the light chain variable domain comprises:

(i) a serine residue seventeen amino acid residues N-terminal to the CDR-L1;

and/or (B) the heavy chain variable domain comprises:

(i) a valine residue twenty-six amino acid residues N-terminal to the CDR-H1;

(ii) a serine residue twenty-four amino acid residues N-terminal to the CDR-H1;

(iii) a lysine residue nineteen amino acid residues N-terminal to the CDR-H1;

(iv) an arginine residue at the amino acid residue directly C-terminal to CDR-H2;

and/or (v) a valine residue seven amino residues C-terminal to CDR-H3.

[2] The antibody or antigen-binding fragment thereof of paragraph [1], wherein the light chain variable domain comprises a serine residue seventeen amino acid residues N-terminal to the CDR-L1.

[3] The antibody or antigen-binding fragment thereof of paragraph [1] or [2], wherein the heavy chain variable domain comprises a valine residue twenty-six amino acid residues N-terminal to the CDR-H1.

[4] The antibody or antigen-binding fragment thereof of any one of paragraphs [1]-[3], wherein the heavy chain variable domain comprises a serine residue twenty-four amino acid residues N-terminal to the CDR-H1.

[5] The antibody or antigen-binding fragment thereof of any one of paragraphs [1]-[4], wherein the heavy chain variable domain comprises a lysine residue nineteen amino acid residues N-terminal to the CDR-H1.

[6] The antibody or antigen-binding fragment thereof of any one of paragraphs [1]-[5], wherein the heavy chain variable domain comprises an arginine residue at the amino acid residue directly C-terminal to CDR-H2.

[7] The antibody or antigen-binding fragment thereof of any one of paragraphs [1]-[6], wherein the heavy chain variable domain comprises a valine residue seven amino residues C-terminal to CDR-H3.

[8] The antibody or antigen-binding fragment thereof of any one of paragraphs [1]-[7], comprising a complementarity-determining region (CDR) light chain 1 (CDR-L1) having the amino acid sequence of SEQ ID NO: 7.

[9] The antibody or antigen-binding fragment thereof of any one of paragraphs [1]-[7], comprising wherein the antibody or antigen-binding fragment thereof comprises a complementarity-determining region (CDR) light chain 1 (CDR-L1) having the amino acid sequence of SEQ ID NO: 8.

[10] The antibody or antigen-binding fragment thereof of any on one of paragraphs [1]-[9], comprising a complementarity-determining region (CDR) light chain 2 (CDR-L2) having the amino acid sequence of SEQ ID NO: 9.

[11] The antibody or antigen-binding fragment thereof of any one of paragraphs [1]-[9], comprising a complementarity-determining region (CDR) light chain 2 (CDR-L2) having the amino acid sequence of SEQ ID NO: 10.

[12] The antibody or antigen-binding fragment thereof of any one of paragraphs [1]-[11], comprising a complementarity-determining region (CDR) heavy chain 2 (CDR-H2) having the amino acid sequence of SEQ ID NO: 11.

[13] The antibody or antigen-binding fragment thereof of any one of paragraphs [1]-[11], comprising a complementarity-determining region (CDR) heavy chain 2 (CDR-H2) having the amino acid sequence of SEQ ID NO: 12.

[14] The antibody or antigen-binding fragment thereof of any one of paragraphs [1]-[13], comprising a threonine residue directly N-terminal to CDR-H3, optionally, wherein CDR-H3 and the amino acid residue directly N-terminal to CDR-H3 together comprise the amino acid sequence of SEQ ID NO: 13.

[15] The antibody or antigen-binding fragment thereof of any one of paragraphs [1]-[14], comprising two threonine residues directly N-terminal to CDR-H3, optionally, wherein CDR-H3 and the two amino acid residues directly N-terminal to CDR-H3 together comprise the amino acid sequence of SEQ ID NO: 14.

[16] The antibody or antigen binding fragment thereof of any one of paragraphs [1]-[15], wherein the framework region of the light chain variable domain that is N-terminal to CDR-L1 comprises the sequence of SEQ ID NO: 36.

[17] The antibody or antigen binding fragment thereof of paragraph [16], wherein the framework region that is N-terminal to CDR-L1 of the light chain variable domain comprises the amino acid sequence of SEQ ID NO: 37 or SEQ ID NO: 38.

[18] The antibody or antigen binding fragment thereof of any one of paragraphs [1]-[17], wherein the framework region that is between CDR-L1 and CDR-L2 of the light chain variable domain comprises the amino acid sequence of SEQ ID NO: 39 or SEQ ID NO: 40.

[19] The antibody or antigen binding fragment thereof of any one of paragraphs [1]-[18], wherein the framework region that is between CDR-L2 and CDR-L3 of the light chain variable domain comprises the amino acid sequence of SEQ ID NO: 41 or SEQ ID NO: 42.

[20] The antibody or antigen binding fragment thereof of any one of paragraphs [1]-[19], wherein the framework region that is C-terminal to CDR-L3 of the light chain variable domain comprises the amino acid sequence of SEQ ID NO: 43 or SEQ ID NO: 44.

[21] The antibody or antigen binding fragment thereof of any one of paragraphs [1]-[20], wherein the framework region of the heavy chain variable domain that is N-terminal to CDR-H1 comprises the sequence of SEQ ID NO: 45.

[22] The antibody or antigen binding fragment thereof of paragraph [21], wherein the framework region that is N-terminal to CDR-H1 of the heavy chain variable domain comprises the amino acid sequence of SEQ ID NO: 46 or SEQ ID NO: 47.

[23] The antibody or antigen binding fragment thereof of any one of paragraphs [1]-[22], wherein the framework region that is between CDR-H1 and CDR-H2 of the heavy chain variable domain comprises the amino acid sequence of SEQ ID NO: 48 or SEQ ID NO: 49.

[24] The antibody or antigen binding fragment thereof of any one of paragraphs [1]-[23], wherein the framework region that is between CDR-H2 and CDR-H3 of the heavy chain variable domain comprises the amino acid sequence of SEQ ID NO: 50 or SEQ ID NO: 51.

[25] The antibody or antigen binding fragment thereof of any one of paragraphs [1]-[24], wherein the framework region that is C-terminal to CDR-H3 of the heavy chain variable domain comprises the amino acid sequence of SEQ ID NO: 52.

[26] The antibody or antigen binding fragment thereof of paragraph [25], wherein the framework region that is C-terminal to CDR-H3 of the heavy chain variable domain comprises the amino acid sequence of SEQ ID NO: 53 or SEQ ID NO: 54.

[27] The antibody or antigen-binding fragment thereof of any one of paragraphs [1]-[26], comprising a light chain variable domain comprising an amino acid sequence with at least 90% sequence identity to the amino acid sequence of any one of SEQ ID NOs: 16-23.

[28] The antibody or antigen-binding fragment thereof of paragraph [27], comprising a light chain variable domain comprising an amino acid sequence with at least 95% sequence identity to the amino acid sequence of any one of SEQ ID NOs: 16-23

[29] The antibody or antigen-binding fragment thereof of paragraph [28], comprising a light chain variable domain having the amino acid sequence of any one of SEQ ID NOs: 16-23.

[30] The antibody or antigen-binding fragment thereof of any one of paragraphs [1]-[26], comprising a heavy chain variable domain comprising an amino acid sequence with at least 90% sequence identity to the amino acid sequence of any one of SEQ ID NOs: 25-35.

[31] The antibody or antigen-binding fragment thereof of any one of paragraph [30], comprising a heavy chain variable domain comprising an amino acid sequence with at least 95% sequence identity to the amino acid sequence of any one of SEQ ID NOs: 25-35.

[32] The antibody or antigen-binding fragment thereof of paragraph [31] comprising a heavy chain variable domain having the amino acid sequence of any one of SEQ ID NOs: 25-35.

[33] The antibody or antigen-binding fragment thereof of any one of paragraph [1]-[32], wherein the antibody or antigen-binding fragment thereof binds specifically to a cis conformation of a phosphorylated-Threonine231-Proline (pThr231-Pro) motif of phosphorylated-Threonine231-tau protein (pThr231-tau).

[34] The antibody or antigen-binding fragment of paragraph [33], wherein the antibody or antigen-binding fragment thereof binds to the cis conformation of the pThr231-Pro motif with at least 10-fold greater affinity than to a trans conformation of the pThr231-Pro motif.

[35] The antibody or antigen-binding fragment of paragraph [17], wherein the antibody or antigen-binding fragment thereof binds to the cis conformation of the pThr231-Pro motif with at least 100-fold greater affinity than to the trans conformation of the pThr231-Pro motif.

[36] The antibody or antigen-binding fragment thereof of any one of paragraphs [1]-[35], wherein the antibody or antigen-binding fragment thereof is selected from the group consisting of a monoclonal antibody or antigen-binding fragment thereof, a polyclonal antibody or antigen-binding fragment thereof, a human antibody or antigen-binding fragment thereof, a humanized antibody or antigen-binding fragment thereof, a primatized antibody or antigen-binding fragment thereof, a bispecific antibody or antigen-binding fragment thereof, a multi-specific antibody or antigen-binding fragment thereof, a dual-variable immunoglobulin domain, a monovalent antibody or antigen-binding fragment thereof, a chimeric antibody or antigen-binding fragment thereof, a single-chain Fv molecule (scFv), a diabody, a triabody, a nanobody, an antibody-like protein scaffold, a domain antibody, a Fv fragment, a Fab fragment, a F(ab')2 molecule, and a tandem scFv (taFv).

[37] The antibody or antigen-binding fragment thereof of paragraph [36], wherein the antibody or antigen-binding fragment thereof is a human, humanized, or chimeric antibody or antigen-binding fragment thereof.

[38] A polynucleotide encoding the antibody or antigen-binding fragment thereof of any one of paragraphs [1]-[37].

[39] A vector comprising the polynucleotide of paragraph [38].

[40] The vector of paragraph [39], wherein the vector is an expression vector.

[41] The vector of paragraph [40], wherein the expression vector is a eukaryotic expression vector.

[42] The vector of paragraph [40], wherein the vector is a viral vector.

[43] The vector of paragraph [42], wherein the viral vector is selected from the group consisting of adenovirus (Ad), retrovirus, poxvirus, adeno-associated virus, baculovirus, herpes simplex virus, and a vaccinia virus.

[44] A host cell comprising the vector of any one of paragraphs [39]-[43].

[45] The host cell of paragraph [44], wherein the host cell is a prokaryotic cell.

[46] The host cell of paragraph [44], wherein the host cell is a eukaryotic cell.

[47] The host cell of paragraph [46], wherein the eukaryotic cell is a mammalian cell.

[48] The host cell of paragraph [47], wherein the mammalian cell is a human cell.

[49] A pharmaceutical composition comprising the antibody or antigen-binding fragment thereof of any one of paragraphs [1]-[37], the polynucleotide of paragraph [38], the vector of any one of paragraphs [39]-[43], or the host cell of any one of paragraphs [44]-[48], and a pharmaceutically acceptable carrier or excipient.

[50] The pharmaceutical composition of paragraph [49], wherein the antibody or antigen-binding fragment thereof is present in the pharmaceutical composition in an amount of from about 0.001 mg/ml to about 200 mg/ml.

[51] A kit comprising an agent selected from the antibody or antigen-binding fragment thereof of any one of paragraphs [1]-[37], the polynucleotide of paragraph [38], the vector of any one of paragraphs [39]-[43], the host cell of any one of paragraphs [44]-[48], or the pharmaceutical composition of paragraph [49] or [50].

[52] The kit of paragraph [51], wherein the kit comprises the antibody or antigen-binding fragment thereof any one of paragraphs [1]-[37].

[53] The kit of paragraph [51], wherein the kit comprises the polynucleotide of paragraph [38].

[54] The kit of paragraph [51], wherein the kit comprises the vector of any one of paragraphs 39-43.

[55] The kit of paragraph [54], wherein the kit further comprises instructions for transfecting the vector into a host cell.

[56] The kit of paragraph [55], wherein the kit further comprises instructions for expressing the antibody, antigen-binding fragment thereof, or construct in the host cell.

[57] The kit of paragraph [51], wherein the kit comprises the host cell of any one of paragraphs [44]-[48].

[58] The kit of paragraph [57], wherein the kit further comprises a reagent that can be used to express the antibody, antigen-binding fragment thereof, or construct in the host cell.

[59] The kit of paragraph [51], wherein the kit comprises the pharmaceutical composition of paragraph [49] or [50].

[60] The kit of paragraph [51], further comprising instructions for administering the agent to a subject.

[61] The kit of paragraph [60], wherein the subject is a human subject.

[62] A method of treating a subject having or at risk of developing a disorder comprising administering to the subject the antibody or antigen-binding fragment thereof of any one of paragraphs [1]-[37], the polynucleotide of paragraph [38], the vector of any one of paragraphs [39]-[43], the host cell of any one of paragraphs [44]-[48], or the pharmaceutical composition of paragraph [49] or [50].

[63] The method of paragraph [62], wherein the disorder is associated with pathogenic accumulation of tau protein.

[64] The method of paragraph [62] or [63], wherein the disorder is associated with an increased level of cis-pThr231-tau as compared to a reference value of cis-pThr231-tau.

[65] The method of paragraph [64], wherein the reference value is the value indicative of a subject not having or not at risk of developing the disorder.

[66] The method of any one of paragraphs [62]-[65], wherein the disorder is associated with an increased ratio of cis-pThr231-tau to trans-pThr231-tau as compared to a reference ratio of cis-pThr231-tau to trans-pThr231-tau.

[67] The method of paragraph [66], wherein the reference ratio of cis-pThr231-tau to trans-pTHr231-tau is indicative of a subject not having or not at risk of developing the disorder.

[68] The method of paragraph any one of paragraphs [62]-[67], wherein the disorder is a neurological disorder.

[69] The method of paragraph [68], wherein the neurological disorder is selected from traumatic brain injury (TBI), chronic traumatic encephalopathy (CTE), mild cognitive impairment, Alzheimer's disease, Parkinson's disease, multiple sclerosis, muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalitis, epilepsy, vascular dementia, age-related dementia, stroke, transient ischemic attacks (TIA), neurofibromatosis, Lewy body disease, amyotrophic lateral sclerosis (ALS), a peripheral neuropathy, diabetic neuropathy, macular degeneration, ischemia-related retinopathy, or diabetic retinopathy.

[70] A method of producing the antibody or antigen-binding fragment thereof of any one of paragraphs [1]-[37] comprising expressing a polynucleotide encoding the antibody or antigen-binding fragment thereof in a host cell and recovering the antibody or antigen-binding fragment thereof from host cell medium.

[71] A method of determining the level of cis-phosphorylated-Threonine231-tau protein (cis-pThr231-tau) in a sample from a subject comprising:

(i) contacting the sample with the antibody or antigen-binding fragment thereof of any one of paragraphs [1]-[37]; and (ii) detecting the level of cis-pThr231-tau in the sample (i) by determining the level of the antibody or antigen-binding fragment thereof bound to the cis-pThr231-tau.

[72] The method of paragraph [71], wherein the method further comprises:

(iii) comparing the level of cis-pThr231-tau detected in (ii) to a reference value of cis-pThr231-tau.

[73] The method of paragraph [72], wherein the reference value is the average level of cis-pThr231-tau in a population of subjects having a neurological disorder.

[74] The method of paragraph [72] or [73], wherein the level of cis-pThr231-tau in the sample that is greater than the reference value of cis-pThr231-tau indicates that the subject has or is at risk of developing a neurological disorder.

[75] The method of paragraph [74], wherein the method further comprises administering a therapeutically effective amount of the antibody or antigen-binding fragment thereof of any one of paragraphs [1]-[37], the polynucleotide of paragraph [38], the vector of any one of paragraphs [39]-[43], the host cell of any one of paragraphs [44]-[48], or the pharmaceutical composition of any one of paragraph [49] or [50] to the subject determined based on the level of cis-pThr231-tau in the sample to have or to be at risk of developing the neurological disorder.

[76] The method of paragraph [71], wherein the method further comprises:

(iii) determining the level of trans-pThr231-tau in the sample; and/or (iv) determining the ratio of cis-pThr231-tau to trans-pThr231-tau.

[77] The method of paragraph [76], wherein the method further comprises:

(v) comparing the ratio of cis-pThr231-tau to trans-pThr231-tau determined in (iv) to a reference value of the ratio of cis-pThr231-tau to trans-p231 Thr-tau.

[78] The method of paragraph [77], wherein the reference value is the average ratio of cis-pThr231-tau to trans-pThr231-tau in a population of subjects having a neurological disorder.

[79] The method of paragraph [77] or [78], wherein the ratio of cis-pThr231-tau to trans-pThr231-tau of greater than the reference ratio of cis-pThr231-tau to trans-pThr231-tau indicates that the subject has or is at risk of developing a neurological disorder.

[80] The method of paragraph [79], wherein the method further comprises administering a therapeutically effective amount of the antibody or antigen-binding fragment thereof of any one of paragraphs [1]-[37], the polynucleotide of paragraph [38], the vector of any one of paragraphs [39]-[43], the host cell of any one of paragraphs [44]-[48], or the pharmaceutical composition of any one of paragraph [49] or [50] to the subject determined based on the ratio of cis-pThr231-tau to trans-pThr231-tau in the sample to have or to be at risk of developing the neurological disorder.

[81] A method of treating a subject having or at risk of developing a neurological disorder comprising administering to the subject an isolated conformation-specific antibody or an antigen-binding fragment thereof that binds specifically to a cis conformation of a phosphorylated-Threonine231-Proline (pThr231-Pro) motif of phosphorylated-Threonine231-tau protein (pThr231-tau), wherein the subject is characterized as lacking any detectable neurofibrillary tangles (NFTs) and as having at least one of:

(i) a detectable level of cis-pThr231-tau in the cerebrospinal fluid (CSF) or blood; and (ii) demyelination and/or neuroinflammation of neurons of the central nervous system.

[82] A method of treating a subject having or at risk of developing a neurological disorder comprising administering to the subject an isolated conformation-specific antibody or an antigen-binding fragment thereof that binds specifically to a cis conformation of a phosphorylated-Threonine231-Proline (pThr231-Pro) motif of phosphorylated-Threonine231-tau protein (pThr231-tau), wherein the subject has been determined to have:

(i) increased expression of one or more genes selected from Meg3, Mme, Lrrc17, Hsd3b2, Phkg1, Grin 2a, Grin 2b, and EphA7; and/or (ii) decreased expression of one or more genes selected from GluI, Slc1a2, Actb, Actg1, Atp6v1 b2, Mbp, Nsf, Ywhag, Kif5a, Actb, Actg1, Pafah1 b1 and Pak1.

[83] A method of treating a subject having or at risk of developing a neurological disorder comprising administering to the subject an isolated conformation-specific antibody or an antigen-binding fragment thereof that specifically binds to a cis conformation of a phosphorylated-Threonine231-Proline (pThr231-Pro) motif of phosphorylated-Threonine231-tau protein (pThr231-tau), wherein the subject has an increased risk of developing the neurological disorders based on the subject's genetic pre-disposition or medical history.

[84] The method of any one of paragraphs [81]-[83], wherein antibody or an antigen-binding fragment thereof is administered to the subject when the subject is pre-symptomatic or asymptomatic.

[85] The method of any one of paragraphs [81]-[84], wherein the subject has one or more relative that have been diagnosed with the neurological disorder.

[86] The method of any one of paragraphs [81]-[85], wherein the subject has previously experienced a head injury.

[87] The method of any one of paragraphs [81]-[86], wherein the neurological disorder is selected from traumatic brain injury (TBI), chronic traumatic encephalopathy (CTE), mild cognitive impairment, Alzheimer's disease, Parkinson's disease, multiple sclerosis, muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalitis, epilepsy, vascular dementia, age-related dementia, stroke, transient ischemic attacks (TIA), neurofibromatosis, Lewy body disease, amyotrophic lateral sclerosis (ALS), a peripheral neuropathy, diabetic neuropathy, macular degeneration, ischemia-related retinopathy, or diabetic retinopathy.

[88] The method of any one of paragraphs [79]-[87], wherein the neurological disorder is a vascular disease of the central nervous system.

[89] The method of paragraph [88], wherein the vascular disease of the central nervous system is selected from vascular dementia, ischemia-related retinopathy, diabetic retinopathy, age-related macular degeneration, diabetic neuropathy, stroke, and transient ischemic attacks (TIA).

[90] A method of treating a subject having or at risk of developing traumatic brain injury comprising administering to the subject an isolated conformation-specific antibody or an antigen-binding fragment thereof that specifically binds to a cis conformation of a phosphorylated-Threonine231-Proline (pThr231-Pro) motif of phosphorylated-Threonine231-tau protein (pThr231-tau), wherein the antibody or an antigen-binding fragment thereof is administered to the subject within 48 hours of a head injury.

[91] The method of paragraph [90], wherein the antibody or an antigen-binding fragment thereof is administered to the subject within 24 hours of the head injury.

[92] The method of paragraph [91], wherein the antibody or an antigen-binding fragment thereof is administered to the subject within 12 hours of the head injury.

[93] The method of any one of paragraphs [81]-[92], wherein the antibody or antigen-binding fragment thereof binds to the cis conformation of the pThr231-Pro motif with at least 10-fold greater affinity than to the trans conformation at the pThr231-Pro motif.

[94] The method of any one of paragraph [93], wherein the antibody or antigen-binding fragment thereof binds to the cis conformation of pThr231-Pro with at least 100-fold greater affinity than to the cis conformation of pThr231-Pro.

[95] The method of any one of paragraphs [81]-[94], wherein the antibody or antigen-binding fragment thereof is an antibody or antigen-binding fragment thereof described by any one of paragraphs [1]-[37].

[96] A method of testing a subject for responsiveness to treatment with a conformation-specific antibody or an antigen-binding fragment thereof that specifically binds to a cis conformation of a phosphorylated-Threonine231-Proline (pThr231-Pro) motif of phosphorylated-Threonine231-tau protein (pThr231-tau), the method comprising detecting an elevated level of cis-pThr231-tau in a sample of blood or cerebrospinal fluid (CSF) from the subject, wherein the level of cis-pThr231-tau in the sample is determined by an immunoassay in which antibody or antigen-binding fragment thereof described by any one of paragraphs [1]-[37] binds to cis-pThr231-tau in the sample.

[97] The method of paragraph [96], wherein the subject is at risk of developing a neurological disorder.

[98] The method of paragraph [97], wherein the subject has suffered a head injury, a stroke, or a vascular injury.

[99] The method of any one of paragraphs [96]-[98], wherein the elevated level of cis-pThr231-tau is any level of cis-pThr231-tau that is above the limit of detection.

[100] The method of any one of paragraphs [96]-[99], wherein the subject is treated with a conformation-specific antibody or an antigen-binding fragment thereof that specifically binds to a cis conformation of a phosphorylated-Threonine231-Proline (pThr231-Pro) motif of phosphorylated-Threonine231-tau protein (pThr231-tau).

[101] The method of paragraph [100], wherein the antibody or antigen-binding fragment thereof is an antibody or antigen-binding fragment thereof described by any one of paragraphs [1]-[37].

[102] A method of monitoring responsiveness to treatment with a conformation-specific antibody or an antigen-binding fragment thereof that specifically binds to a cis conformation of a phosphorylated-Threonine231-Proline (pThr231-Pro) motif of phosphorylated-Threonine231-tau protein (pThr231-tau), the method comprising determining a level of cis-pThr231-tau in a sample of blood or cerebrospinal fluid (CSF) from the subject prior to treatment with the antibody or an antigen-binding fragment thereof and determining a level of cis-pThr231-tau in a sample of blood or CSF from the subject after to treatment with the antibody or an antigen-binding fragment thereof, wherein the level of cis-pThr231-tau in the sample is determined by an immunoassay in which antibody or antigen-binding fragment thereof described by any one of paragraphs [1]-[37] binds to cis-pThr231-tau in the sample.

[103] The method of paragraph [102], further comprising comparing the level of cis-pThr231-tau prior to treatment with the level of cis-pThr231-tau after treatment.

[104] The method of paragraph [103], wherein a decrease in the level of cis-pThr231-tau after treatment as compared to the level of cis-pThr231-tau prior to treatment is indicative of responsiveness to treatment.

[105] The method of any one of paragraphs [102]-[104], wherein the subject is at risk of developing a neurological disorder.

[106] The method of paragraph [105], wherein the subject has suffered a head injury, a stroke, or a vascular injury.

Definitions

To facilitate the understanding of this disclosure, a number of terms are defined below. Terms defined herein have meanings as commonly understood by a person of ordinary skill in the areas relevant to the disclosure. Terms such as "a", "an," and "the" are not intended to refer to only a singular entity, but include the general class of which a specific example may be used for illustration. The terminology herein is used to describe specific embodiments of the disclosure, but their usage does not limit the disclosure, except as outlined in the claims.

As used herein, the term "about" refers to a value that is no more than 10% above or below the value being described. For example, the term "about 5 nM" indicates a range of from 4.5 nM to 5.5 nM.

As used herein, any values provided in a range of values include both the upper and lower bounds and any values contained within the upper and lower bounds.

As used herein, the term "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration a vaccine. Examples of chemical compounds used as adjuvants include, but are not limited to, aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

As used herein, the term "antigen" is meant a molecule to which an antibody or fragment thereof can selectively bind. The target antigen may be a protein (e.g., an antigenic peptide), carbohydrate, nucleic acid, lipid, hapten, or other naturally occurring or synthetic compound. The target antigen may be a polypeptide (e.g., a polypeptide containing a pThr-Pro motif) or peptide mimics (e.g., a polypeptide containing a pThr-Proline analog motif). An antigen may also be administered to an animal to generate an immune response in the animal.

As used herein, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, primatized antibodies, heteroconjugate antibodies (e.g., bi- tri- and quad-specific antibodies, diabodies, triabodies, and tetrabodies), and antigen-binding fragments of antibodies, including e.g., Fab', $F(ab')_2$, Fab, Fv, rIgG, and scFv fragments. Moreover, unless otherwise indicated, the term "monoclonal antibody" (mAb) is meant to include both intact molecules, as well as antibody fragments (such as, for example, Fab and $F(ab')_2$ fragments) that are capable of specifically binding to a target protein. Fab and $F(ab')_2$ fragments lack the Fc fragment of an intact antibody, clear more rapidly from the circulation of the animal, and may have less non-specific tissue binding than an intact antibody (see Wahl et al., J. Nucl. Med. 24:316, 1983; incorporated herein by reference).

The term "antigen-binding fragment," as used herein, refers to one or more fragments of an antibody that retain the ability to specifically bind to a target antigen (e.g., as measured by binding affinity). The antigen-binding function of an antibody can be performed by fragments of a full-length antibody. The antibody fragments can be a Fab, $F(ab')_2$, scFv, SMIP, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the VL, VH, CL, and CH1 domains; (ii) a $F(ab')_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment (Ward et al., Nature 341:544-546, 1989), which consists of a VH domain; (vii) a dAb which consists of a VH or a VL domain; (viii) an isolated complementarity determining region (CDR); and (ix) a combination of two or more isolated CDRs which may optionally be joined by a synthetic linker. Furthermore, although the two domains of the Fv fragment, VL and VH, are coded for by separate genes, they can be joined, using recombinant methods, by a linker that enables them to be made as a single protein chain in which the VL and VH regions pair to form monovalent molecules (known as single-chain Fv (scFv); see, e.g., Bird et al., Science 242:423-426, 1988, and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in some embodiments, by chemical peptide synthesis procedures known in the art.

As used herein, the term "binding affinity" is meant the strength of the total noncovalent interactions between a single binding site of a molecule (e.g., an antibody) and its binding partner (e.g., an antigen or antigenic peptide). Unless otherwise indicated, as used herein, "binding affinity" refers to intrinsic binding affinity, which reflects a specific interaction between members of a binding pair (e.g., antibody and antigen). The affinity of a molecule X for its partner Y can generally be represented by the dissociation constant (Kd). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "chimeric" antibody refers to an antibody having variable domain sequences (e.g., CDR sequences) derived from an immunoglobulin of one source organism, such as rat or mouse, and constant regions derived from an immunoglobulin of a different organism (e.g., a human, another primate, pig, goat, rabbit, hamster, cat, dog, guinea pig, member of the bovidae family (such as cattle, bison, buffalo, elk, and yaks, among others), cow, sheep, horse, or bison, among others). Methods for producing chimeric antibodies are known in the art. See, e.g., Morrison, 1985, Science 229(4719): 1202-7; Oi et al, 1986, BioTechniques 4:214-221; Gillies et al, 1985, J. Immunol. Methods 125:191-202; U.S. Pat. Nos. 5,807,715; 4,816,567; and 4,816,397; incorporated herein by reference.

As used herein, the term "complementarity determining region" (CDR) refers to a hypervariable region found both in the light chain and the heavy chain variable domains. The more highly conserved portions of variable domains are called the framework regions (FRs). As is appreciated in the art, the amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may including modifications in these hybrid hypervariable positions. The variable domains of native heavy and light chains each include four framework regions that primarily adopt a p-sheet configuration, connected by three CDRs, which form loops that connect, and in some cases form part of, the p-sheet structure. The CDRs in each chain are held together in close proximity by the FR regions in the order FR1-CDR1-FR2-CDR2-FR3-CDR3-FR4 and, with the CDRs from the other antibody chains, contribute to the formation of the target binding site of antibodies (see Kabat et al, Sequences of Proteins of Immunological Interest (National Institute of Health, Bethesda, Md. 1987; incorporated herein by reference). As used herein, numbering of immunoglobulin amino acid residues is done according to the immunoglobulin amino acid residue numbering system of Kabat et al, unless otherwise indicated.

As used herein, the term "conformation-specific antibody" is an antibody or fragment thereof that recognizes and specifically binds to a particular conformation (e.g., a conformational isomer or conformer) of its complementary antigen. For example, as described herein, the conformation-specific antibody may specifically bind to the cis conformation of a pThr-Pro motif, such as the pThr231-Pro motif of the phosphorylated tau protein but will not specifically bind to the trans conformation of the same pThr-Pro motif. The conformation-specific antibody may have, for example, at least 10- to 500-fold greater affinity to the cis conformation than to the trans conformation of pThr23n-Pro of the phosphorylated tau protein.

As used herein, the terms "conservative mutation," "conservative substitution," or "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume† |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | nonpolar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in $A^3$: 50-100 is small, 100-150 is intermediate, 150-200 is large, and >200 is bulky From this table it is appreciated that the conservative amino acid families include, e.g., (i) G, A, V, L, I, P, and M; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

Amino acid substitutions may be represented herein using the convention: (AA1)(N)(AA2), where "AA1" represents the amino acid normally present at particular site within an amino acid sequence, "N" represents the residue number within the amino acid sequence at which the substitution occurs, and "AA2" represents the amino acid present in the amino acid sequence after the substitution is effectuated. For example, the notation "C232S" in the context of an antibody hinge region, such as an IgG2 antibody hinge region, refers to a substitution of the naturally-occurring cysteine residue for a serine residue at amino acid residue 232 of the indicated hinge amino acid sequence. Likewise, the notation "C233S" in the context of an antibody hinge region, such as an IgG2 antibody hinge region, refers to a substitution of the naturally-occurring cysteine residue for a serine residue at amino acid residue 233 of the indicated hinge amino acid sequence.

As used herein, the term "conjugate" refers to a compound formed by the chemical bonding of a reactive functional group of one molecule with an appropriately reactive functional group of another molecule.

As used herein, the term "derivatized antibodies" refers to antibodies that are modified by a chemical reaction so as to cleave residues or add chemical moieties not native to an isolated antibody. Derivatized antibodies can be obtained by glycosylation, acetylation, pegylation, phosphorylation, amidation, derivatization by addition of known chemical protecting/blocking groups, proteolytic cleavage, linkage to a cellular ligand or other protein. Any of a variety of chemical modifications can be carried out by known techniques, including, without limitation, specific chemical cleavage, acetylation, formylation, metabolic synthesis of tunicamycin, etc. using established procedures. Additionally, the derivative can contain one or more non-natural amino acids, e.g., using amber suppression technology (see, e.g., U.S. Pat. No. 6,964,859; incorporated herein by reference).

As used herein, the term "diabodies" refers to bivalent antibodies including two polypeptide chains, in which each polypeptide chain includes $V_H$ and $V_L$ domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabodies" refers to trivalent antibodies including three peptide chains, each of which contains one VH domain and one VL domain joined by a linker that is exceedingly short (e.g., a linker composed of 1-2 amino acids) to permit intramolecular association of VH and VL domains within the same peptide chain. In order to fold into their native structure, peptides configured in this way typically trimerize so as to position the VH and VL domains of neighboring peptide chains spatially proximal to one another to permit proper folding (see Holliger et al., Proc. Natl. Acad. Sci. USA 90:6444-48, 1993; incorporated herein by reference).

As used herein, the term "disorder" refers to any condition, disease, or state of pathogenic abnormal biological function in a subject. In particular, the disclosure provides disorders associated with pathogenic tau protein, which includes an increase in soluble pathogenic cis-pTau and/or an increase in tau neurofibrillary tangles. Particular disorders of the disclosure include neurological disorder and vascular disease of the central nervous system, as defined herein.

As used herein, the term "epitope" refers to a portion of an antigen that is recognized and bound by a polypeptide, such as an antibody, antigen-binding fragment thereof, single-chain polypeptide, or construct as described herein. In the context of a protein antigen (such as p-Tau), an epitope may be a continuous epitope, which is a single, uninterrupted segment of one or more amino acids covalently linked to one another by peptide bonds in which all of the component amino acids bind the polypeptide (e.g., antibody, antigen-binding fragment thereof, single-chain polypeptide, or construct thereof). Continuous epitopes may be composed, for instance, of 1, 5, 10, 15, 20, or more amino acids within an antigen. In some embodiments, an epitope may be a discontinuous epitope, which contains two or more segments of amino acids each separated from one another in an antigen's amino acid sequence by one or more intervening amino acid residues. Discontinuous epitopes may be composed, for instance, of 1, 2, 3, 4, 5, 6, 7, 8, 9, 10, or more such segments of amino acid residues. Despite this separation by intervening amino acids, the segments that compose a discontinuous epitope may be, for instance, spatially proximal to one another in the three-dimensional conformation of the antigen. An epitope may be defined not just by its amino acid compositions, but also by the post-translation state of an amino acid of the epitope (e.g., phosphorylation) or the bond geometry of a peptide bond between two amino acids in the epitope (e.g., cis or trans).

As used herein, the term "framework region" or "FW region" includes amino acid residues that are adjacent to the CDRs. FW region residues may be present in, for example, human antibodies, rodent-derived antibodies (e.g., murine antibodies), humanized antibodies, primatized antibodies, chimeric antibodies, antibody fragments (e.g., Fab fragments), single-chain antibody fragments (e.g., scFv fragments), antibody domains, and bispecific antibodies, among others.

As used herein, the term "fusion protein" refers to a protein that is joined via a covalent bond to another molecule. A fusion protein can be chemically synthesized by, e.g., an amide-bond forming reaction between the N-terminus of one protein to the C-terminus of another protein. Alternatively, a fusion protein containing one protein covalently bound to another protein can be expressed recombinantly in a cell (e.g., a eukaryotic cell or prokaryotic cell) by expression of a polynucleotide encoding the fusion protein, for example, from a vector or the genome of the cell. A fusion protein may contain one protein that is covalently bound to a linker, which in turn is covalently bound to another molecule. Examples of linkers that can be used for the formation of a fusion protein include peptide-containing linkers, such as those that contain naturally occurring or non-naturally occurring amino acids. In some embodiments, it may be desirable to include D-amino acids in the linker, as these residues are not present in naturally-occurring proteins and are thus more resistant to degradation by endogenous proteases. Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage (Leriche et al., Bioorg. Med. Chem., 20:571-582, 2012).

As used herein, the term "heterospecific antibodies" refers to monoclonal, preferably human or humanized, antibodies that have binding specificities for at least two different antigens. Traditionally, the recombinant production of heterospecific antibodies is based on the co-expression of two immunoglobulin heavy chain-light chain pairs, where the two heavy chains have different specificities (Milstein et al., Nature 305:537, 1983). Similar procedures are disclosed, e.g., in WO 93/08829, U.S. Pat. Nos. 6,210,668; 6,193,967; 6,132,992; 6,106,833; 6,060,285; 6,037,453; 6,010,902; 5,989,530; 5,959,084; 5,959,083; 5,932,448; 5,833,985; 5,821,333; 5,807,706; 5,643,759, 5,601,819; 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986); incorporated herein by reference. Heterospecific antibodies can include Fc mutations that enforce correct chain association in multi-specific antibodies, as described by Klein et al, mAbs 4(6):653-663, 2012; incorporated herein by reference.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A human antibody can be produced in a human cell (e.g., by recombinant expression), or by a non-human animal or a prokaryotic or eukaryotic cell that is capable of expressing functionally rearranged human immunoglobulin (e.g., heavy chain and/or light chain) genes. Further, when a human antibody is a single-chain antibody, it can include a linker peptide that is not found in native human antibodies. For example, an Fv can include a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. See U.S. Pat. Nos. 4,444,887 and 4,716,111; and PCT publications WO 1998/46645; WO 1998/50433; WO 1998/24893; WO 1998/16654; WO 1996/34096; WO 1996/33735; and WO 1991/10741; incorporated herein by reference. Human antibodies can also be produced using transgenic mice that are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598; incorporated by reference herein.

As used herein, the term "humanized" antibody refers to forms of non-human (e.g., murine) antibodies that are chimeric immunoglobulins, immunoglobulin chains or fragments thereof (such as Fv, Fab, Fab', $F(ab')_2$ or other target-binding subdomains of antibodies) which contain minimal sequences derived from non-human immunoglobulin. In general, the humanized antibody will include substantially all of at least one, and typically two, variable domains, in which all or substantially all of the CDR regions correspond to those of a non-human immunoglobulin. All or substantially all of the FR regions may also be those of a human immunoglobulin sequence. The humanized antibody can also include at least a portion of an immunoglobulin constant region (Fc), typically that of a human immunoglobulin consensus sequence. Methods of antibody humanization are known in the art. See, e.g., Riechmann et al., Nature 332:323-7, 1988; U.S. Pat. Nos. 5,530,101; 5,585,089; 5,693,761; 5,693,762; and 6,180,370 to Queen et al; EP239400; PCT publication WO 91/09967; U.S. Pat. No. 5,225,539; EP592106; and EP519596; incorporated herein by reference.

As used herein, the term "hydrophobic side-chain" refers to an amino acid side-chain that exhibits low solubility in water relative due to, e.g., the steric or electronic properties of the chemical moieties present within the side-chain. Examples of amino acids containing hydrophobic side-chains include those containing unsaturated aliphatic hydrocarbons, such as alanine, valine, leucine, isoleucine, proline, and methionine, as well as amino acids containing aromatic ring systems that are electrostatically neutral at physiological pH, such as tryptophan, phenylalanine, and tyrosine.

As used herein, the term "monoclonal antibody" refers to an antibody that is derived from a single clone, including any eukaryotic, prokaryotic, or phage clone, and not the method by which it is produced.

As used herein, the term "neurological disorder" refers to a condition having as a component a disturbance in the structure or function of the nervous system. Neurological disorders may result from developmental abnormalities, disease, genetic defects, age, or injury. These disorders may affect the central nervous system (e.g., the brain, brainstem, cerebellum, and spinal cord), the peripheral nervous system (e.g., the cranial nerves, spinal nerves, and sympathetic and parasympathetic nervous systems), and/or the autonomic nervous system (e.g., the part of the nervous system that regulates involuntary to action and that is divided into the sympathetic and parasympathetic nervous systems). In particular, neurological disorders of the present disclosure may be associated with the pathogenic accumulation of tau protein (e.g., increased cis p-Tau and/or increased soluble cis p-Tau). Exemplary neurological disorders include traumatic brain injury (TBI), chronic traumatic encephalopathy (CTE), mild cognitive impairment, Alzheimer's disease, Parkinson's disease, multiple sclerosis, muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalitis, epilepsy, vascular dementia, age-related dementia, stroke, transient ischemic attacks (TIA, also commonly referred to as mini strokes), neurofibromatosis, Lewy body disease, amyotrophic lateral sclerosis (ALS), a peripheral neuropathy, diabetic neuropathy, macular degeneration, ischemia-related retinopathy, and diabetic retinopathy.

As used herein, the term "non-native constant region" refers to an antibody constant region that is derived from a source that is different from the antibody variable region or that is a human-generated synthetic polypeptide having an amino sequence that is different from the native antibody constant region sequence. For instance, an antibody containing a non-native constant region may have a variable region derived from a non-human source (e.g., a mouse, rat, or rabbit) and a constant region derived from a human source (e.g., a human antibody constant region), or a constant region derived from another primate, pig, goat, rabbit, hamster, cat, dog, guinea pig, member of the bovidae family (such as cattle, bison, buffalo, elk, and yaks, among others), cow, sheep, horse, or bison, among others).

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, the term "primatized antibody" refers to an antibody including framework regions from primate-derived antibodies and other regions, such as CDRs and/or constant regions, from antibodies of a non-primate source. Methods for producing primatized antibodies are known in the art. See e.g., U.S. Pat. Nos. 5,658,570; 5,681,722; and 5,693,780; incorporated herein by reference. For instance, a primatized antibody or antigen-binding fragment thereof described herein can be produced by inserting the CDRs of a non-primate antibody or antigen-binding fragment thereof into an antibody or antigen-binding fragment thereof that contains one or more framework regions of a primate.

As used herein, the term "proline analog" is meant a molecule substantially similar in function to either an entire proline amino acid residue or to a fragment thereof. For example, the present invention contemplates the use of proline analogs wherein a side chain is lengthened or shortened while still providing a carboxyl, amino, or other reactive precursor functional group, as well as proline analogs having variant side chains with appropriate functional groups. Exemplary proline analogs include, without limitation, homoproline (i.e., pipecolic acid (PIP)), azetidine-2-carboxylic acid (Aze), tert-butyl-L-proline (TBP), trans-4-fluoro-L-proline (t-4F-Pro), or cis-4-fluoro-L-proline (c-4F-Pro).

As used herein, the term "operatively linked" in the context of a polynucleotide fragment is intended to mean that the two polynucleotide fragments are joined such that the amino acid sequences encoded by the two polynucleotide fragments remain in-frame.

As used herein, the term "pharmacokinetic profile" refers to the absorption, distribution, metabolism, and clearance of a drug over time following administration of the drug to a patient.

As used herein, the term "regulatory sequence" includes promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, CA, 1990); incorporated herein by reference.

As used herein, the term "reference value" refers to a value, metric, or level that is used for comparison purposes. For example, when a level of protein expression (e.g., soluble cis-pTau expression) is determined for a subject, the level may be compared to a reference value to determine whether the is elevated, unchanged, or reduced. Likewise, a "reference ratio," as used herein, is the ratio of two values, metrics, or levels, where the ratio may be used for comparison purposes to another ratio. For example, when a ratio of cis-pTau:trans-pTau is determined for a subject, the ratio may be compared to a reference ratio to determine whether the ratio determined for the subject is elevated, unchanged, or reduced. A reference value or reference ratio can be determined, for example, from a prior sample taken from the same subject prior to the development of the disorder or of symptoms suggestive of the disorder; from a sample from a subject not having the disorder; from a sample from a subject not having symptoms of the disorder; or from a sample of a purified reference polypeptide in a given conformation at a known normal concentration (i.e., not indicative of the disorder). As used herein, the term "scFv" refers to a single-chain Fv antibody in which the variable domains of the heavy chain and the light chain from an antibody have been joined to form one chain. scFv fragments contain a single polypeptide chain that includes the variable region of an antibody light chain (VL) (e.g., CDR-L1, CDR-L2, and/or CDR-L3) and the variable region of an antibody heavy chain (VH) (e.g., CDR-H1, CDR-H2, and/or CDR-H3) separated by a linker. The linker that joins the VL and VH regions of a scFv fragment can be a peptide linker composed of proteinogenic amino acids. Alternative linkers can be used to so as to increase the resistance of the scFv fragment to proteolytic degradation (e.g., linkers containing D-amino acids), in order to enhance the solubility of the scFv fragment (e.g., hydrophilic linkers such as polyethylene glycol-containing linkers or polypeptides containing repeating glycine and serine residues), to improve the biophysical stability of the molecule (e.g., a linker containing cysteine residues that form intramolecular or intermolecular disulfide bonds), or to attenuate the immunogenicity of the scFv fragment (e.g., linkers containing glycosylation sites). scFv molecules are known in the art and are described, e.g., in U.S. Pat. No. 5,892,019, Flo et al., (Gene 77:51, 1989); Bird et al., (Science 242:423, 1988); Pantoliano et al., (Biochemistry 30:10117, 1991); Milenic et al., (Cancer Research 51:6363, 1991); and Takkinen et al., (Protein Engineering 4:837, 1991). The VL and VH domains of a scFv molecule can be derived from one or more antibody molecules. It will also be understood by one of ordinary skill in the art that the variable regions of the scFv molecules described herein can be modified such that they vary in amino acid sequence from the antibody molecule from which they were derived. For example, in one embodiment, nucleotide or amino acid substitutions leading to conservative substitutions or changes at amino acid residues can be made (e.g., in CDR and/or framework residues). Alternatively, or in addition, mutations are made to CDR amino acid residues to optimize antigen binding using art recognized techniques. scFv fragments are described, for example, in WO 2011/084714; incorporated herein by reference.

As used herein, the phrase "specifically binds" refers to a binding reaction which is determinative of the presence of an antigen in a heterogeneous population of proteins and other biological molecules that is recognized, e.g., by an antibody or antigen-binding fragment thereof, with particularity. An antibody or antigen-binding fragment thereof that specifically binds to an antigen will bind to the antigen with a $K_D$ of less than 100 nM. For example, an antibody or antigen-binding fragment thereof that specifically binds to an antigen will bind to the antigen with a $K_D$ of up to 100 nM (e.g., between 1 μM and 100 nM). An antibody or antigen-binding fragment thereof that does not exhibit specific binding to a particular antigen or epitope thereof will exhibit a $K_D$ of greater than 100 nM (e.g., greater than 500 nm, 1 μM, 100 μM, 500 μM, or 1 mM) for that particular antigen or epitope thereof. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of immunoassay formats and conditions that can be used to determine specific immunoreactivity.

As used herein, the terms "subject" and "patient" refer to an organism that receives treatment for a particular disease or condition as described herein (such as a neurological disorder). Examples of subjects and patients include mammals, such as humans, primates, pigs, goats, rabbits, hamsters, cats, dogs, guinea pigs, members of the bovidae family (such as cattle, bison, buffalo, elk, and yaks, among others), cows, sheep, horses, and bison, among others, receiving treatment for diseases or conditions.

As used herein, the term "transfection" refers to any of a wide variety of techniques commonly used for the introduction of exogenous DNA into a prokaryotic or eukaryotic host cell, e.g., electroporation, lipofection, calcium-phosphate precipitation, DEAE-dextran transfection and the like.

As used herein, the terms "treat" or "treatment" refer to therapeutic treatment, in which the object is to prevent or slow down (lessen) an undesired physiological change or disorder, such as the progression of a neurological disorder described herein. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in which the condition or disorder is to be prevented. To treat, as used throughout this application, therefore also refers to reducing likelihood of occurrence in a subject at risk of developing a disorder (e.g., relative to a subject not treated with an antibody described herein and/or relative to a subject treated with an alternative therapy).

As used herein the term "variable region CDR" includes amino acids in a CDR or complementarity determining region as identified using sequence or structure-based methods. As used herein, the term "CDR" or "complementarity determining region" refers to the noncontiguous antigen-binding sites found within the variable regions of both heavy and light chain polypeptides. These particular regions have been described by Kabat et al., J. Biol. Chem. 252:6609-6616, 1977 and Kabat, et al., Sequences of Proteins of Immunological Interest, Fifth Edition, U.S. Department of Health and Human Services, NIH Publication No. 91-3242, 1991; by Chothia et al., (J. Mol. Biol. 196:901-917, 1987), and by MacCallum et al., (J. Mol. Biol. 262:732-745, 1996) where the definitions include overlapping or subsets of amino acid residues when compared against each other. The term "CDR" may be, for example, a CDR as defined by Kabat based on sequence comparisons.

As used herein, the term "vascular disease of the central nervous system (CNS)" refers to neuronal deficiencies involving a loss, damage, or inadequate or suboptimal function of neurons, astrocytes, endothelial cells, microglia, and any other cell-type of the central nervous system, where the neuronal deficiencies are associate with lack of supply of oxygen (e.g., hypoxia or ischemia) or lack of supply of nutrients to the affected CNS tissue (e.g., a lack of supply of oxygen or supply of nutrients to the brain). Exemplary vascular diseases of the CNS include vascular dementia, ischemia-related retinopathy, diabetic retinopathy, age-related macular degeneration, diabetic neuropathy, stroke, and transient ischemic attacks (TIA).

As used herein, the term "vector" includes a nucleic acid vector, e.g., a DNA vector, such as a plasmid, a RNA vector, virus or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO 1994/11026; incorporated herein by reference. Expression vectors described herein contain a polynucleotide sequence as well as, e.g., additional sequence elements used for the expression of proteins and/or the integration of these polynucleotide sequences into the genome of a mammalian cell. Certain vectors that can be used for the expression of antibodies and antibody fragments described herein include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements include, e.g., 5' and 3' untranslated regions, an internal ribosomal entry site (IRES), and polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "VH" refers to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain of a native antibody has at the amino terminus a variable domain (VH) followed by a number of constant domains. Each light chain of a native antibody has a variable domain at the amino terminus (VL) and a constant domain at the carboxy terminus.

BRIEF DESCRIPTION OF THE DRAWINGS

This patent or application file contains at least one drawing in color. Copies of this patent or patent application publication with color drawings will be provided by the Office upon request and payment of the necessary fee.

FIG. 1D is an image showing an alignment of the amino acid sequences of the light chain variable domains from C113 (a previously described murine cis-pTau monoclonal antibody (see, e.g., U.S. Pat. No. 9,688,747); SEQ ID NO:15); HT13 (a mouse-human chimera antibody; SEQ ID NO: 15) and humanized cis-mAbs described herein (SEQ ID NOs: 16-23). The alignment is annotated to show, in order, the framework region that is N-terminal to CDR-L1 (FW region 1); CDR-L1; the framework region that is between CDR-L1 and CDR-L2 (FW region 2); CDR-L2; the framework region that is between CDR-L2 and CDR-L3 (FW region 3); CDR-L3; and the framework region that is C-terminal to CDR-L3 (FW region 4).

FIG. 13A shows representative infrared (IR) immunofluorescence images of cis P-tau in the cortex overlying the corpus callosum (Ctx-CC) of aged-matched normal control human brains and in VaD human brains.

FIG. 13B is a graph of the quantified levels of cis P-tau measured with IR immunofluorescence images of cis P-tau in human normal control and VaD brains.

TG) along with WT littermate controls were subject to immunoblotting with Pin1 antibody.

Figure 31A:
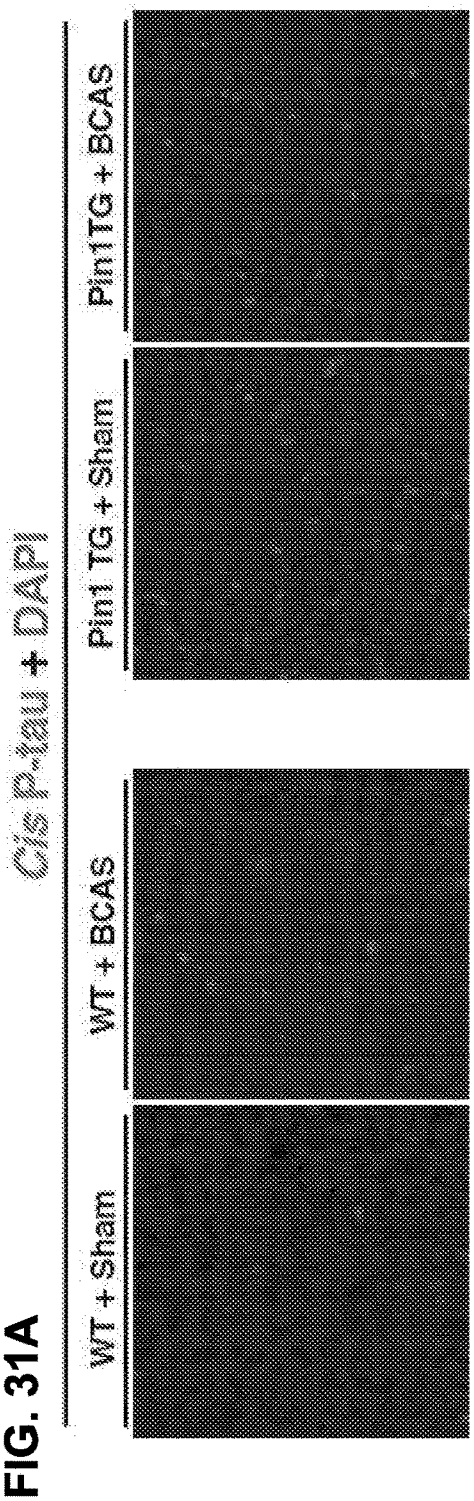
Figure 31B:
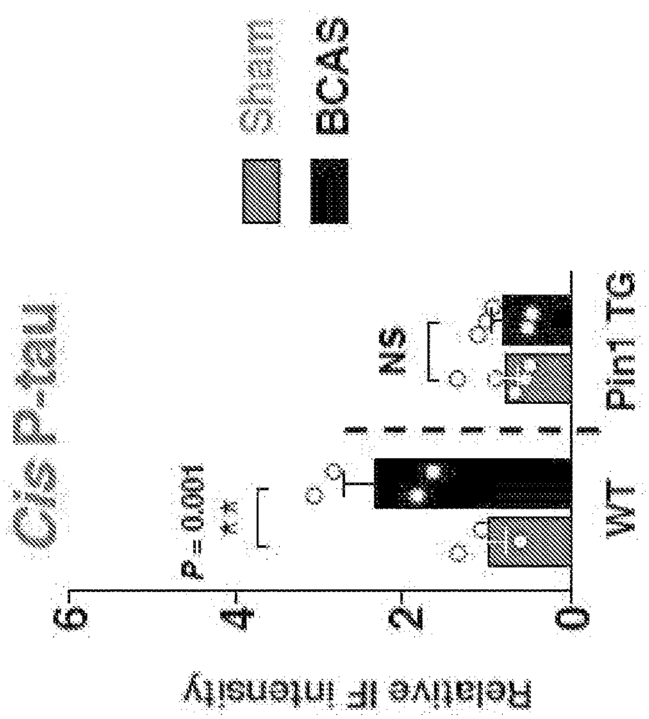
Figure 33A:
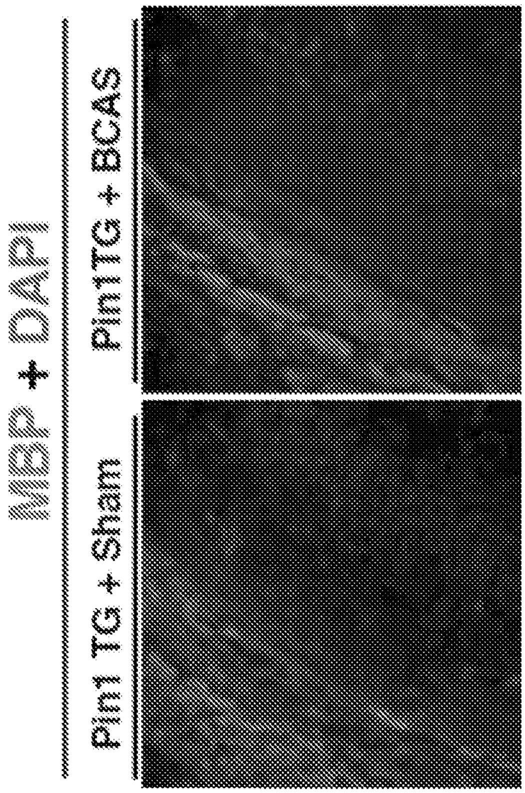
Figure 33B:
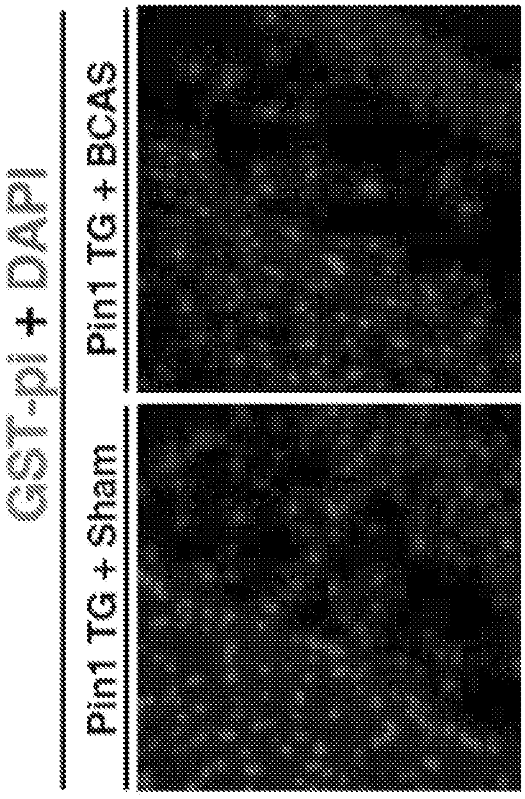
Figure 33D:
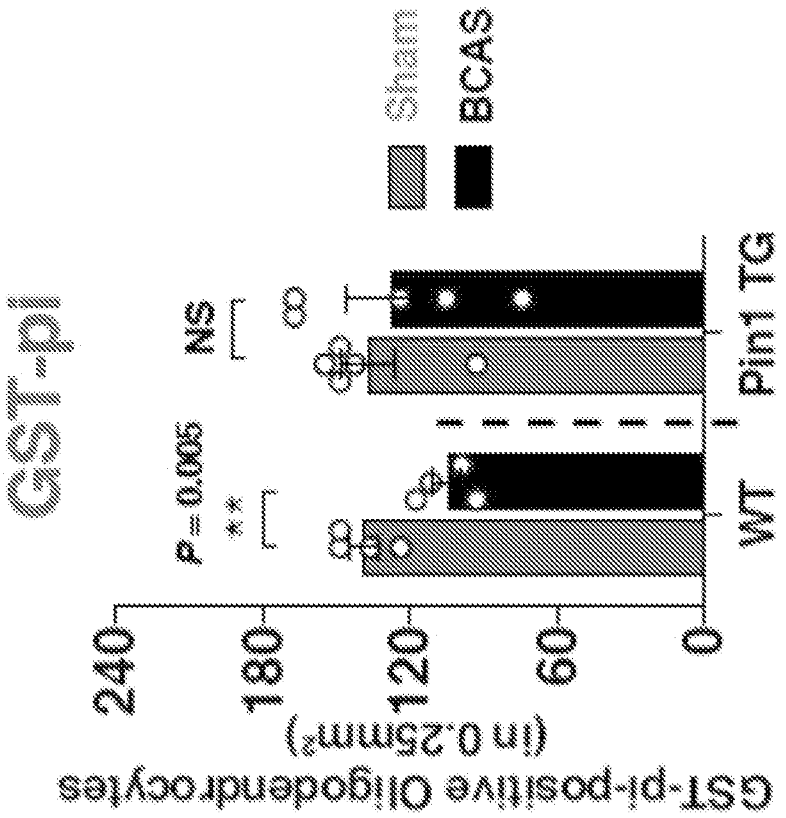
Figure 33C:
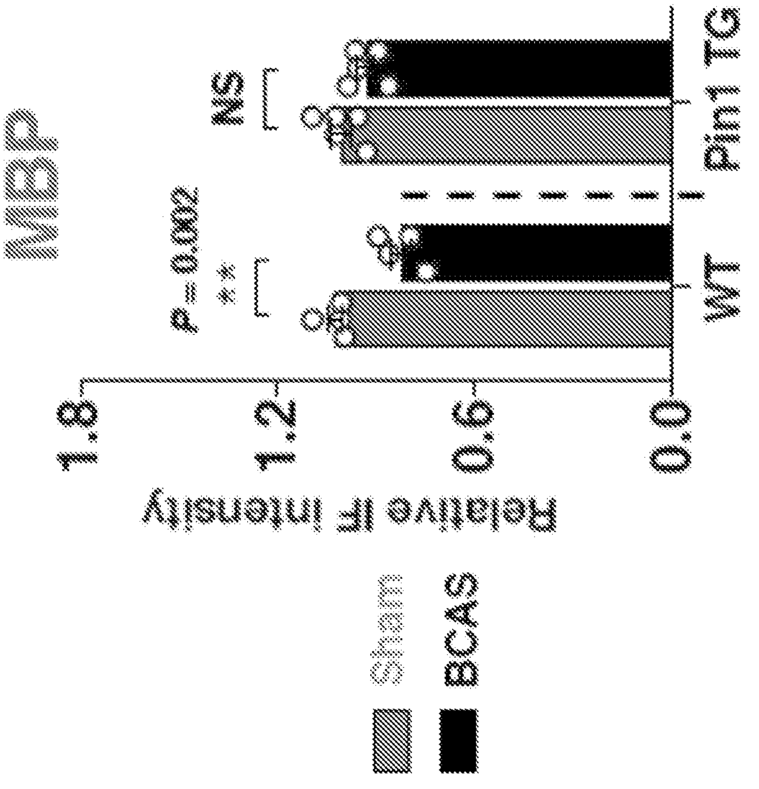

FIGS. 31A-31B show immunofluorescence staining results (FIG. 31A), and their accompanying quantification graphs (FIG. 31B), describing that brain-specific Pin1 overexpression reduces cis P-tau in BCAS mice at 28 days. Mouse brain sections were analyzed by IF using cis P-tau antibodies followed by quantifying signal intensity in the corpus callosum at 28 days after surgery.

FIGS. 32A-32D show immunofluorescence staining results from GFAP (FIG. 32A) and Iba1 (FIG. 32B), and the accompanying quantification graphs for GFAP (FIG. 32C) and Iba1 (FIG. 32D), describing that brain-specific Pin1 overexpression inhibits neuroinflammation in BCAS mice at 28 days. Mouse brain sections were analyzed by IF using GFAP and Iba1 antibodies followed by quantifying signal intensity in the corpus callosum at 28 days after surgery.

FIGS. 33A-33D show immunofluorescence staining results from MBP (FIG. 33A) and GST-pi (FIG. 33B), and their accompanying quantification graphs for MBP (FIG. 33C) and GST-pi (FIG. 33D), describing that brain-specific Pin1 overexpression inhibits demyelination in BCAS mice at 28 days. Mouse brain sections were analyzed by IF using MBP and GST-pi antibodies followed by quantifying signal intensity in the corpus callosum at 28 days after surgery.

Figure 34B:
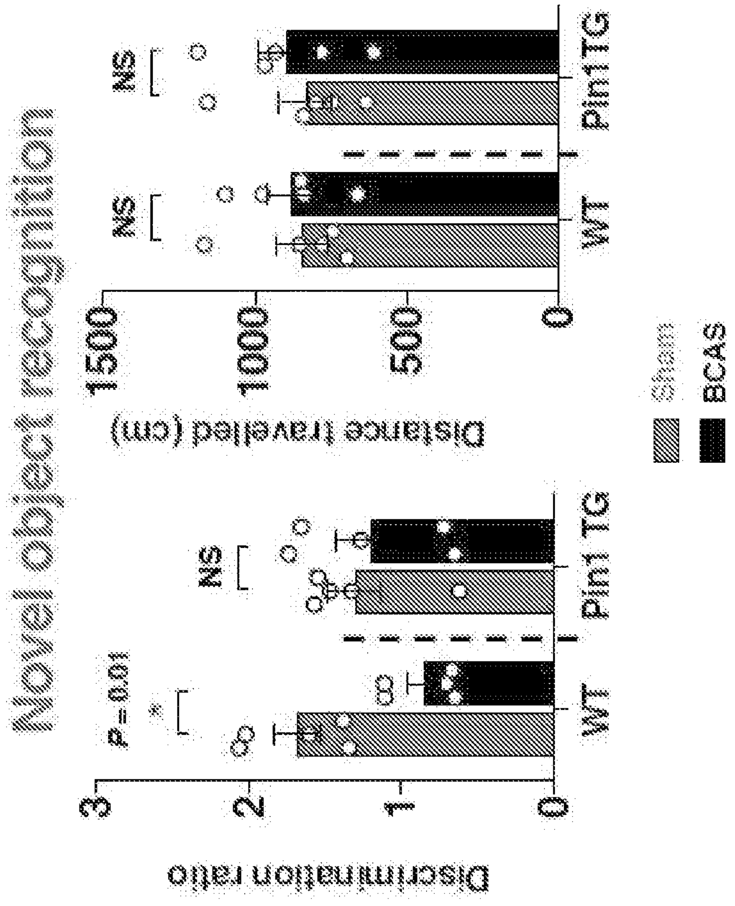
Figure 34A:
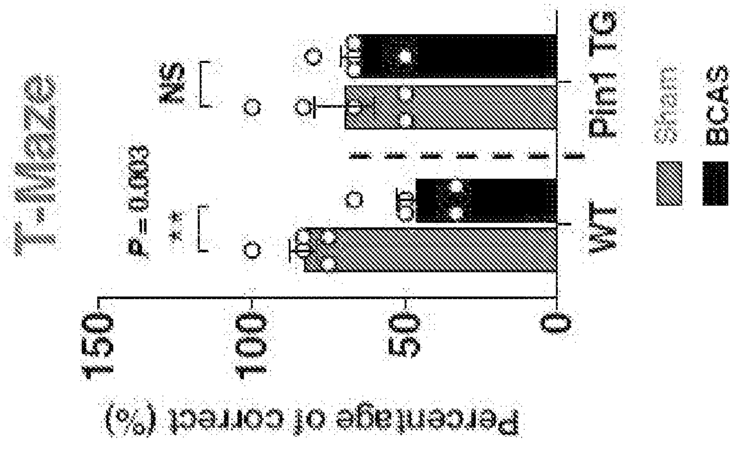

FIGS. 34A-34B are graphs describing that Pin1 overexpression restores working memory deficits in BCAS mice. Behavioral changes were assayed using the T-maze (FIG. 34A) and novel object location recognition (FIG. 34B) tests at 28 days after BCAS.

Figure 35A:
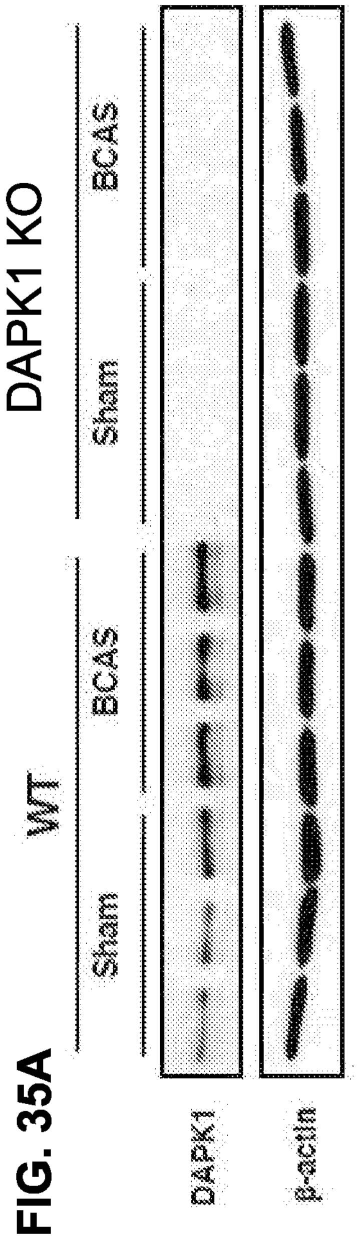

FIG. 35A shows immunoblotting results indicating that DAPK1 is activated in BCAS mice. Lysates of the cortex overlaying the corpus callosum from DAPK1 knockout mice, along with WT littermate controls, were collected and subject to immunoblotting with DAPK1 and p-actin antibodies.

Figure 35B:
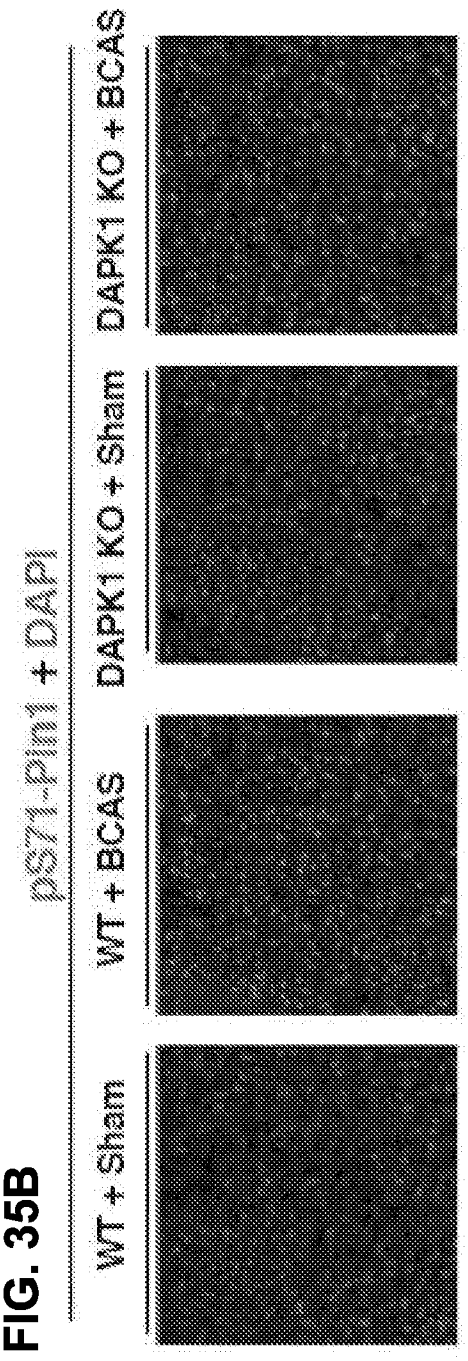
Figure 35C:
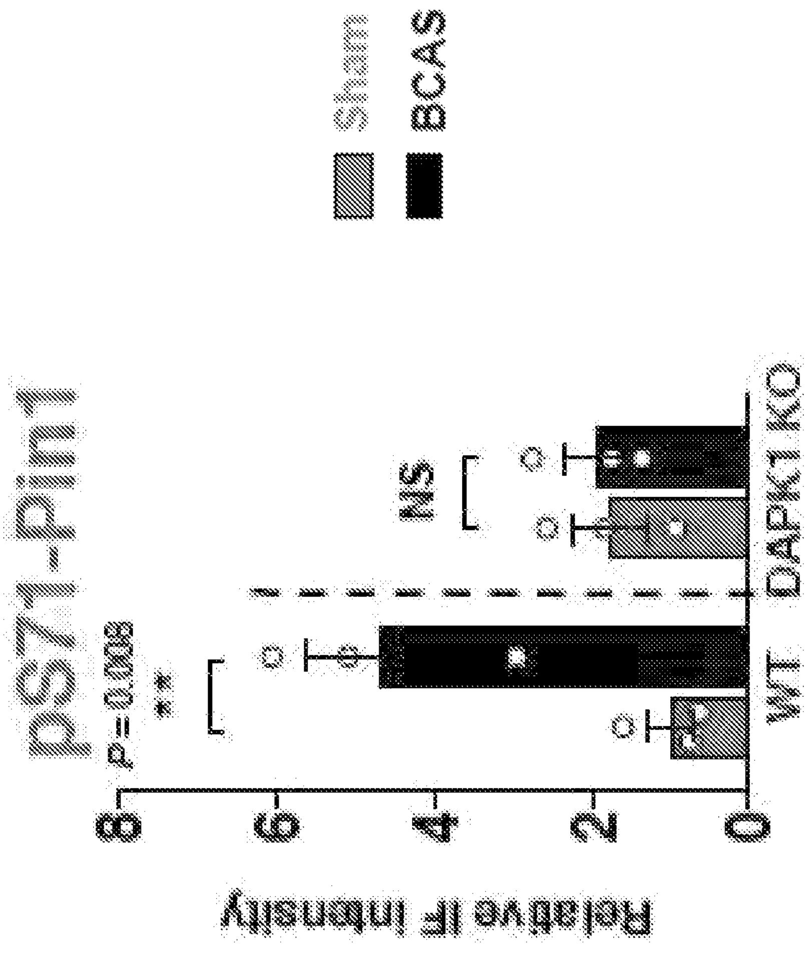

FIGS. 35B-35C show immunofluorescence results (FIG. 35B), and their accompanying quantification graphs (FIG. 35C), indicating that DAPK1 KO suppresses Pin1 inhibition in BCAS mice. Mouse brain sections were analyzed by IF for S71 phosphorylation followed by quantifying signal intensity in the cortex overlaying corpus callosum at 28 days after surgery.

Figure 36A:
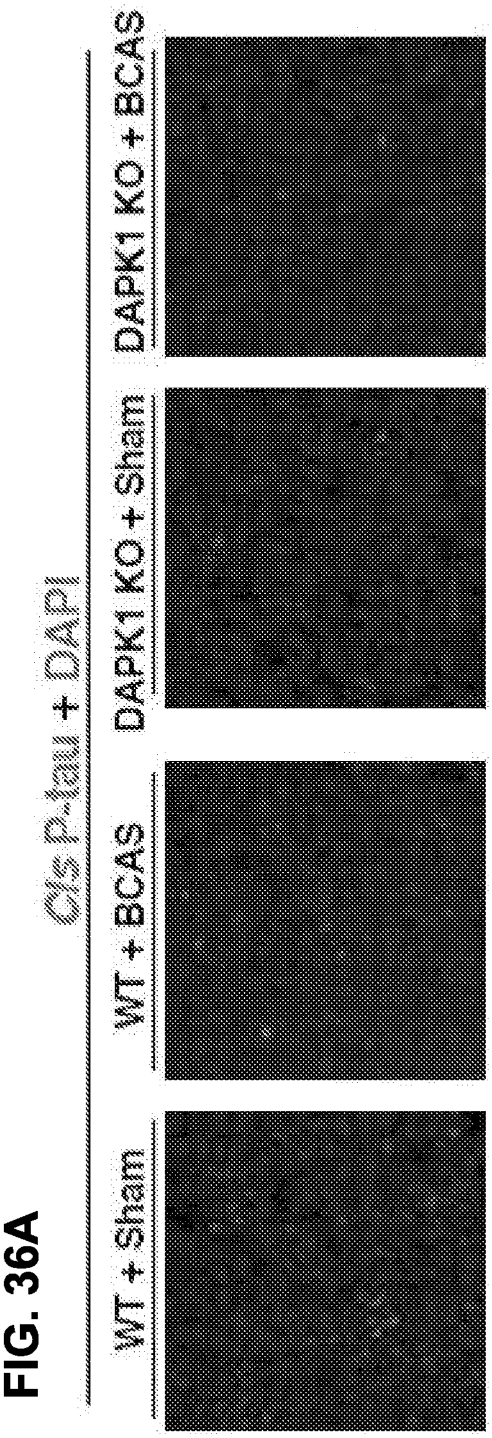
Figure 36B:
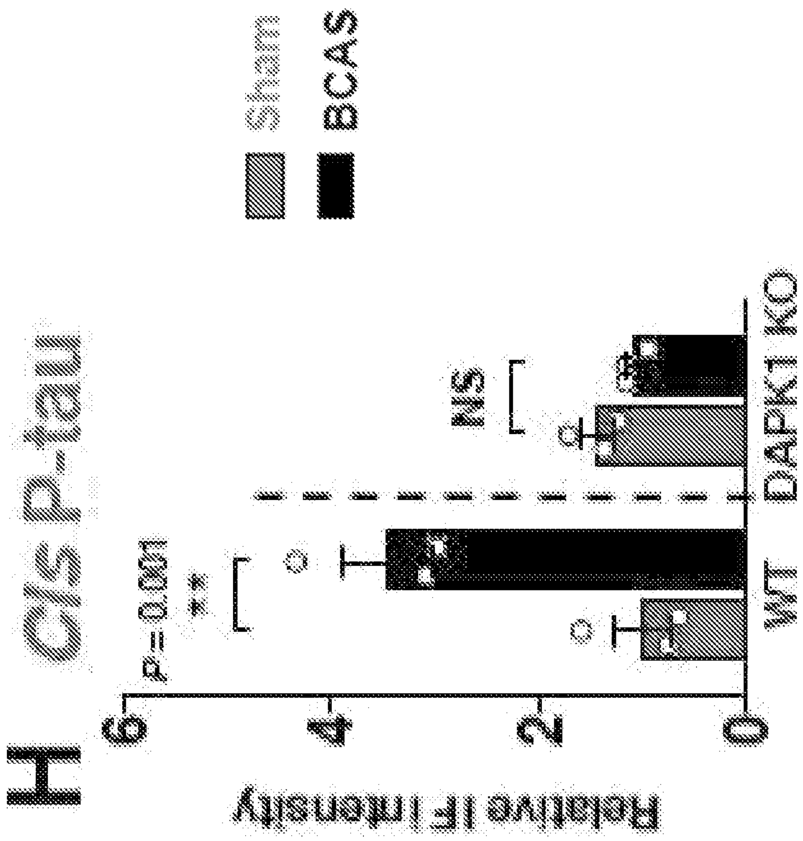
Figure 37A:
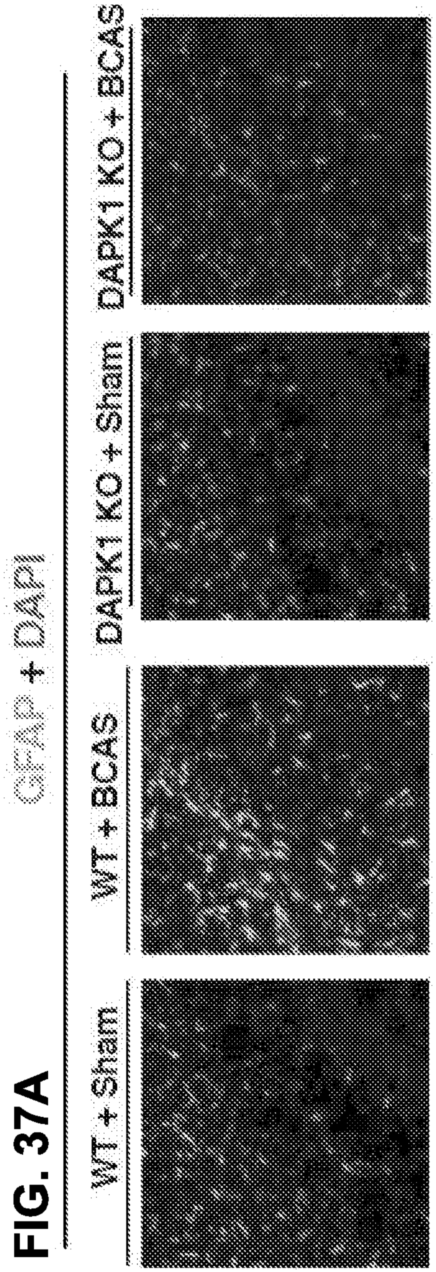
Figure 37B:
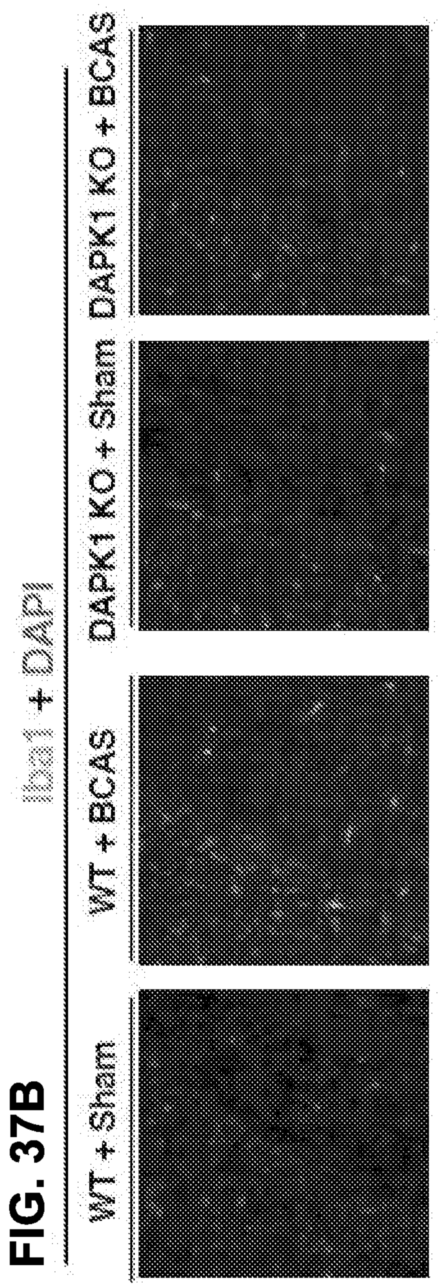
Figure 37D:
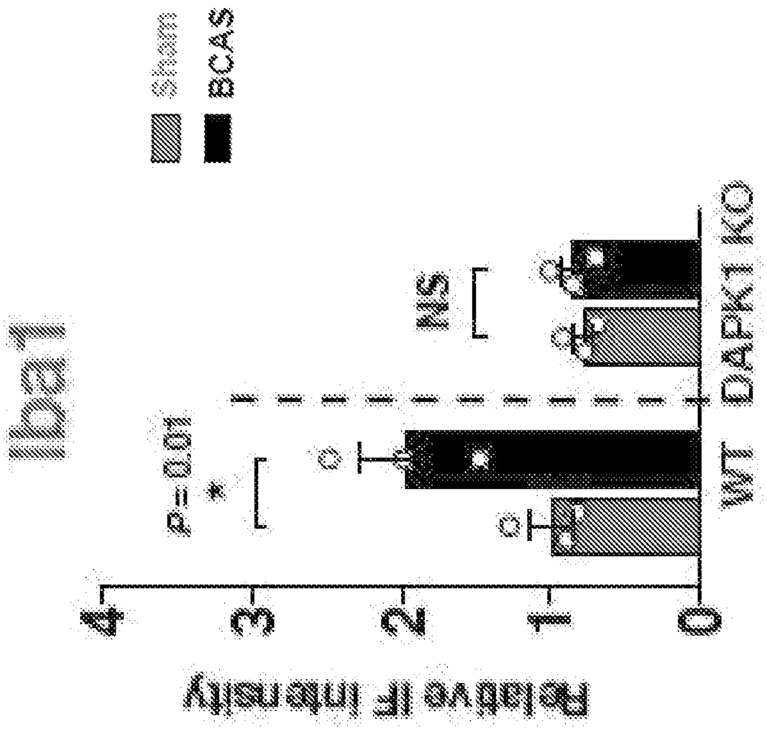
Figure 37C:
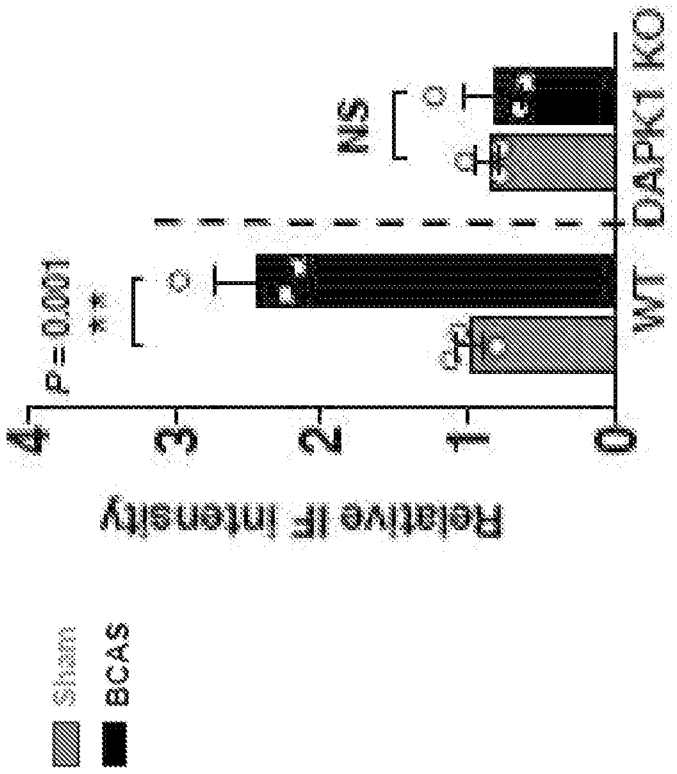

FIGS. 36A-36B show immunofluorescence results (FIG. 36A), and their accompanying quantification graphs (FIG. 36B), indicating that DAPK1 KO suppresses cis P-tau induction in BCAS mice. Mouse brain sections were analyzed by IF for cis P-tau followed by quantifying signal intensity in the cortex overlaying corpus callosum at 28 days after surgery.

FIGS. 37A-37D show immunofluorescence results for GFAP (FIG. 37A) and Iba1 (FIG. 37B), and their accompanying quantification graphs for GFAP (FIG. 37C) and Iba1 (FIG. 37D), indicating that DAPK1 KO suppresses neuroinflammation in BCAS mice. Mouse brain sections were analyzed by IF for GFAP and Iba1 followed by quantifying signal intensity in the cortex overlaying corpus callosum at 28 days after surgery.

Figure 38A:
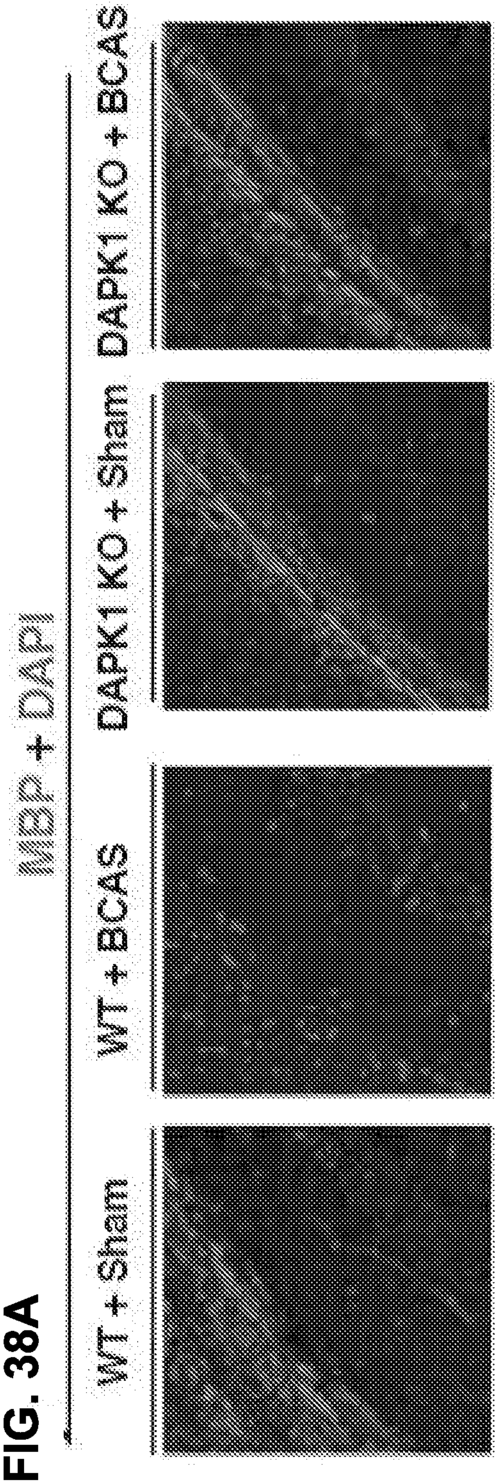
Figure 38B:
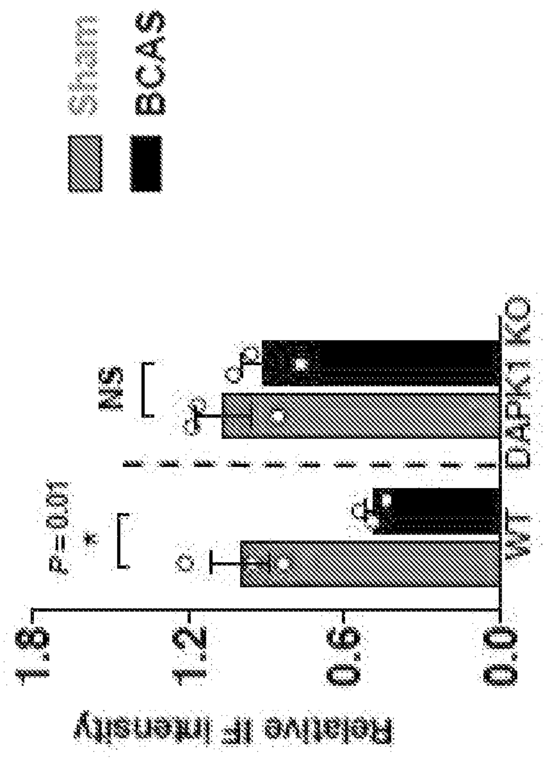

FIGS. 38A-38B show immunofluorescence results (FIG. 38A), and their accompanying quantification graphs (FIG. 38B), indicating that DAPK1 KO suppresses demyelination in BCAS mice. Mouse brain sections were analyzed by IF for MBP followed by quantifying signal intensity in the cortex overlaying corpus callosum at 28 days after surgery.

Figures 39A, 39B:
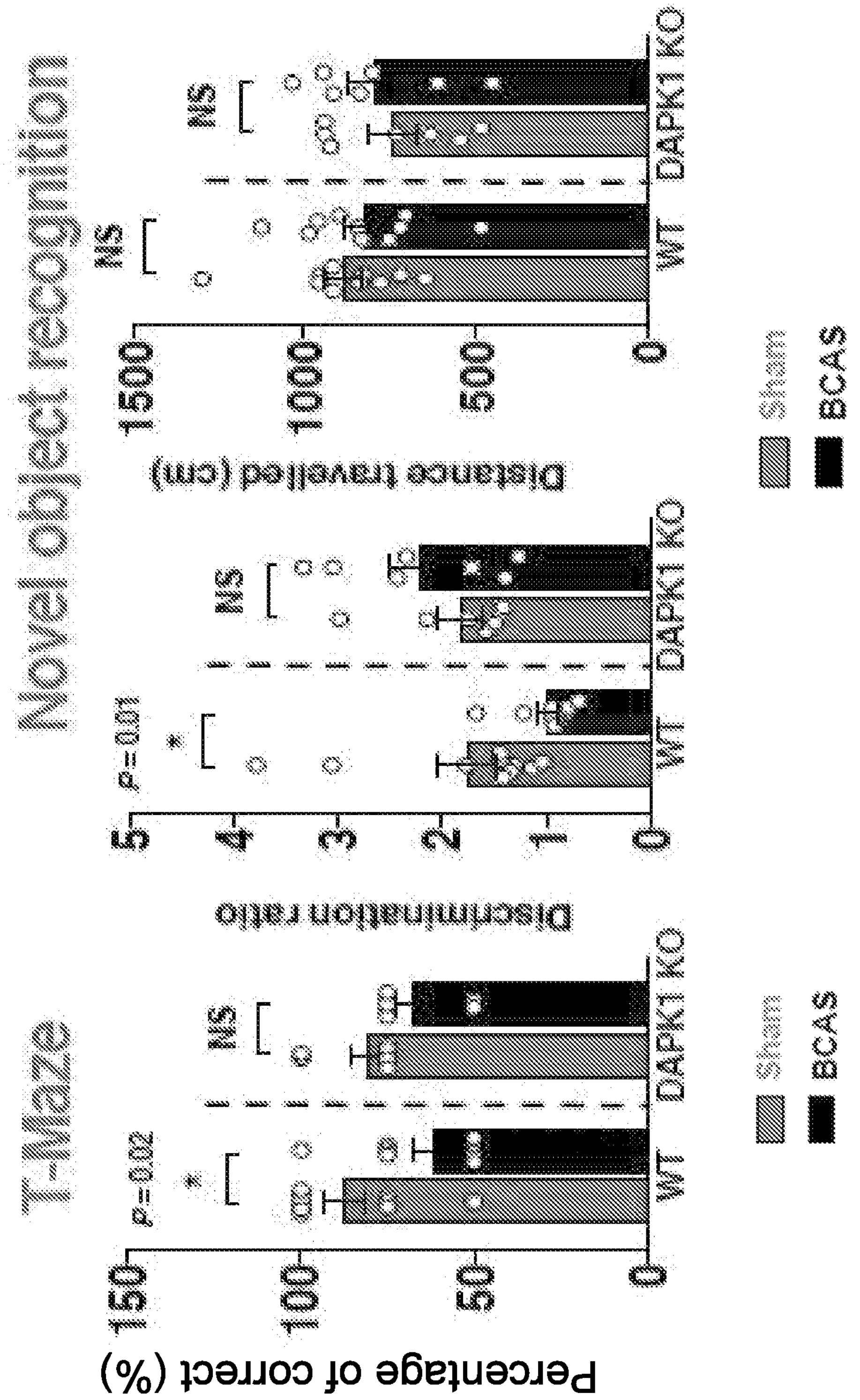

FIGS. 39A-39B are graphs describing that DAPK1 KO restores the working memory deficits in BCAS mice. Behavioral changes were analyzed using the T-maze (FIG. 39A) and novel object location recognition (FIG. 39B) tests at 28 days after BCAS. NS: not significant. The p values were calculated using two-way ANOVA with Bonferroni correction and unpaired two tailed parametric Student's t-test. #$p<0.05$; *$p<0.05$, $p<0.01$, *$p<0.001$.

Figure 40A:
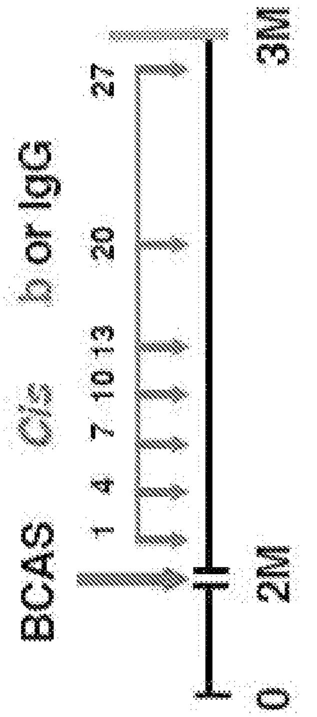

FIG. 40A is a schematic of the timeline used to assess brain gene expression changes with single-nucleus RNA-seq experiments in BCAS mice treated with IgG or cis mAb, with sham littermate as controls to assess the effects on gene expression.

Figure 40B:
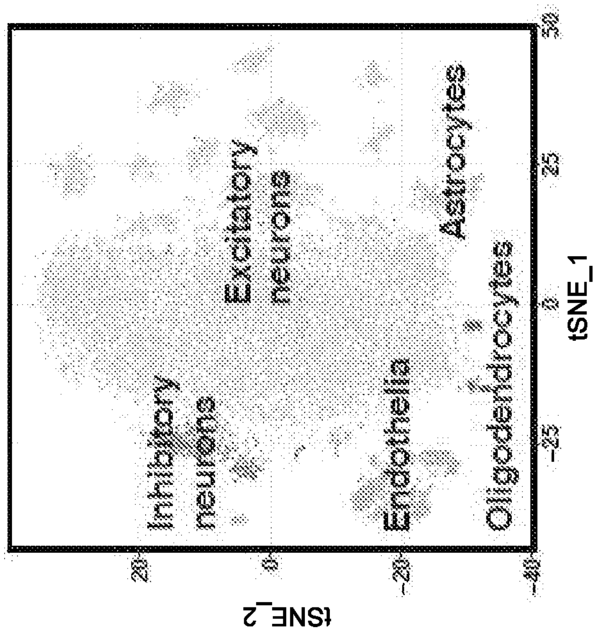

FIG. 40B is a graph describing t-distributed stochastic neighbor embedding (tSNE) plots of color coded different cortical cell types from BCAS mice treated with IgG or cis mAb, with sham littermate as controls.

Figure 40C:
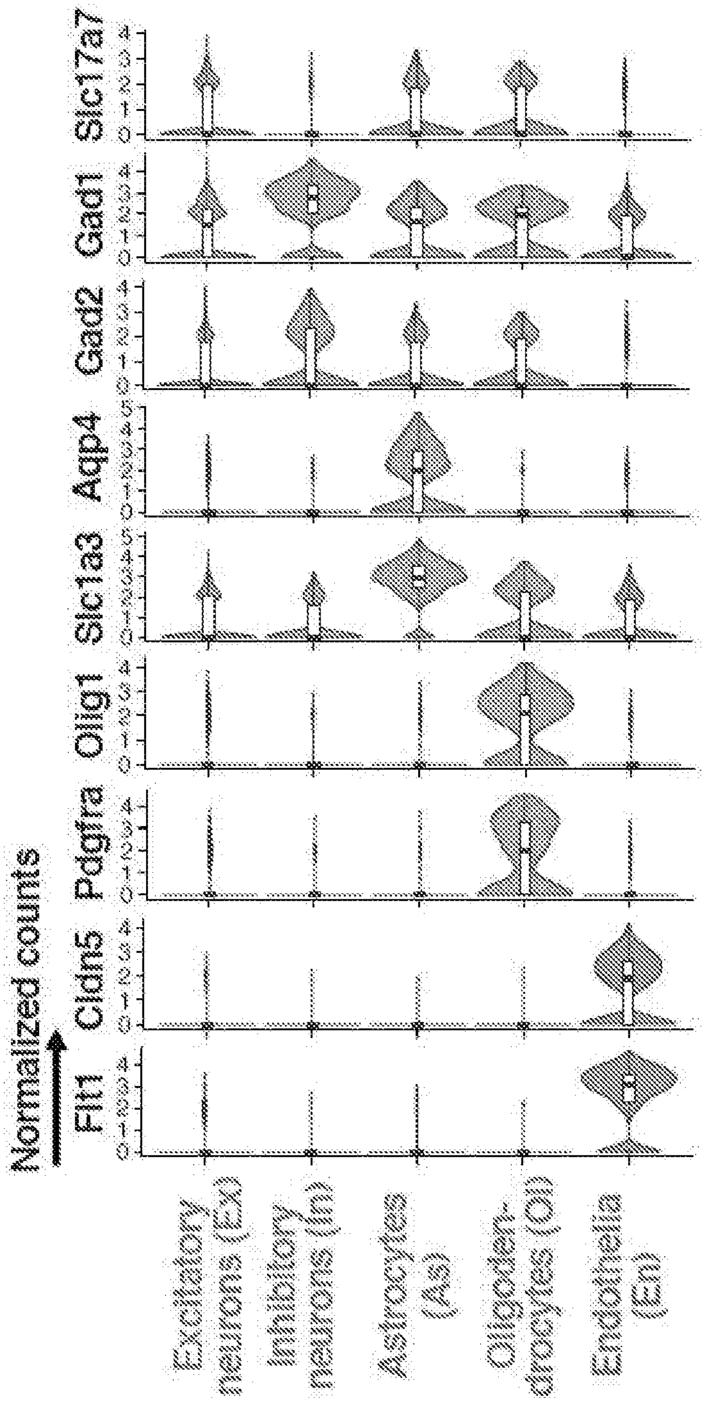
Figure 41A:
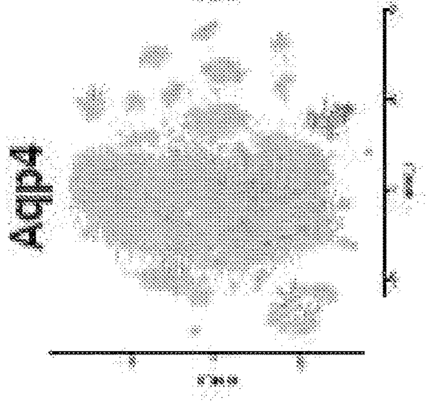
Figure 41B:
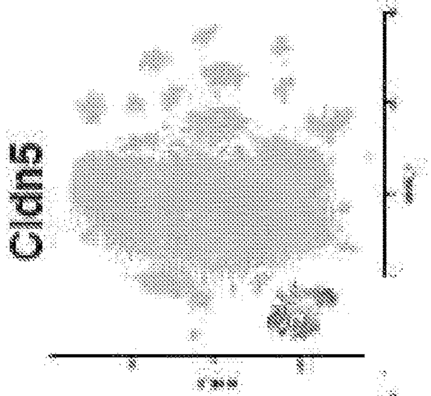
Figure 41C:
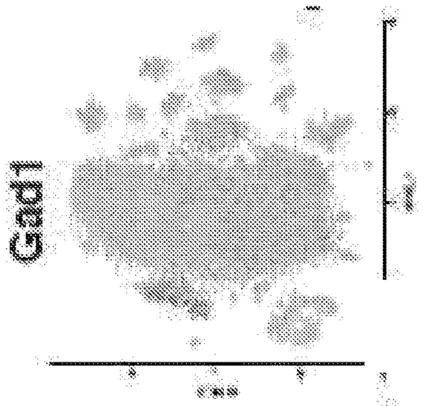
Figure 41D:
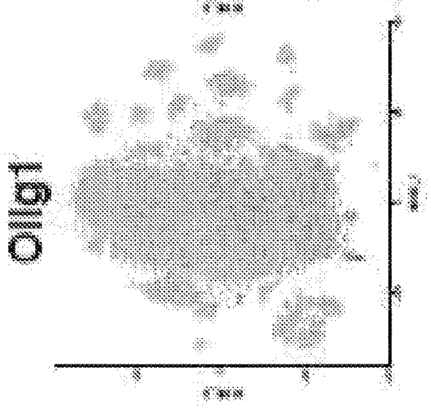
Figure 41E:
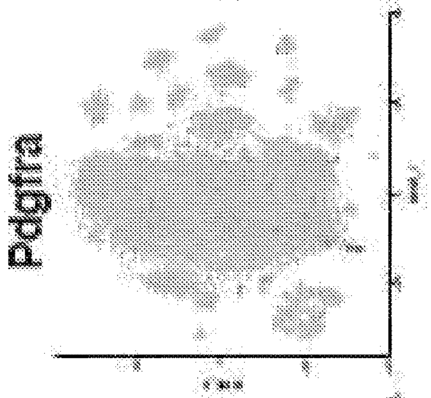
Figure 41F:
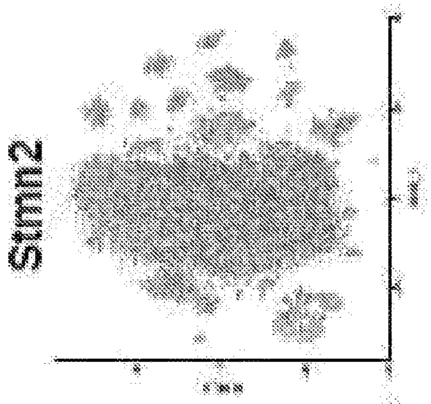

FIG. 40C is a graph describing violin plots showing normalized expression of marker genes for different cell types. Slc17a7 (glutamatergic neurons, Ex), Gad1 and Gad2 (GABAergic neurons, In), Aqp4 and Slc1a3 (astrocytes, As), Olig1 and Pdgfra (oligodendrocytes and their progenitor cells, OI), and Cldn5 and Flt1 (endothelia, En).

FIGS. 41A-41F are a series of graphs describing expression patterns of cell-type specific marker genes across cell clusters in BCAS scRNA-seq experiments (Sham, BCAS+IgG, BCAS+cis mAb). Expression patterns for astrocyte marker Aqp4 (FIG. 41A), endothelia marker Cldn5 (FIG. 41B), inhibitory neuron marker Gad1 (FIG. 41C), oligodendrocyte markers Olig1 (FIG. 41D) and Pdgfra (FIG. 41E) and neuronal marker Stmn2 (FIG. 41F) are shown in heatmaps. Each cell is color coded by the relative expression of the indicated gene from minimal (grey) to maximal (blue).

Figure 42:
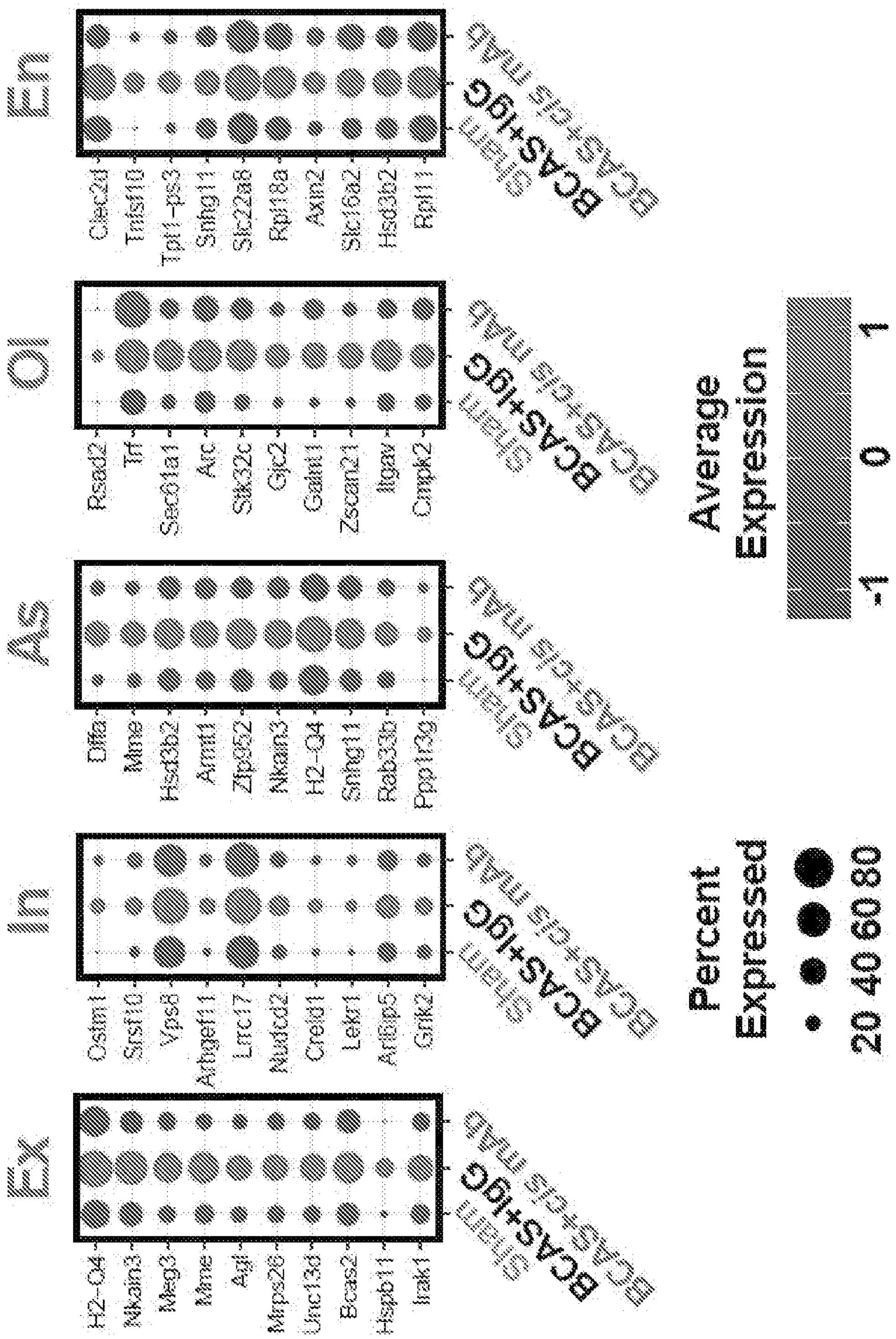

FIG. 42 is a series of graphs, shown as dot plots of average expression (color coded) and percentage of cells expressing the gene (dot size), that describe the top up-regulated differentially expressed genes (DEGs) in five major brain cell types in BCAS mice rescued by cis mAb.

Figure 43:
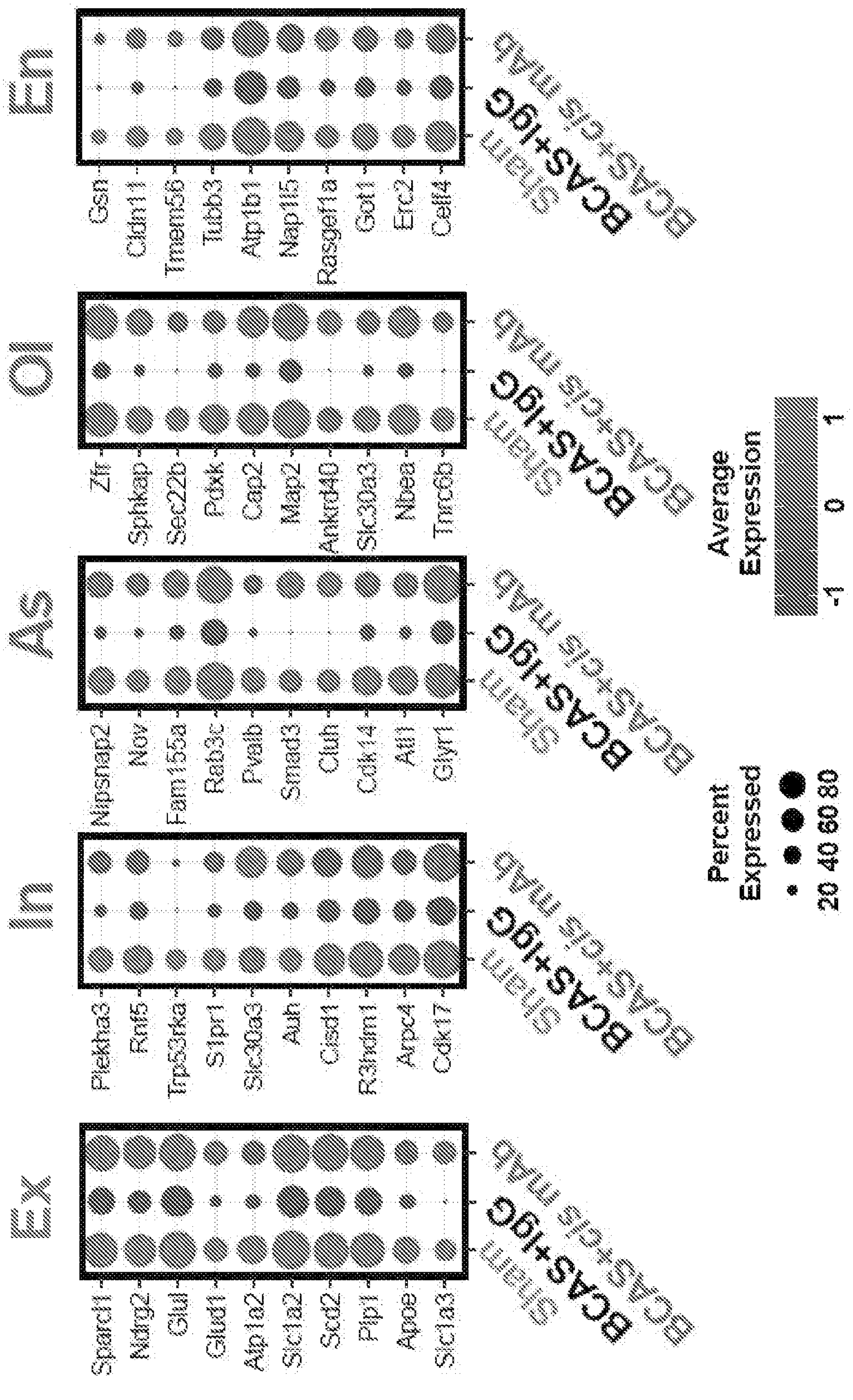

FIG. 43 is a series of graphs, shown as dot plots of average expression (color coded) and percentage of cells expressing the gene (dot size), that describe the top down-regulated differentially expressed genes (DEGs) in five major brain cell types in BCAS mice rescued by cis mAb.

Figure 44:
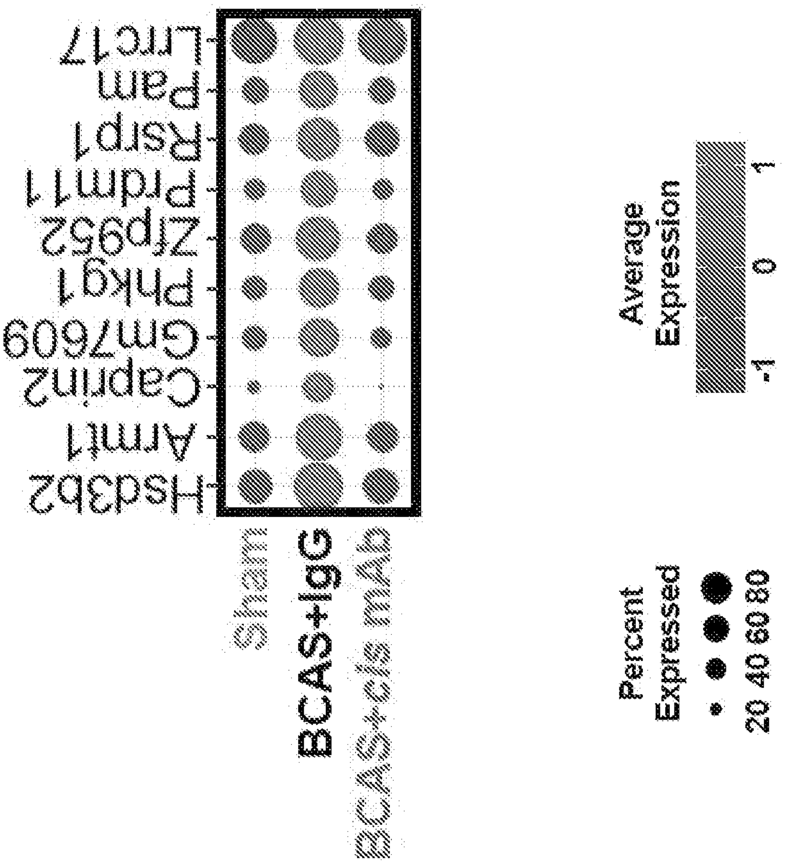
Figure 45A:
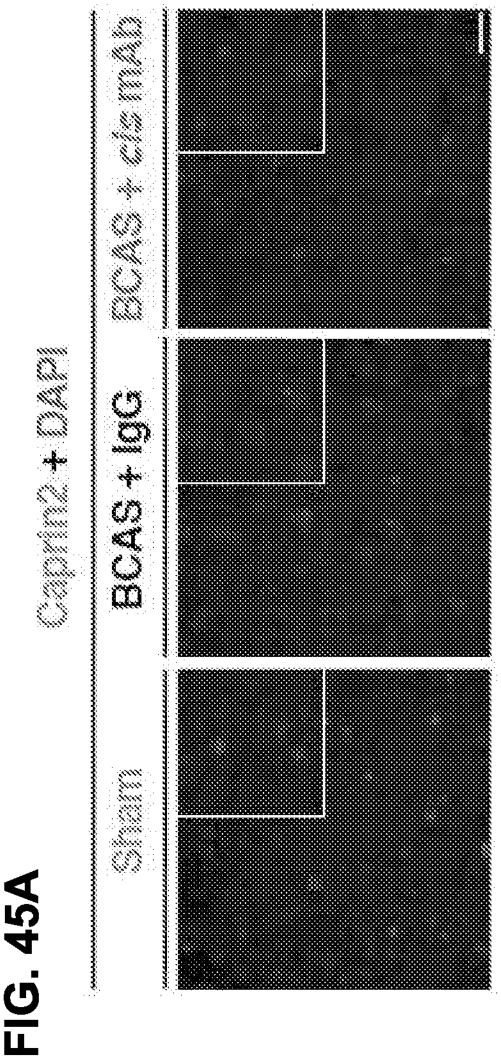
Figure 45B:
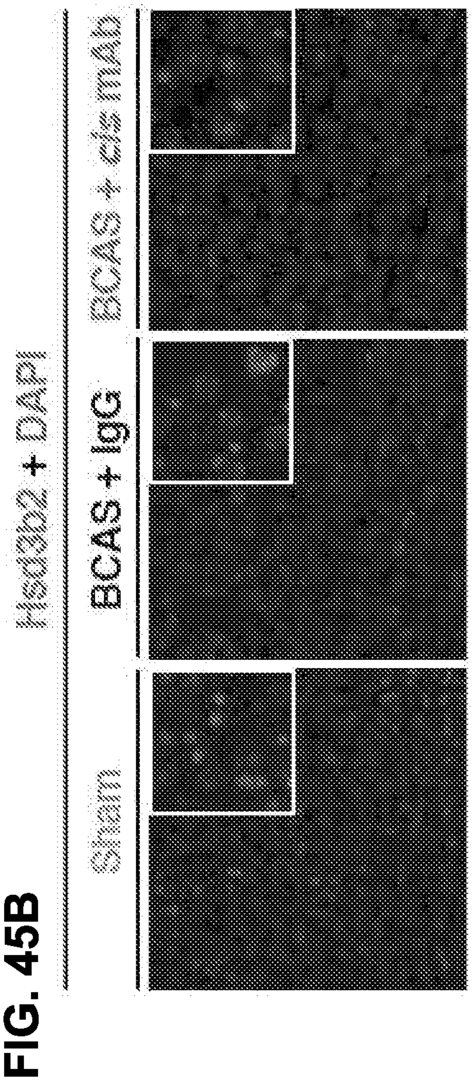
Figure 45D:
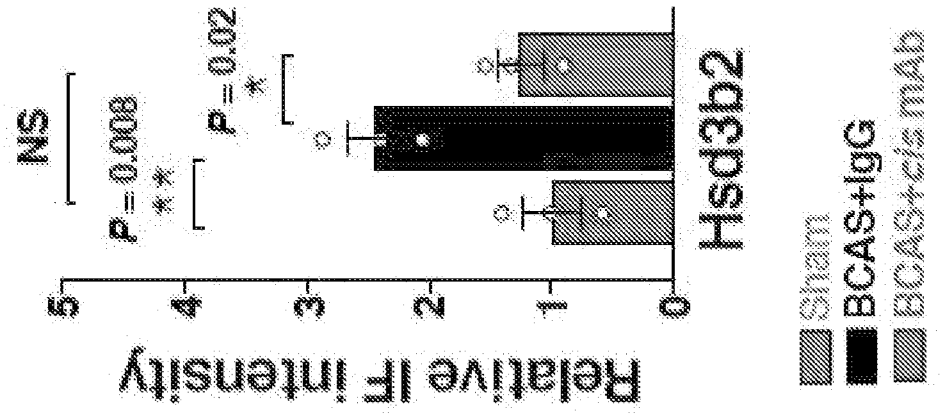
Figure 45C:
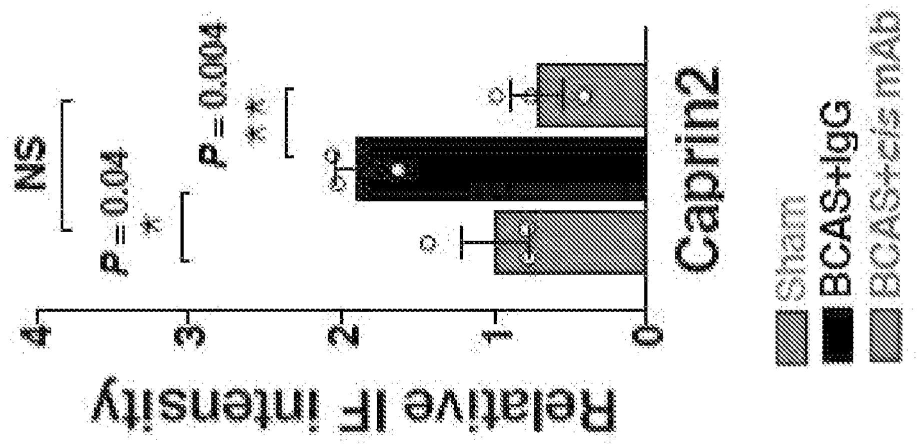

FIG. 44 is a graph, shown as dot plots of average expression (color coded) and percentage of cells expressing the gene (dot size), that describes a list of novel DEGs that are up-regulated in excitatory neurons but have never been linked to neurodegeneration or stroke.

Figure 46A:
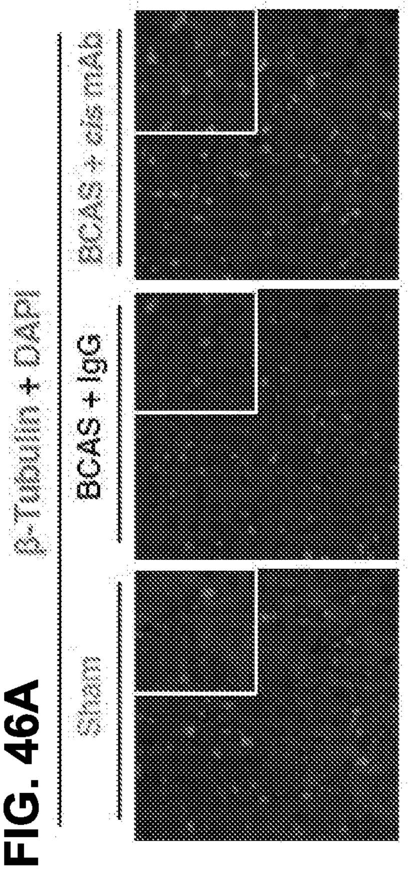
Figure 46B:
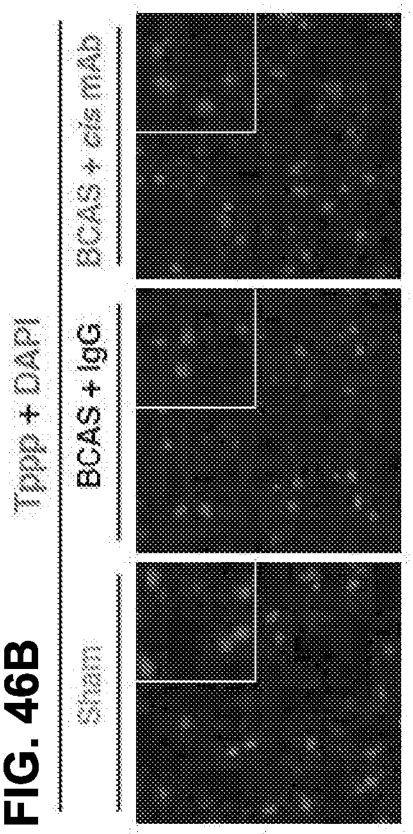
Figure 46C:
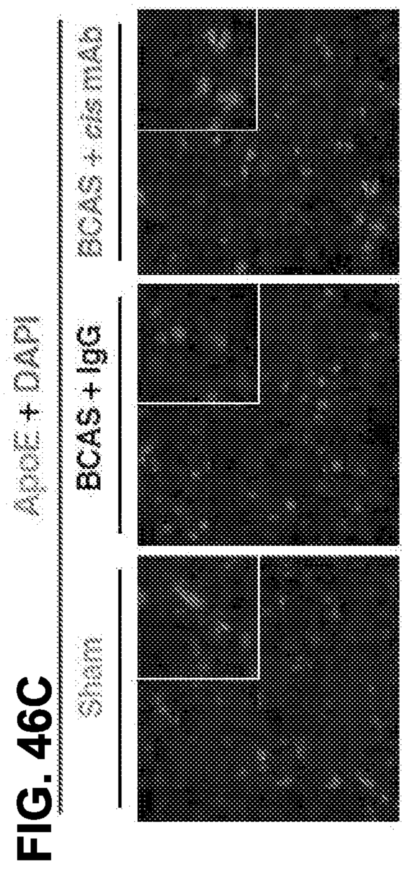
Figure 46D:
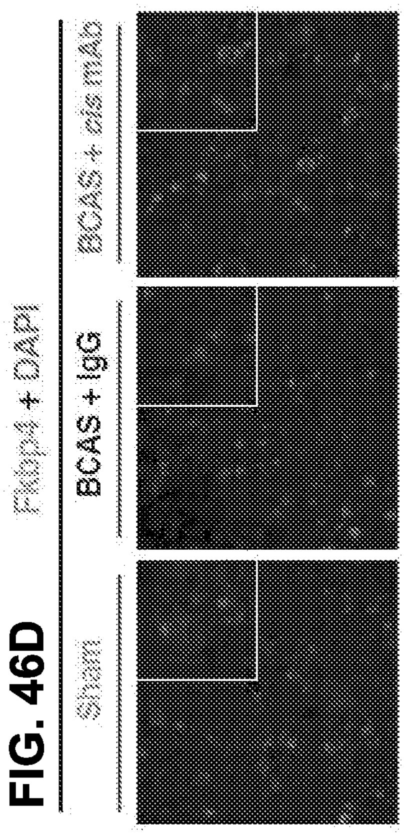
Figures 47A, 47B, 47C, 47D:
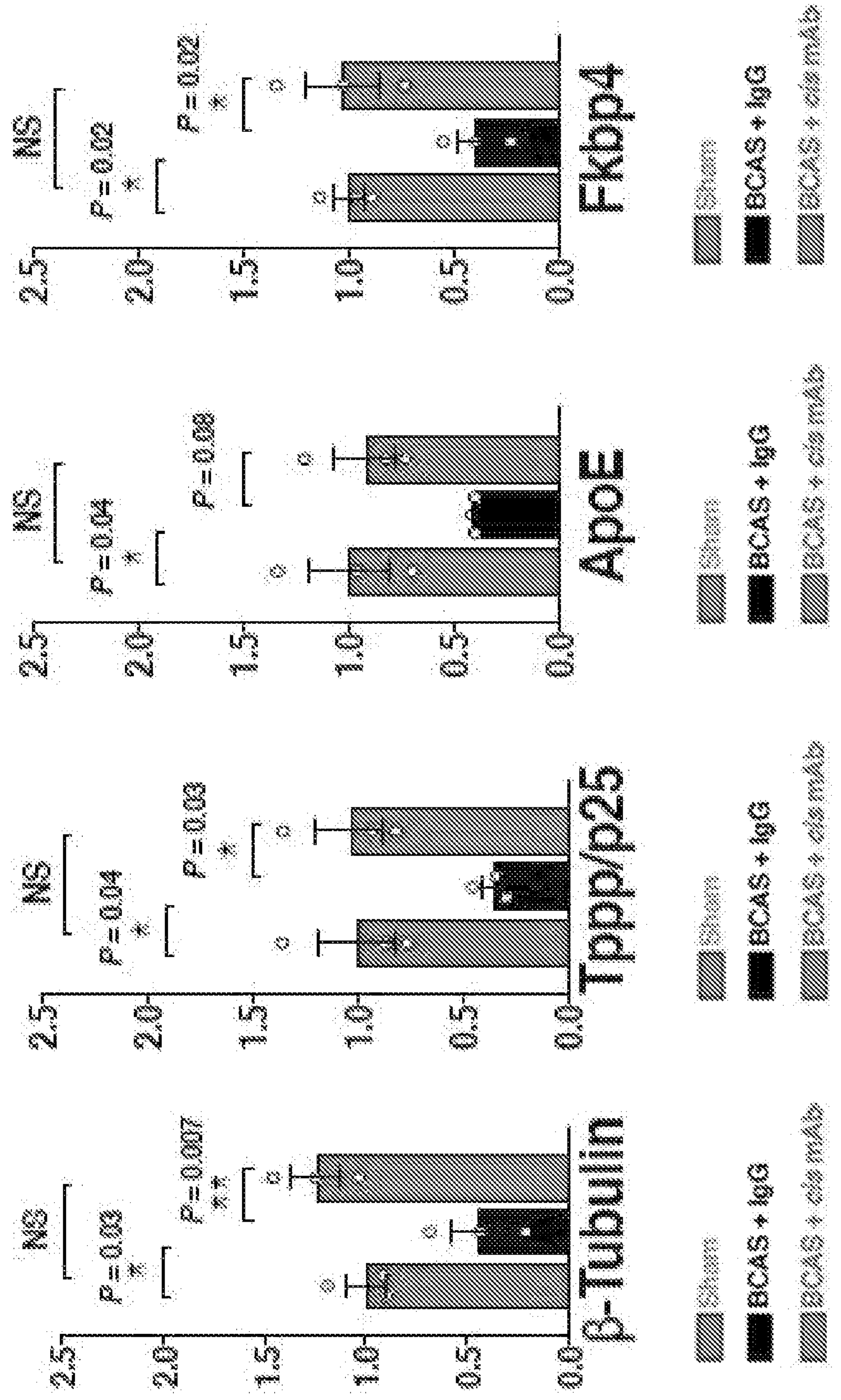

FIGS. 45A-45D show immunofluorescence results, and their accompanying quantification graphs, indicating the validation of two novel DEGs Caprin2 and Hsd3b2 with immunofluorescence staining with their relative fluorescence intensity quantified. Immunofluorescent staining with Caprin 2 (FIG. 45A) and Hsd3b2 (FIG. 45B) is shown, with the corresponding quantification for Caprin2 (FIG. 46C) and Hsdb2 (FIG. 45D) also provided.

FIGS. 46A-46D show immunofluorescence results indicating the down-regulation of four micro-tubule related genes, 13-Tubulin (FIG. 46A), Tppp (FIG. 46B), ApoE (FIG. 46C), and Fkbp4 (FIG. 46D) in BCAS mice treated with IgG which are recovered by cis mAb treatment.

FIGS. 47A-47D is a series of graphs indicating the quantified levels of indicating the down-regulation of four micro-tubule related genes, 13-Tubulin (FIG. 47A), Tppp (FIG. 47B), ApoE (FIG. 47C) and Fkbp4 (FIG. 47D) in BCAS mice treated with IgG which are recovered by cis mAb treatment.

Figure 48A:
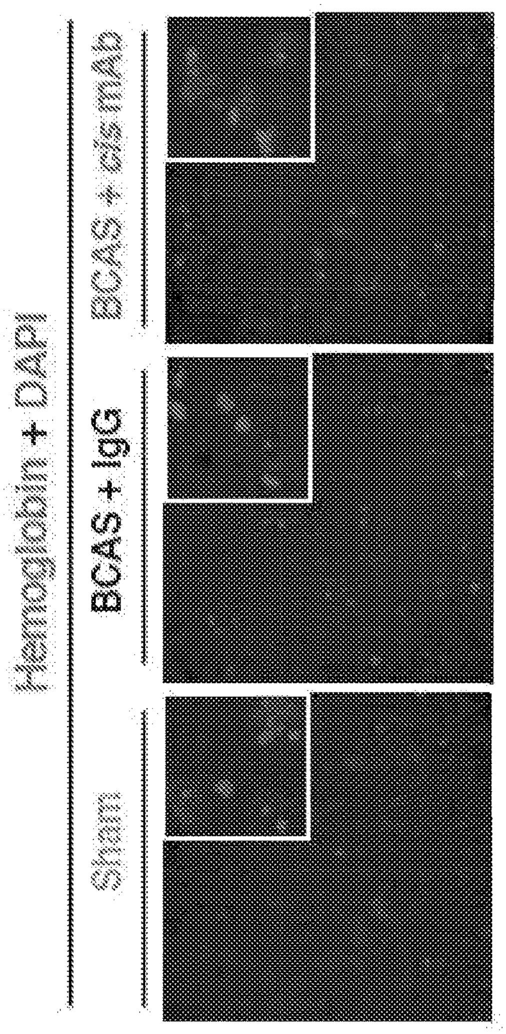
Figure 48B:
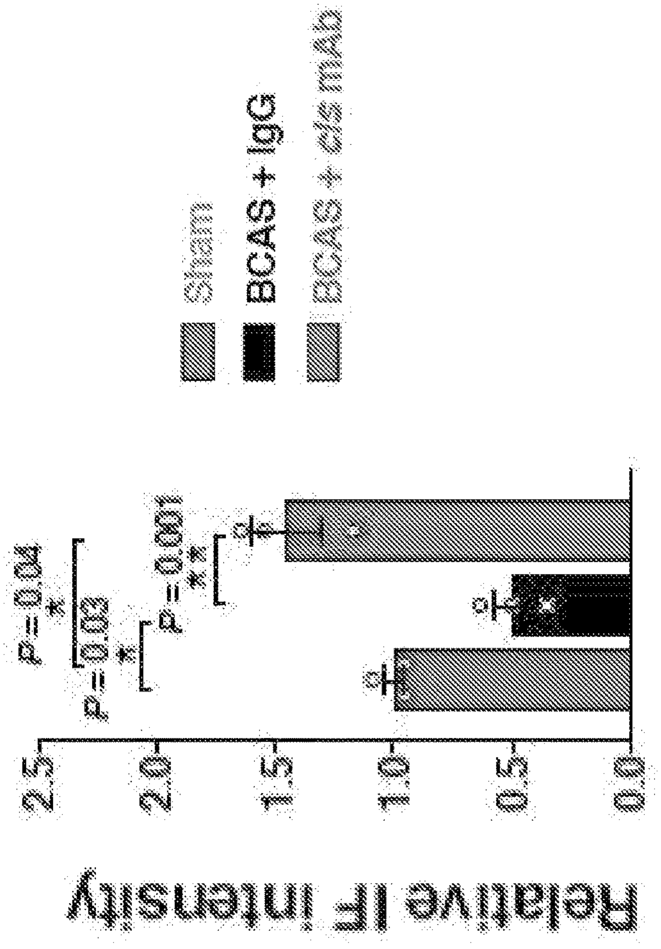

FIGS. 48A-48B shows immunofluorescence results (FIG. 48A), and their accompanying quantification graph (FIG. 48B), indicating the up-regulation of hemoglobin in BCAS mice treated with cis mAb.

Figure 49A:
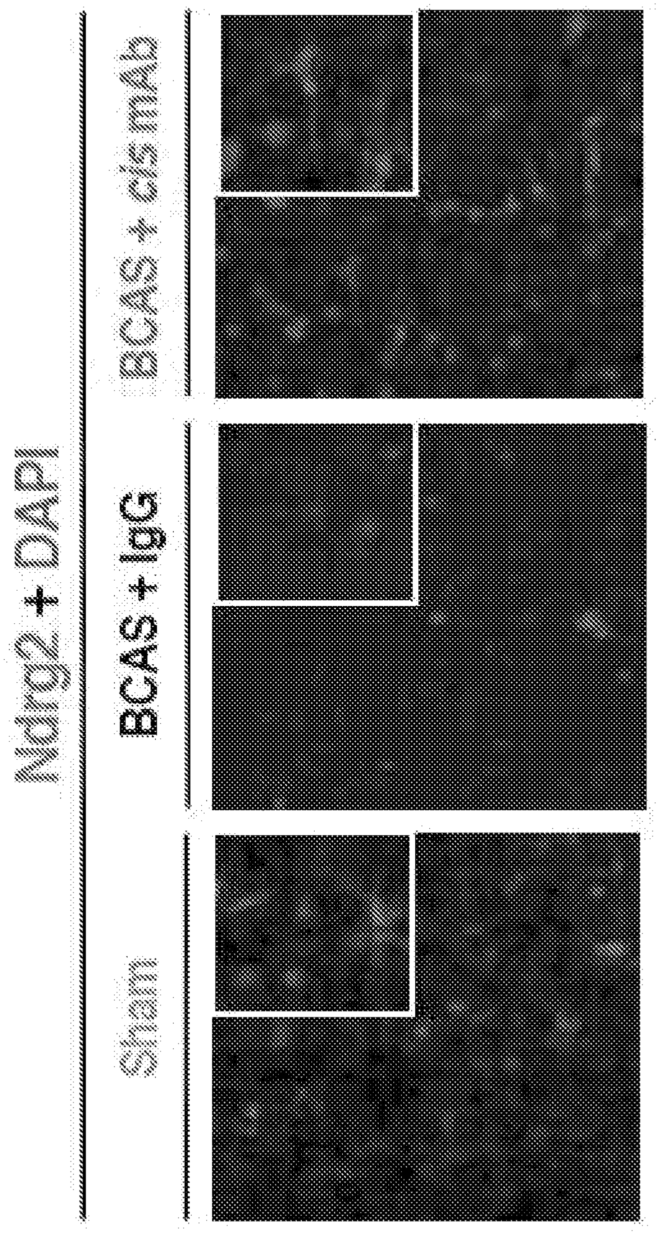
Figure 49B:
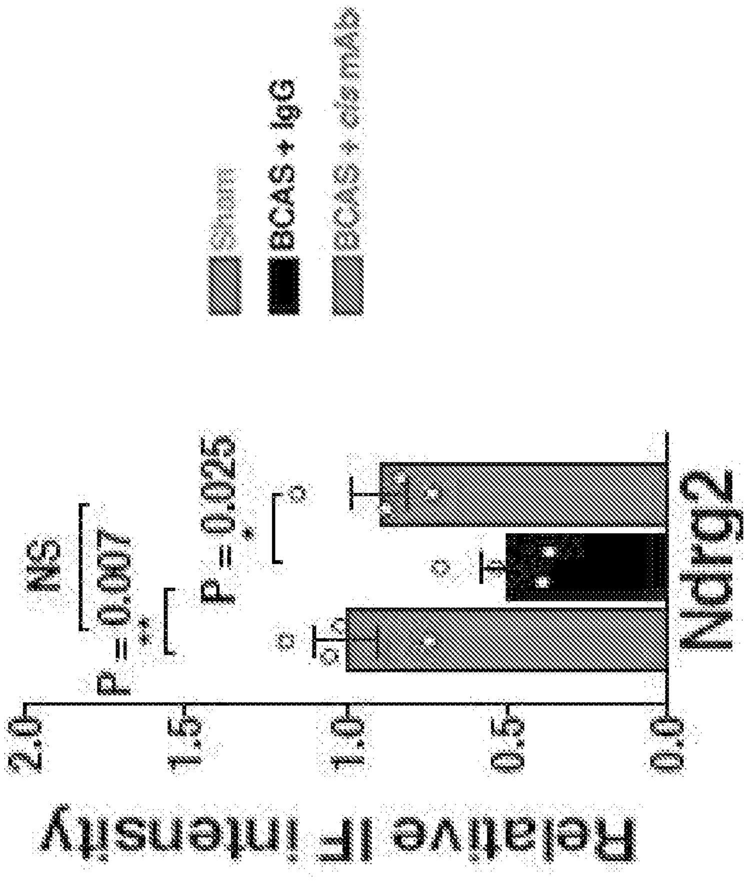

FIGS. 49A-49B shows immunofluorescence results (FIG. 49A), and their accompanying quantification graph (FIG. 49B), indicating the up-regulation of Ndrg2 in BCAS mice treated with cis mAb.

Figure 50:
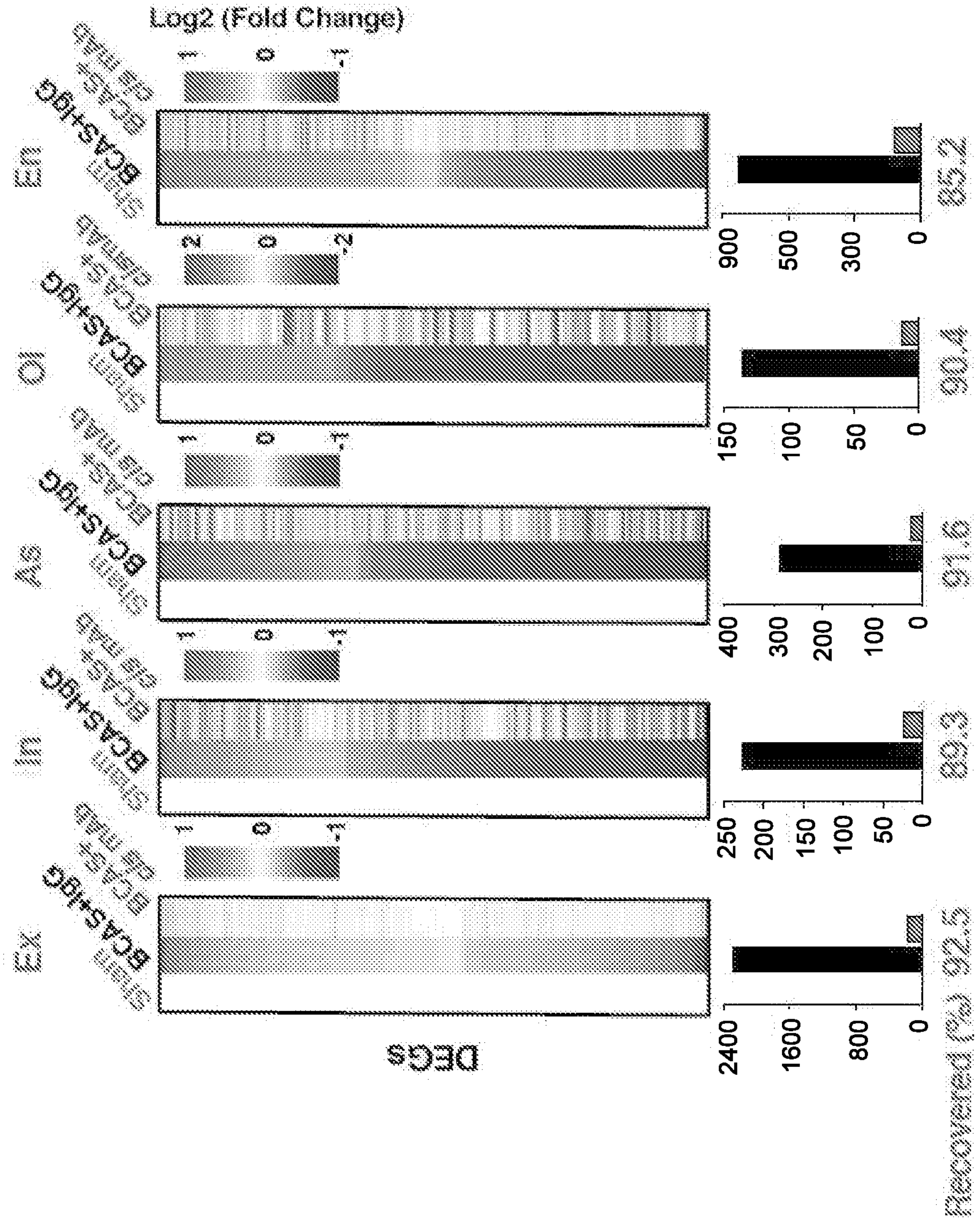

FIG. 50 is a series of graphs that indicate the differential gene expression profiles of BCAS mice based on expressed hundreds to thousands of genes in five major cortical cell types, 85%-92% of which are recovered by cis mAb (2117/2289 for excitatory neurons, 201/225 for inhibitory neurons, 263/287 for astrocytes, 122/135 for oligodendrocytes, 702/824 for endothelia). Top: Relative normalized expression of each gene compared to sham is log 2 transformed and used for generating the heatmaps using Morpheus. Cell types are labeled on the top, excitatory neurons (Ex), inhibitory neurons (In), astrocytes (As), oligodendrocytes (01) and endothelial cells (En). Bottom: Number of DEGs (p value <0.01 for inhibitory neurons, oligodendrocytes, astrocytes, endothelia, fdr adjusted p value <0.0001 for excitatory neurons) are as shown in bar graphs. Genes that are differentially expressed in BCAS+IgG, but not in BCAS+cis mAb mice referencing to sham mice are defined as recovered genes. Recovered percentage was calculated as the number of recovered genes vs the number of DEGs.

Figure 51:
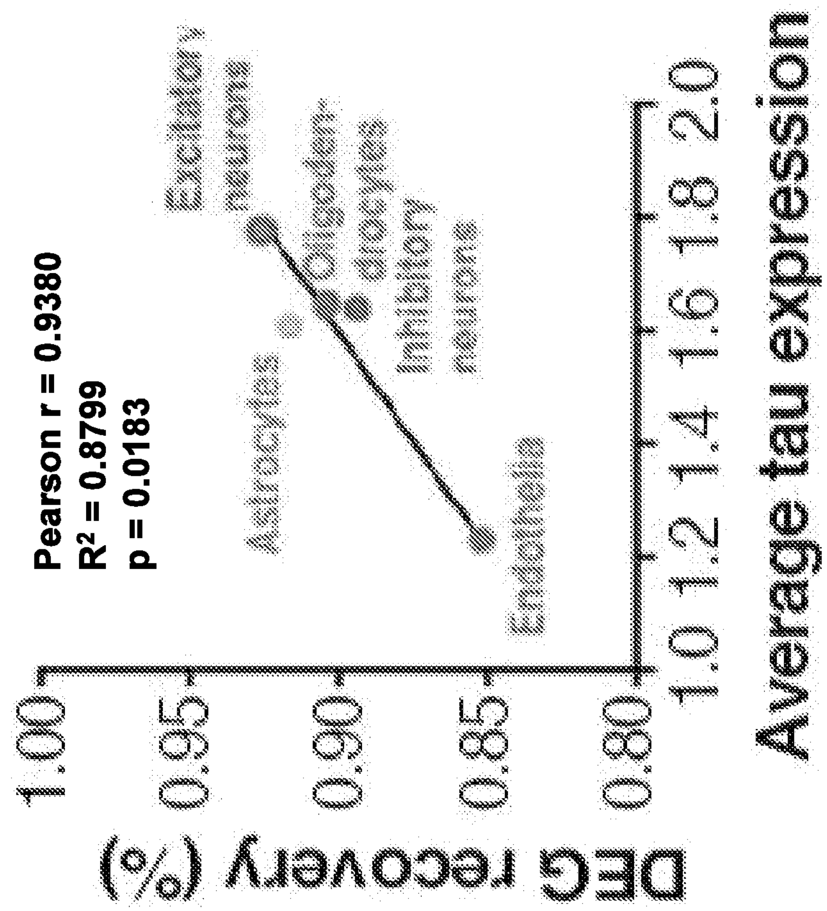

FIG. 51 is a graph that describes the extent of the recovery in different cell types correlated with their cellular tau expression.

Figure 52:
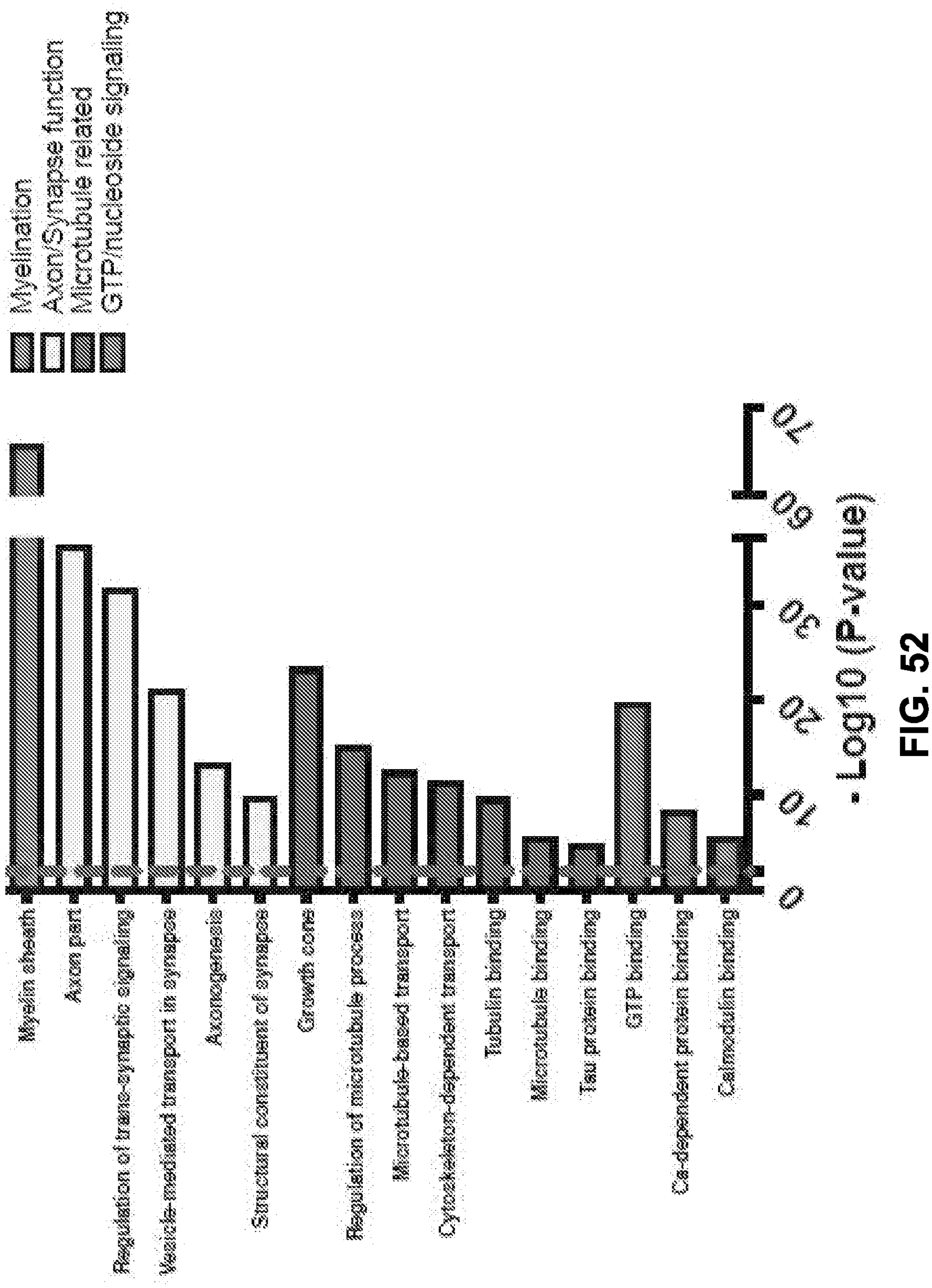

FIG. 52 is a graph that describes the effect of BCAS in downregulation of genes (fdr adjusted p-value <0.0001) related to myelination, axon/synapses, microtubule function and GTP/nucleoside signaling in the excitatory neurons. Enriched gene-ontology (GO) terms are showed in bar graphs with terms associated with different classes color coded.

Figure 53:
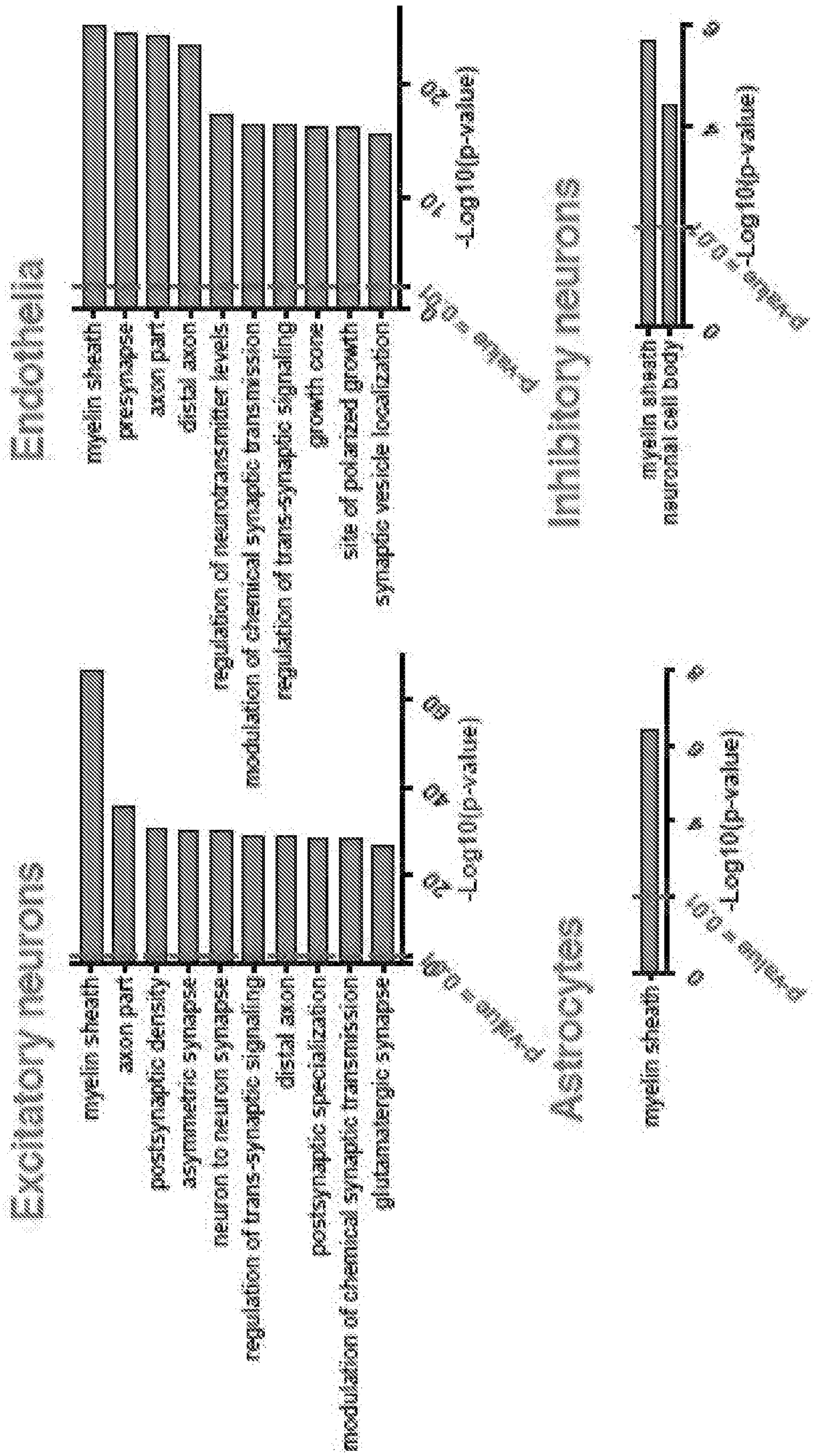

FIG. 53 is a series of graphs that demonstrate that most downregulated DEGs in diverse cortical cell types in BCAS mice are associated with the myelin sheath.

Figure 54:
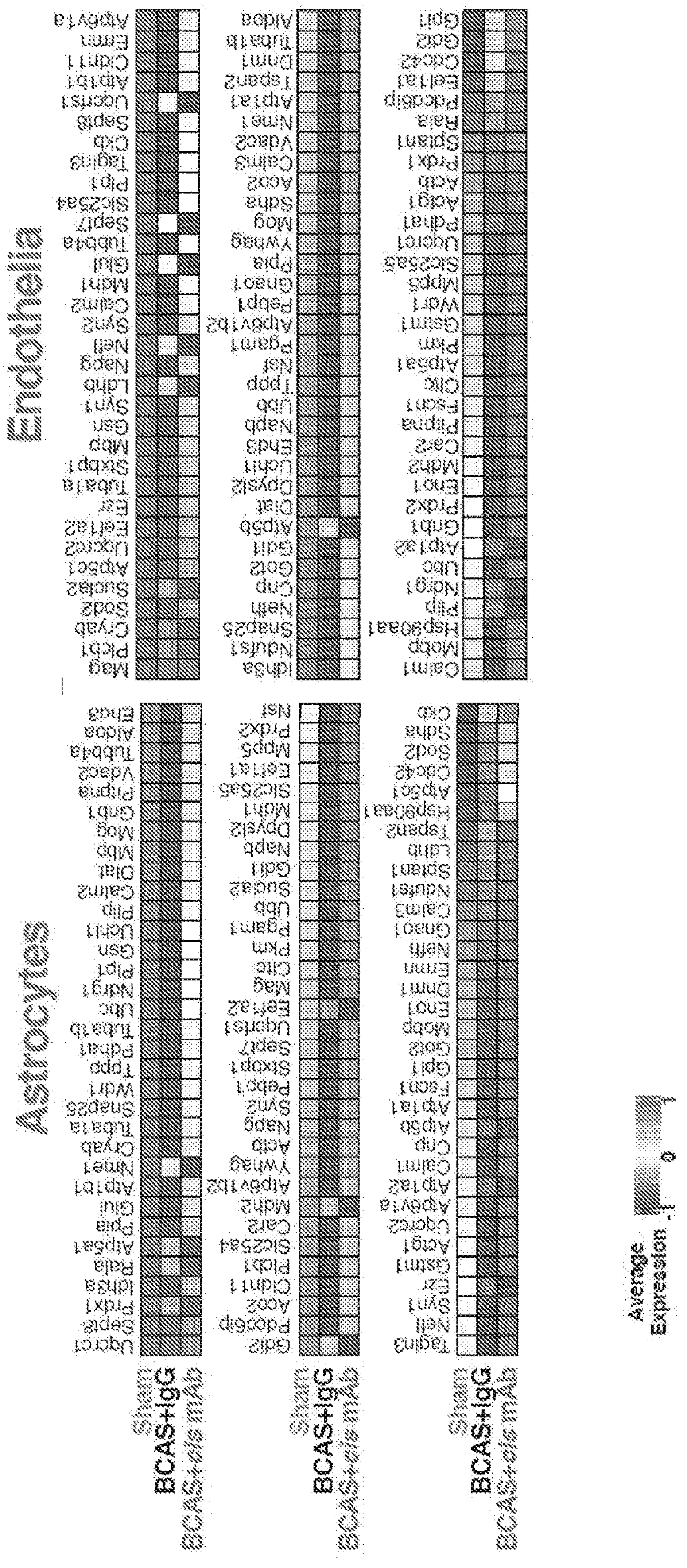
Figure 54:
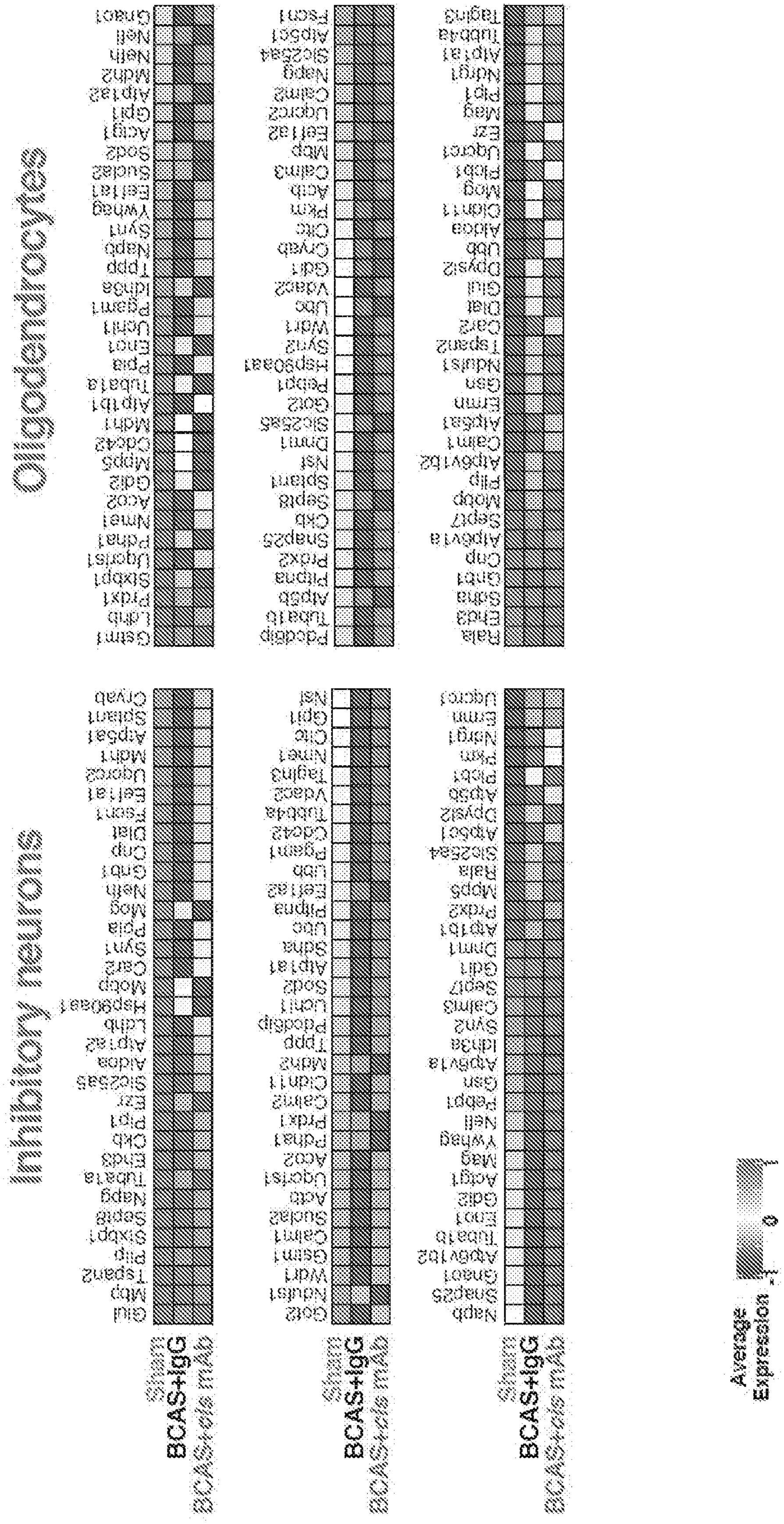

FIG. 54 is a series of heatmap graphs that demonstrate the association of gene expression, for individual genes, in diverse cortical cell types in BCAS mice, inhibitory neurons (In), astrocytes (As), oligodendrocytes (OI) and endothelial cells (En) with the myelin sheath gene-ontology and recovery with cis mAb.

Figure 55:
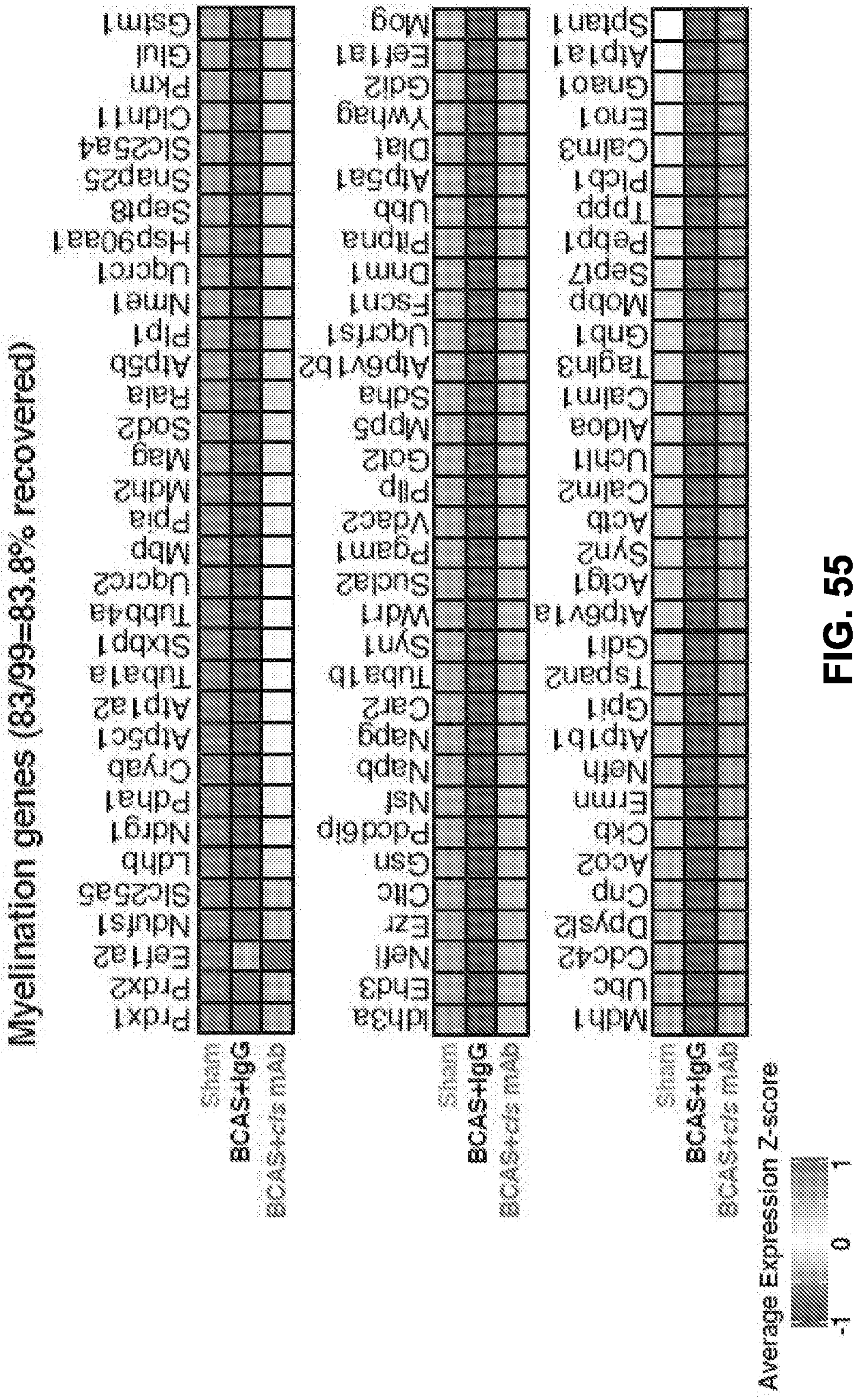

FIG. 55 is a series of heatmap graphs that demonstrate the effect of BCAS on widely down-regulation of myelination related genes in excitatory neurons, which are largely recovered by cis mAb. 99 BCAS down-regulated genes in the excitatory neurons associated with the gene-ontology term myelin sheath are chosen for the analysis. The heatmap is color coded with average expression Z-score. 83/99 (83.8%) of the analyzed genes are recovered by cis mAb.

Figure 56:
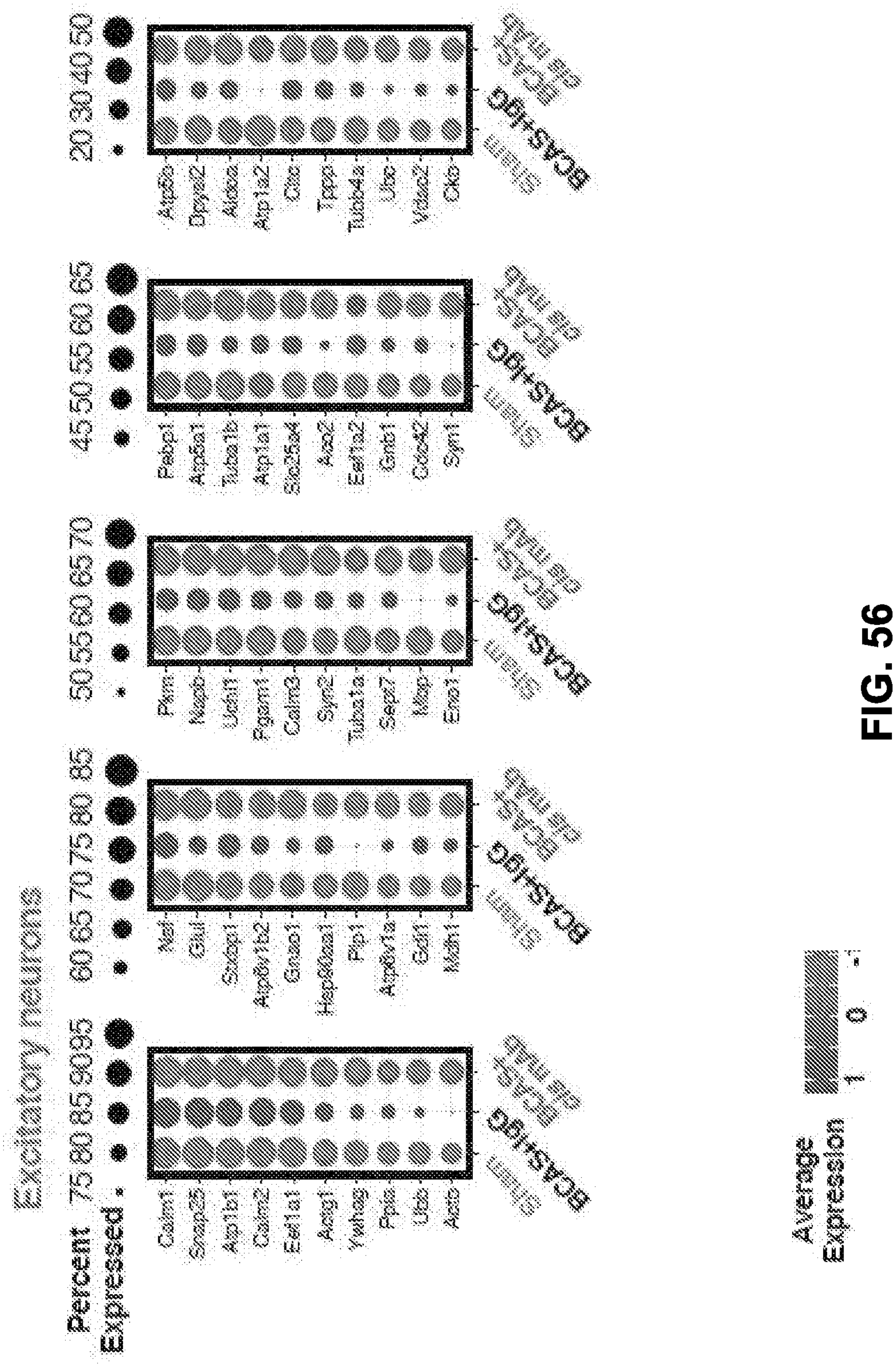
Figure 56:
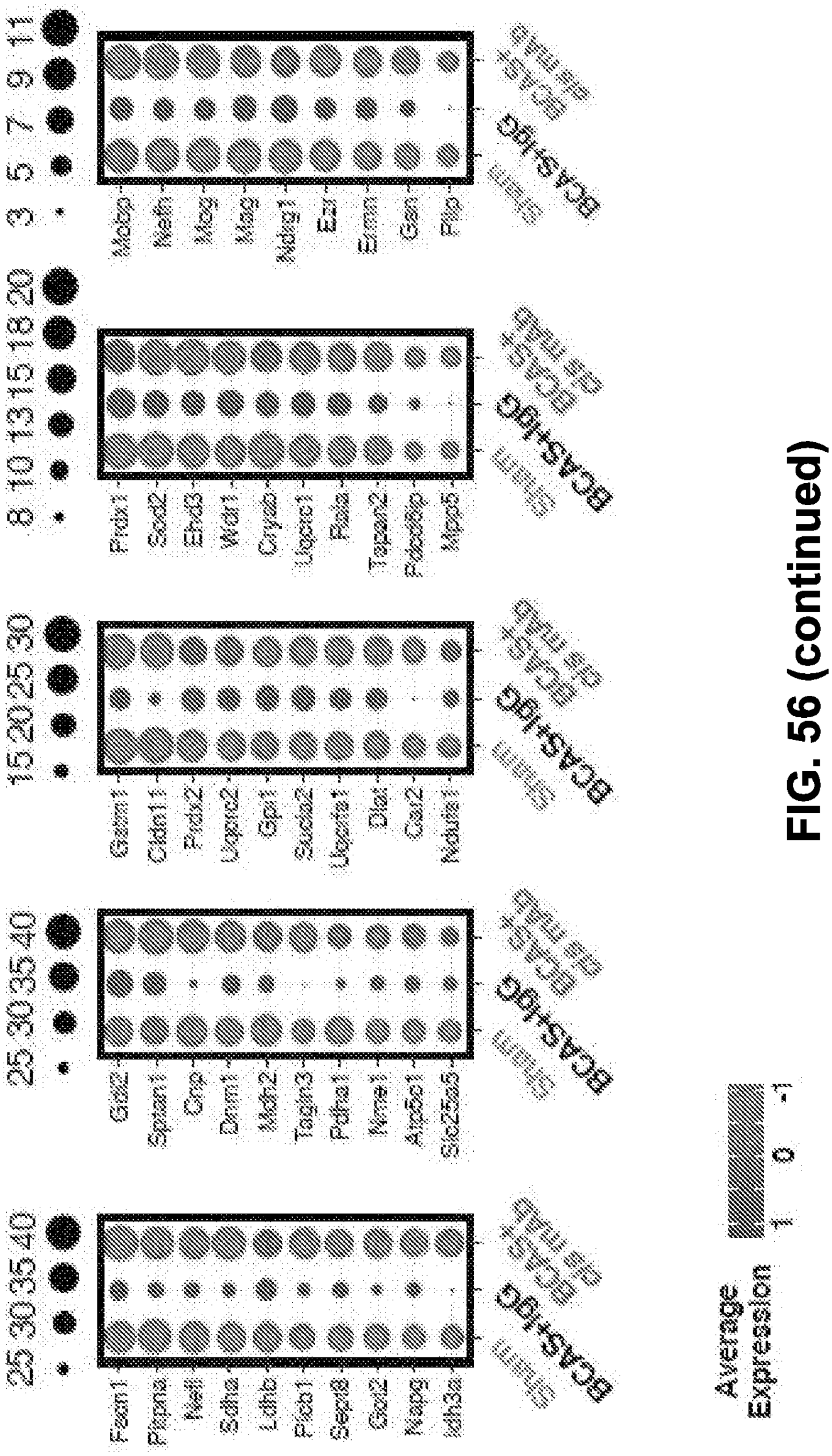

FIG. 56 is a series of graphs, shown as dot plots of average expression (color coded) and percentage of cells expressing the gene (dot size), that describe the expression of myelination genes (associated with myelin sheath gene ontology term) that are down-regulated in BCAS cortical excitatory neurons and recovered by cis mAb. The 99 myelin sheath genes were ranked from the most highly expressed (top left) to the least expressed (bottom right) in dot plots using Seurat 3. The color scales from low relative expression (blue) to high relative expression (red).

Figure 57:
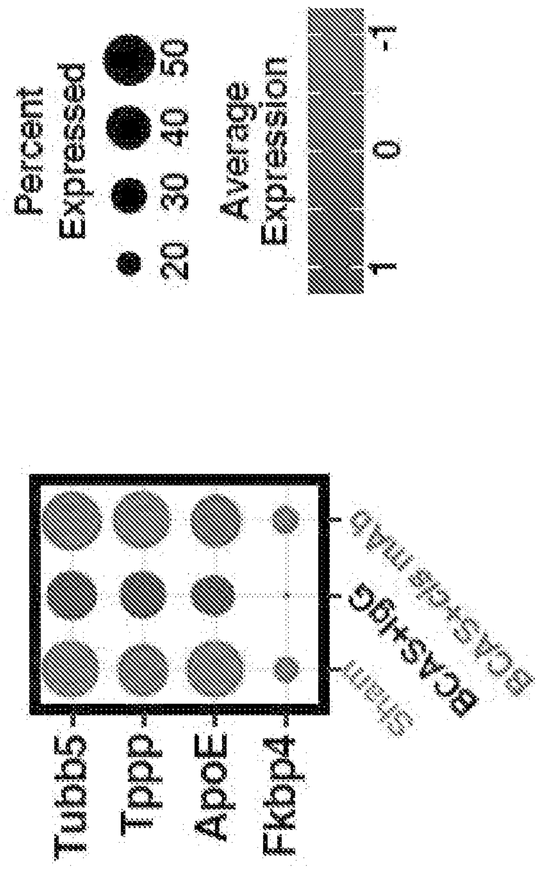

FIG. 57 is a graph, shown as a dot plot of average expression (color coded) and percentage of cells expressing the gene (dot size), that describes single-cell transcriptome profiling revealing down regulation of four examples of microtubule related genes in BCAS mice treated with IgG, which are recovered by cis mAb treatment, referencing to sham controls.

Figure 58:
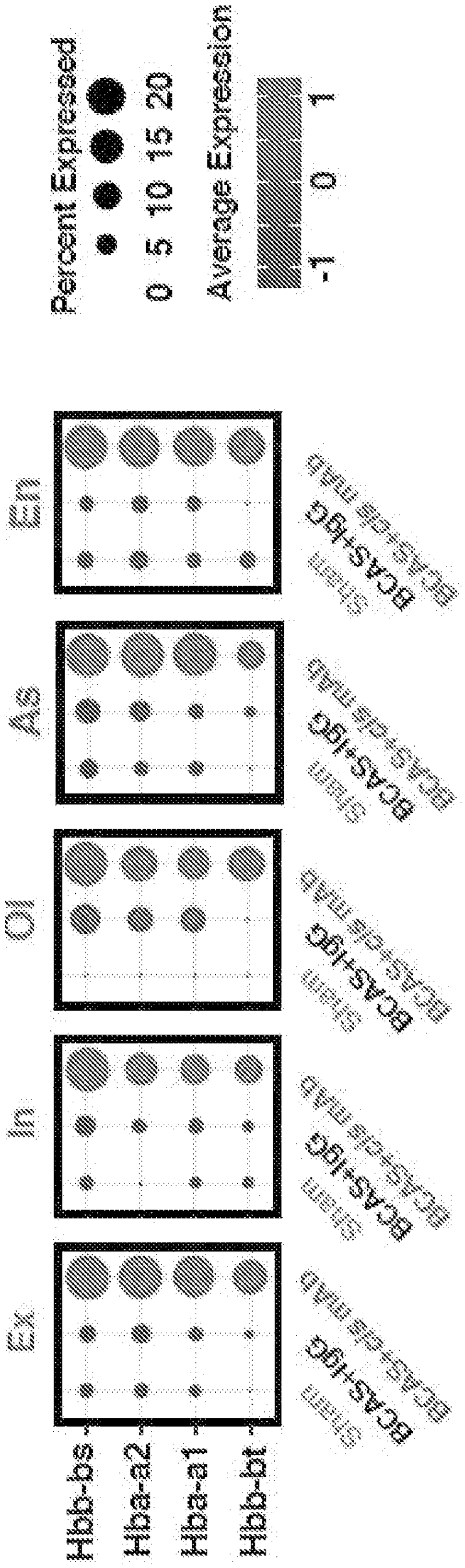

FIG. 58 is a series of graphs, shown as dot plots of average expression (color coded) and percentage of cells expressing the gene (dot size), describing that the expression of hemoglobin in BCAS mice are highly induced after cis mAb treatment in excitatory neurons (Ex), inhibitory neurons (In), oligodendrocytes (O), astrocytes (As) and endothelia (En) both at the average expression and the number of cells expressing hemoglobin.

Figure 59:
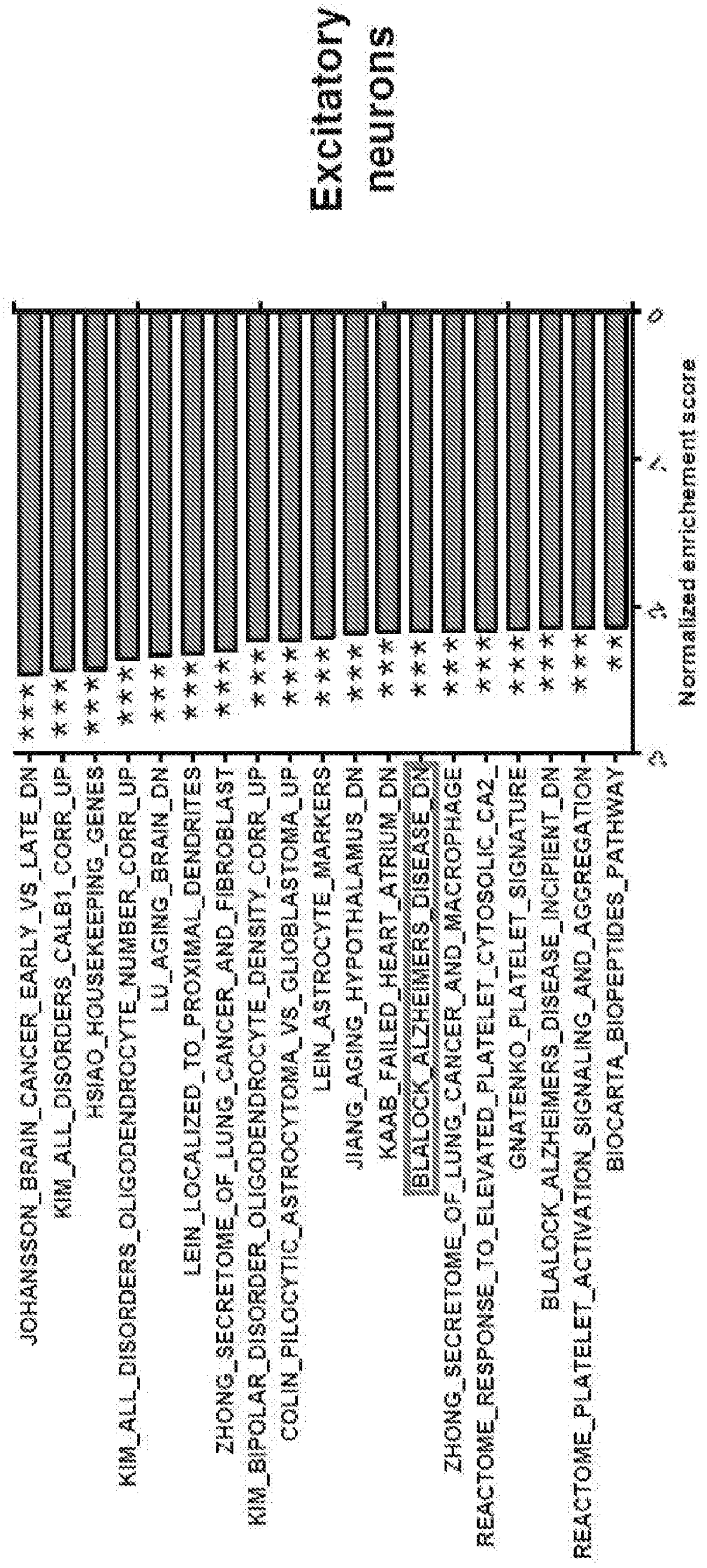

FIG. 59 is a graph showing the results from gene set enrichment analysis in excitatory neurons.

Figure 60:
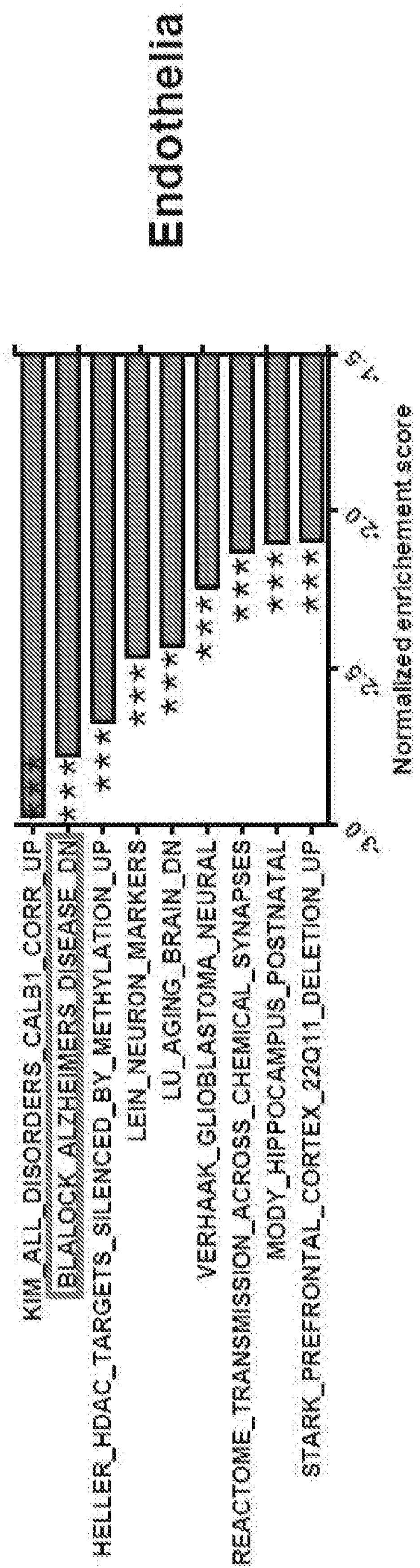

FIG. 60 is a graph showing the results from gene set enrichment analysis in endothelia.

Figure 61:
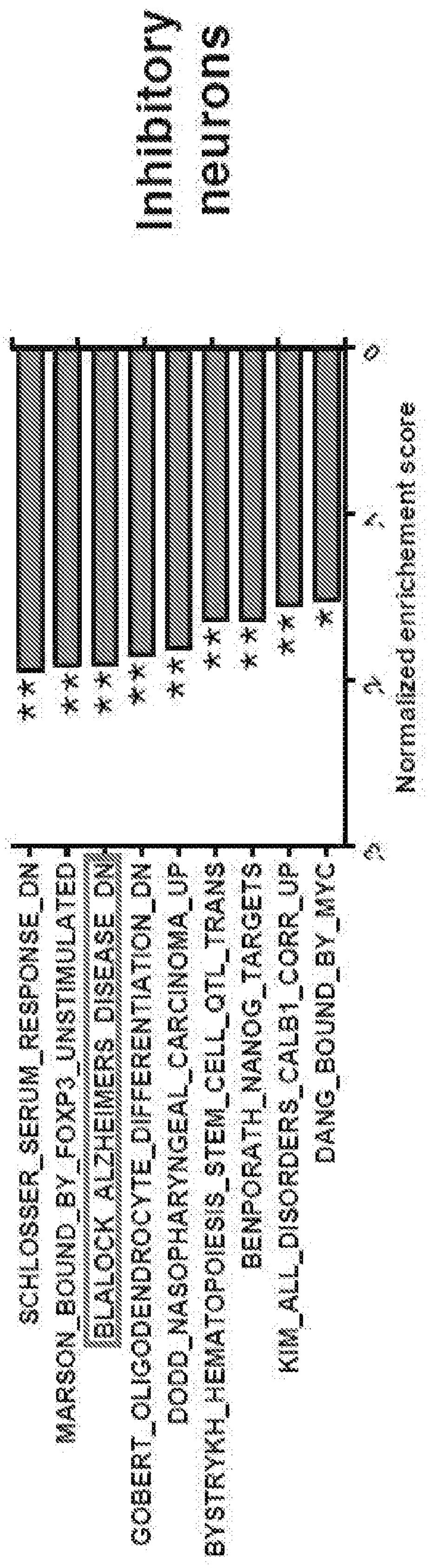

FIG. 61 is a graph showing the results from gene set enrichment analysis in inhibitory neurons.

Figure 62:
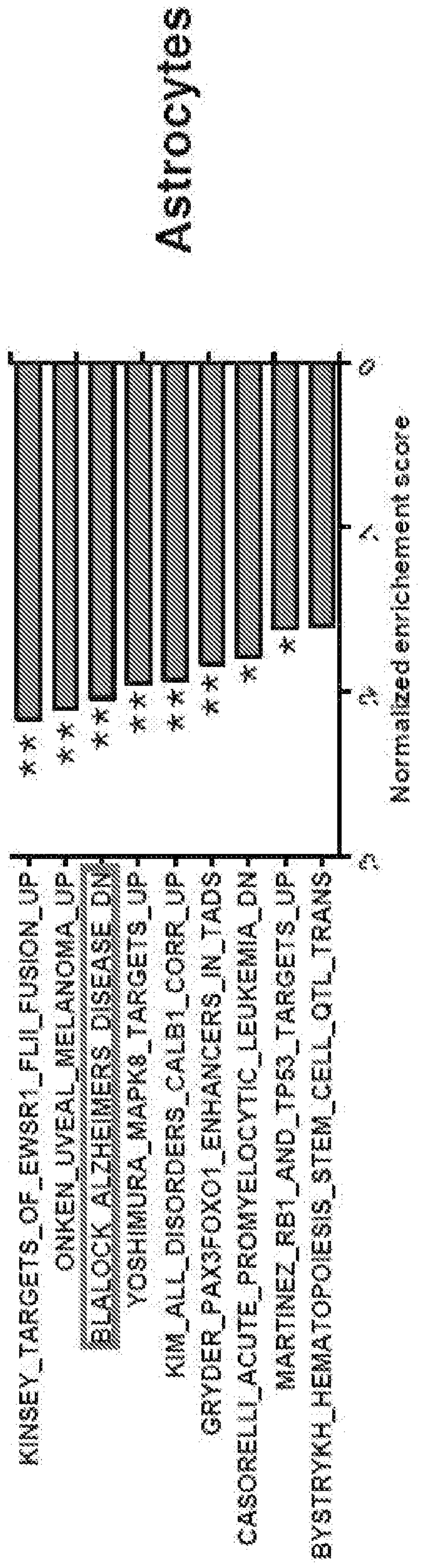

FIG. 62 is a graph showing the results from gene set enrichment analysis in astrocytes.

Figure 63:
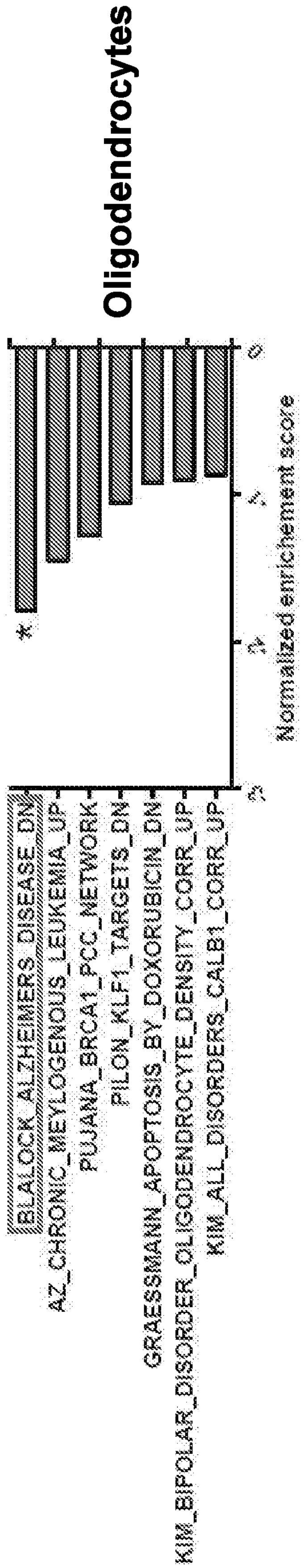

FIG. 63 is a graph showing the results from gene set enrichment analysis in oligodendrocytes.

Figure 64B:
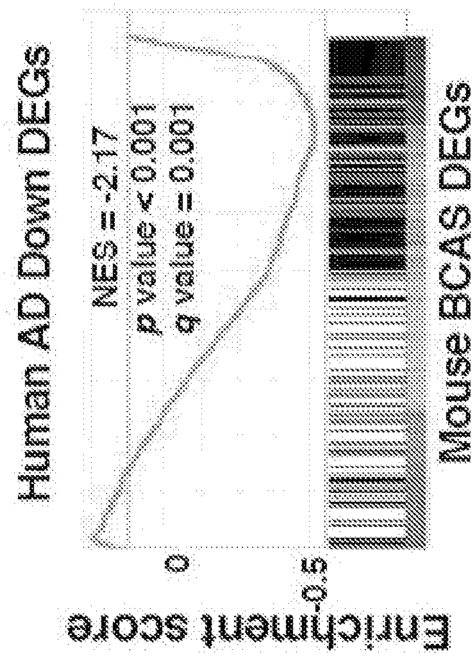
Figure 64A:
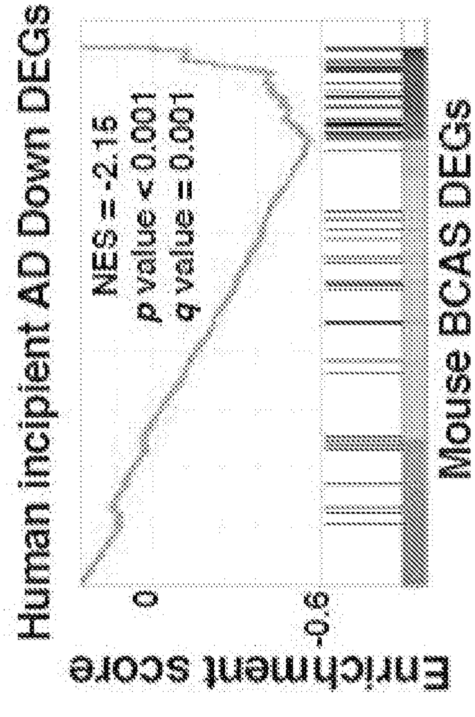

FIGS. 64A-64B are graphs that describe gene-set enrichment analyses that revealed significant negative enrichment of incipient AD (FIG. 64A) and AD (FIG. 64B) altered genes in human patients and in mouse BCAS DEGs in excitatory neurons, with normalized enrichment score (NES)=−2.15 and −2.17, respectively; p values <0.001 and fdr adjusted p (q) value=0.001. Notably, the genes-sets that are down-regulated in human incipient AD and AD patients were both highly enriched in our BCAS down-regulated DEGs in the excitatory neurons (p value <0.001).

Figure 65A:
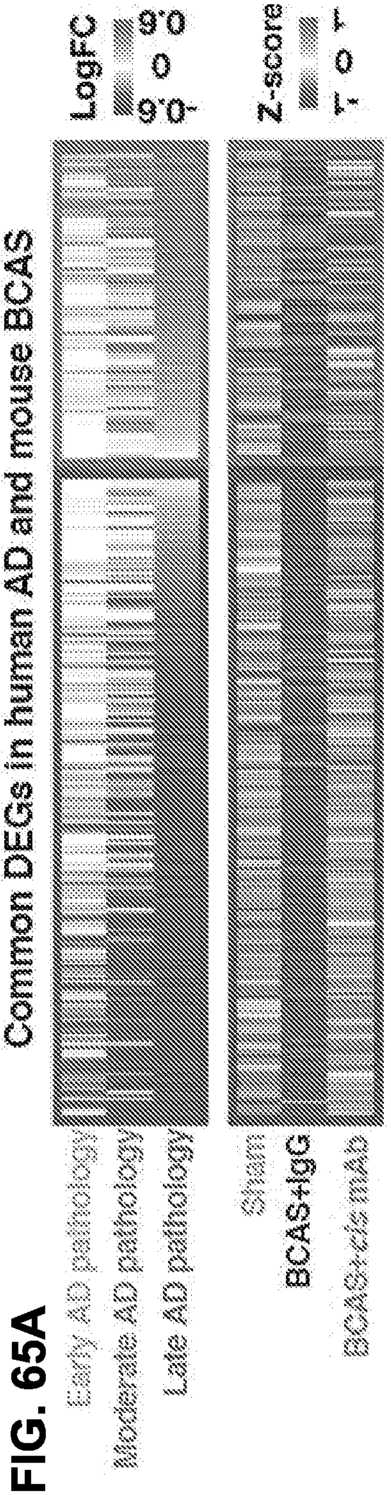

FIG. 65A is a gene expression profile graph that describes the shared DEGs in excitatory neurons in young BCAS mice and human AD patients.

Figure 65B:
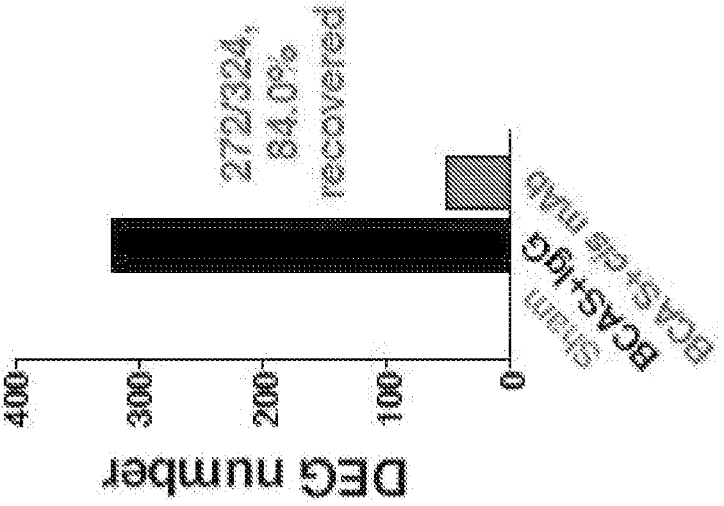

FIG. 65B is a graph of the recovered expression of DEGs in BCAS mice treated with cis mAbs (272/324 were recovered, 84.0%).

Figure 66B:
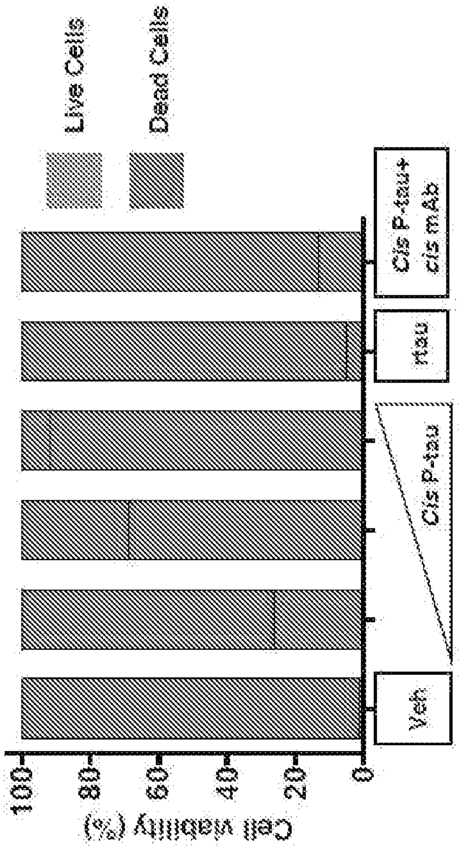
Figure 66A:
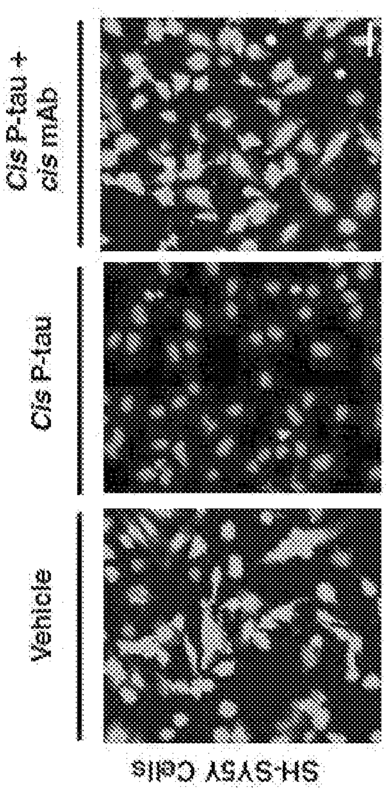

FIG. 66A shows immunofluorescence staining results that describe the neurotoxicity testing of purified cis P-tau in vitro. Purified cis P-tau or recombinant human tau (rtau) was added to growing neuroblastoma cells (SH-SY5Y) for 48 hours, followed by live and dead cell assay. Live cells are in green, dead cells are in red.

FIG. 66B is a graph of dose dependent neurotoxicity responses of neuroblastoma cells to the addition of purified cis P-tau, vehicle control, recombinant human tau (rtau), and the improvement in cell viability when treated with cis mAbs for 48 hours followed by live-dead cell assay.

Figure 67:
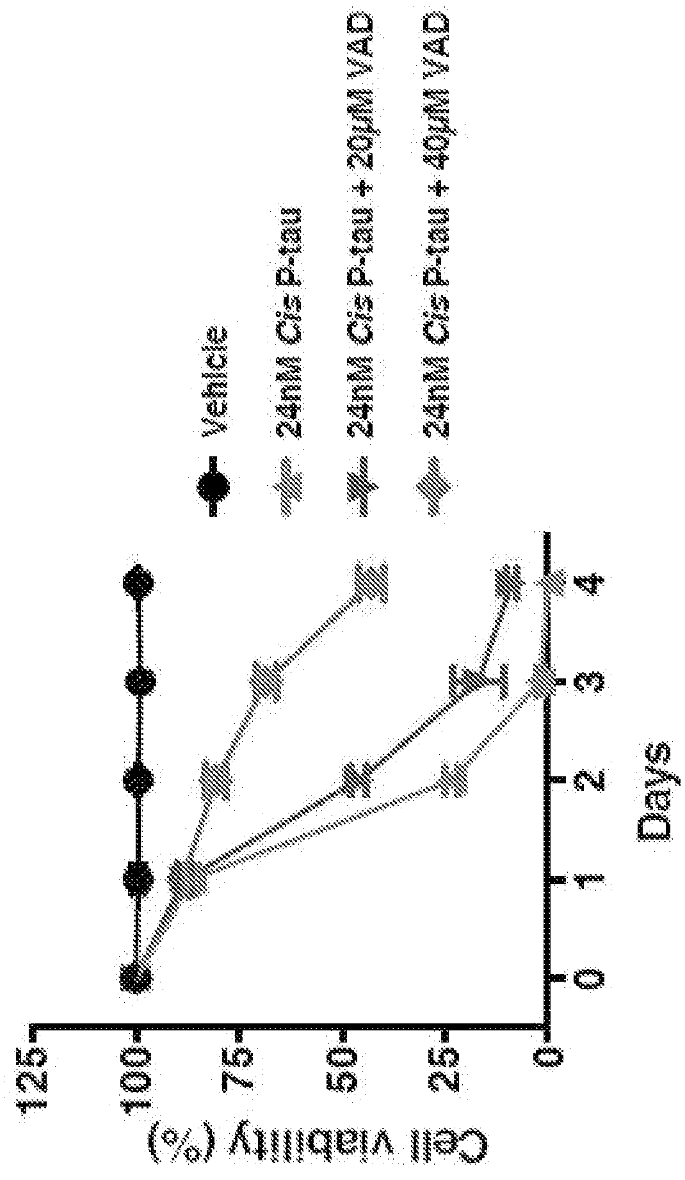

FIG. 67 is a graph of dose dependent neurotoxicity responses of primary neurons to the addition of purified cis P-tau, vehicle control and the improvement in cell viability when treated with Z-VAD-FMK inhibitor.

Figures 68A, 68B, 68C:
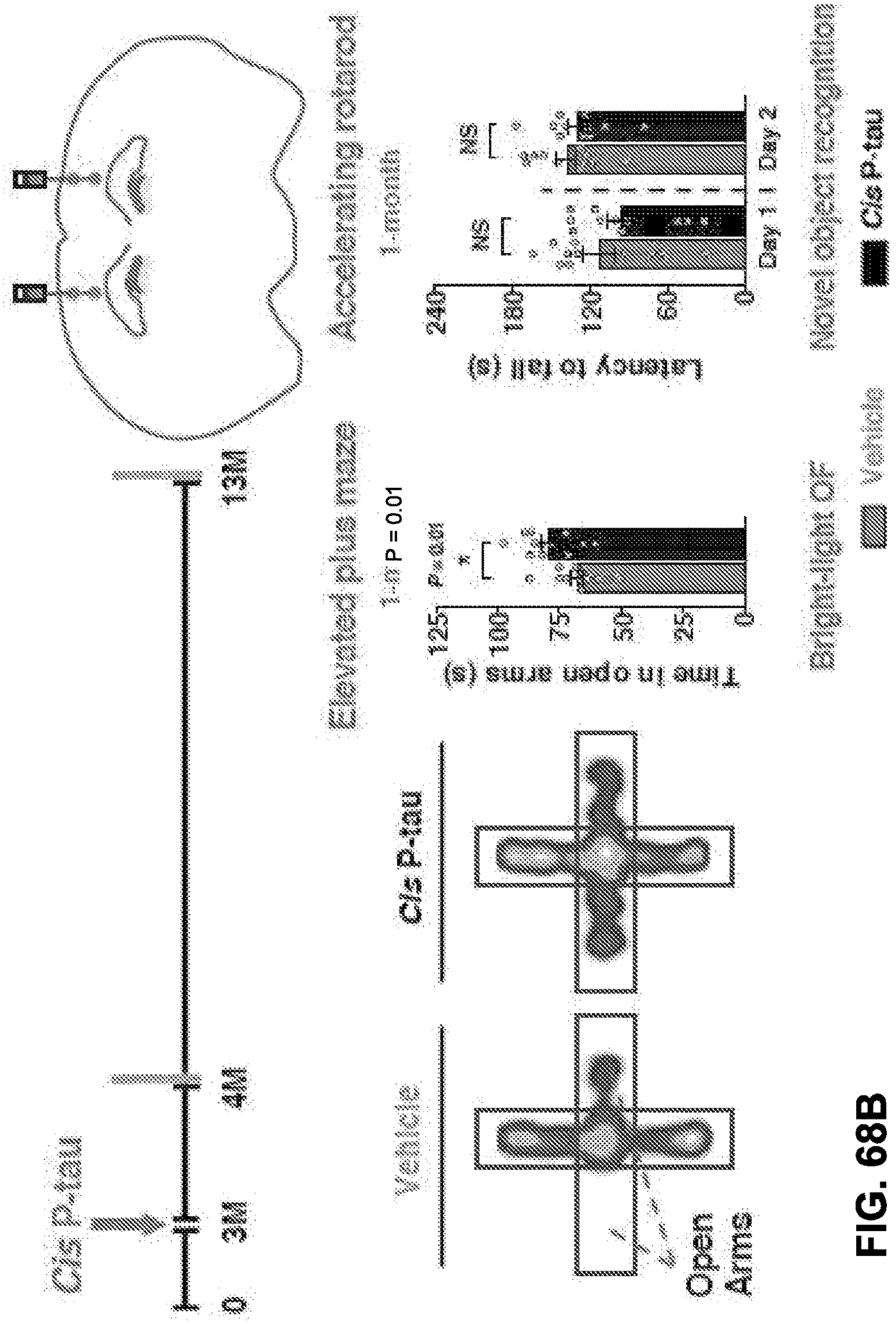

FIG. 68A is a schematic of the timeline used to assess whether stereotaxic cortical injection of purified soluble cis P-tau is sufficient to induce progressive neurodegeneration and brain dysfunction. Three-month-old (3M) WT mice were stereotaxically microinjected with purified cis P-tau or control vehicle bilaterally into the upper & lower layer of the neocortex (Red arrow, stereotaxic injection; green lines, functional assays).

FIG. 68B is a top down view of the risk-taking behaviors, and accompanying quantification graph, assayed by elevated plus maze of mice 1 month after injection with either vehicle control or cis P-tau. The time in open arms shown in the graph was significantly elevated in the mice that received cis P-tau compared to vehicle controls.

FIG. 68C is a graph that describes the responses to the accelerating rotarod behavioral assay in mice 1 month after injection with either vehicle control or cis P-tau. The latency to fall was not significantly different in the two groups at Day 1 and Day 2 of evaluation.

Figures 69A, 69B, 69C, 69D:
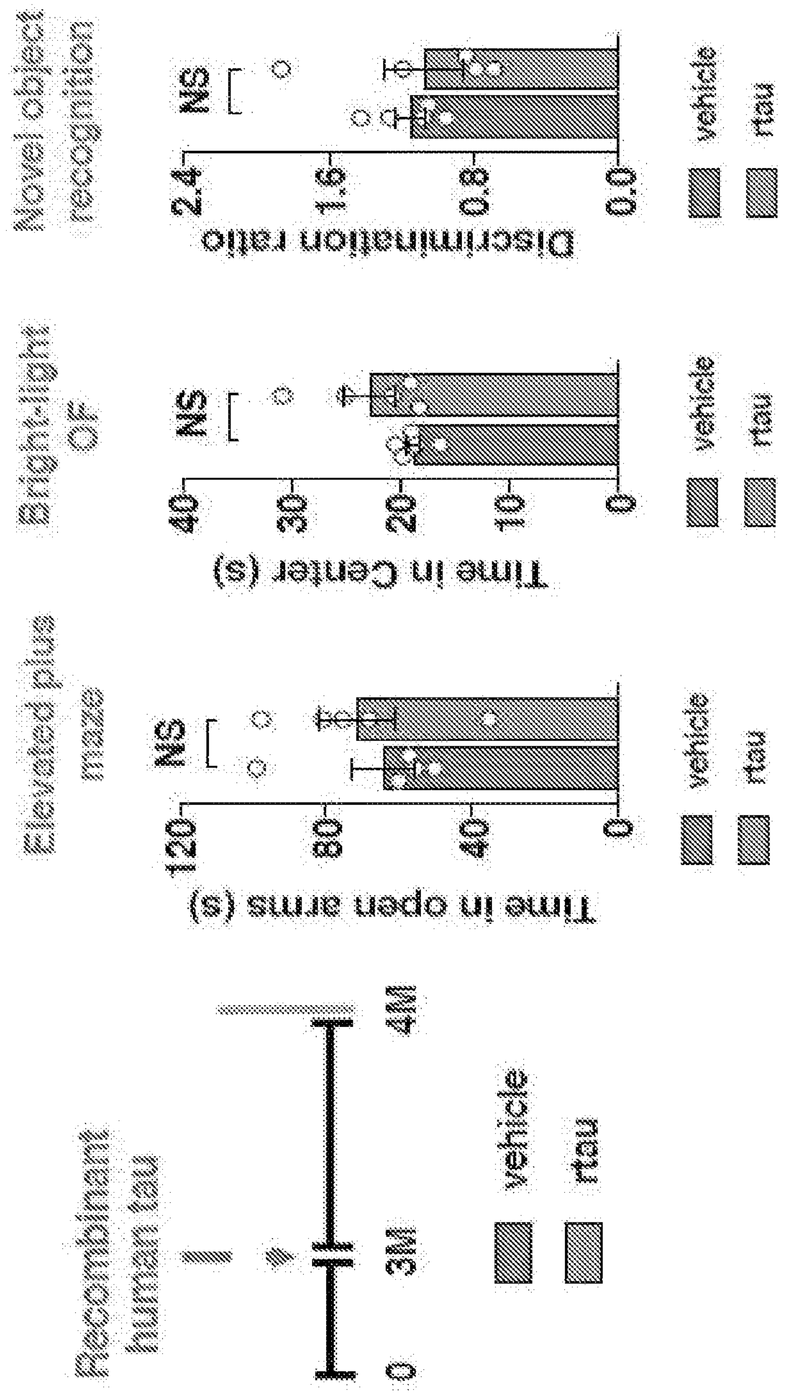

FIG. 69A is a schematic of the timeline used to assess the behavioral responses to stereotaxic infusion with recombinant human tau (rtau) (0.4 μg/μl) or vehicle bilaterally into the upper & lower layer of the neocortex. Red arrow shows the timepoint of the stereotaxic injection; green lines show the timepoint of the functional assays.

FIGS. 69B-69D are graphs that describe the behavioral performance of affective and cognitive behavior at 1-month after injection with recombinant tau (rtau) evaluated by elevated plus maze (FIG. 69B), bright-light open field (FIG. 69C), and novel object location recognition (FIG. 69D) tests, respectively. The data were presented as means±SEM. The p values were calculated using two-way ANOVA with Bonferroni correction, one-way ANOVA and unpaired two-tailed parametric Student's t-test. NS: not significant.

Figure 70A:
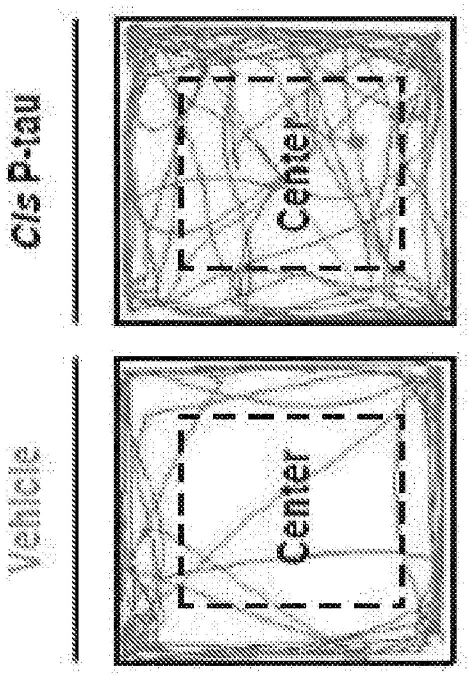

FIG. 70A shows behavioral tracking data of mice subjected to a bright-light open field assay. One group was injected with vehicle control while another group was injected with cis P-tau.

Figure 70B:
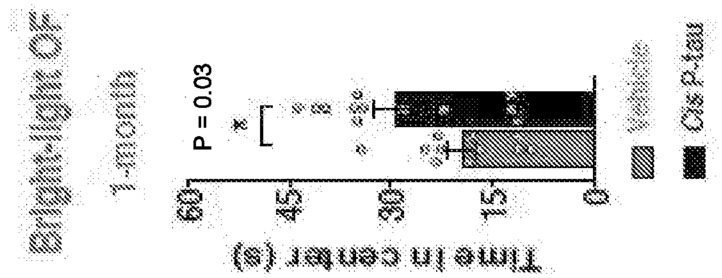

FIG. 70B is a graph of the quantified tracking data of mice subjected to a bright-light open field assay following injection of either vehicle control or cis P-tau. At 1 month from the injection, mice that received cis P-tau showed significantly higher residence within the center of the arena (black bar) compared to the vehicle control mice (green bar).

Figure 70C:
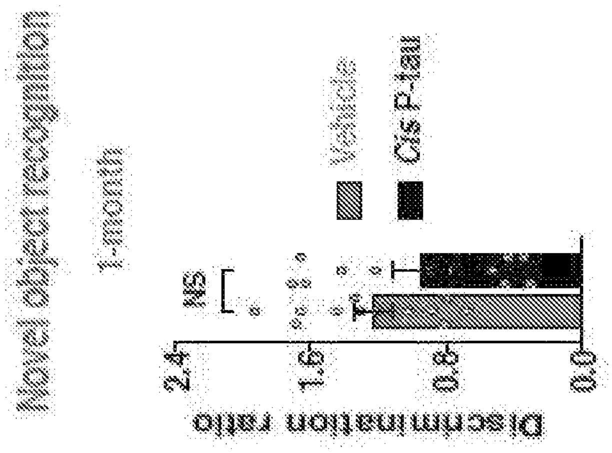

FIG. 70C is a graph of the behavioral data of mice subjected to novel object recognition assays following injection of either vehicle control or cis P-tau. At 1 month from the injection, mice that received cis P-tau showed significantly lower discrimination ratio (black bar) compared to the vehicle control mice (green bar).

Figures 71A, 71B, 71C, 71D:
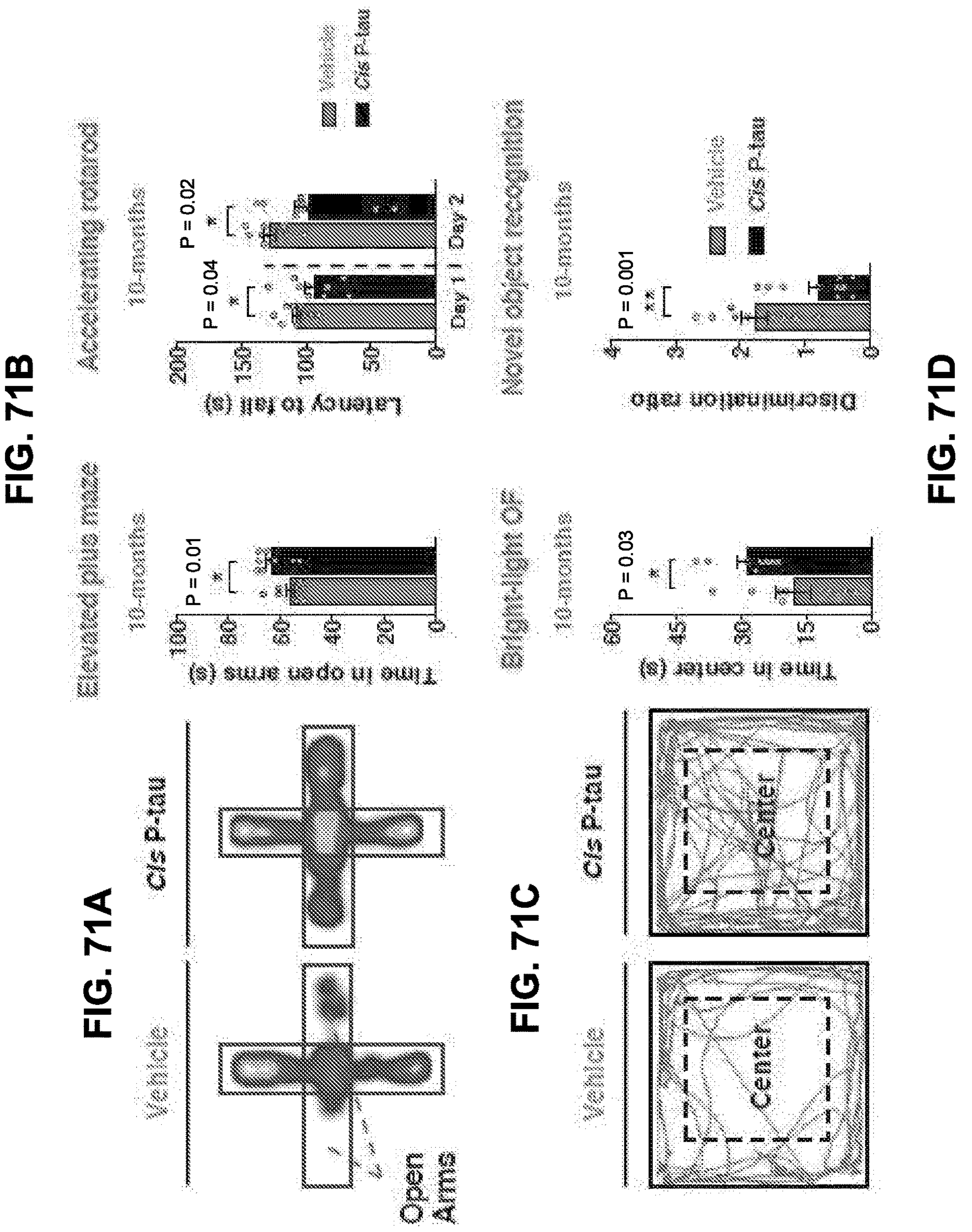

FIG. 71A is a top down view of the risk-taking behaviors, and accompanying quantification graph, assayed by elevated plus maze of mice 10 month after injection with either vehicle control or cis P-tau. The parameter time in open arms shown in the graph was significantly elevated in the mice that received cis P-tau compared to vehicle controls.

FIG. 71B is a graph that describes the responses to the accelerating rotarod behavioral assay in mice 10 months after injection with either vehicle control or cis P-tau. The latency to fall was significantly reduced in the mice that received cis P-tau at Day 1 and Day 2 of evaluation.

FIG. 71C is a graph of the quantified tracking data of mice subjected to a bright-light open field assay following injection of either vehicle control or cis P-tau. At 10 months from the injection, mice that received cis P-tau showed significantly higher residence within the center of the arena (black bar) compared to the vehicle control mice (green bar).

FIG. 71D is a graph of the behavioral data of mice subjected to novel object recognition assays following injection of either vehicle control or cis P-tau. At 10 months from the injection, mice that received cis P-tau showed significantly lower discrimination ratio (black bar) compared to the vehicle control mice (green bar).

Figure 72:
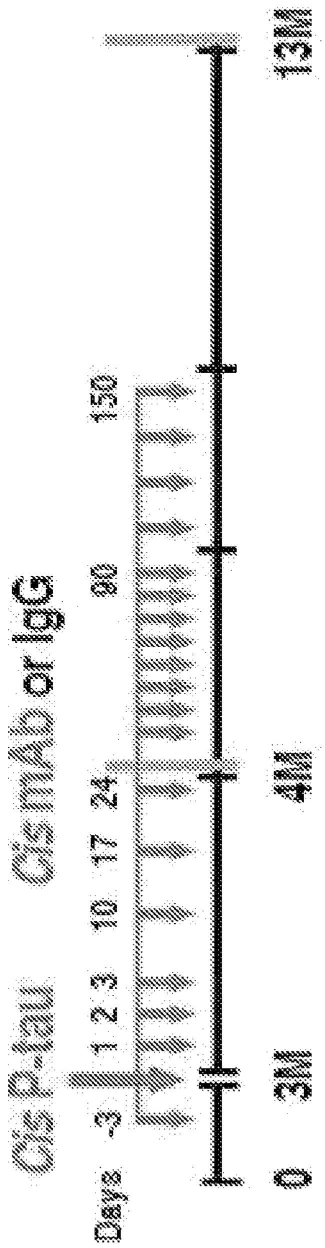

FIG. 72 is a schematic of the timeline used to assess whether treatment with cis mAb rescues the behavioral changes observed in mice that received cis P-tau. 3-month old mice were injected with cis P-tau and were injected with either cis mAb or IgG control at the timepoints represented by the multi-arrow marks. Functional assays were then performed at 1 month and at 10 months after the cis P-tau injection.

Figure 73B:
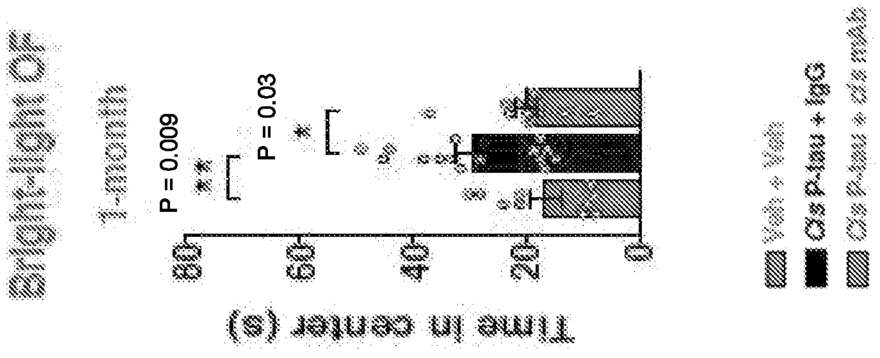
Figure 73A:
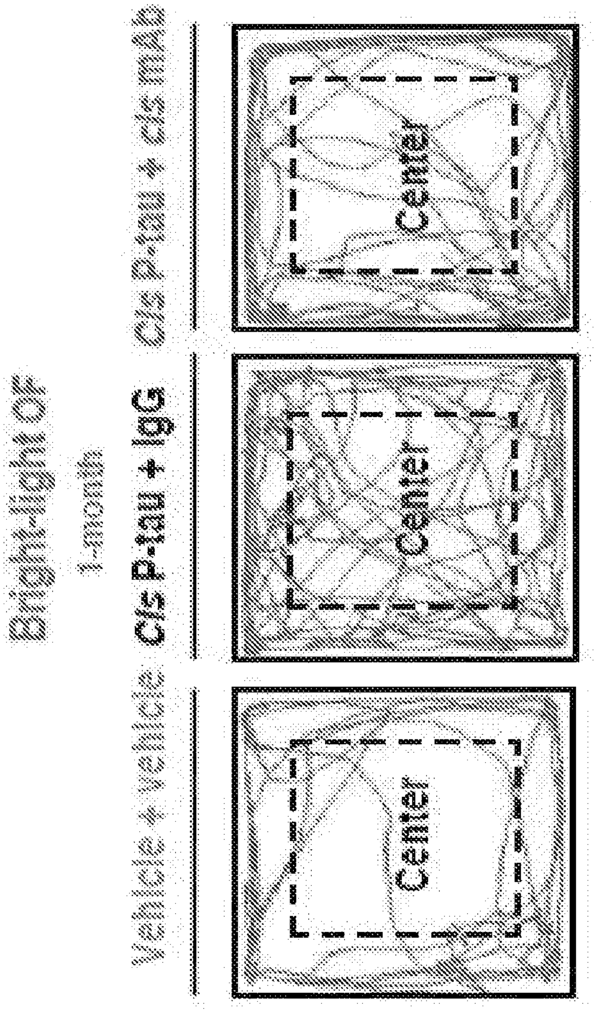

FIG. 73A shows behavioral tracking data of mice subjected to a bright-light open field assay after 1 month of cis P-tau or vehicle control injection. One group was injected with vehicle controls while another group was injected with cis P-tau and the third group received both cis P-tau and cis mAb.

FIG. 73B is a graph of the quantified tracking data of mice subjected to a bright-light open field assay following injection of either vehicle controls (green), cis P-tau+IgG (black) or cis P-tau+cis mAb (red). At 1 month from the injections, mice that received cis P-tau+IgG showed significantly higher residence within the center of the arena (black bar) compared to the vehicle control mice (green bar). Mice that received cis P-tau+cis mAb had improved performance compared to the cis P-tau+IgG controls.

Figure 74A:
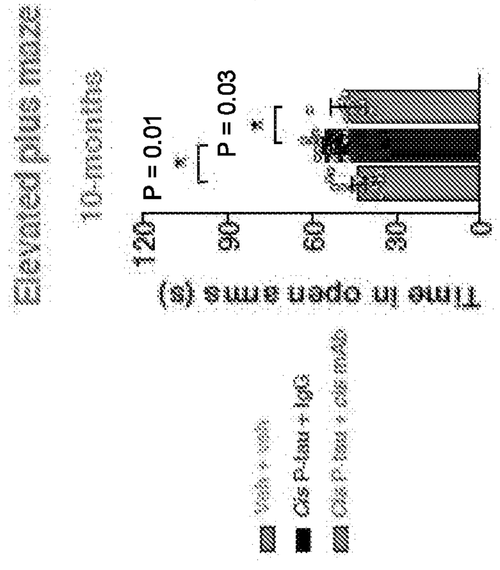

FIG. 74A is a graph describing the time in open arms measured using elevated plus maze after 10 months from cis P-tau injection in the three groups of mice, vehicle controls (green), cis P-tau+IgG (black) or cis P-tau+cis mAb (red).

Figure 74B:
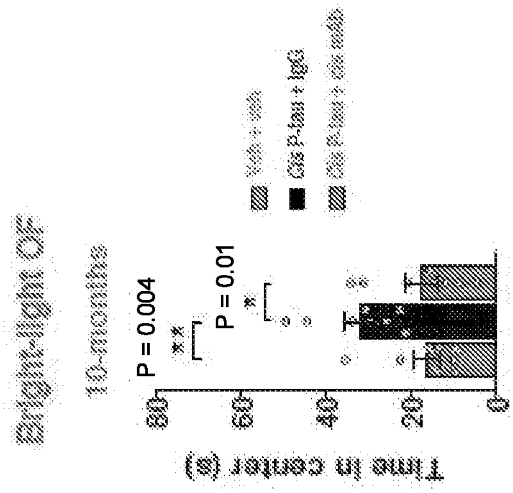

FIG. 74B is a graph describing the time in center measured using the bright-light open field assay after 10 months from cis P-tau injection in the three groups of mice, vehicle controls (green), cis P-tau+IgG (black) or cis P-tau+cis mAb (red).

Figure 74C:
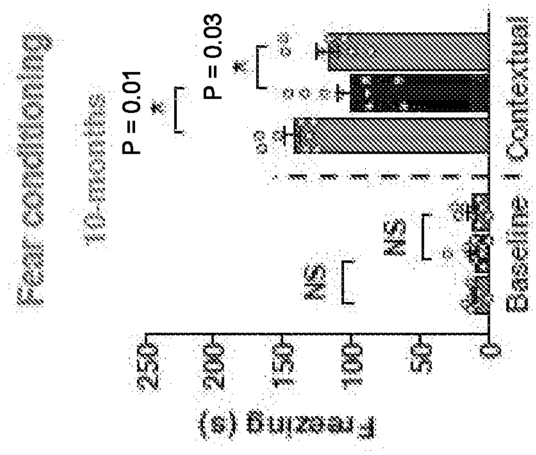

FIG. 74C is a graph describing fear conditioning data after 10 months from cis P-tau injection in the three groups of mice, vehicle controls (green), cis P-tau+IgG (black) or cis P-tau+cis mAb (red).

Figure 74D:

FIG. 74D is a graph that describes the responses to the accelerating rotarod behavioral assay in mice 10 months after injection with vehicle controls (green), cis P-tau+IgG (black) or cis P-tau+cis mAb (red).

Figure 74E:
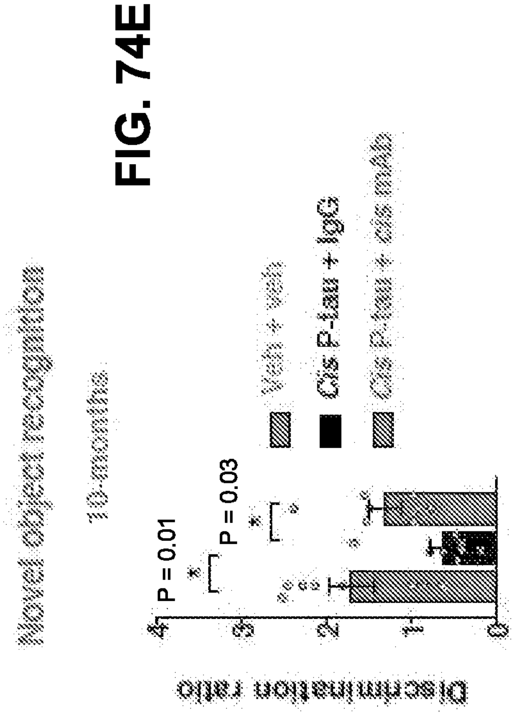

FIG. 74E is a graph that describes the behavioral data of mice subjected to novel object recognition assays following injection with vehicle controls (green), cis P-tau+IgG (black) or cis P-tau+cis mAb (red).

Figure 75B:
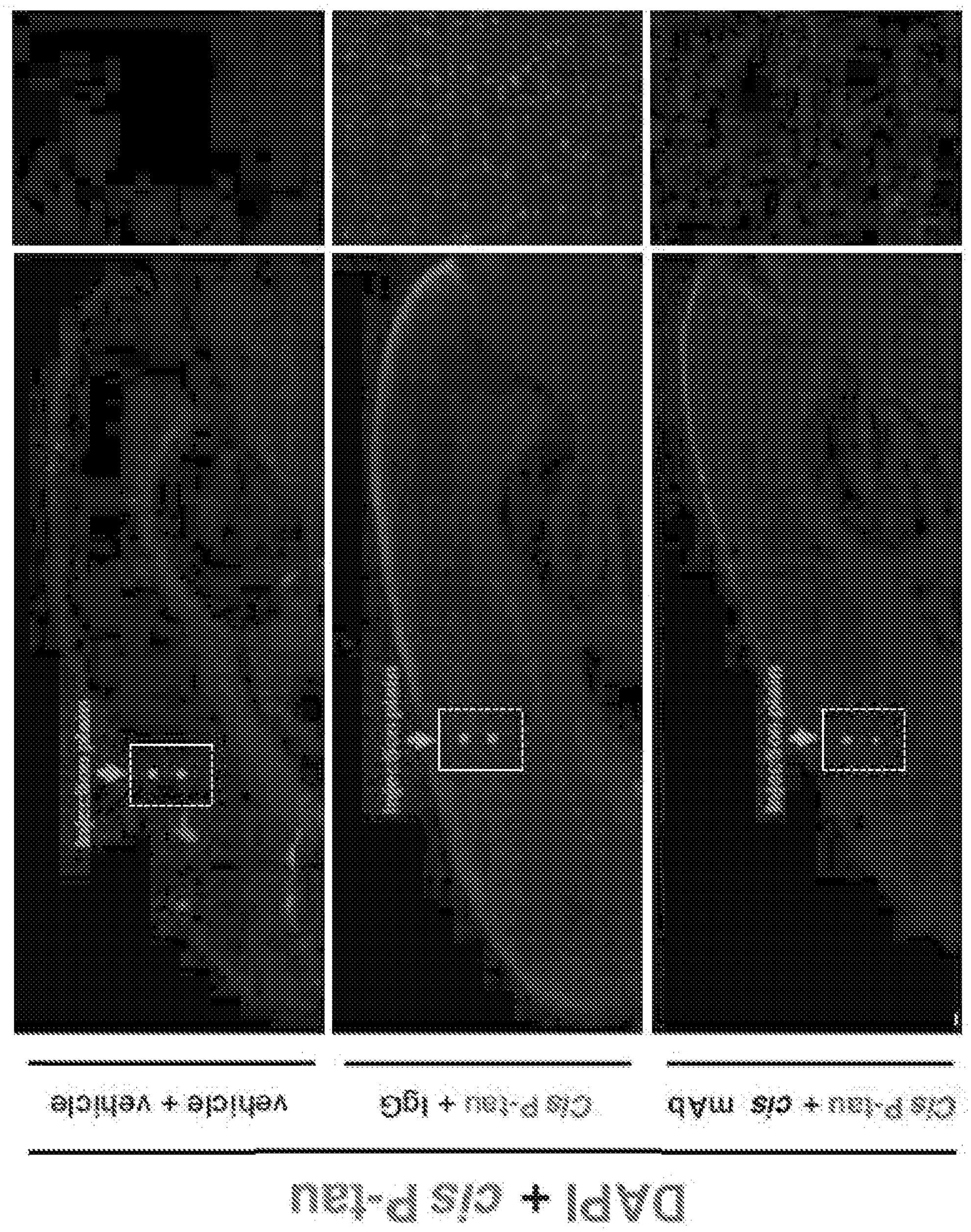
Figure 75A:
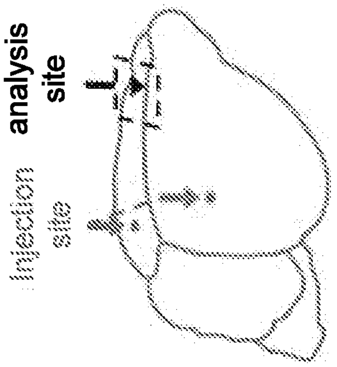

FIG. 75A is a schematic of a mouse brain and the locations of injected cis P-tau and site of analysis to assess whether cis P-tau induction spreads in wild-type mouse brains and whether treatment with cis mAb blocks this spread.

FIG. 75B show immunofluorescence results of cis P-tau spreads in WT mouse brains injected with cis P-tau, which is blocked by cis mAb. Three-month-old (3M) WT mice underwent stereotaxic intra cortical injection of purified soluble cis P-tau or vehicle, and were continuously subjected to treatment regimens of cis mAb, IgG isotype or vehicle controls over 5-months, followed by immunofluorescence staining of cis P-tau immunoreactivity in whole brain sections to detect cis P-tau spreading over the cortex at 10-months after injection. Inset images (right) are high magnifications of representative areas. Scale bar, 400 μm.

Figure 76A:
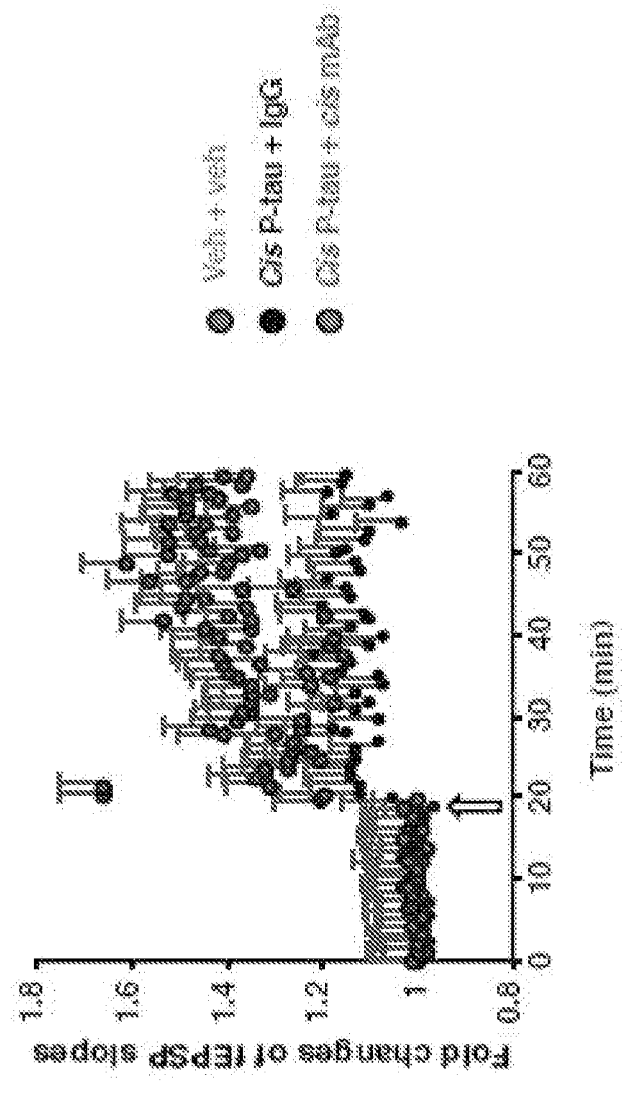

FIG. 76A is a graph that describes impaired synaptic plasticity via recording field excitatory postsynaptic potentials (fEPSP) at 10 months after stereotaxic injection with vehicle controls (green), cis P-tau+IgG (black) or cis P-tau+cis mAb (red). Treatment with cis mAb neutralizes cortical axonal long-term potentiation. A stable fEPSP slope for at least 20 min was recorded as baseline.

Figure 76B:
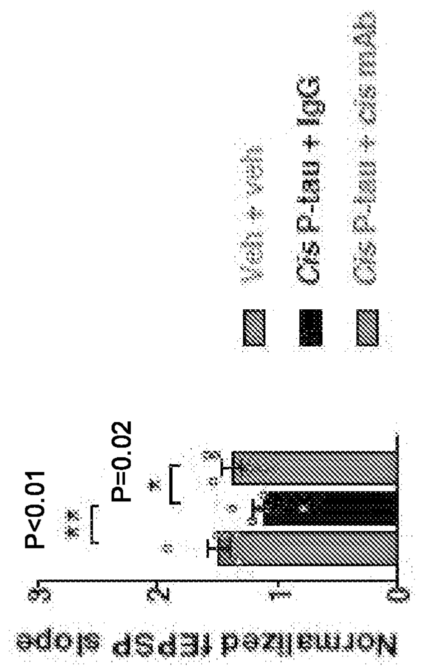

FIG. 76B is a graph of the field excitatory postsynaptic potential (fEPSP) measurements recorded in acute brain slices at 10 months after stereotaxic injection with vehicle controls (green), cis P-tau+IgG (black) or cis P-tau+cis mAb (red).

Figure 76C:
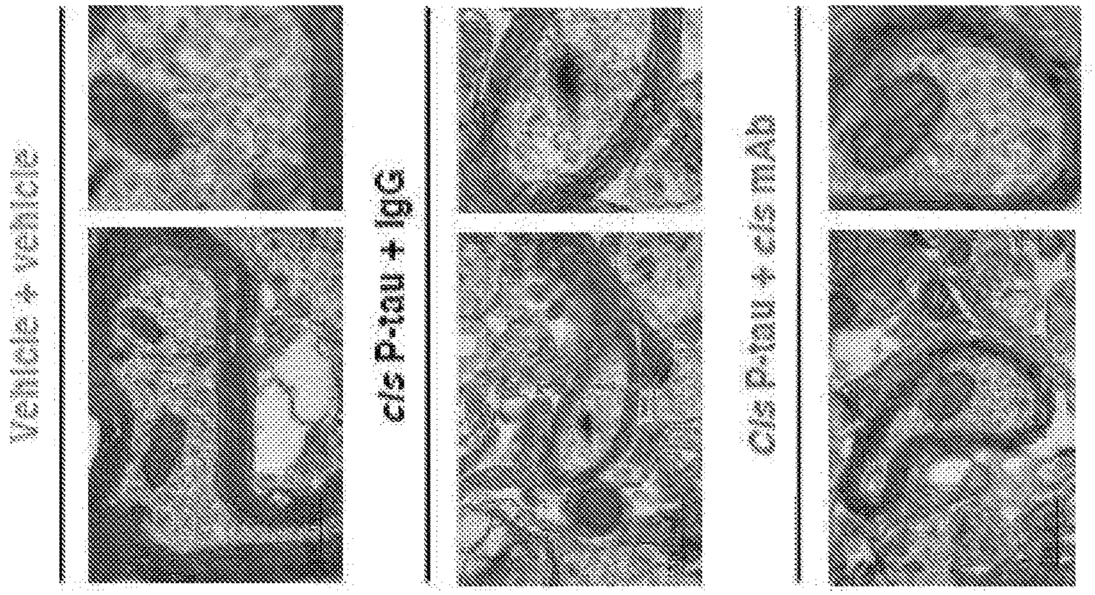

FIG. 76C is a series of histological images recorded using scanning electron microscopy of brain sections from mice that were injected with vehicle controls (green), cis P-tau+

IgG (black) or cis P-tau+cis mAb (red). The images show ultrastructural pathologies of disrupted axonal microtubules and mitochondria in mice injected with cis P-tau. Ultrastructural changes were rescued in mice that received cis mAb. Inset shows higher magnification.

Figure 77A:
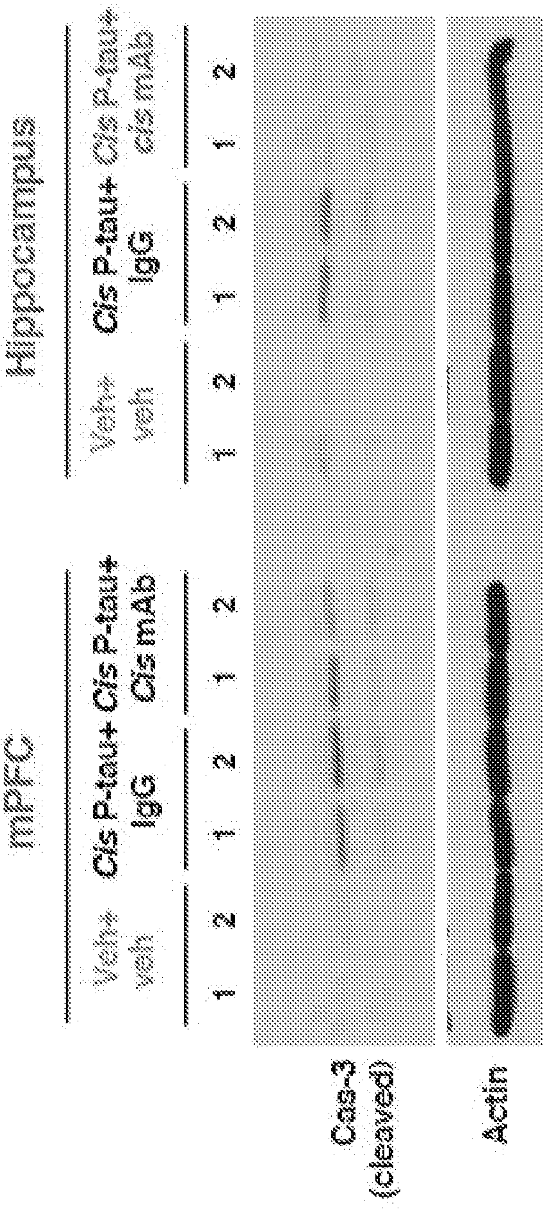

FIG. 77A shows immunoblotting of cleaved caspase-3 to detect relative apoptotic activity in the medial prefrontal cortex (mPFC) and hippocampus of mice injected with vehicle controls (green), cis P-tau+IgG (black) or cis P-tau+cis mAb (red). Three-month old wild-type mice underwent stereotaxic intra-cortical injection of purified cis P-tau or vehicle and were continuously subjected to treatment regimens of cis mAb IgG isotype or vehicle controls over 5 months.

Figure 77B:
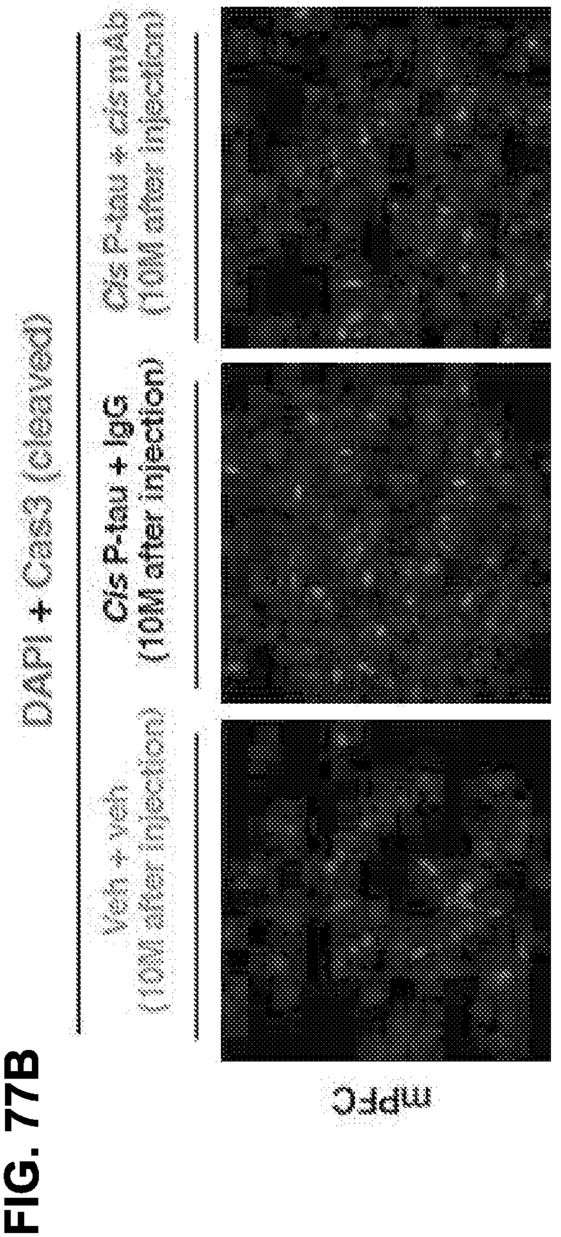

FIG. 77B shows immunofluorescence staining images of cleaved caspase-3 (red) to detect relative apoptotic activity in the medial prefrontal cortex (mPFC) of mice injected with vehicle controls (green), cis P-tau+IgG (black) or cis P-tau+cis mAb (red). Blue denotes DAPI nuclear staining to report all cells. Scale bar, 20 μm.

Figure 78A:
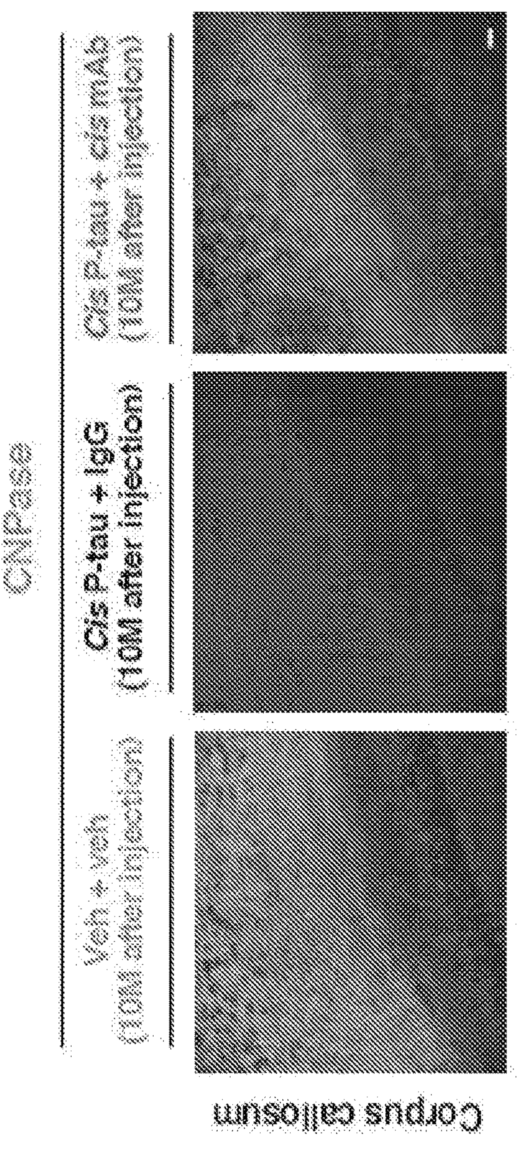

FIG. 78A shows immunofluorescence staining images of CNPase to detect demyelination in the corpus callosum of mice injected with vehicle controls (green), cis P-tau+IgG (black) or cis P-tau+cis mAb (red). Scale bar, 20 μm.

Figure 78B:
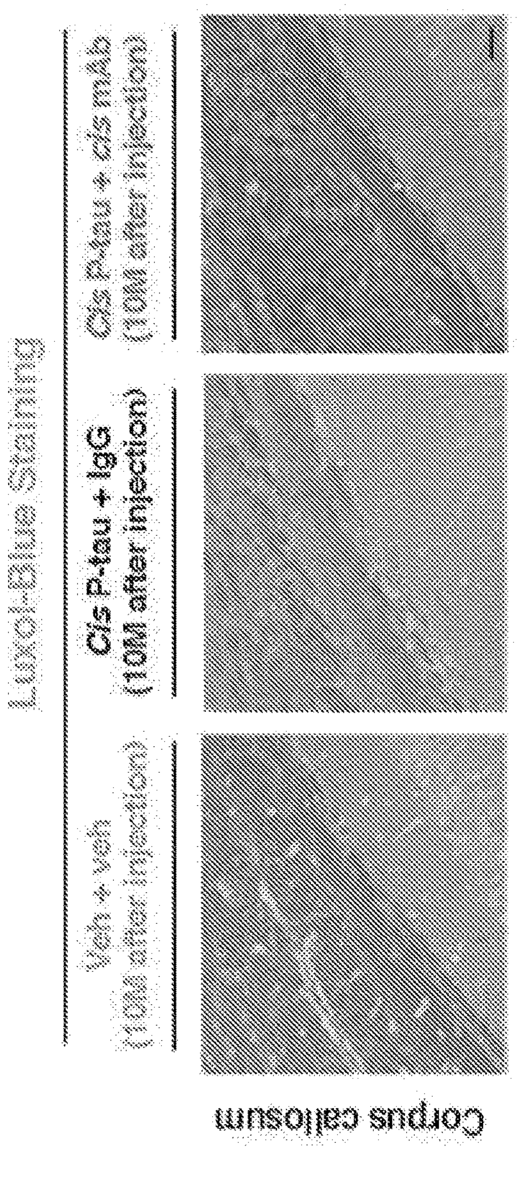

FIG. 78B shows histological staining images with Luxol-Blue to detect demyelination in the corpus callosum of mice injected with vehicle controls (green), cis P-tau+IgG (black) or cis P-tau+cis mAb (red). Scale bar, 20 μm.

Figures 79A, 79B:
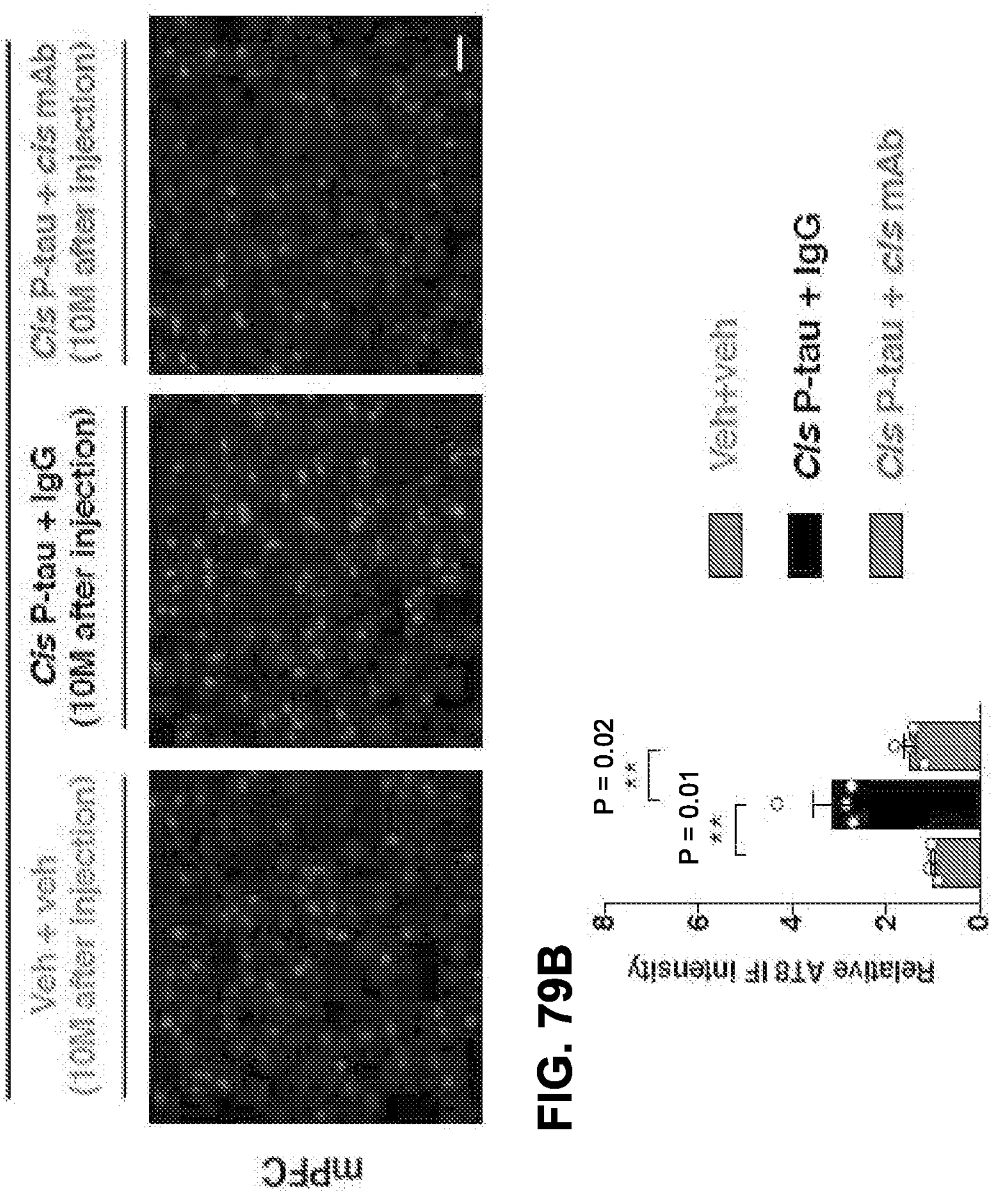

FIG. 79A shows immunofluorescence staining results of AT8 to detect early tangle-like epitopes in the medial prefrontal cortex of mice injected with vehicle controls (green), cis P-tau+IgG (black) or cis P-tau+cis mAb (red). Scale bar, 20 μm.

FIG. 79B is a graph of the quantified relative AT8 immunofluorescence signal intensity in the medial prefrontal cortex of mice injected with vehicle controls (green), cis P-tau+IgG (black) or cis P-tau+cis mAb (red). The p-values were calculated using one-way ANOVA and unpaired two-tailed parametric Student's t-tests. **, $p<0.01$.

Figure 80A:
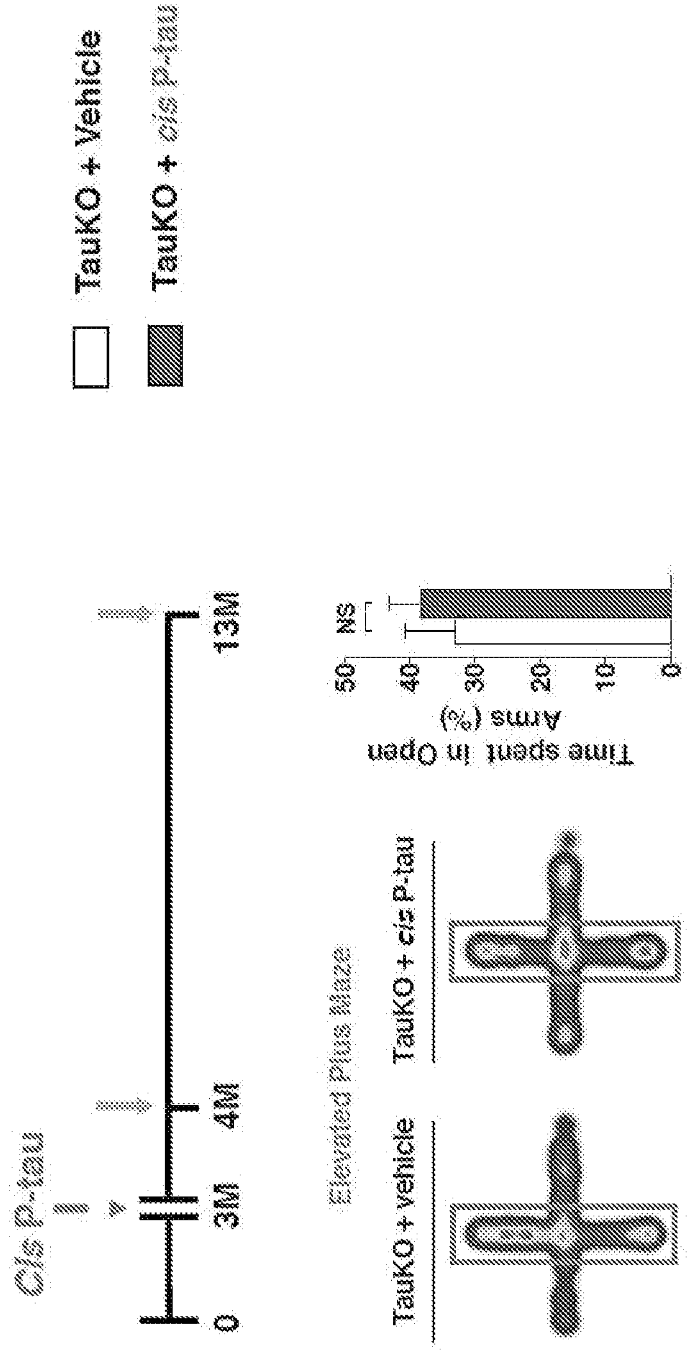

FIG. 80A is a schematic of the experimental timeline used to evaluate the effects of purified cis P-tau in Tau knockout (TauKO) mice. TBI-purified cis P-tau (0.1 μg/μl) or vehicle control were injected bilaterally into the upper (DV, −0.8 mm) & lower (DV, −1.0 mm) layer of the neocortex of three-month-old TauKO mice. Red arrow indicates timepoint of stereotaxic surgery; green line indicates timepoint of functional assays.

Figure 80B:
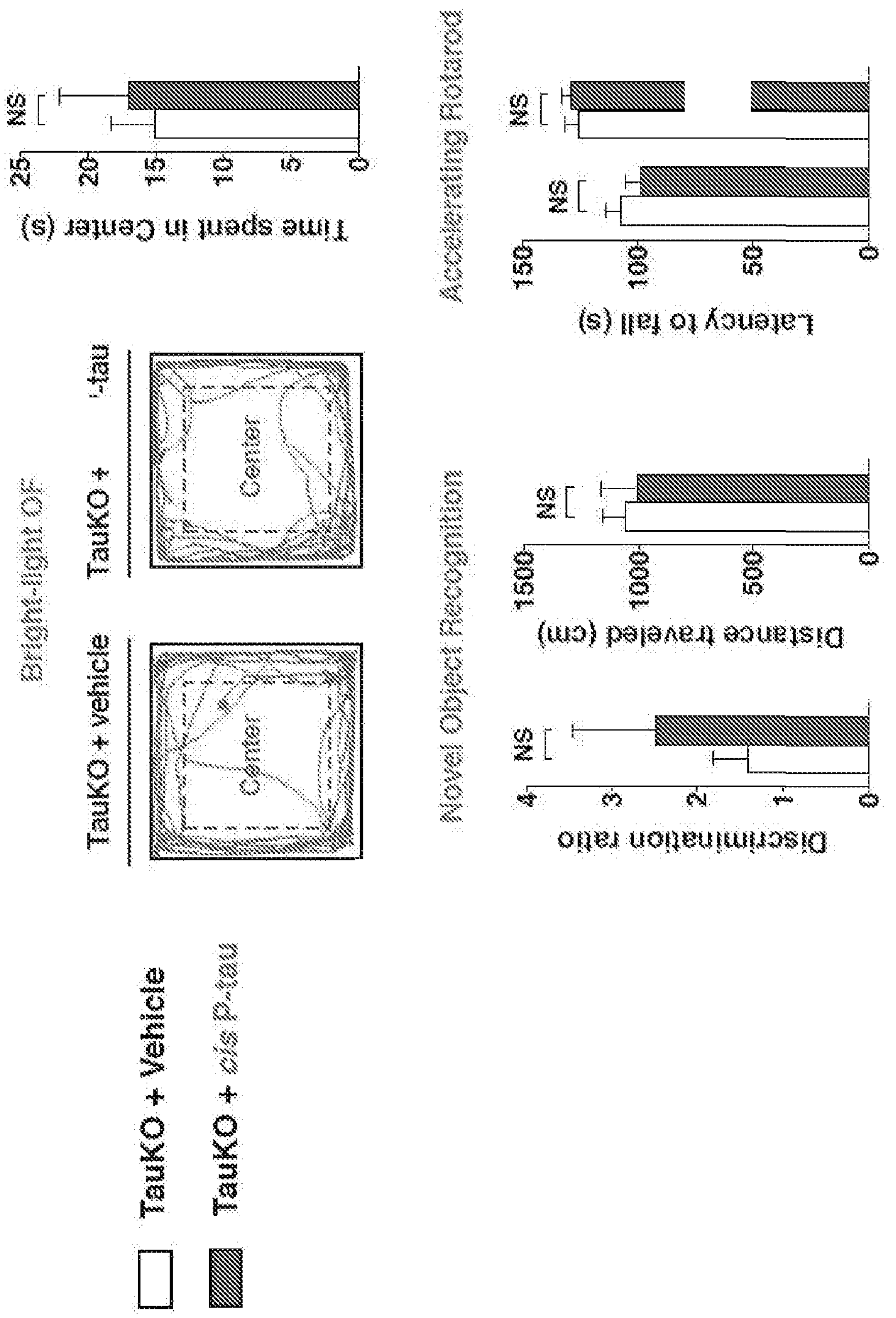
Figure 80C:
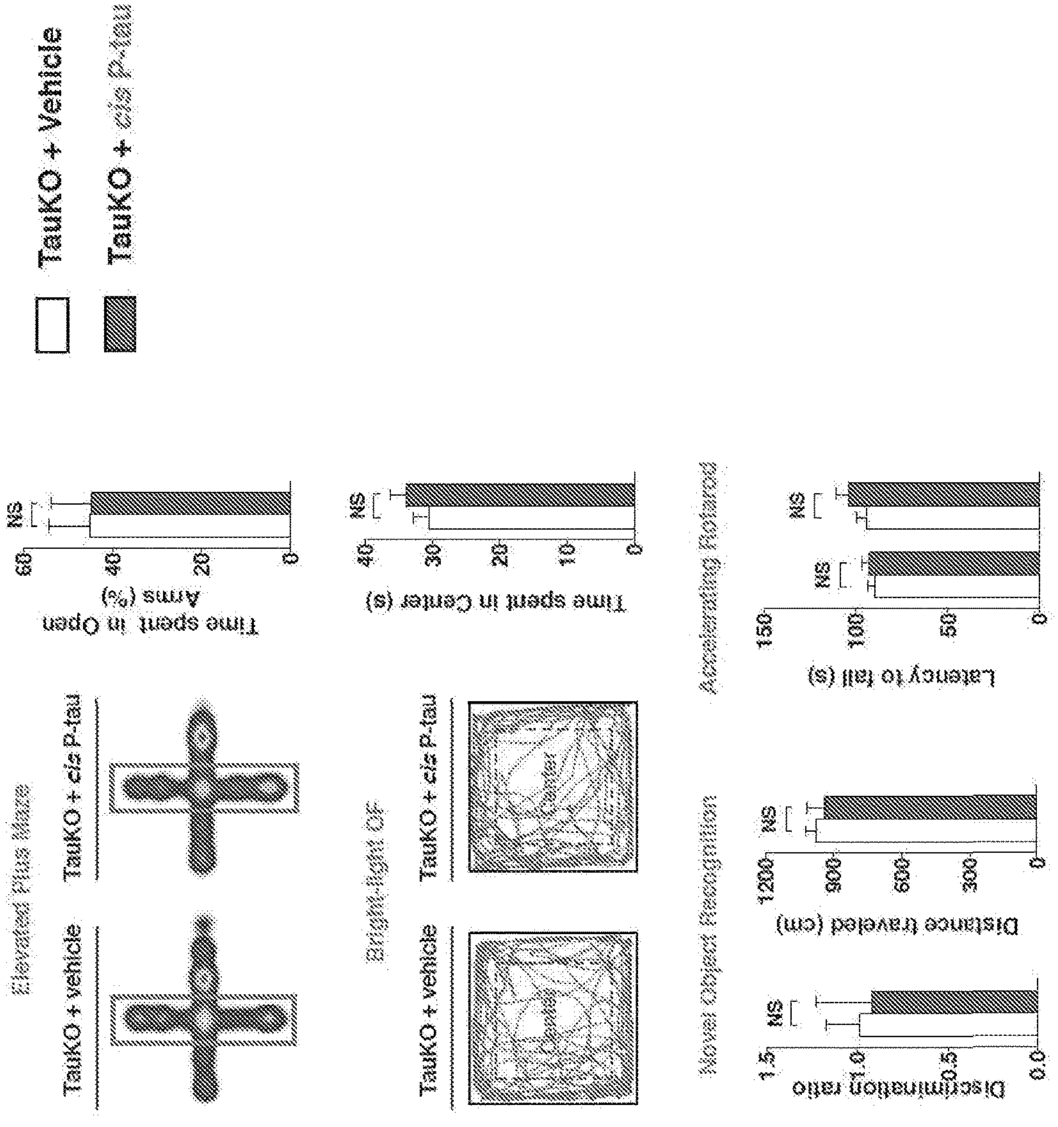

FIGS. 80B-80C are a series of behavioral results that show that cortical injection of purified cis P-tau has no significant behavioral effect in TauKO mice. Assessment of behavioral changes of cis P-tau or vehicle injected Tau KO mice using the Elevated plus maze, bright-light open field, novel object recognition and Accelerating rotarod tests at 1 month (B) and 10 months (C) after surgery. NS: not significant. 8-10 mice per group were included in each of the behavioral tests. The data were presented as means±SEM. The p-values were calculated using unpaired two-tailed parametric Student's t-test.

Figure 81A:
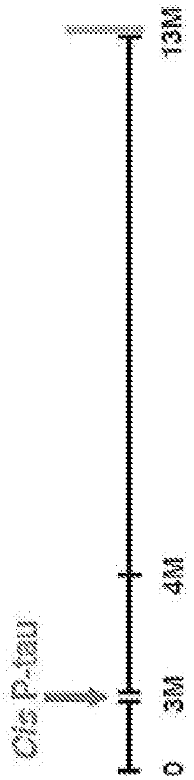

FIG. 81A is a schematic of the experimental timeline used to evaluate the effects of injected cis P-tau in the induction of transcriptomic changes in the brain. Three-month-old mice were injected stereotaxically with cis P-tau or vehicle control. Single nucleus RNA-seq experiments performed 10 months after injection.

Figure 81B:
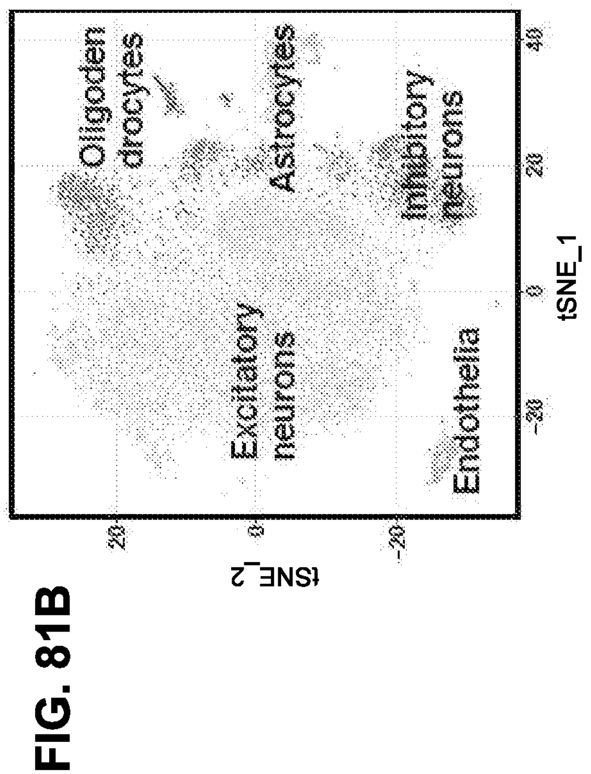

FIG. 81B is a graph describing a t-distributed stochastic neighbor embedding (tSNE) plot of color coded cortical cell types from mice injected with cis P-tau.

Figure 81C:
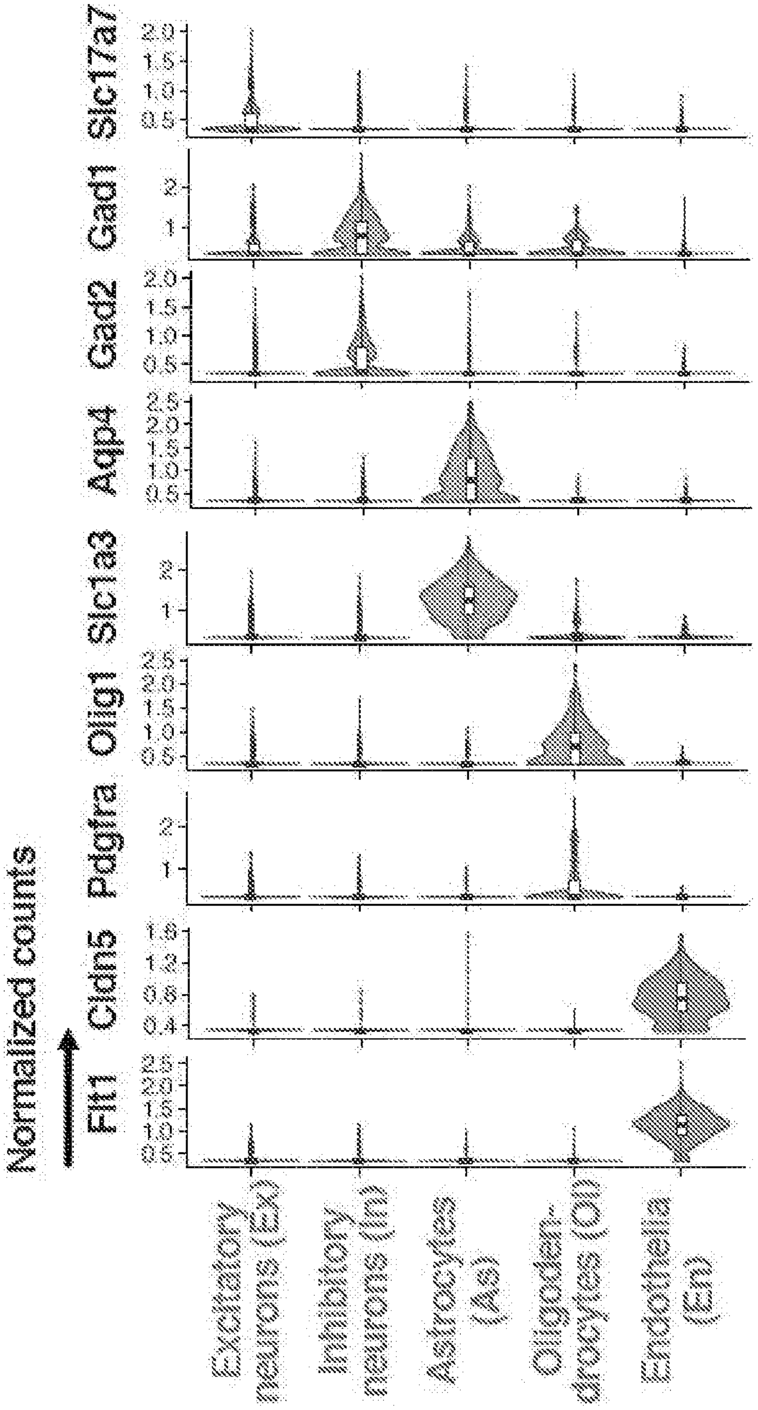
Figure 82A:
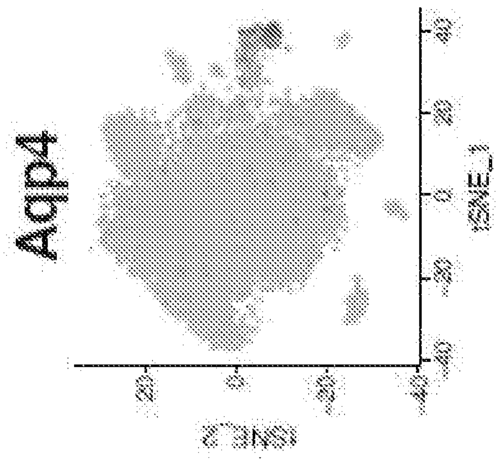
Figure 82B:
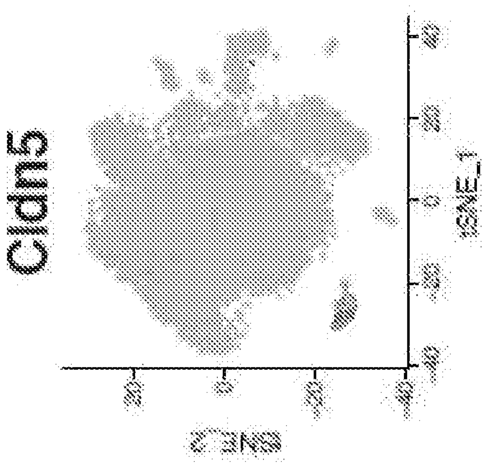
Figure 82C:
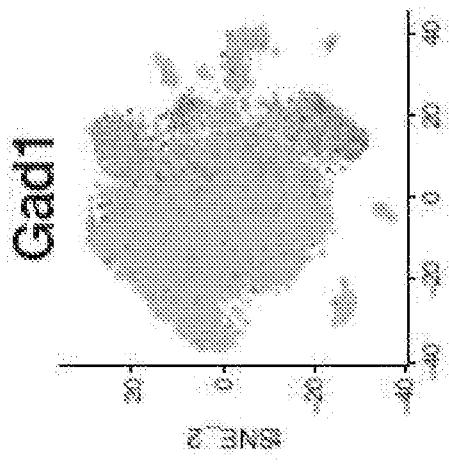
Figure 82D:
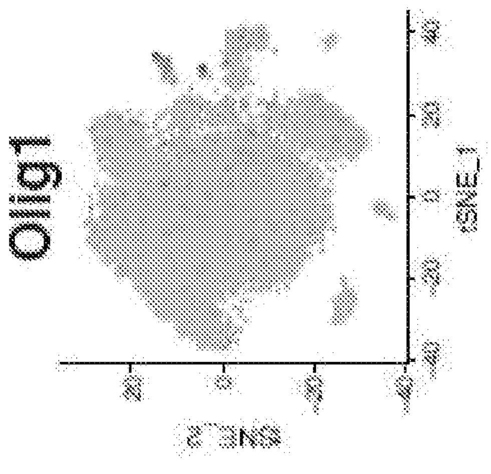
Figure 82E:
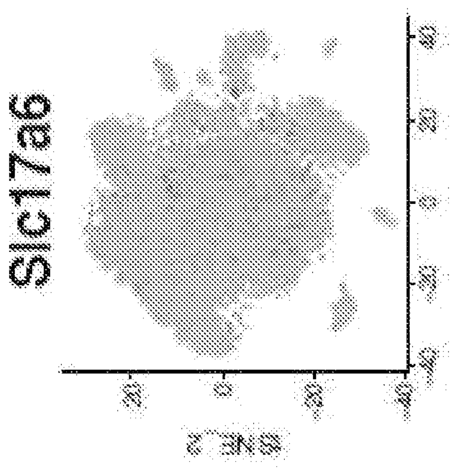
Figure 82F:
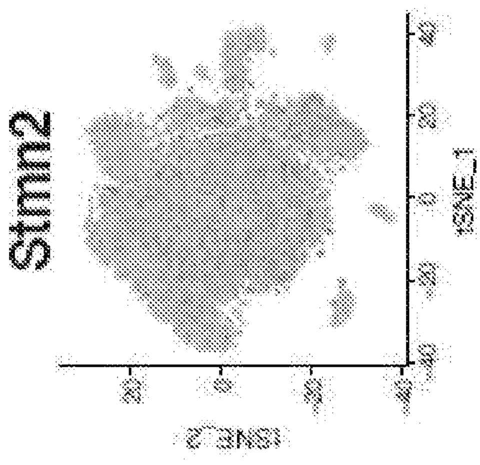

FIG. 81C is a graph describing violin plots showing normalized expression of marker genes for different cell types from mice injected with cis P-tau. Slc17a7 (glutamatergic neurons, Ex), Gad1, Gad2 (GABAergic neurons, In), Aqp4, Slc1a3 (astrocytes, As), Olig1, Pdgfra (oligodendrocytes and their progenitor cells, Ol), Cldn5, Flt1 (endothelia, En).

FIGS. 82A-82F show expression pattern profiles of cell-type specific marker genes across cell clusters in mice stereotaxically injected with cis P-tau or vehicle control. Expression patterns for astrocyte marker Aqp4 (FIG. 82A), endothelia marker Cldn5 (FIG. 82B), inhibitory neuron marker Gad1 (FIG. 82C), oligodendrocyte markers Olig1 (FIG. 82D), excitatory neuronal markers Slc17a6 (FIG. 82E) and Stmn2 (FIG. 82F) are shown in heatmaps.

Figure 83:
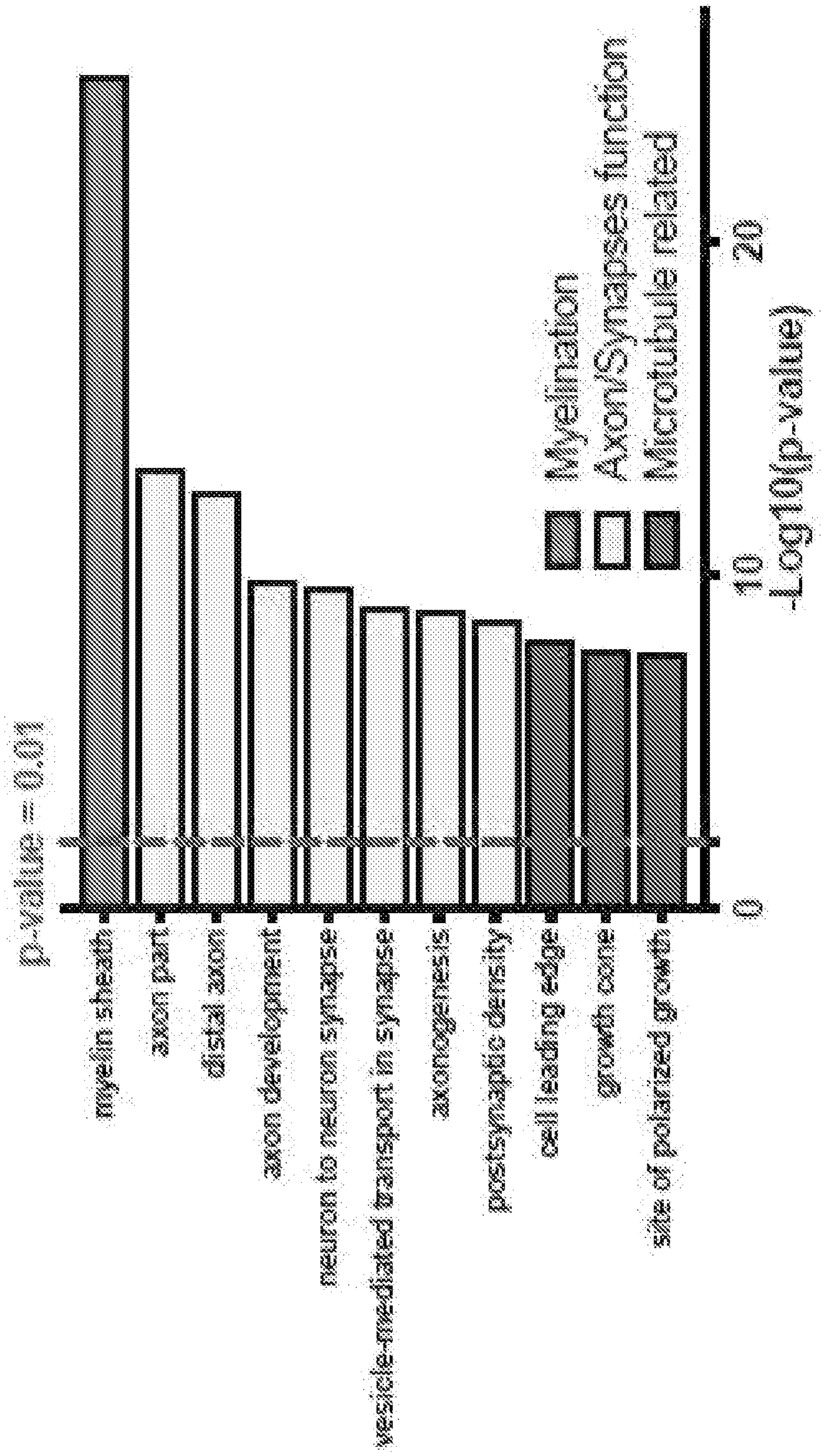

FIG. 83 is a graph showing that cis P-tau injection down-regulated genes (p value <0.05) are widely associated with myelination, axon/synapses and microtubule function in excitatory neurons from mice after cis P-tau injection. Enriched gene-ontology terms are showed in bar graphs with terms associated with different classes color coded.

Figure 84A:
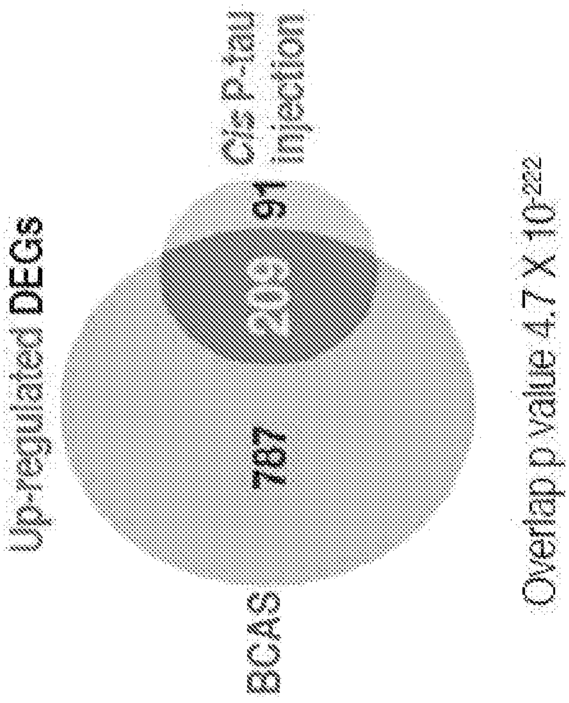

FIG. 84A is a graph showing that the up-regulated DEGs in cis P-tau injected excitatory neurons significantly correlate with BCAS DEGs (fdr adjusted p value <0.00001). Fisher's exact test is implemented to compute the p-values for the overlap, as described (Mathys et al., 2019).

Figure 84B:
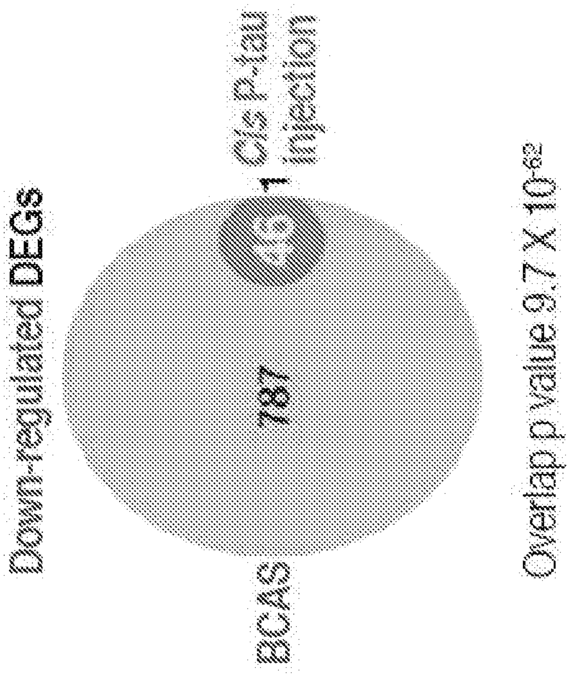

FIG. 84B is a graph showing that the down-regulated DEGs in cis P-tau injected excitatory neurons significantly correlate with BCAS DEGs (fdr adjusted p value <0.00001). Fisher's exact test is implemented to compute the p values for the overlap, as described (Mathys et al., 2019).

Figure 85A:
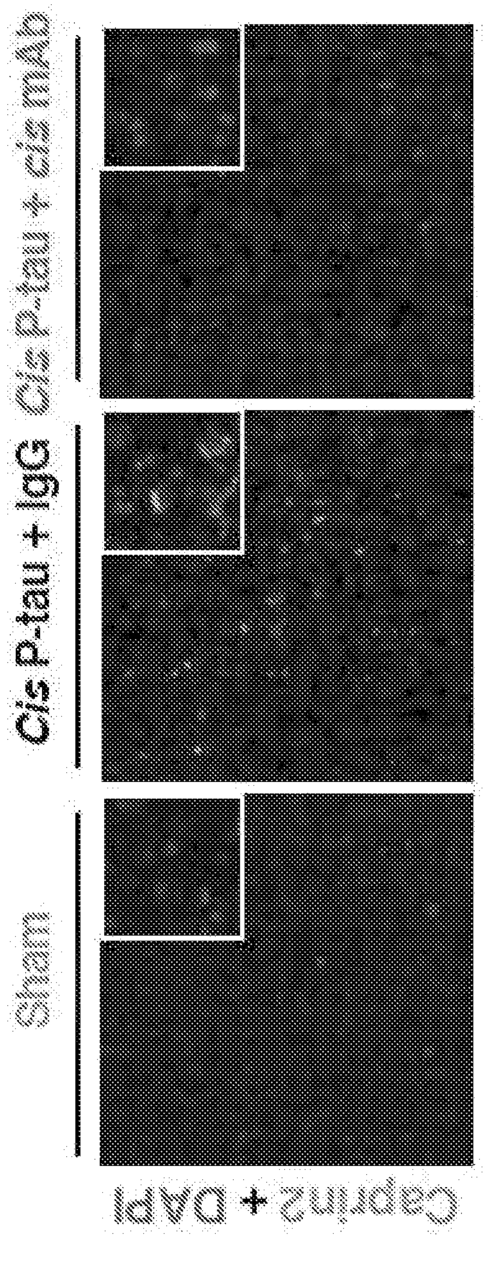

FIG. 85A shows immunofluorescence results of the elevated levels of Caprin2 and the rescue of the elevated Caprin2 signal in response to cis mAb. Inset shows higher magnification. Blue denotes DAPI nuclear staining to report all cells.

Figure 85B:
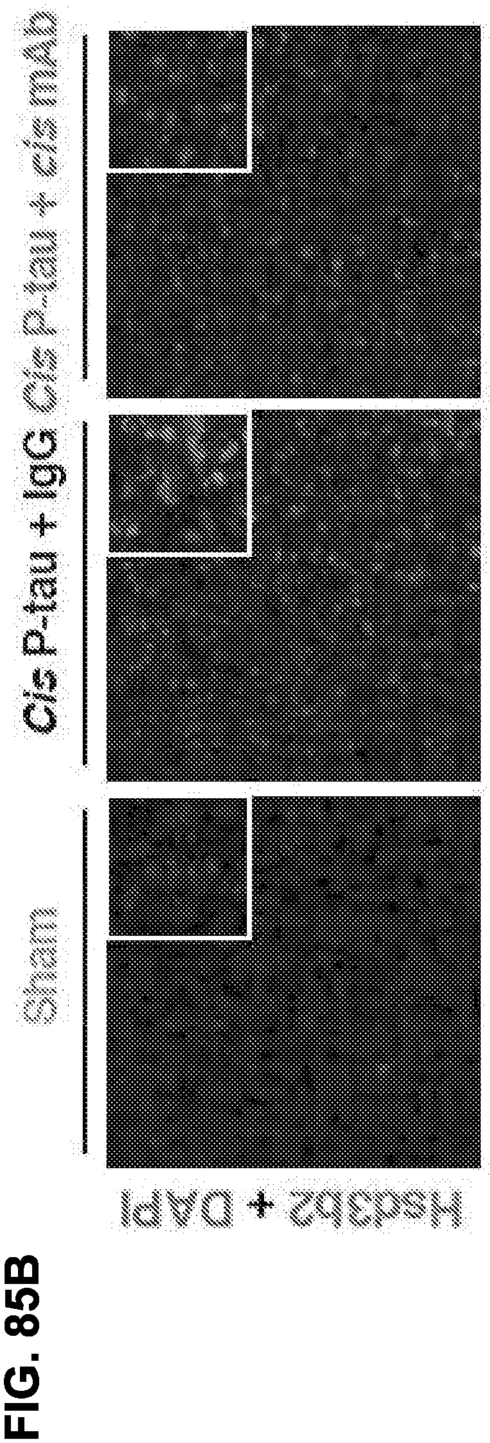

FIG. 85B shows immunofluorescence results of the elevated levels of Hsd3b2 and the rescue of the elevated Caprin2 signal in response to cis mAb. Inset shows higher magnification. Blue denotes DAPI nuclear staining to report all cells.

Figure 85C:
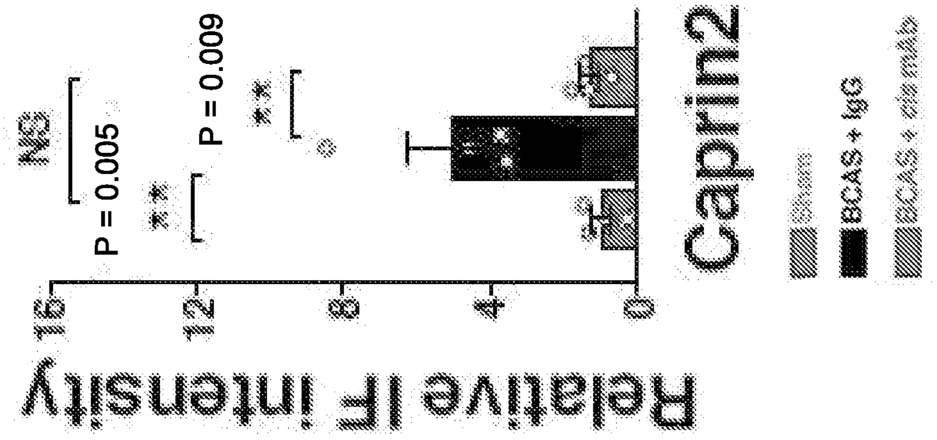

FIG. 85C is a graph of the quantified levels Caprin2 measured with immunofluorescence images of Caprin2 in brains of Sham controls (green), cis P-tau+IgG (black) and cis P-tau+cis mAb mice (red).

Figure 85D:
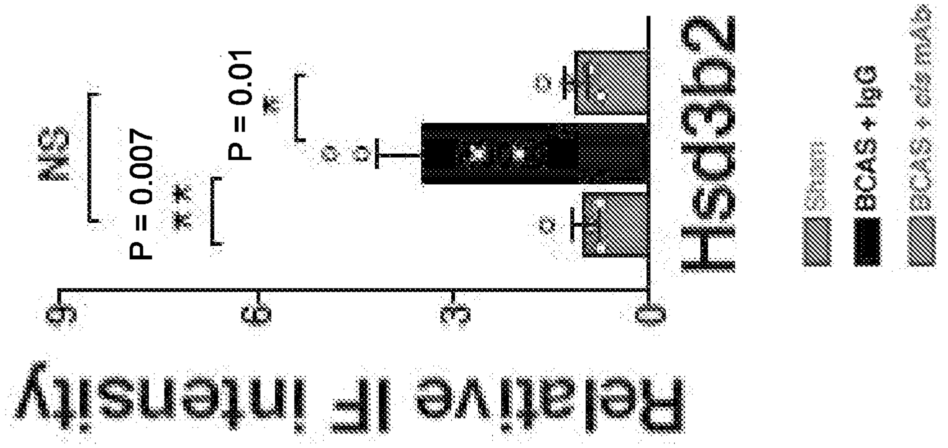

FIG. 85D is a graph of the quantified levels Hsd3b2 measured with immunofluorescence images of Hsd3b2 in brains of Sham controls (green), cis P-tau+IgG (black) and cis P-tau+cis mAb mice (red).

Figure 86A:
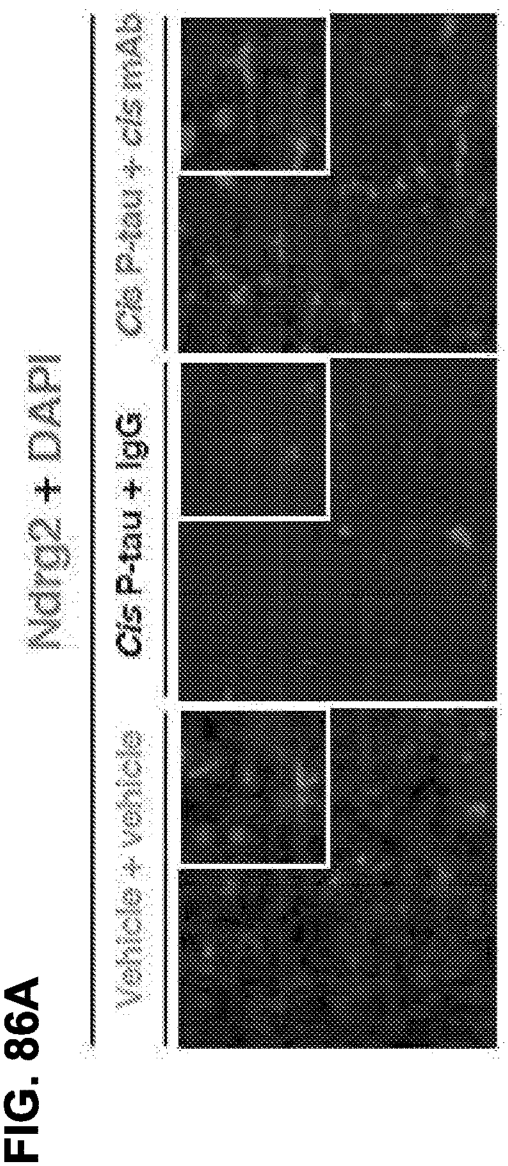

FIG. 86A shows immunofluorescence results of the decreased levels of Ndrg2 and the rescue of the decreased Ndrg2 signal in response to cis mAb. Inset shows higher magnification. Blue denotes DAPI nuclear staining to report all cells.

Figure 86B:
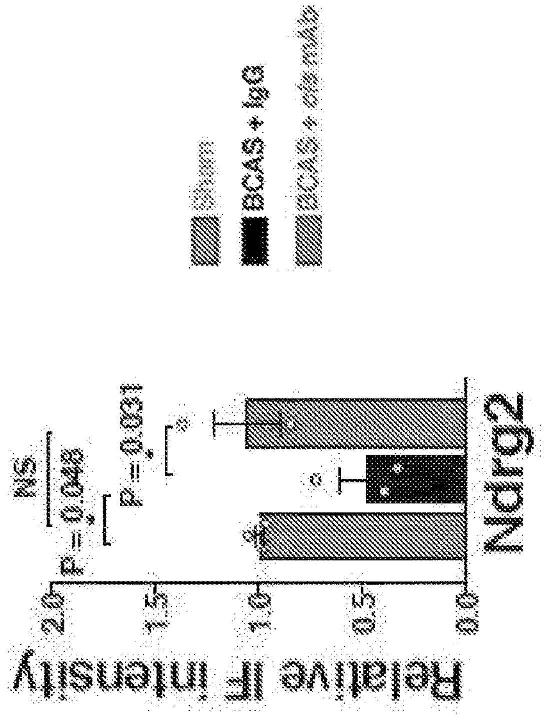

FIG. 86B is a graph of the quantified levels Ndrg2 measured with immunofluorescence images of Ndrg2 in brains of Sham controls (green), cis P-tau+IgG (black) and cis P-tau+cis mAb mice (red).

Figure 86C:
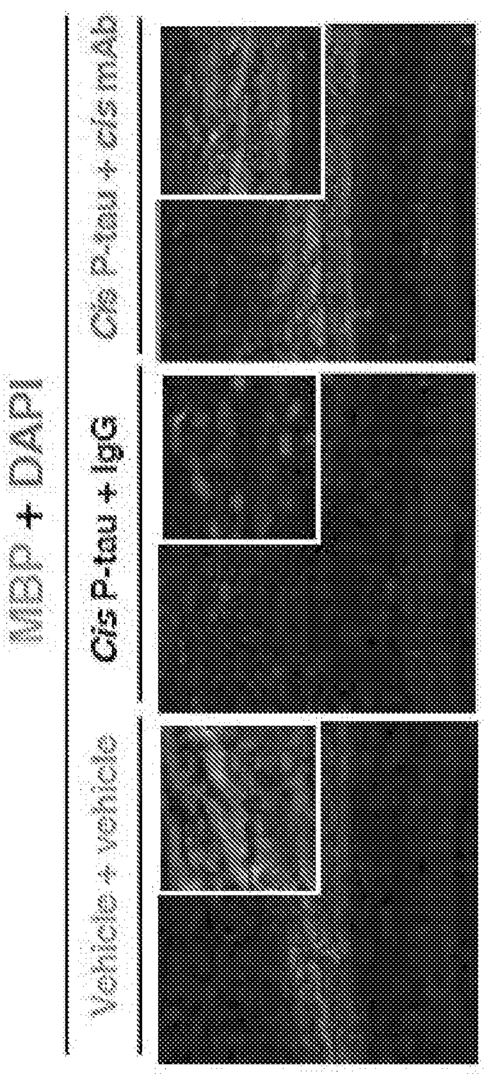

FIG. 86C shows immunofluorescence results of the decreased levels of Mbp and the rescue of the decreased Mbp signal in response to cis mAb. Inset shows higher magnification. Blue denotes DAPI nuclear staining to report all cells.

Figure 86D:
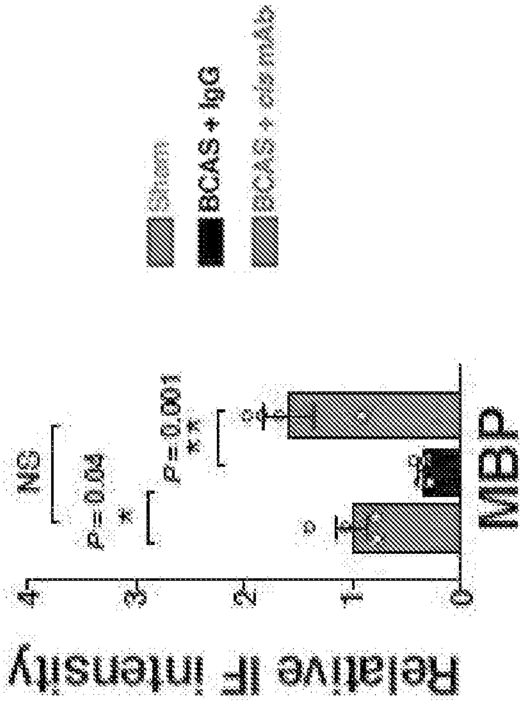

FIG. 86D is a graph of the quantified levels Mbp measured with immunofluorescence images of Mbp in brains of Sham controls (green), cis P-tau+IgG (black) and cis P-tau+cis mAb mice (red).

Figure 87:
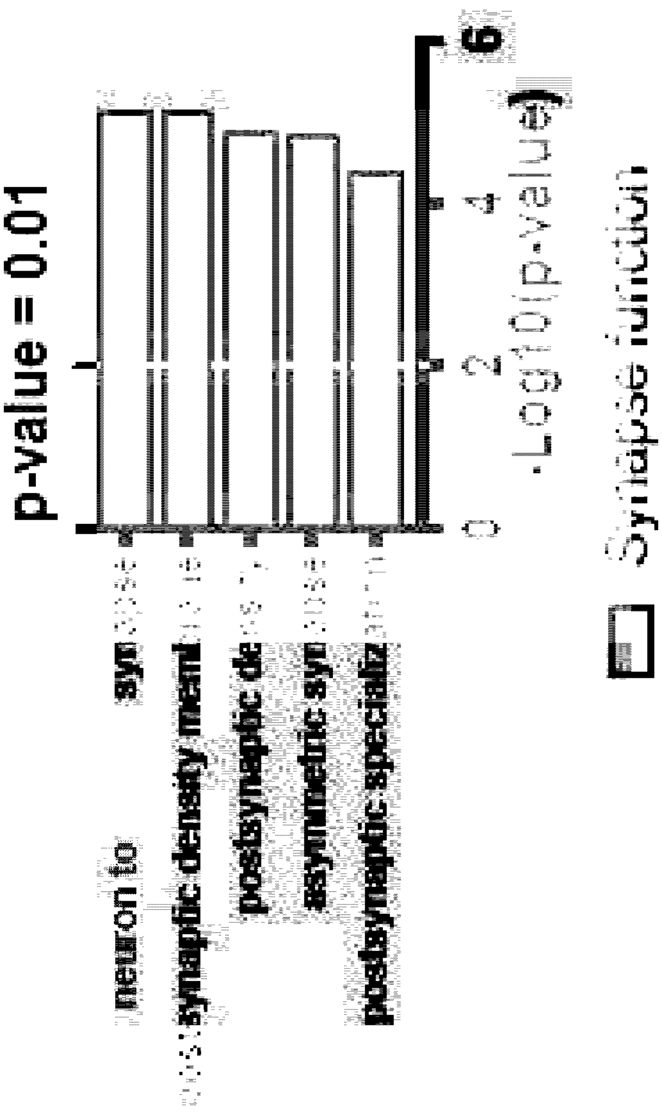

FIG. 87 is a graph showing that the 209 commonly up-regulated genes between cis P-tau injection and BCAS are enriched in genes related to synapse function. The p-values for the enriched gene-ontology terms are showed in bar graphs.

Figure 88A:
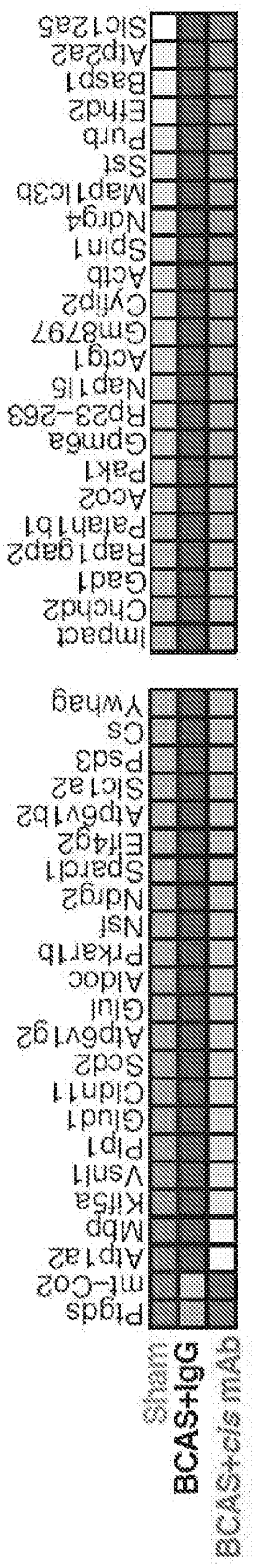

FIG. 88A shows heatmap graphs that demonstrate the that the vast majority of cis P-tau altered genes are similarly altered in BCAS mice brains and recovered by cis mAb. 46 genes that are commonly down-regulated by BCAS and cis P-tau injection were identified and rescued by cis mAb.

Figure 88B:
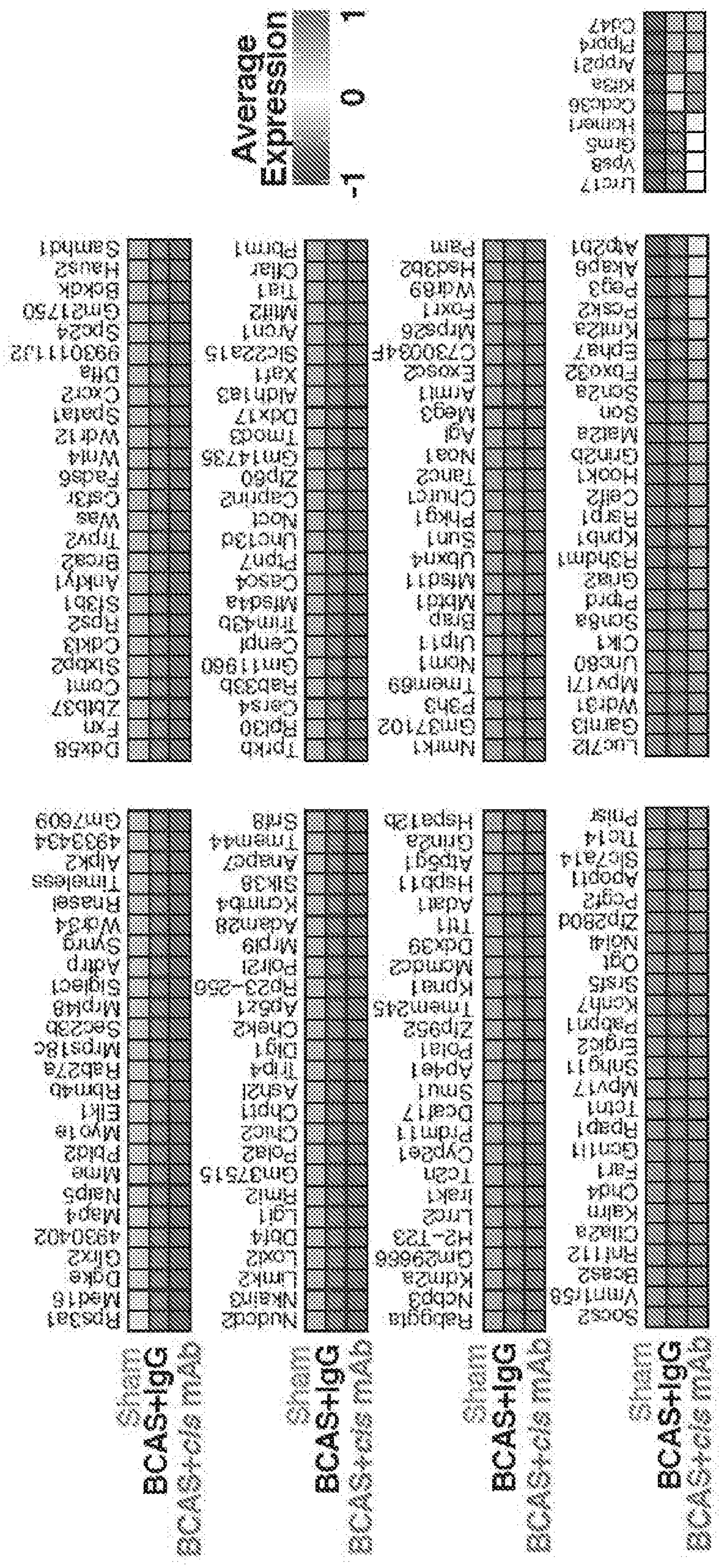

FIG. 88B shows heatmap graphs demonstrating that the vast majority of cis P-tau altered genes are similarly altered in BCAS mice brains and recovered by cis mAb. 209 genes that are commonly up-regulated by BCAS and cis P-tau injection were identified and rescued by cis mAb.

Figure 89:
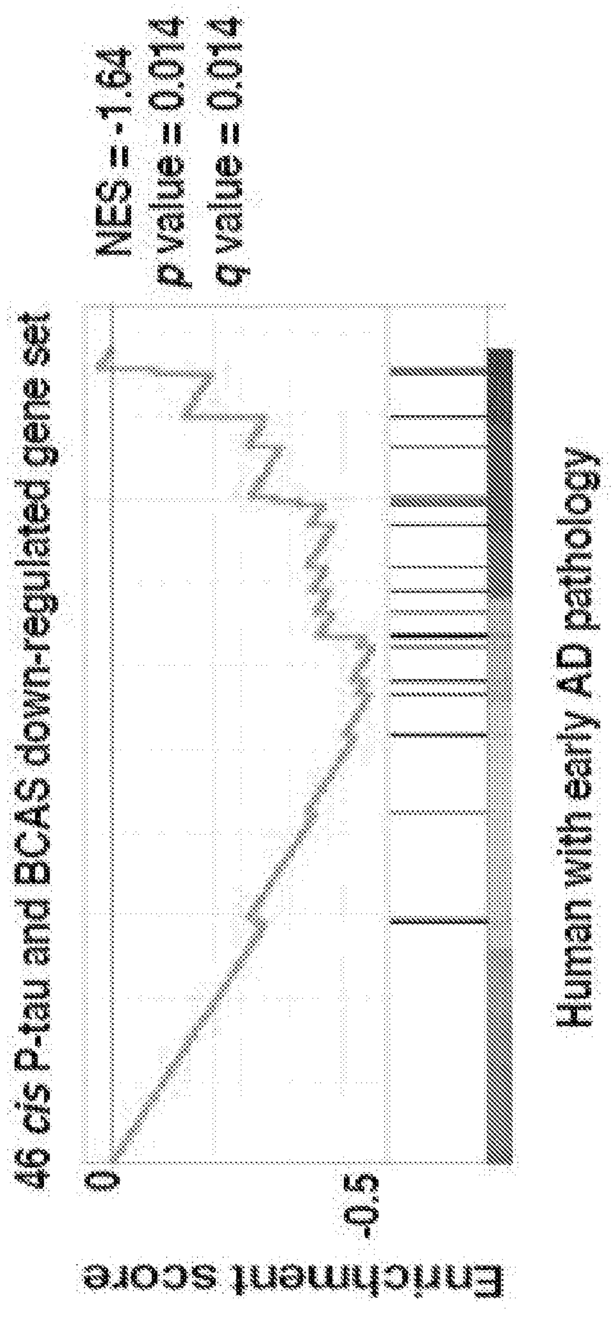

FIG. 89 is a graph showing gene set enrichment analysis of 46 commonly down-regulated genes by BCAS and cis P-tau injection that are also negatively enriched (down-regulated) in human AD with early pathology, with normalized enrichment score (NES)=−1.64, p values=0.01 and fdr adjusted p (q) value=0.01.

Figure 90:
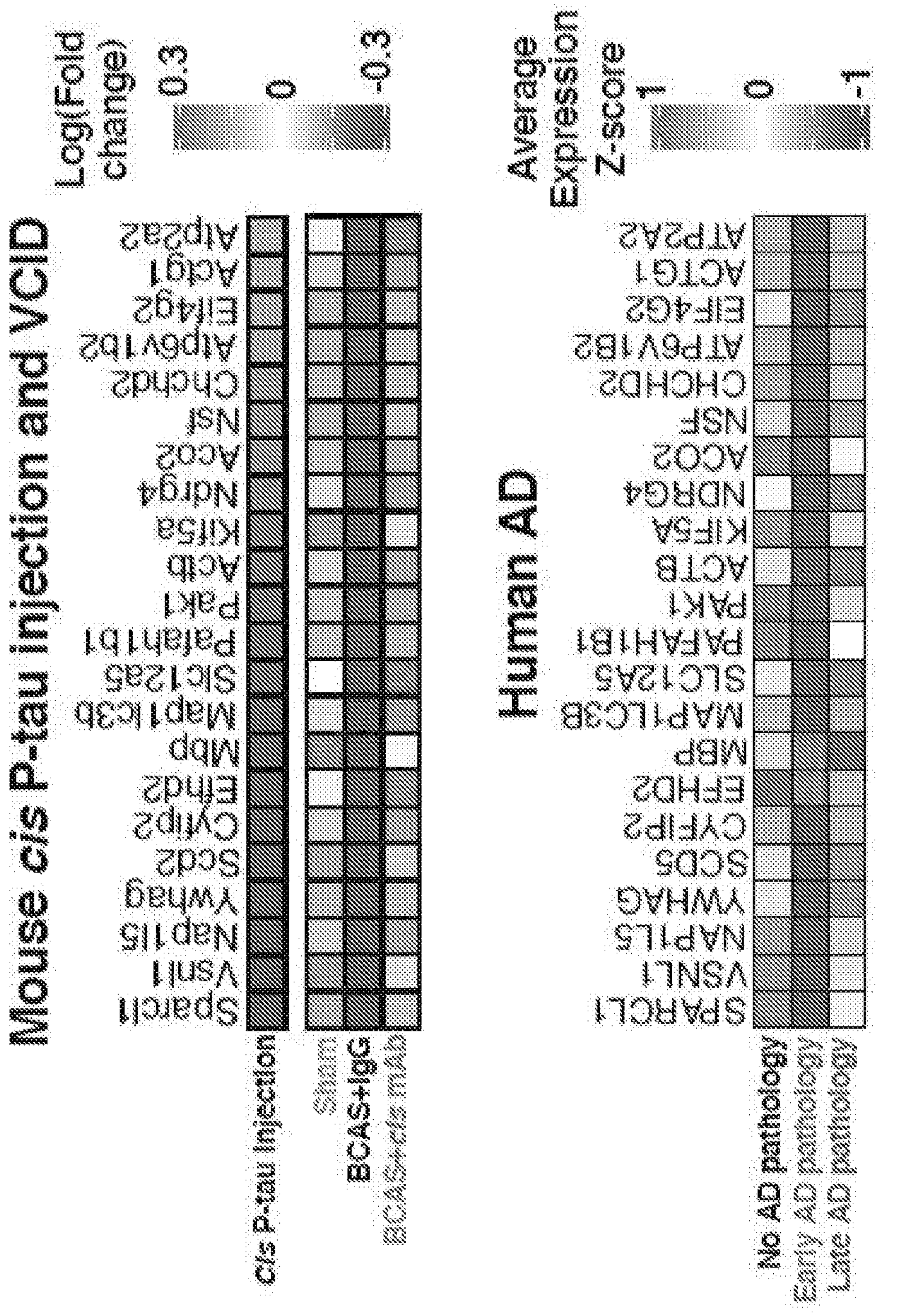

FIG. 90 shows heatmap graphs demonstrating 24 conserved genes that are commonly down-regulated in the excitatory neurons of cis P-tau injected mice, BCAS mice and human patients only with early, but not late AD pathology.

Figure 91:
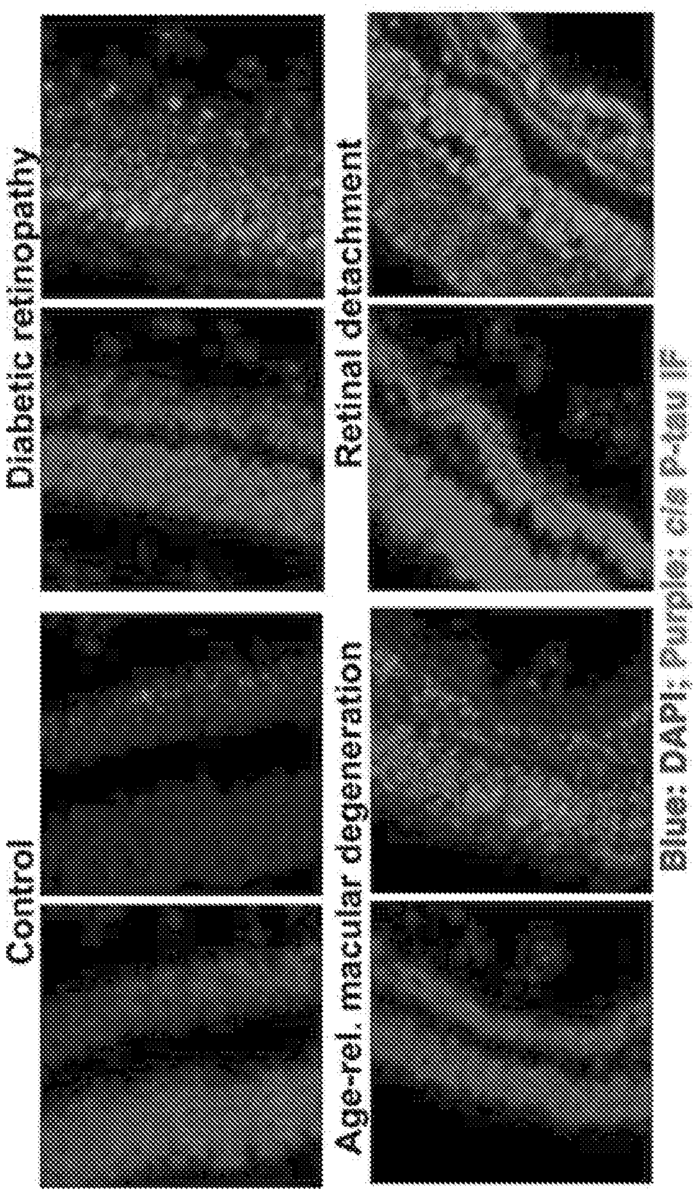

FIG. 91 shows immunofluorescence staining results of elevated levels of cis P-tau in human age-related macular degeneration, diabetic retinopathy and retinal detachment.

Figure 92A:
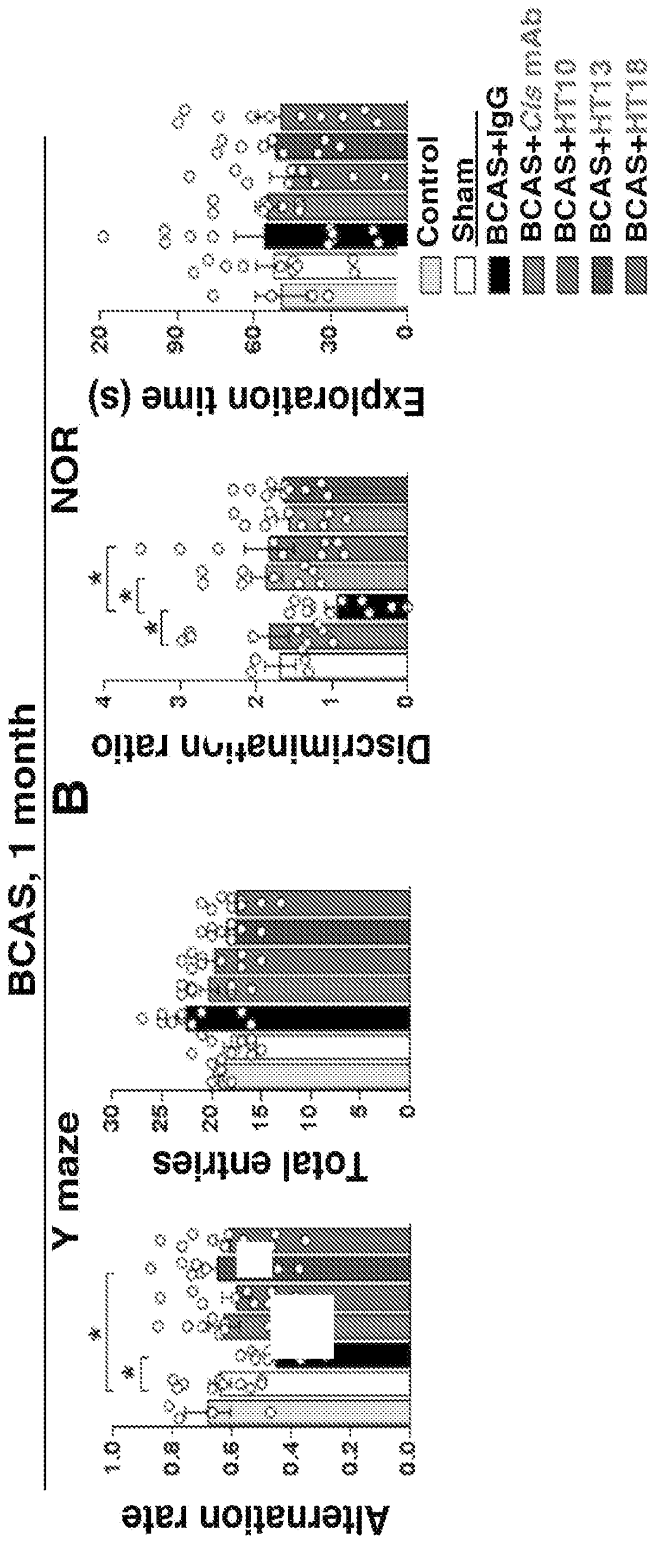
Figure 92B:
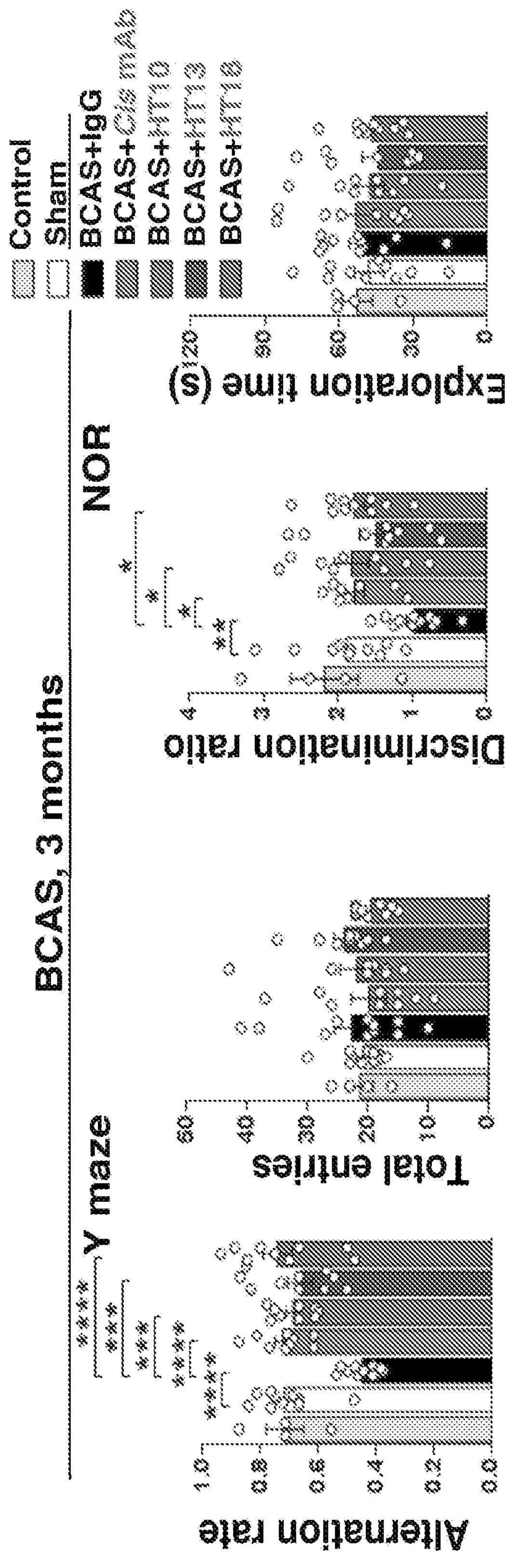
Figure 92C:
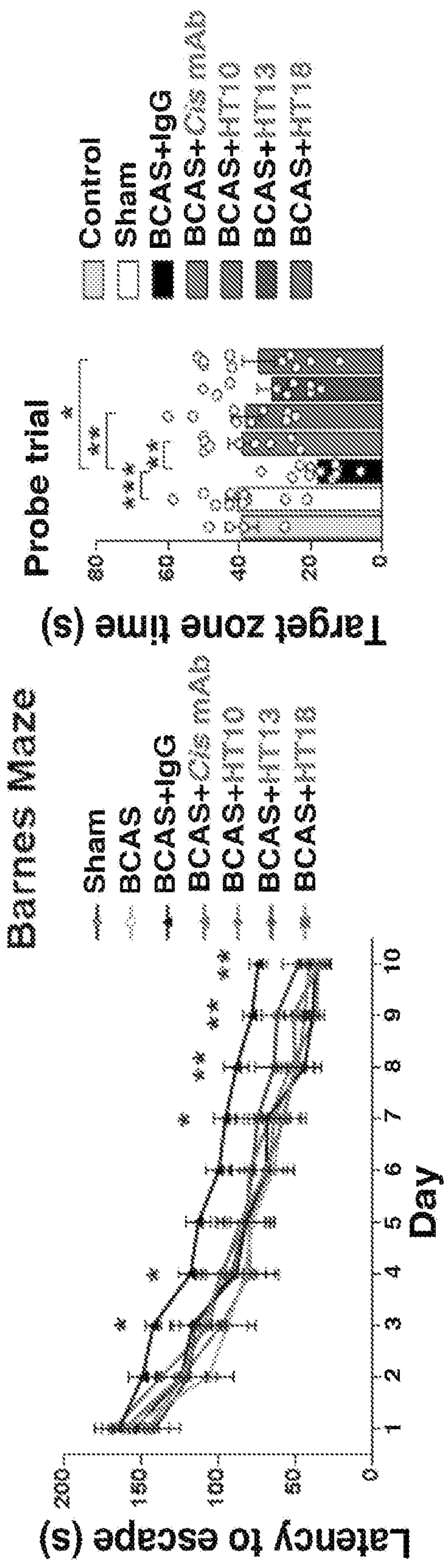

FIGS. 92A-92C shows that humanized cis P-tau mAb variants have potent therapeutic efficacy in Vascular contributions to Cognitive Impairment and Dementia (VCID) mice. BCAS mice were treated with novel humanized cis mAbs (HT10 and HT18), murine cis mAb C113 (as described in, e.g., U.S. Pat. No. 9,688,747, positive control), mouse-human chimeric HT13 (positive control), or IgG (negative control). Behavioral changes were assay by Y-maze and novel object recognition (NOR) at 1 month after BCAS (FIG. 92A); by Y-maze and NOR at 3 months after BCAS (FIG. 92B); and by Barnes maze at 3 months after BCAS (FIG. 92C). *, $p<0.05$; , $p<0.01$; *, $p<0.001$; ****, $p<0.0001$.

Figure 93:
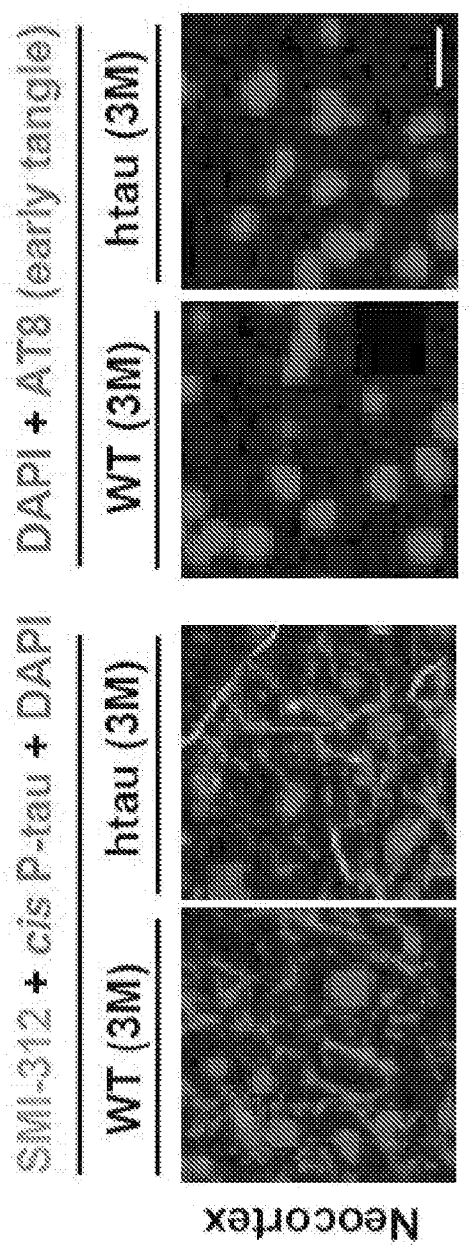

FIG. 93 shows immunofluorescence staining results of three-month-old (3M) htau mouse brain sections that were subjected to double Immunofluorescence (IF) with axon marker SMI-312 and cis P-tau; or single IF with early tangle marker AT8 along with DAPI, scale bar=20 μm.

Figures 94A, 94B, 94C:
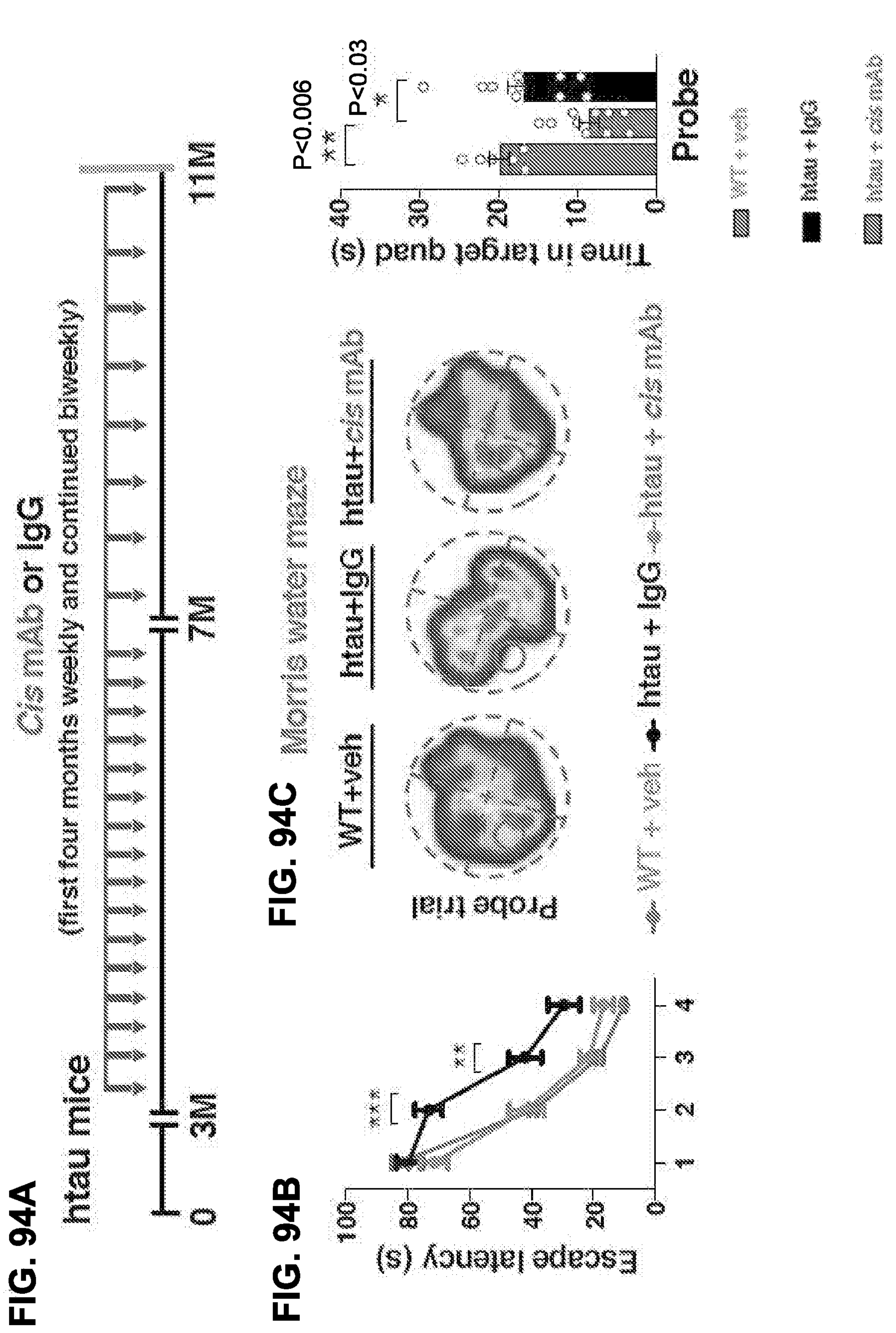

FIG. 94A is a schematic diagram showing the experimental setup (Black arrows, antibody injection; green lines, functional or pathological assays). Three-month-old htau mice were subjected to treatment regimens of cis mAb or IgG controls for 8-months, followed by functional and pathological examinations.

FIGS. 94B-94C are graphs showing that cis mAb treatment prevents the development of cognitive deficits in htau mice, as assayed by the Morris water maze after 8 months of treatment in htau mice escape latency (FIG. 94B) in the acquisition trials and trajectories and time spent in target quadrant in the probe trial (FIG. 94C).

Figure 95A:
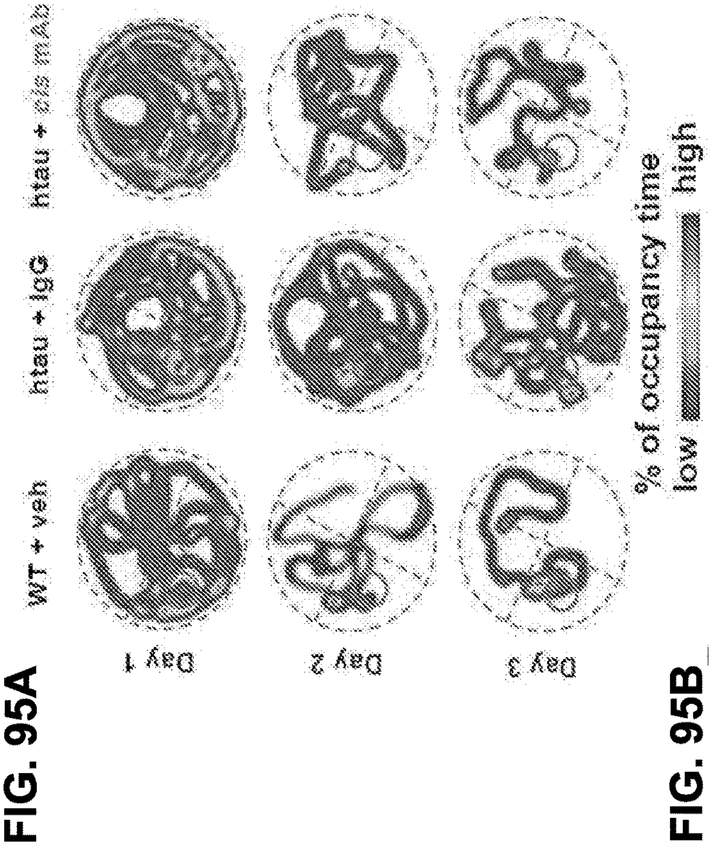
Figure 95B:
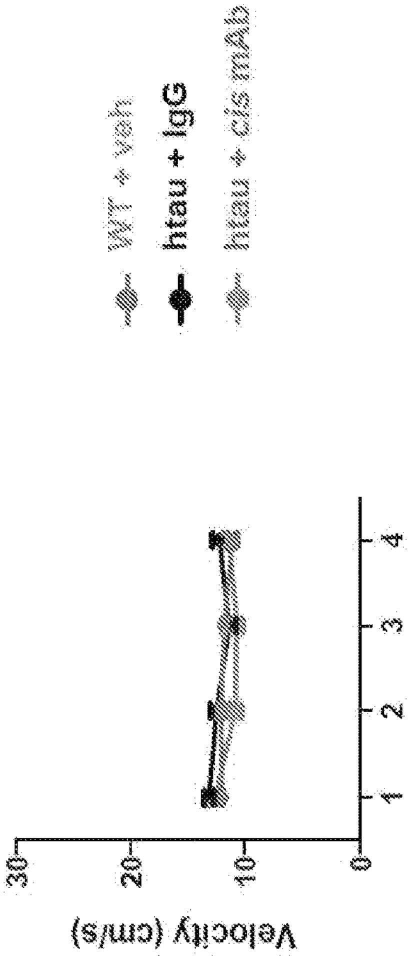
Figure 95C:
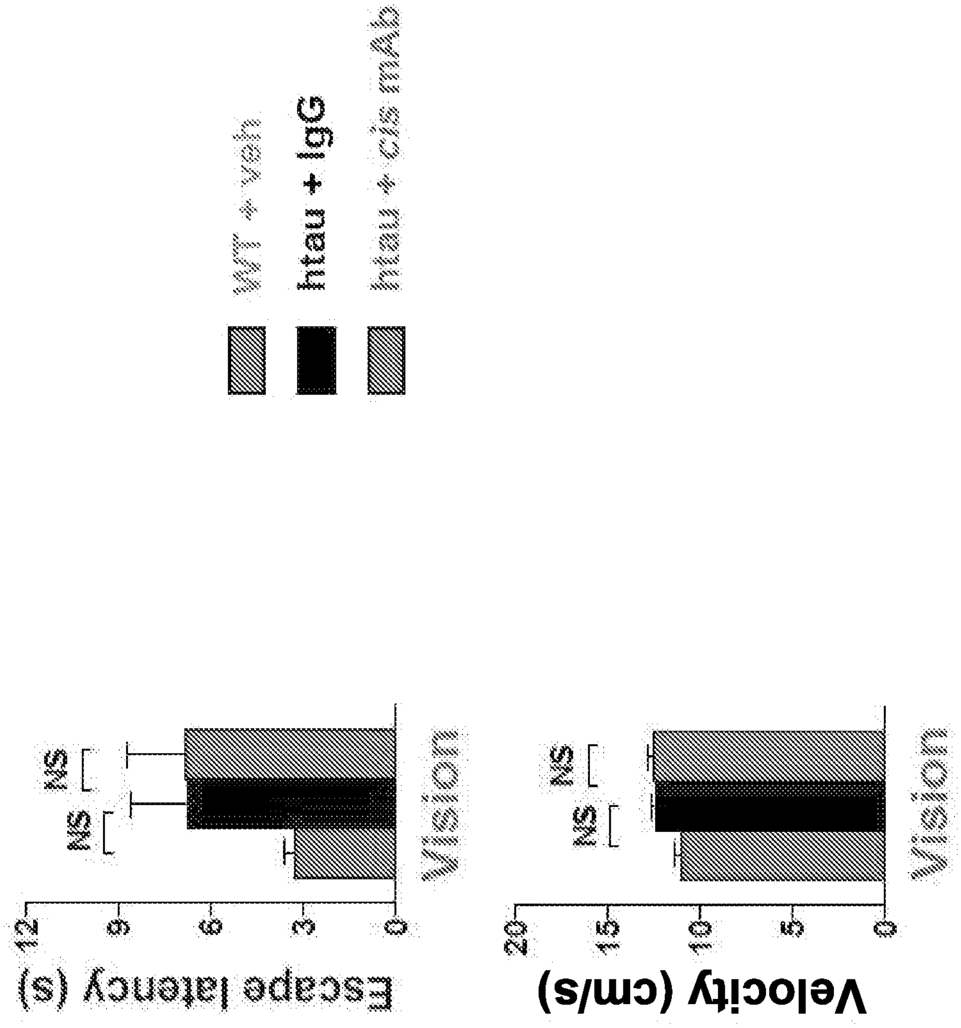

FIGS. 95A-95C are graphs showing results of the Morris water maze after 8 months of cis mAb treatment in htau mice showing trajectories (FIG. 95A) and velocity (FIG. 95B) in the acquisition trial. No differences were observed in the motivation of finding the platform in vision trial of the Morris water maze test between the groups (FIG. 95C). Scale bar, 20 μm. NS: not significant.

Figure 96:
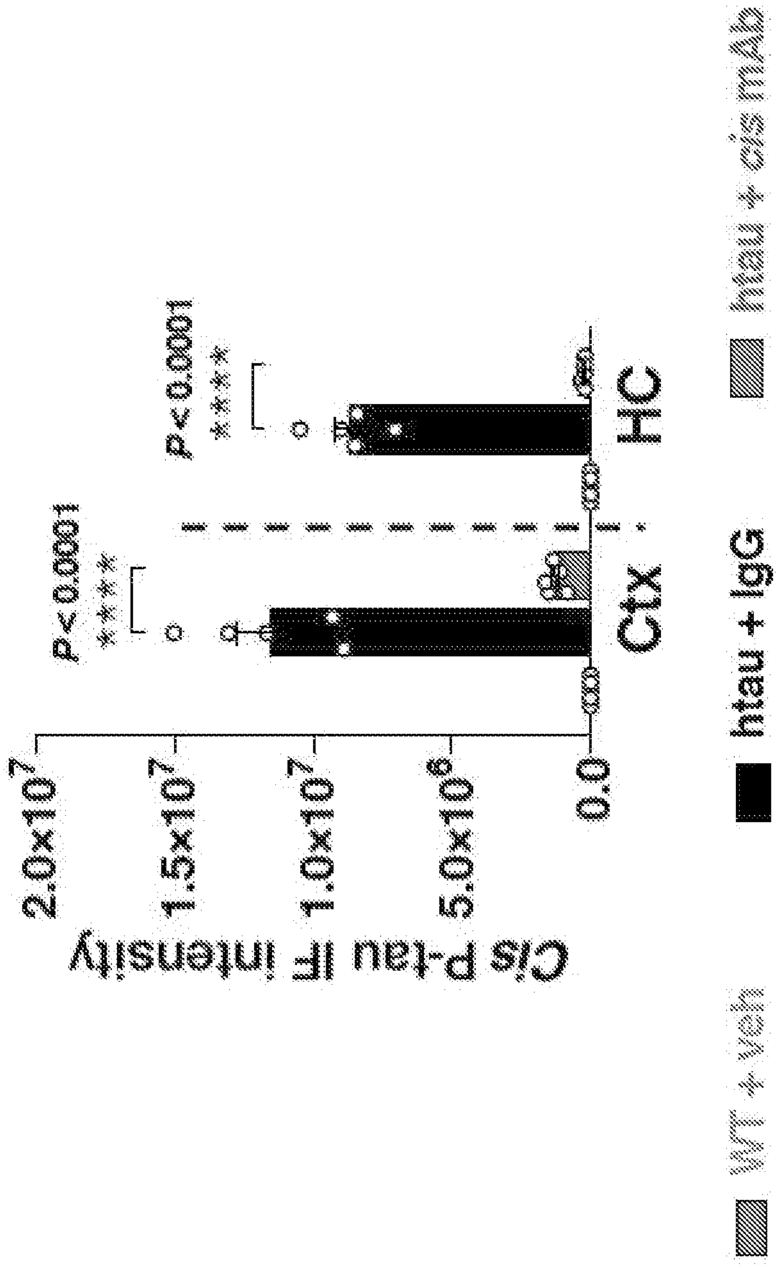

FIG. 96 is a graph showing that cis mAb treatment prevents the accumulation of cis P-tau and the development of tangle-like pathology in htau mice as assayed by immunofluorescence (IF) staining of cis P-tau in the neocortex (Ctx) and hippocampus (HC). The data were presented as means±SEM and the p values were calculated using two-way ANOVA with Bonferroni correction, one-way ANOVA and unpaired two-tailed parametric Student's t-test. NS, not significant; *, $p<0.05$; , $p<0.01$; and **, $p<0.0001$.

Figure 97:
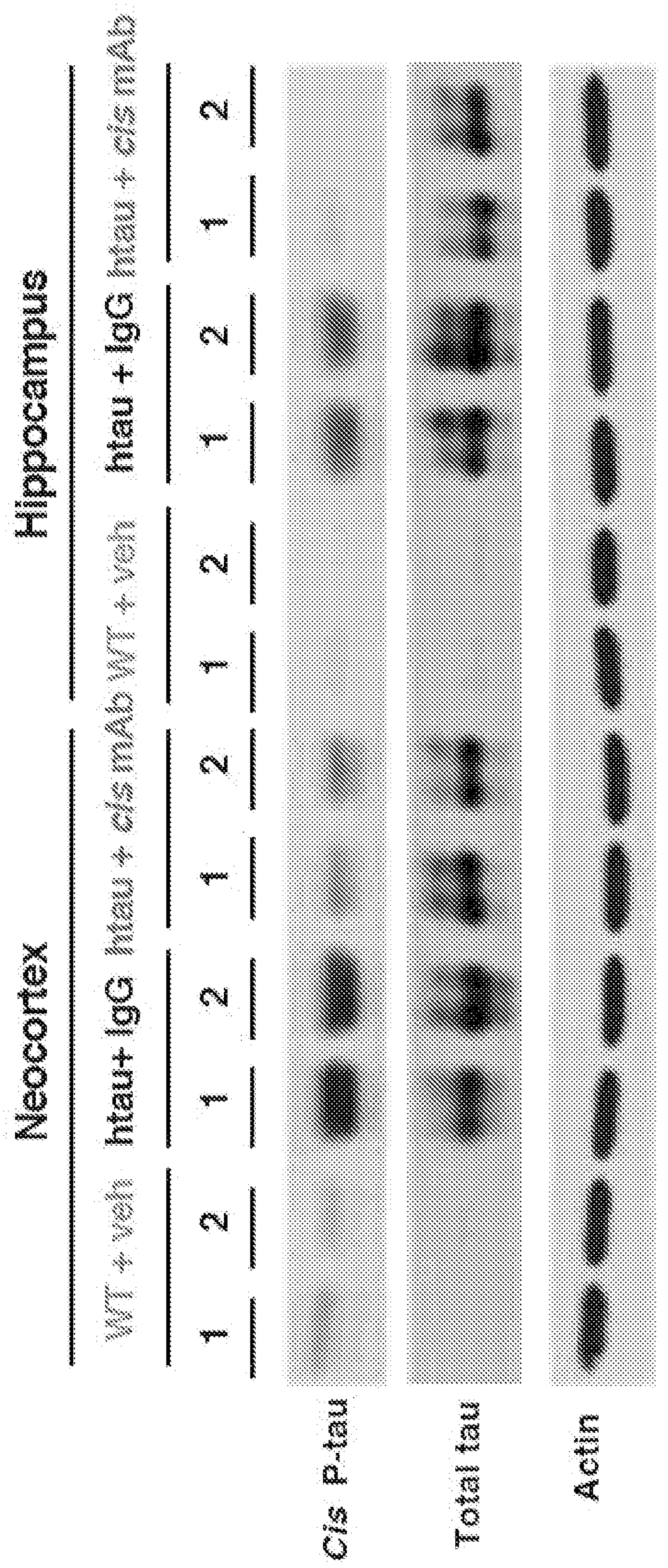

FIG. 97 is a photographic image showing that cis mAb treatment prevents the accumulation of cis P-tau and the development of tangle-like pathology in htau mice as assayed by immunoblotting of cis P-tau and total tau.

Figure 98:
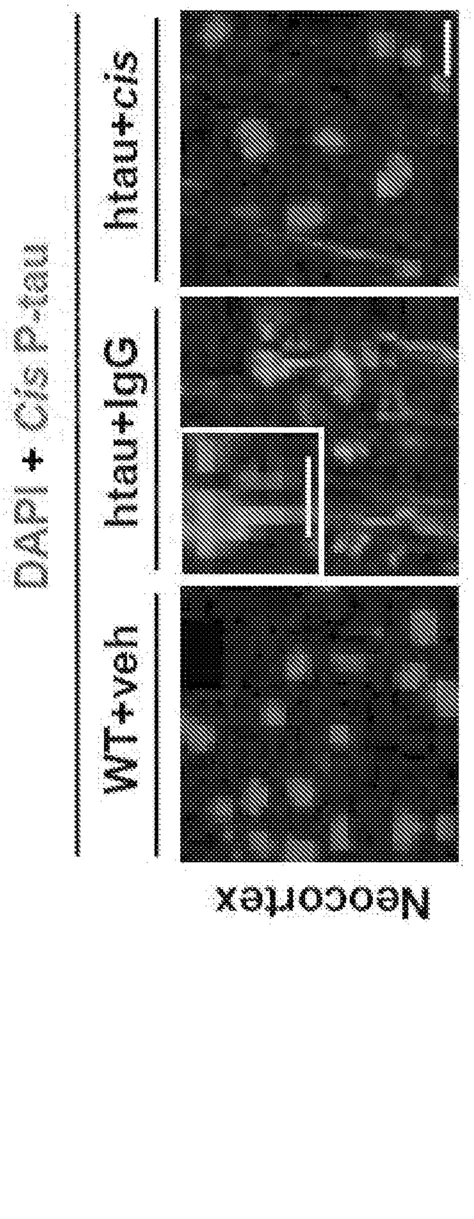

FIG. 98 shows immunofluorescence staining results showing that cis mAb treatment prevented the accumulation of cis P-tau in young htau mice. Scale bar, 20 μm. NS: not significant.

Figure 99B:
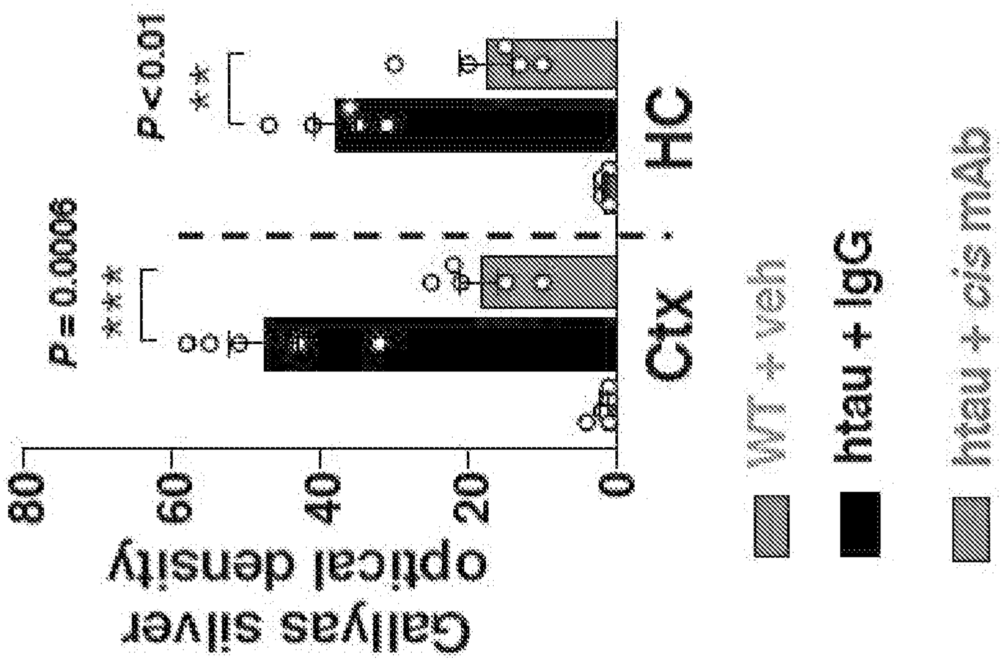
Figure 99A:
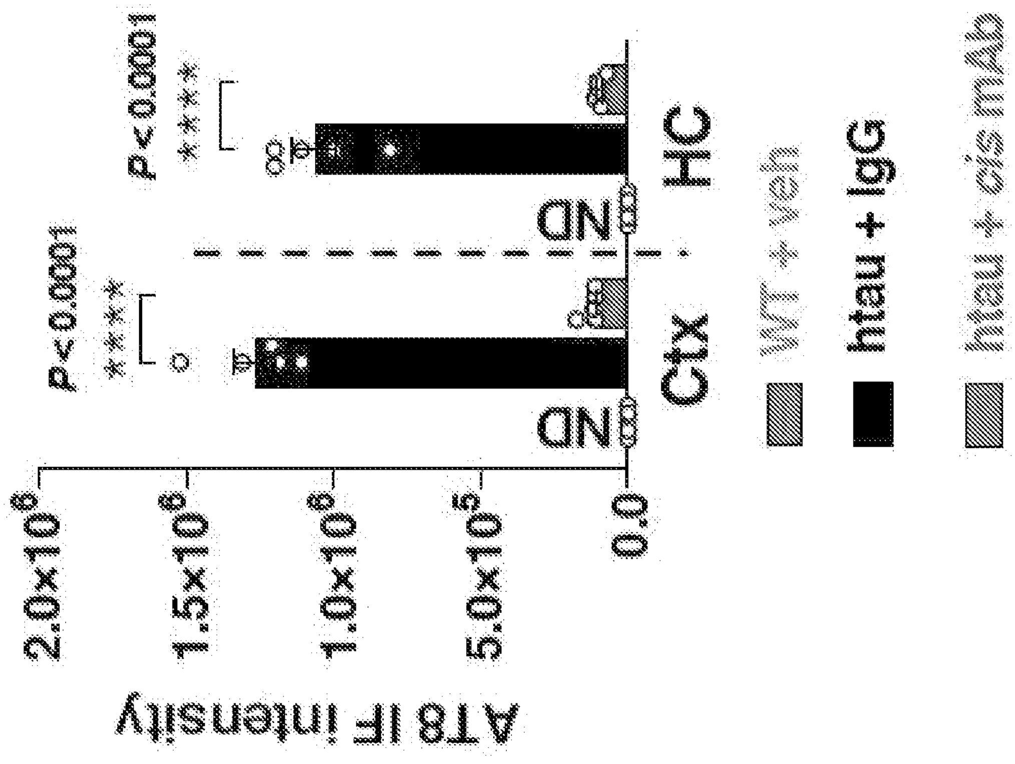
Figure 100A:
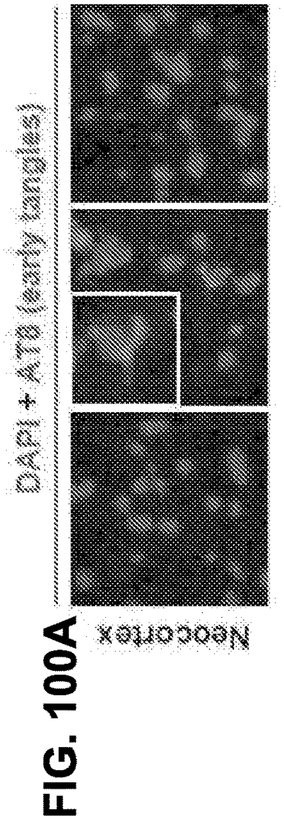
Figure 100B:
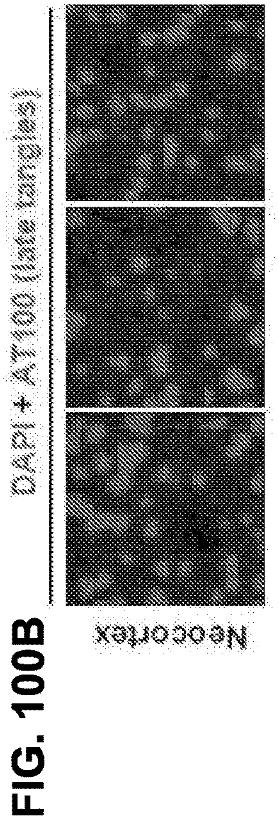
Figure 100C:
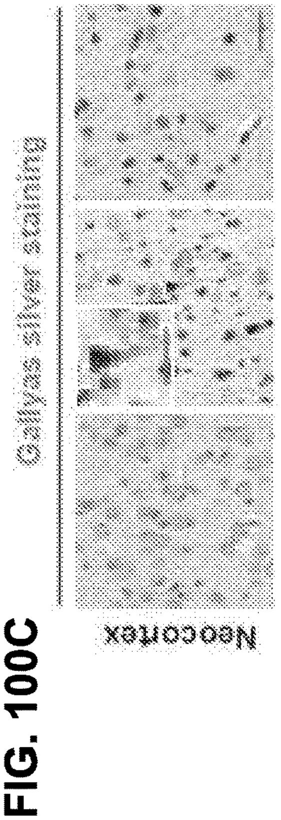
Figure 100D:
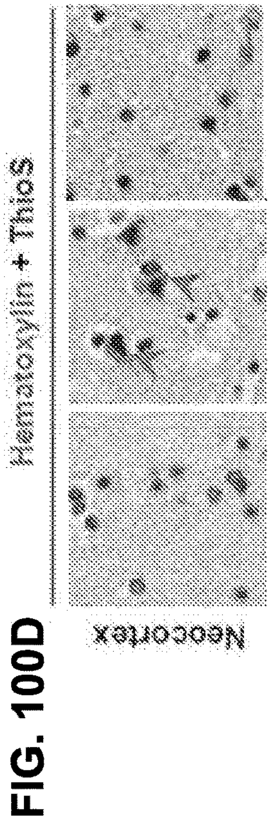

FIGS. 99A-99B show immunofluorescence staining results showing that cis mAb treatment prevents the accumulation of cis P-tau and the development of tangle-like pathology in htau mice as assayed by immunofluorescence with AT8 antibody (FIG. 99A) and Gallyas silver staining (FIG. 99B) to detect tangle-like pathology in neocortex and hippocampus after 8 months of treatment.

FIGS. 100A-100D are images showing that cis mAb treatment prevented the development of tangle-like pathologies detected by AT8 antibody (FIG. 100A), AT100 antibody (FIG. 1001B), Gallyas silver staining (FIG. 1000), and ThioS staining (FIG. 100D) in neocortex of htau mice compared with IgG controls, as visualized by confocal microscopy. Higher magnification images of representative structures are provided in the insets. Neurofibrillary tangles indicated with red arrows in thioflavin S staining. Scale bar, 20 μm.

Figure 101:
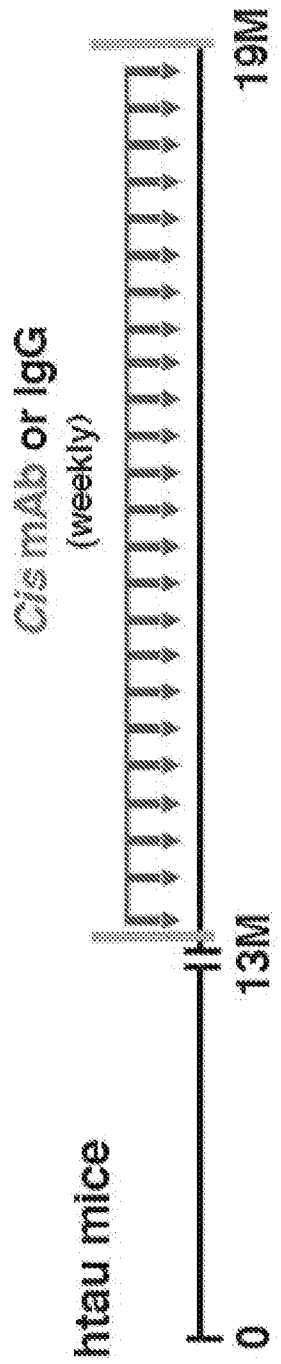

FIG. 101 is a schematic of the timeline of the experimental setup (brown arrows, antibody injection; green lines, functional or pathological assays). Thirteen-month-old (13M) htau mice were subjected to treatment regimens of cis mAb or IgG isotype control for 6-months.

Figure 102B:
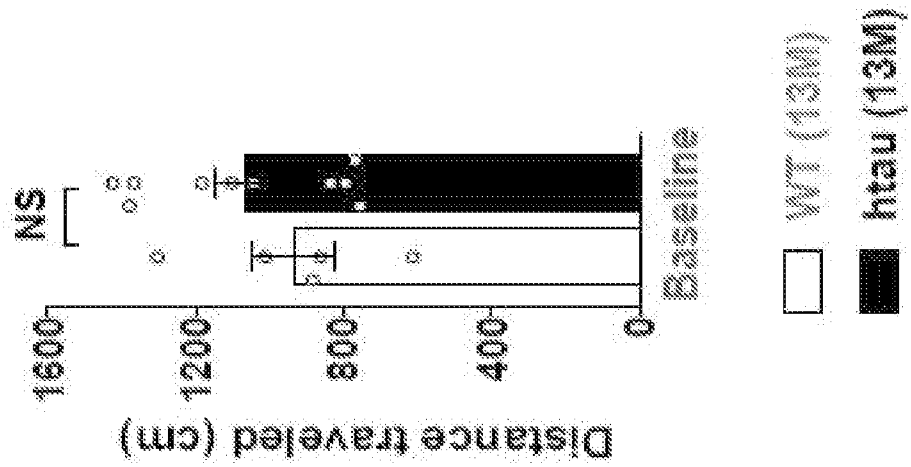
Figure 102A:
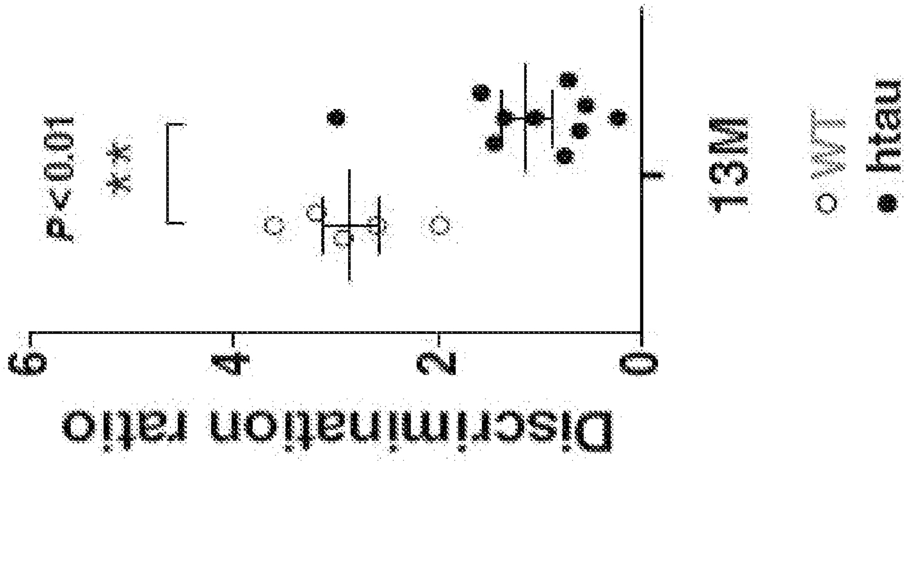

FIGS. 102A-102B are graphs showing cognitive impairment in aged htau mice. On the novel location recognition test, 13M htau mice had poorer cognitive skills compared with age-matched WT controls prior to cis mAb treatment (FIG. 102A). No differences were observed in distance traveled in the novel object location recognition tests between the 13-month-old htau mice and WT controls (FIG. 102B).

Figure 103B:
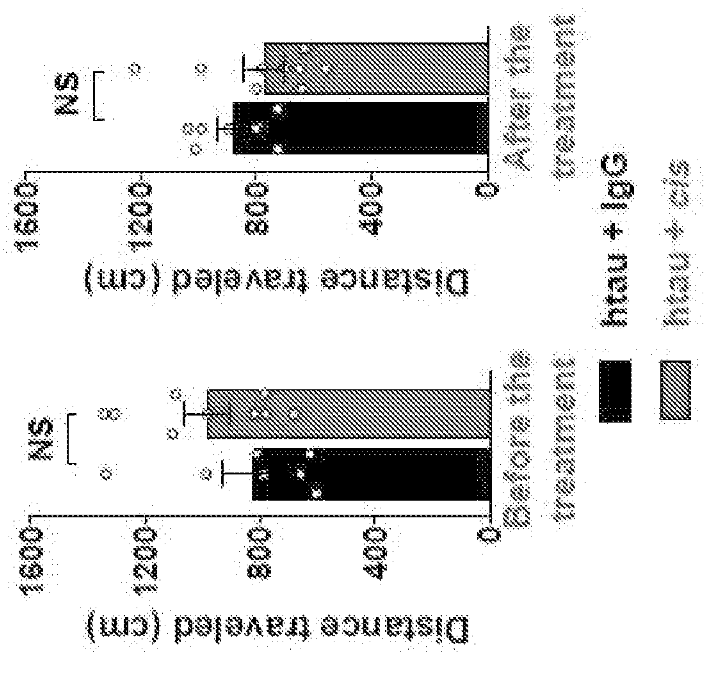
Figure 103A:
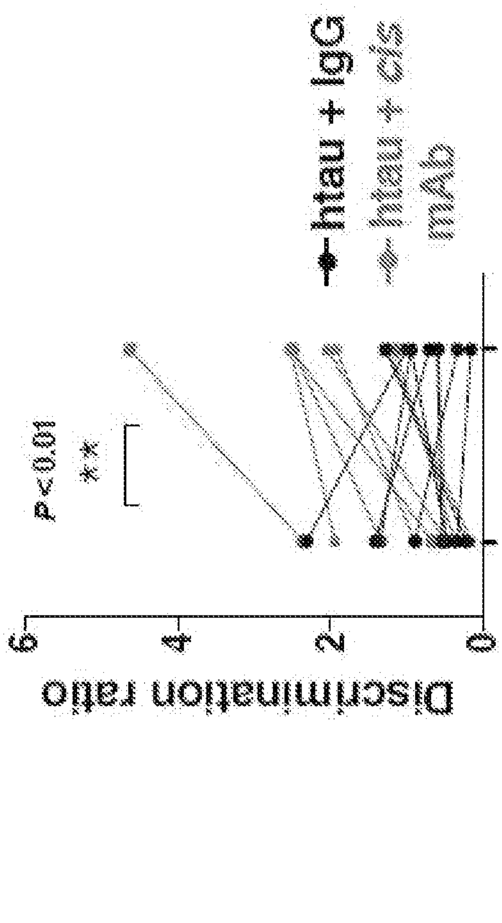

FIGS. 103A-103B are graphs showing that cis mAb treatment of aged htau mice improves learning and memory. Longitudinal assessment of novel location recognition test for mice before and after treatment with either cis mAb (red) or control (black) (FIG. 103A). No differences were observed in distance traveled in the novel object location recognition tests before and after treatment (FIG. 103B).

Figure 104:
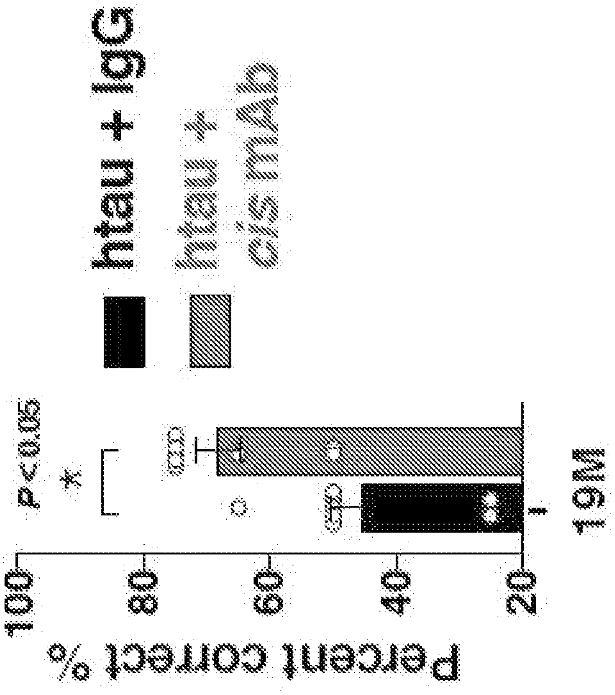

FIG. 104 is a graph showing that cis mAb treatment of aged htau mice improves learning and memory, as assessed by the T-maze test maze after treatment. 6-10 mice per group were included in each of the behavioral tests. The data were presented as means±SEM and the p values were calculated using two-way ANOVA with Bonferroni correction, one-way ANOVA and unpaired two-tailed parametric Student's t-test. NS, not significant; *, $p<0.05$; , $p<0.01$; and **, $p<0.0001$.

Figure 105A:
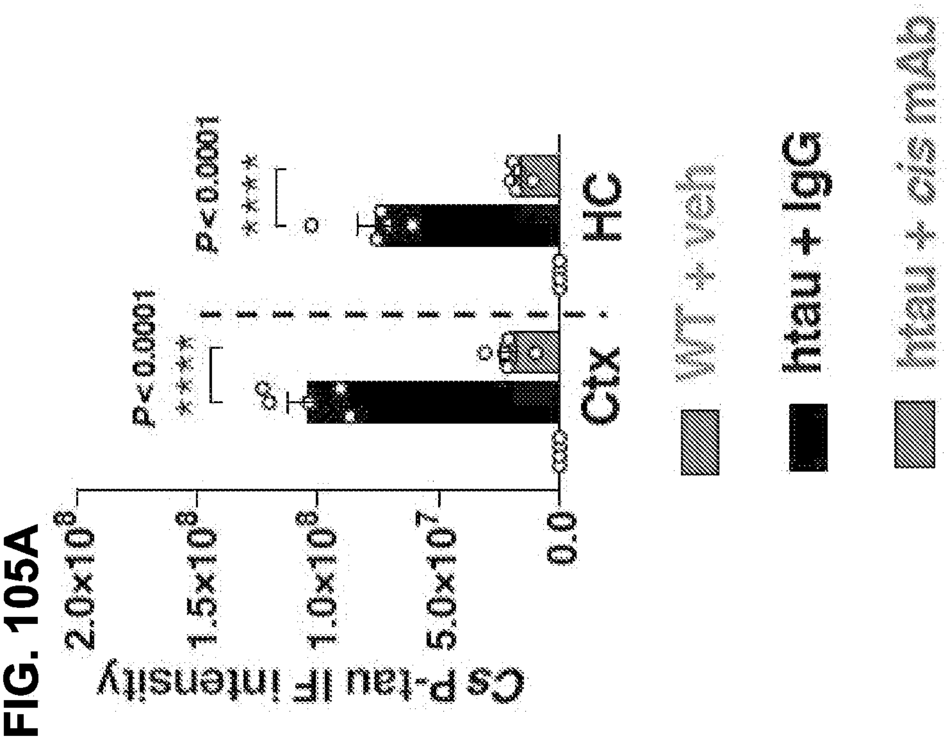
Figure 105B:
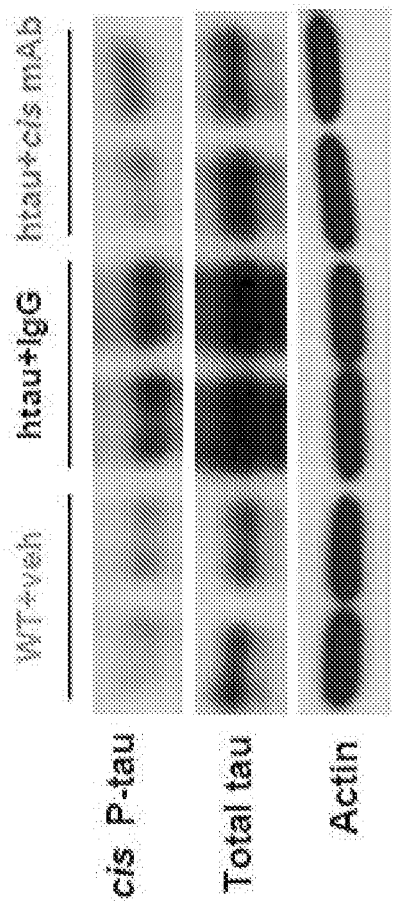

FIG. 105A is a graph showing that cis mAb treatment of aged htau mice reduces the accumulation of cis P-tau and neuronal loss without clearance of tangle-like pathology, as shown by immunofluorescence staining (IF) for cis P-tau, FIG. 105B is an immunoblotting photograph showing cis mAb treatment of aged htau mice reduces the accumulation of cis P-tau after 6 months treatment of aged htau mice and total tau in the hippocampus. Actin blotting shown as control.

Figure 105C:
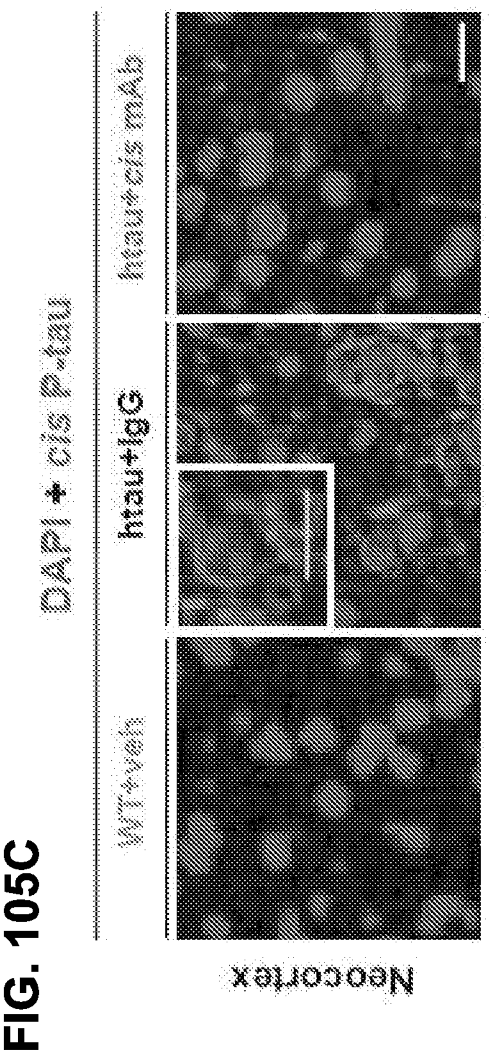

FIG. 105C is immunofluorescence staining images showing that cis mAb treatment of aged htau mice reduces the accumulation of cis P-tau. After 6 months treatment of aged htau mice, immunofluorescence staining (IF) for cis P-tau in the neocortex was performed. Scale bar, 20 μm.

Figure 106A:
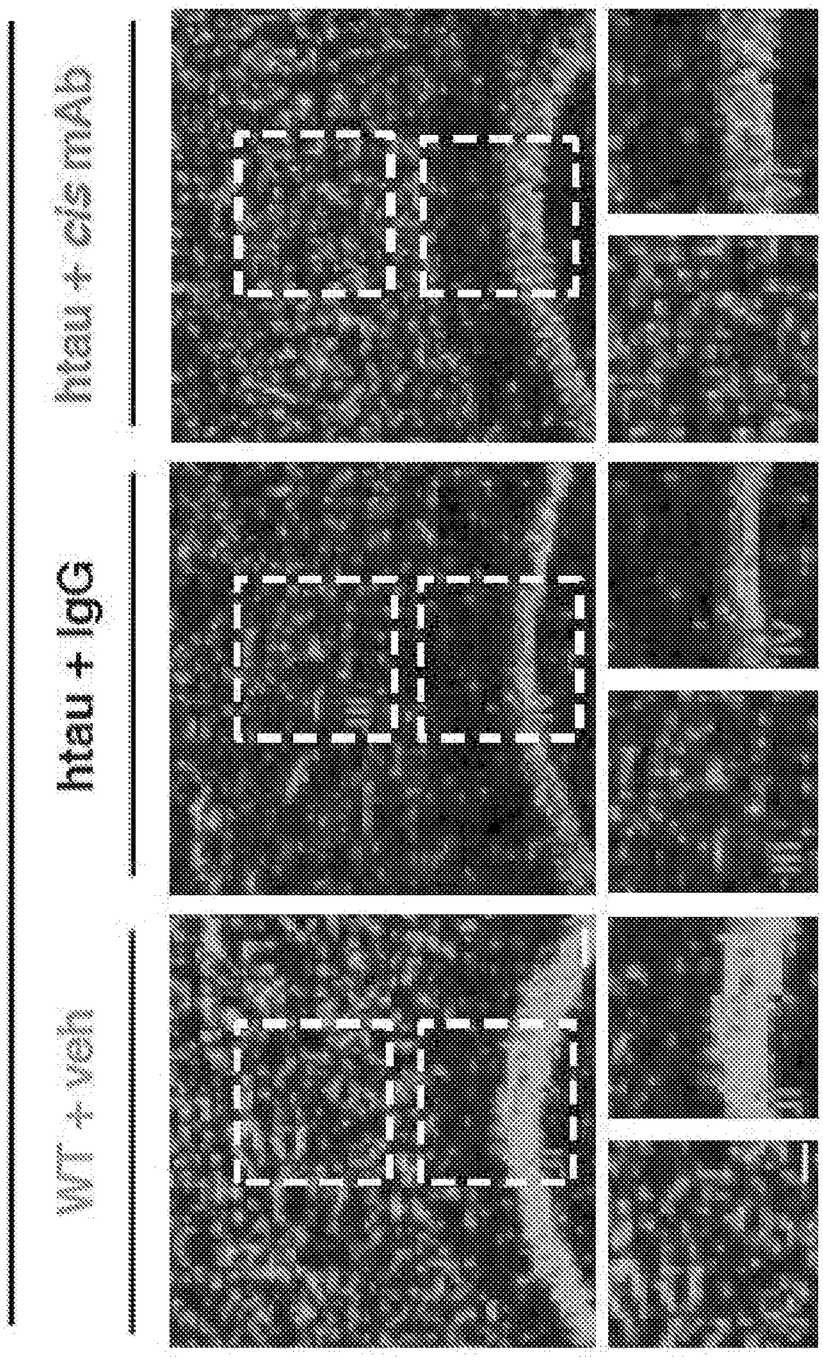
Figure 106B:
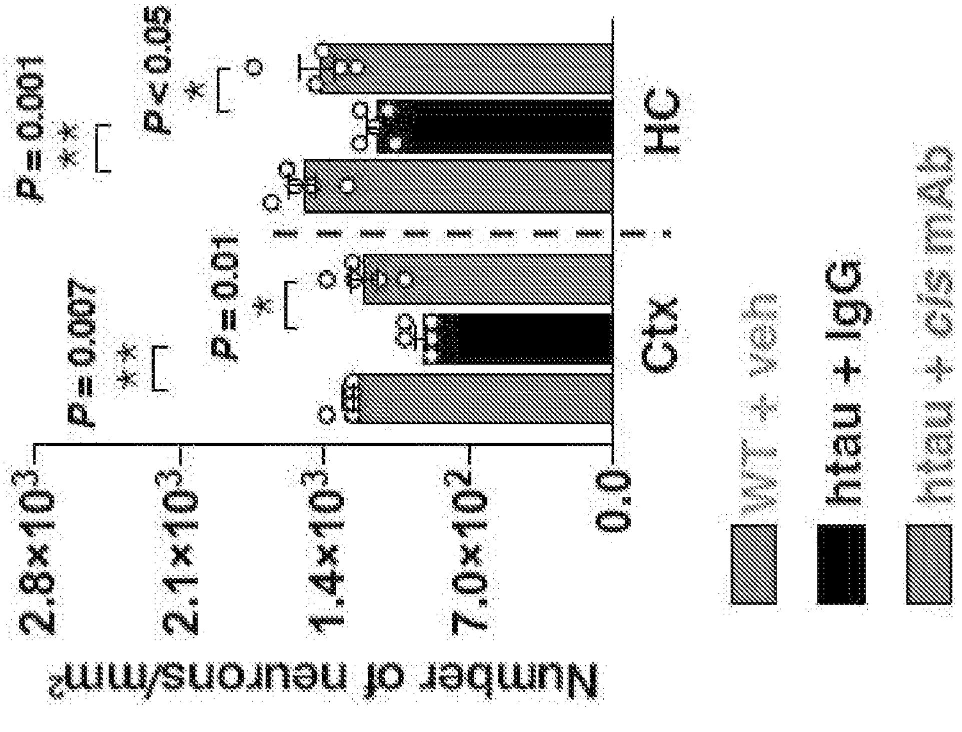

FIGS. 106A-106B are a series of immunofluorescence images and a graph showing cis mAb treatment of aged htau mice reduces the accumulation of cis P-tau and neuronal loss without clearance of tangle-like pathology, as shown by immunofluorescence staining (IF) for NeuN antibody (FIG. 106A) to detect neuronal loss in neocortex and hippocampus. Inset images are high magnifications of representative areas. Statistical data for NeuN-positive neurons are provided in (FIG. 106B). Scale bar, 20 μm; Ctx, neocortex; HC, hippocampus; ND, not detectable. Brains from 4-5 male mice were studied for immunohistochemistry, 6-10 mice per group were included in each of the behavioral tests. The data were presented as means±SEM and the p values were calculated using two-way ANOVA with Bonferroni correction, one-way ANOVA and unpaired two-tailed parametric Student's t-test. NS, not significant; *, $p<0.05$; , $p<0.01$; and **, $p<0.0001$.

Figure 107A:
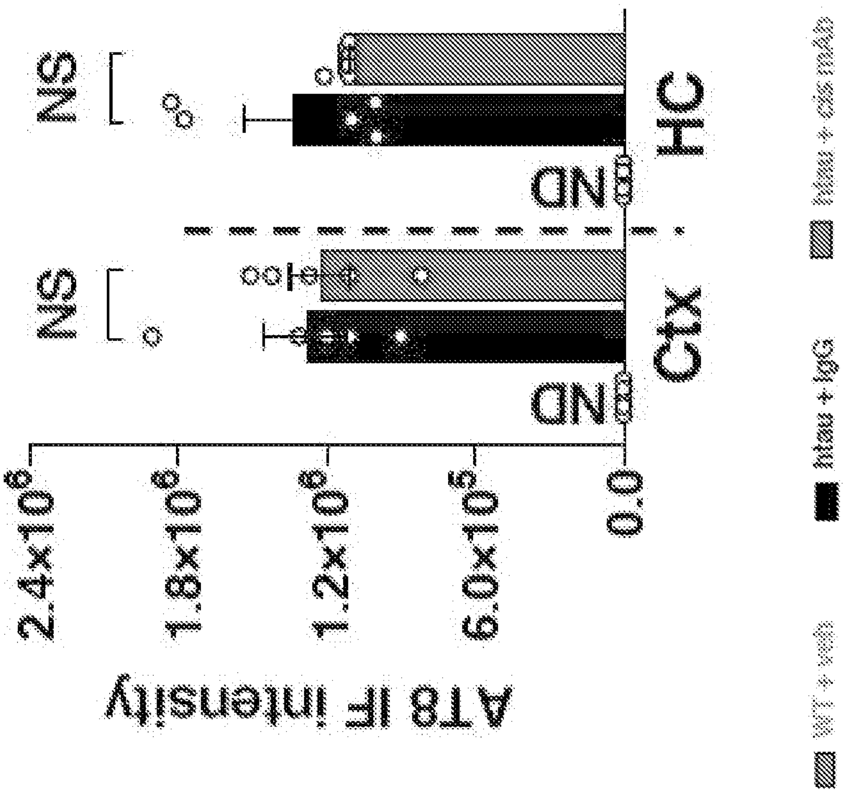
Figure 107B:
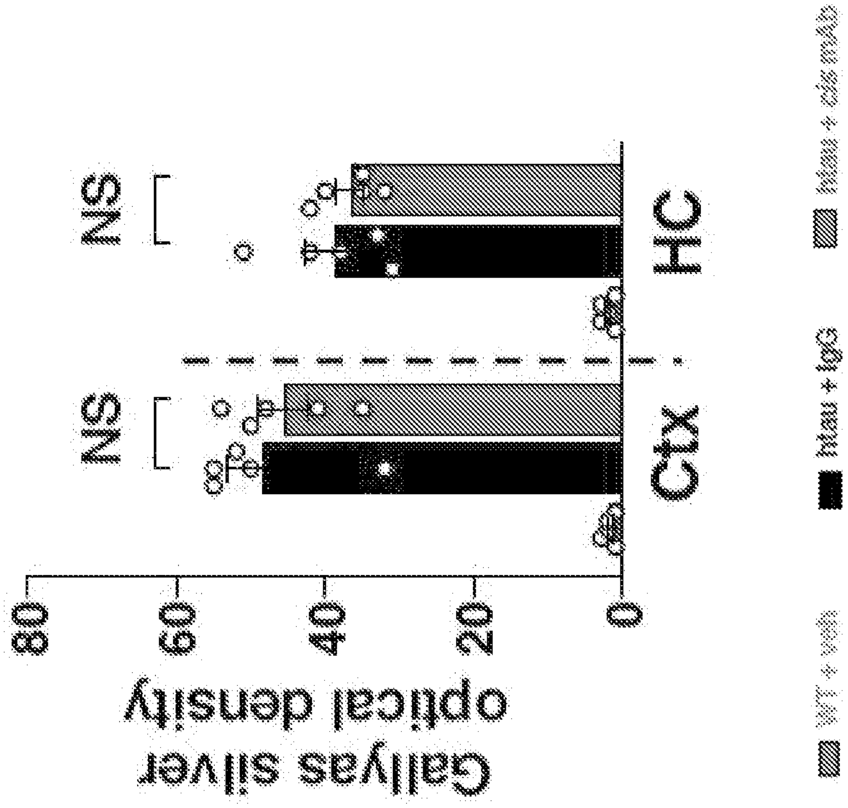

FIGS. 107A-107B are graphs showing that cis mAb treatment of aged htau mice reduces the accumulation of cis P-tau and neuronal loss without clearance of tangle-like pathology, as shown by immunofluorescence staining (IF) staining with AT8 mAb (FIG. 107A), Gallyas silver staining (FIG. 107B) to detect tangle-like pathology in neocortex and hippocampus. Inset images are high magnifications of representative areas. Statistical data for NeuN-positive neurons are provided in (I). Scale bar, 20 μm; Ctx, neocortex; HC, hippocampus; ND, not detectable. Brains from 4-5 male mice were studied for immunohistochemistry, 6-10 mice per group were included in each of the behavioral tests. The data were presented as means±SEM and the p values were calculated using two-way ANOVA with Bonferroni correction, one-way ANOVA and unpaired two-tailed parametric Student's t-test. NS, not significant; *, $p<0.05$; , $p<0.01$; and **, $p<0.0001$.

Figure 108A:
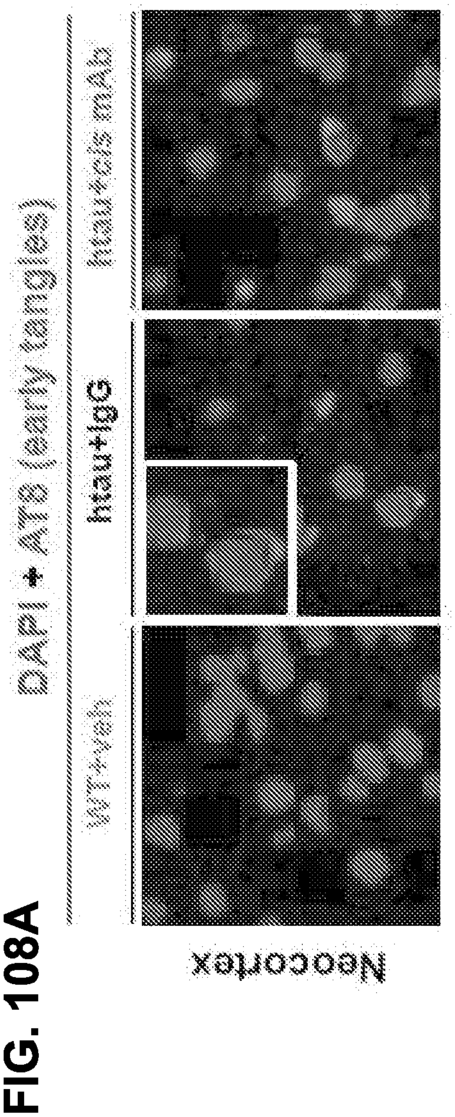
Figure 108B:
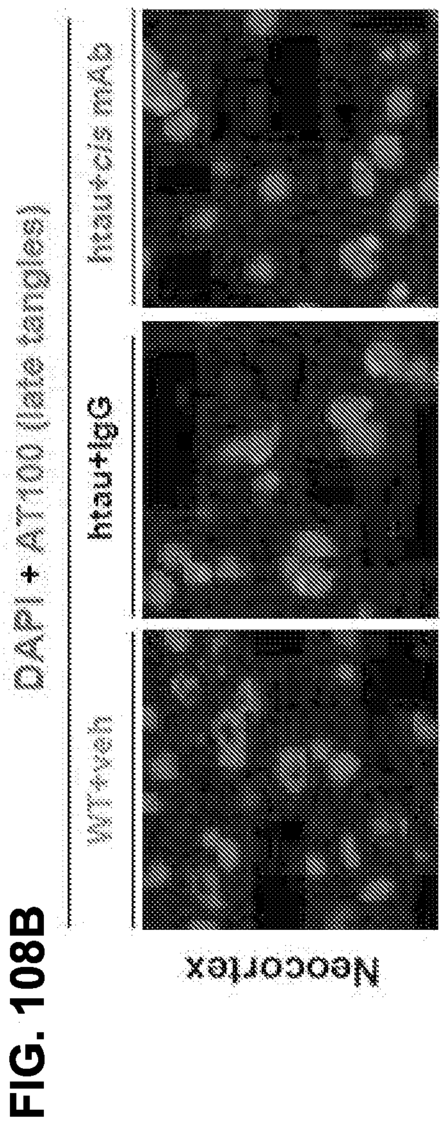

FIGS. 108A-108B are immunofluorescence images showing Cis mAb treatment did not change the accumulation of tangle-like pathologies detected by AT8 antibody (FIG. 108A) and AT100 antibody (FIG. 108B) in neocortex and hippocampus of the mice, as visualized by confocal microscopy. Higher magnification images of representative structures are provided in the insets. Neurofibrillary tangles indicated with red arrows in thioflavin S staining. Scale bar, 20 μm.

Figure 108C:
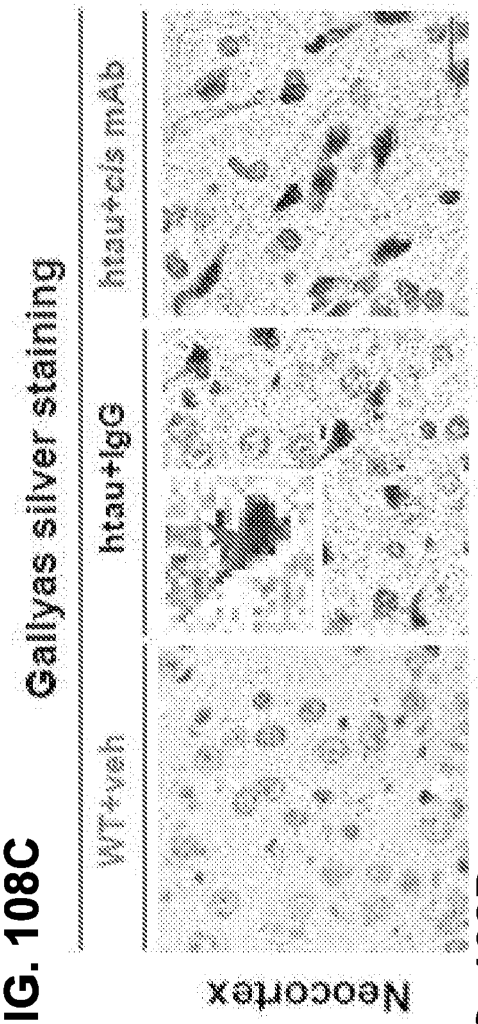
Figure 108D:
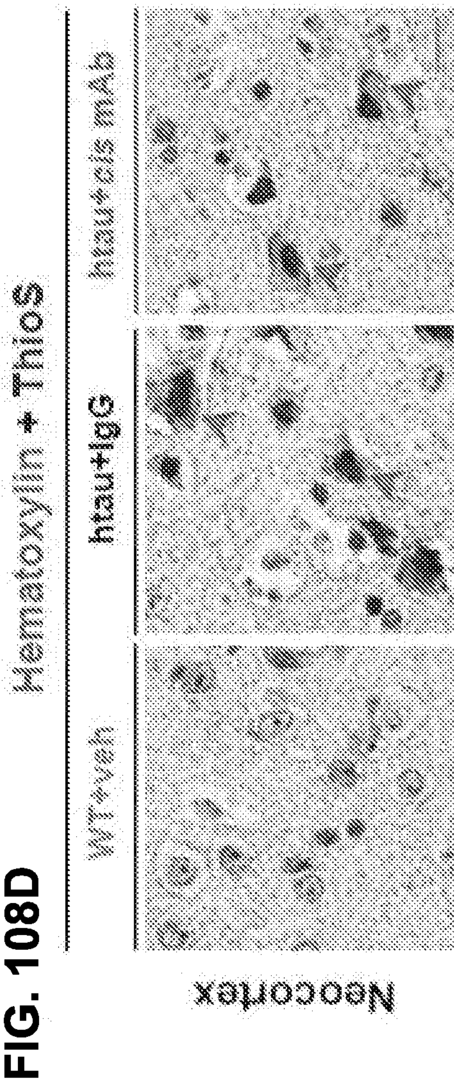

FIGS. 108C-108D are histological images showing Cis mAb treatment did not change the accumulation of tangle-like pathologies detected by Gallyas silver staining (FIG. 108C) and ThioS staining (FIG. 108D) in neocortex and hippocampus of the mice, as visualized by confocal microscopy. Higher magnification images of representative structures are provided in the insets. Neurofibrillary tangles indicated with red arrows in thioflavin S staining. Scale bar, 20 μm.

Figure 109:
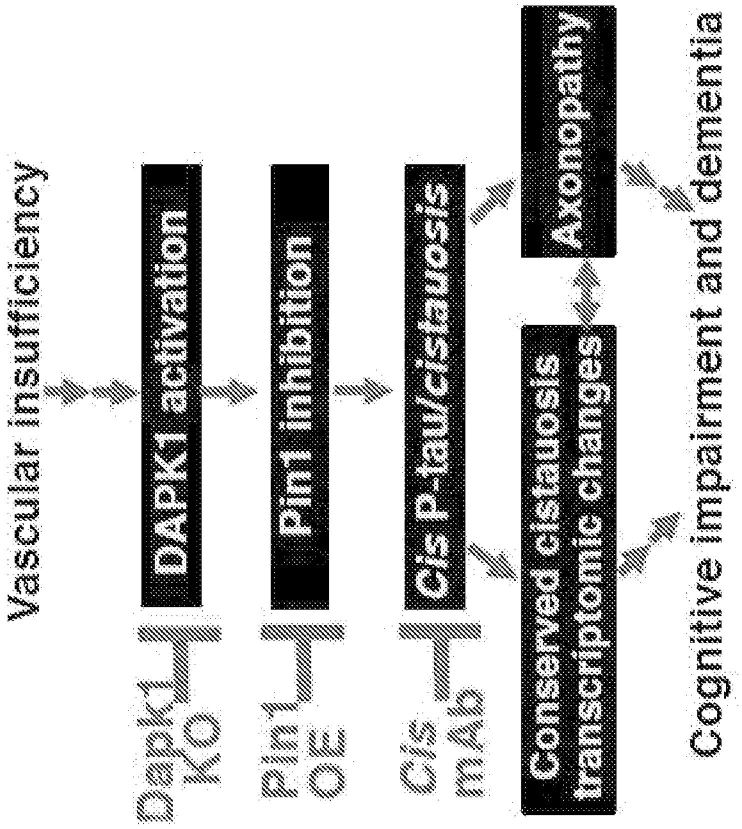

FIG. 109 is a schematic model for Pin1 and cis P-tau in VCID. Neurovascular insufficiency activates DAPK to inhibit Pin1, which fails to repress the induction of cis P-tau. Cis P-tau induction can be attenuated by cis mAb treatment, Pin1 overexpression (OE) or DAPK knockout (KO). If not attenuated, cis P-tau induces the conserved transcriptomic changes, cistauosis and axonopathy, eventually leading to cognitive impairment and dementia. Double arrow indicate possible involvement of multiple molecular events in between.

Figure 110:
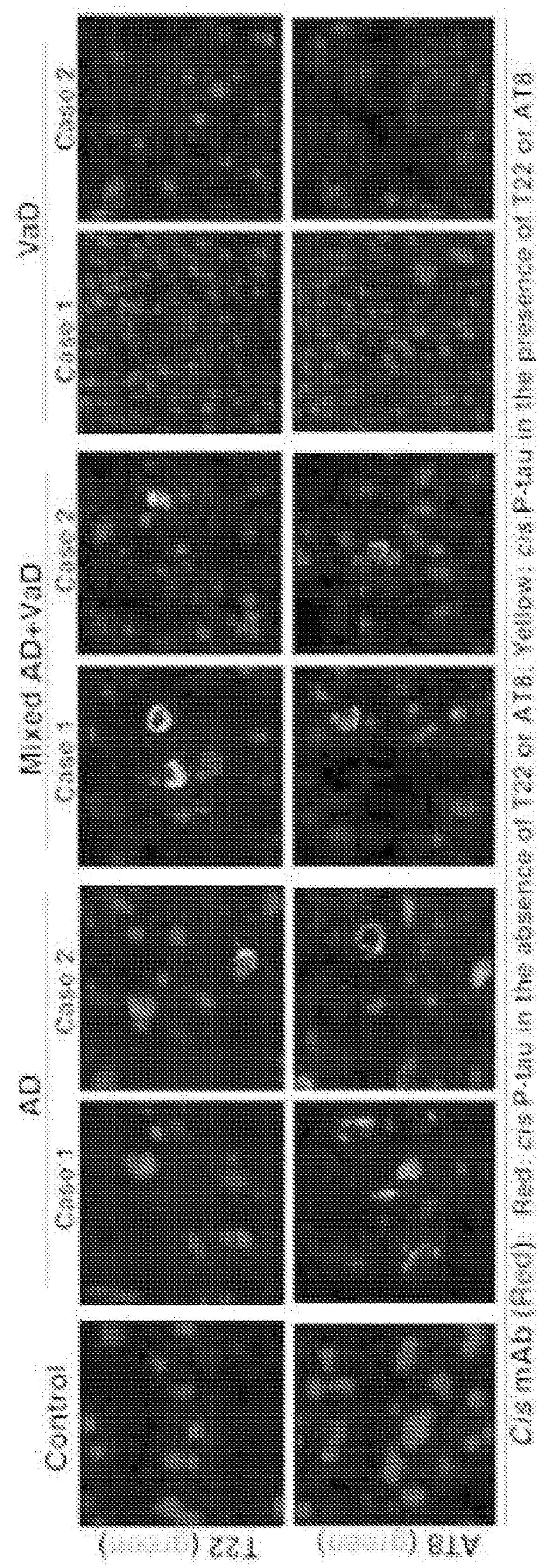

FIG. 110 is a series of immunofluorescence images showing robust cis P-tau present in the pure VaD patients and partially colocalizes with tau oligomers (T22) and tangle epitopes (AT8) in AD and mixed AD and VaD patients. Cis P-tau, tau oligomers and tangles are absent in the brain of age matched non-dementia control patients. Robust cis P-tau (red), tau oligomers and tangles (green) are present and partially co-localize in AD and mixed AD and VaD patients. Robust cis P-tau is present in the pure VaD patients in the absence of tau oligomers or tangles in verified VaD human brains.

Figure 111B:
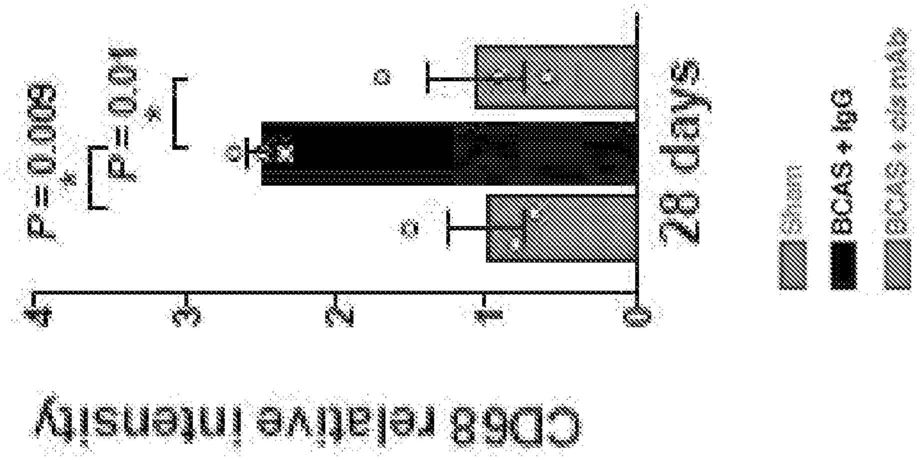
Figure 111A:
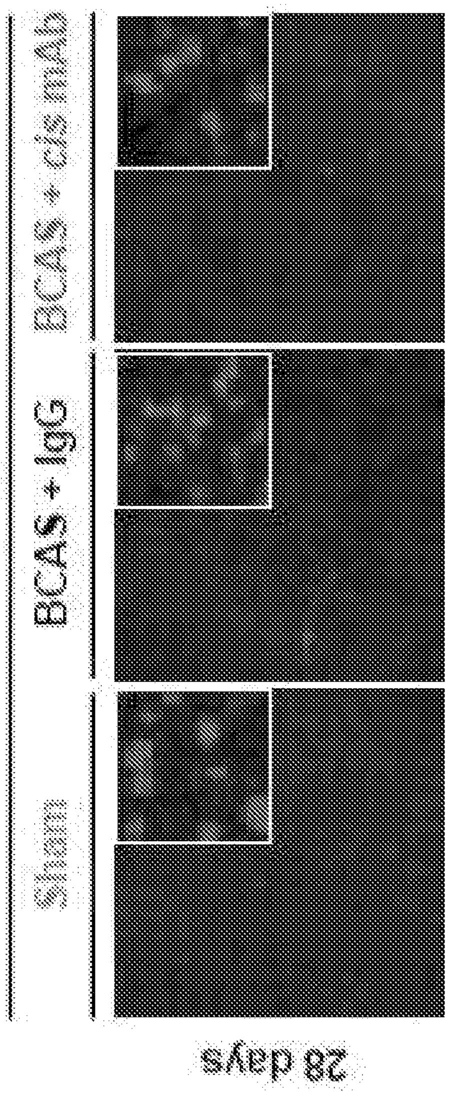

FIGS. 111A-111B is a group of immunofluorescence images showing cis mAb treatment of BCAS mice inhibits markers consistent with neuroinflammation at 28 days, as examined by immunofluorescence staining for microglia marker CD68 (FIG. 111A), followed by quantitation of signal intensity (FIG. 111B). Scale bar, 10 μm. CC: corpus callosum; Neo-Ctx: neocortex. Scale bar, 50 μm. The data were presented as means±SEM and the p values were calculated one-way ANOVA and using unpaired two-tailed parametric Student's t-test. NS, not significant; *, $p<0.05$; , $p<0.001$; *, $p<0.0001$.

Figure 112A:
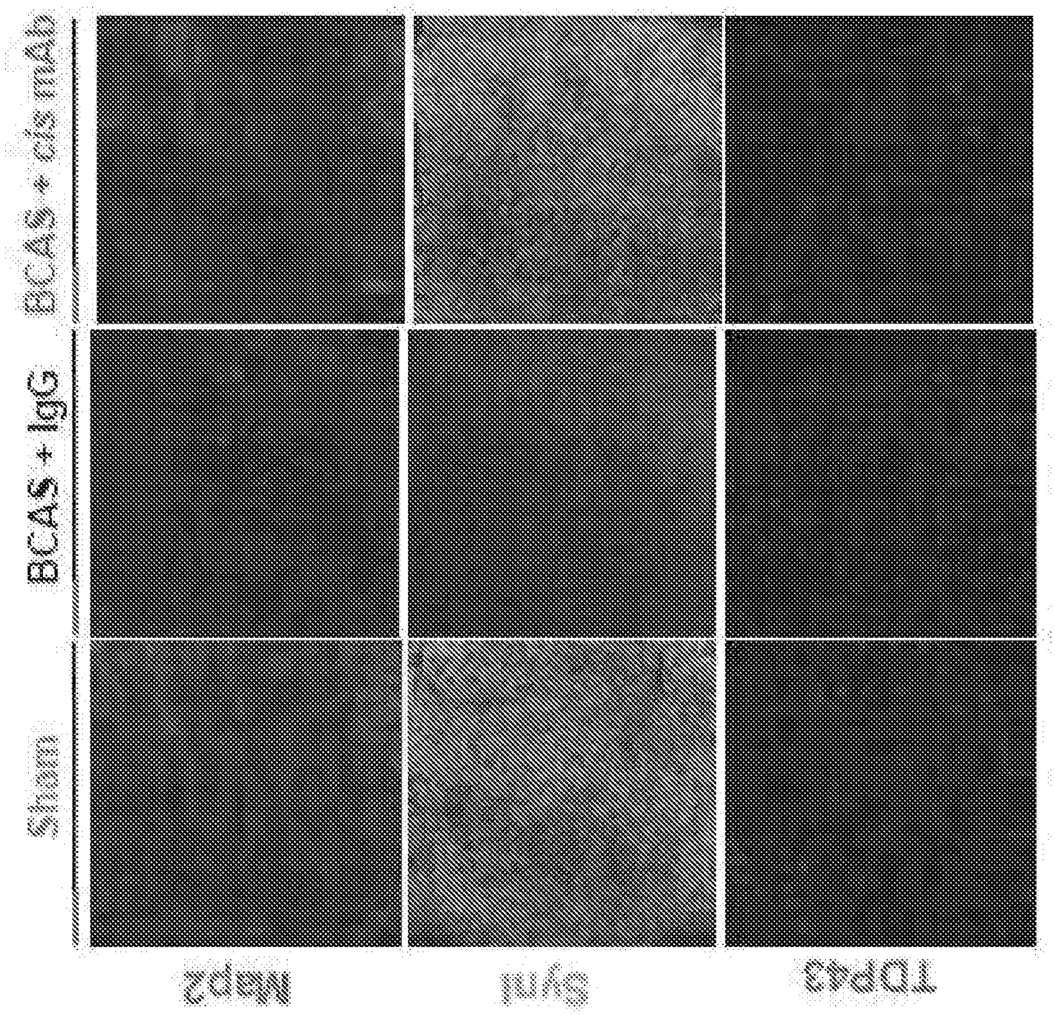
Figure 112B:
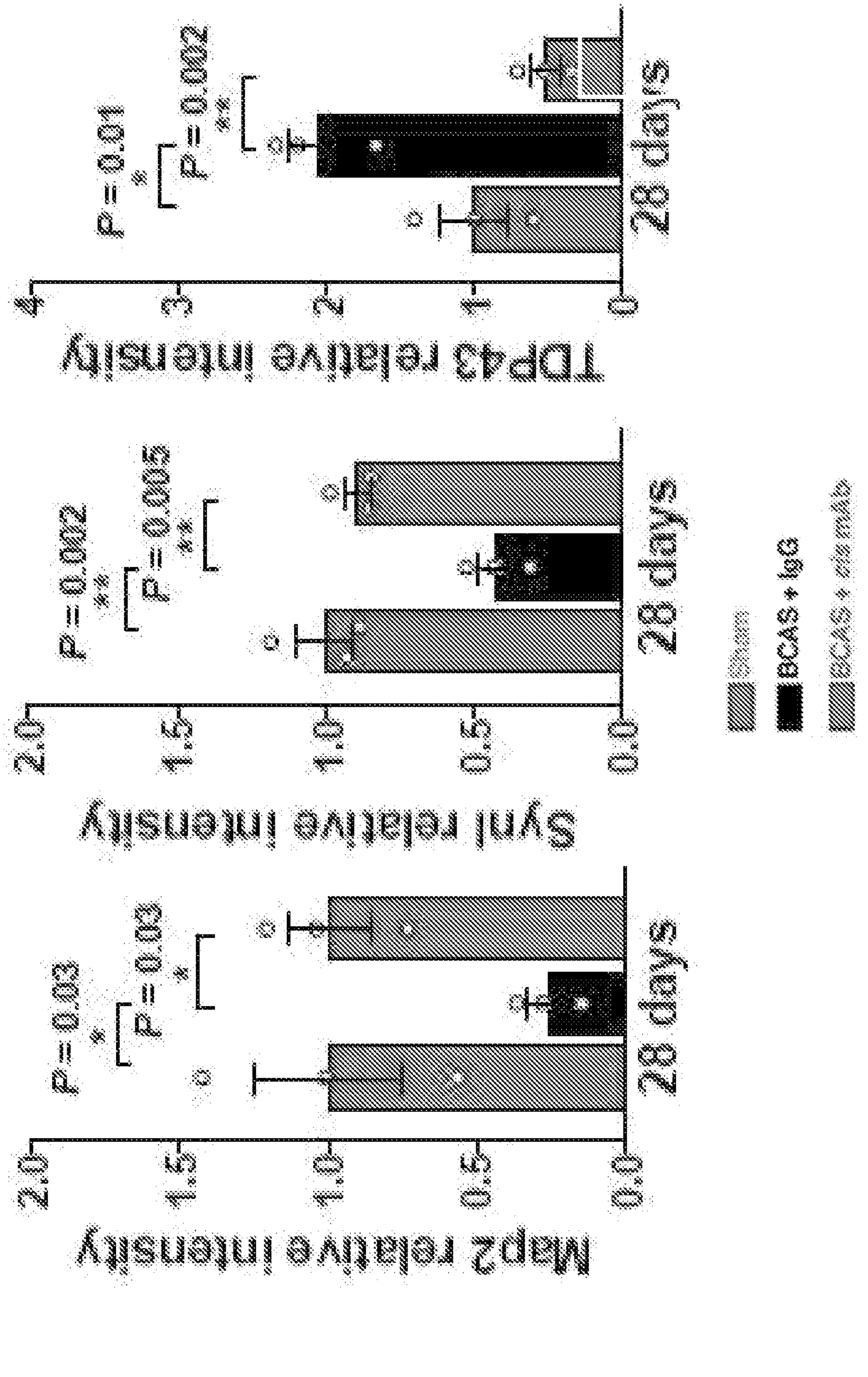

FIGS. 112A-112B is a group of immunofluorescence images showing cis mAb treatment of BCAS mice rescues markers consistent with neurodegeneration, including decreased expression of neuronal marker Map2 and synapses marker Synapsin I, and neurodegenerative marker TDP43, as examined by immunofluorescence staining (FIG. 112A) followed by quantitation (FIG. 112B). Scale bar, 10 μm. CC: corpus callosum; Neo-Ctx: neocortex. Scale bar, 50 μm. The data were presented as means±SEM and the p values were calculated one-way ANOVA and using unpaired two-tailed parametric Student's t-test. NS, not significant; *, $p<0.05$; , $p<0.001$; *, $p<0.0001$.

Figures 113A, 113B:
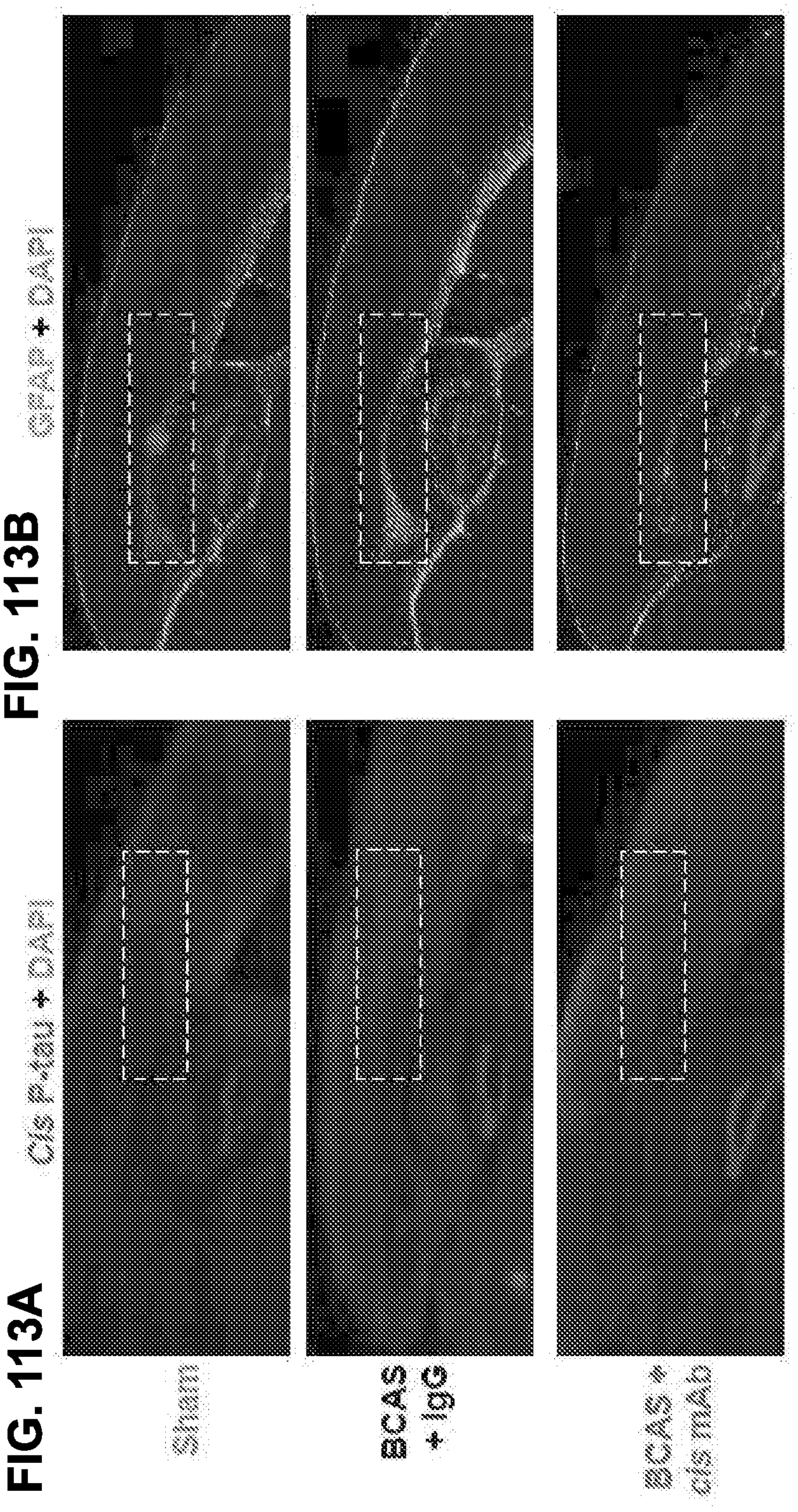

FIGS. 113A-113B are immunofluorescence images showing increased cis P-tau (FIG. 113A) and increased GFAP (FIG. 113B) induced in BCAS mice in the cortex overlaying corpus callosum. Low power images to show specific and robust increased Cis P-tau and GFAP in the cortex and corpus callosum overlaying area in the BCAS mice and rescued by cis mAb.

Figures 114A, 114B:
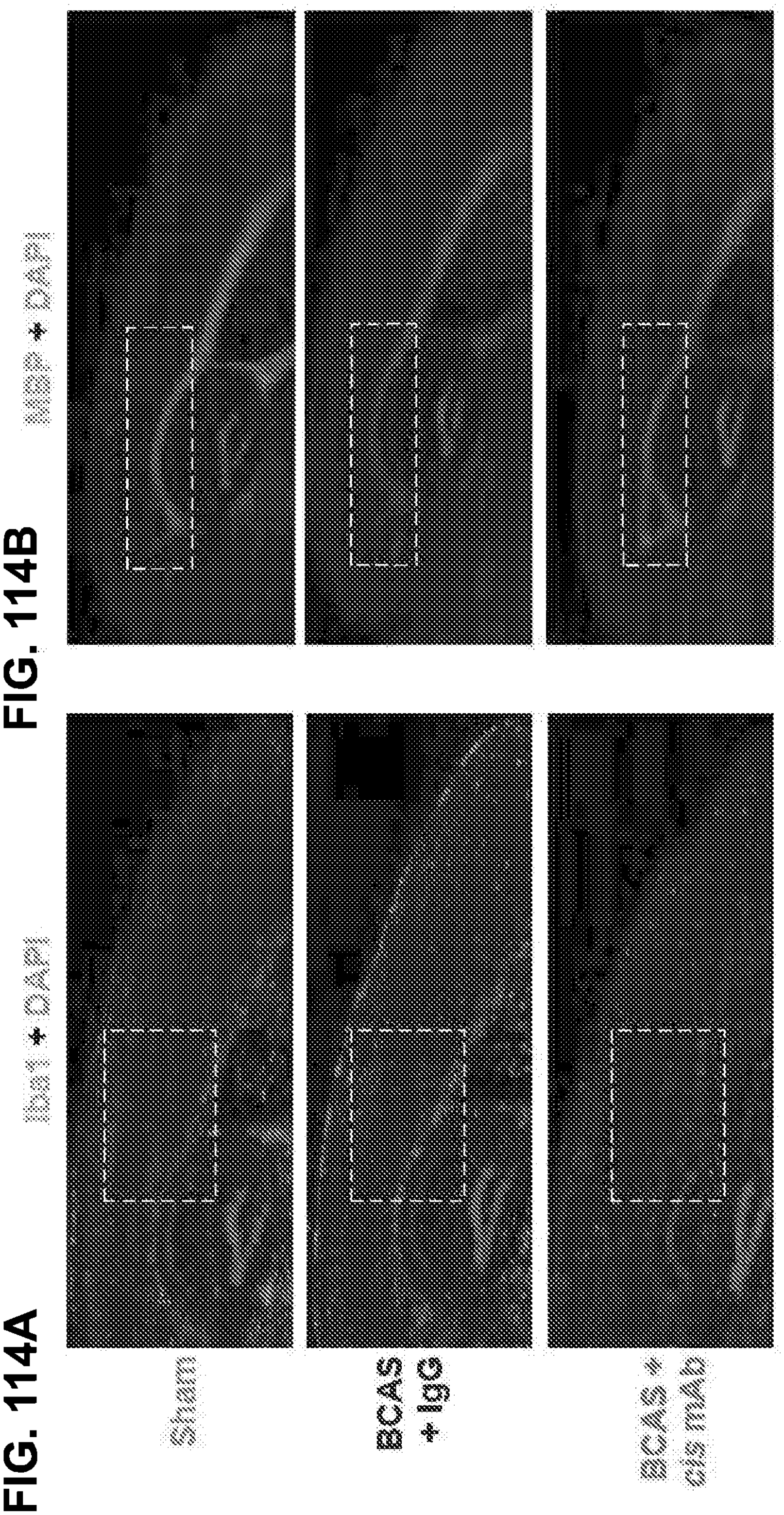

FIGS. 114A-114B are immunofluorescence images showing increased Iba1 (FIG. 114A) and decreased MBP immunoreactivity (FIG. 114B) induced in the BCAS mice in the cortex overlaying corpus callosum. Low power images to show specific and robust increased Iba1 and decreased MBP immunoreactivity in the cortex and corpus callosum overlaying area in the BCAS mice and rescued by cis mAb.

Figure 115A:
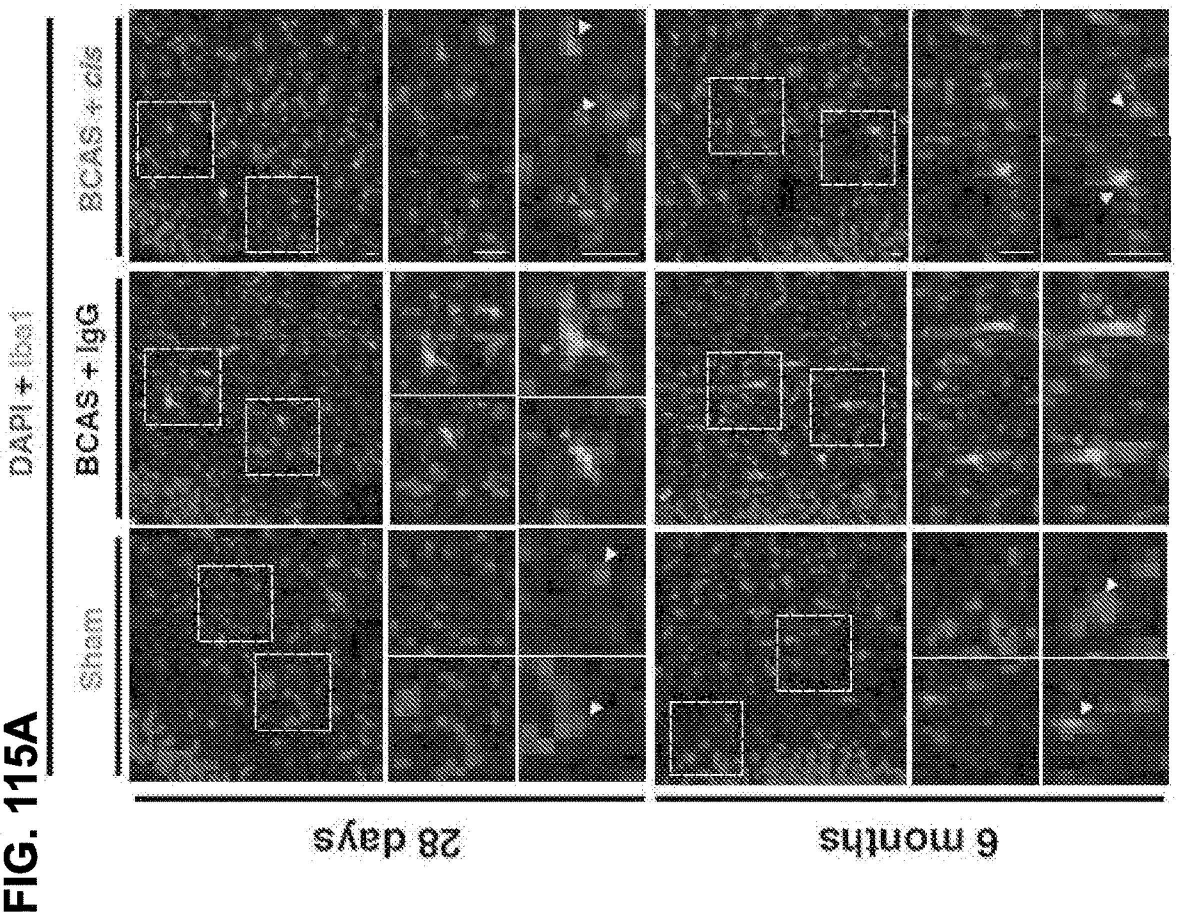

FIG. 115A is a group of immunofluorescence images showing microglia are time dependently activated in the cortical region overlaying corpus callosum in BCAS mice and recovered by cis mAb for up to 6-month after surgery. Representative micrographs of Iba-1 positive microglial cells depicting morphological stages of microglial activation ("ramified-resting" form—white arrow; "intermediate" form-yellow arrow; "amoeboid-activated" form—red arrow) are shown. Ramified form of microglia is characterized by thin processes with small cell bodies. Intermediate form of microglia is characterized by slightly thicker processes and enlarged cell bodies. Amoeboid form of microglia is characterized rounded macrophage-like morphology with no or few processes. Scale bar, 10 μm.

Figure 115B:
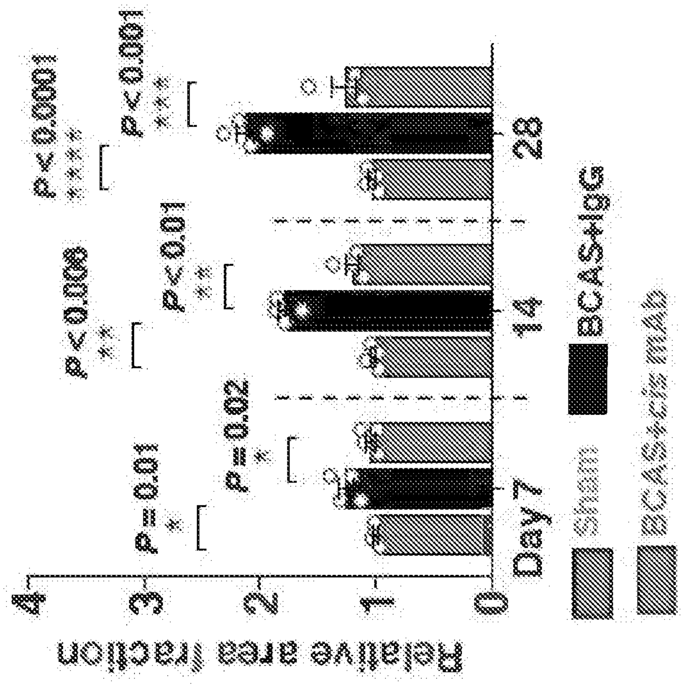
Figure 115C:
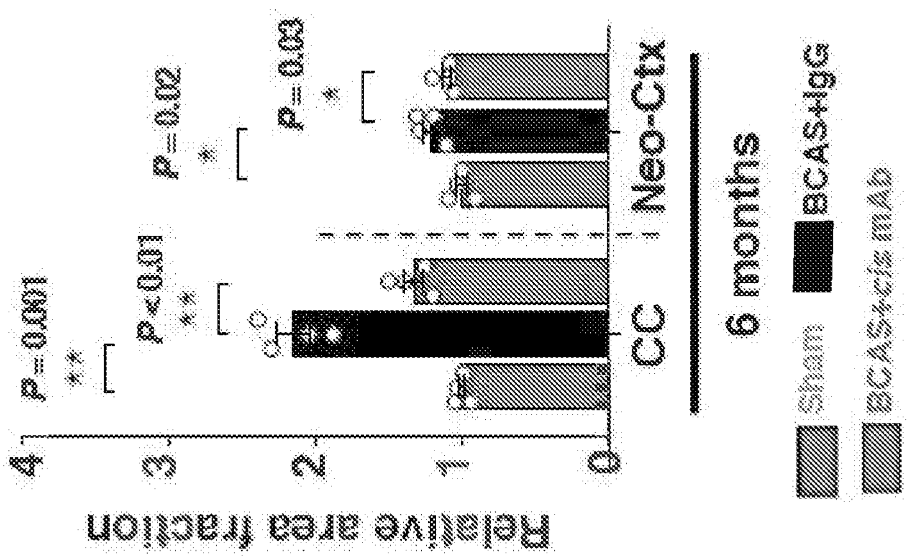

FIGS. 115B-115C are graphs showing Microglia are time dependently activated in the cortical region overlaying corpus callosum in BCAS mice and recovered by cis mAb for up to 6-month after surgery. Quantifications of relative area fraction are shown for 28 days (FIG. 115B) and for 6 months (FIG. 115C). The data were presented as means±SEM and the p values were calculated one-way ANOVA and using unpaired two-tailed parametric Student's t-test. NS, not significant; *, p<0.05; , p<0.001; *, p<0.0001.

Figure 116:
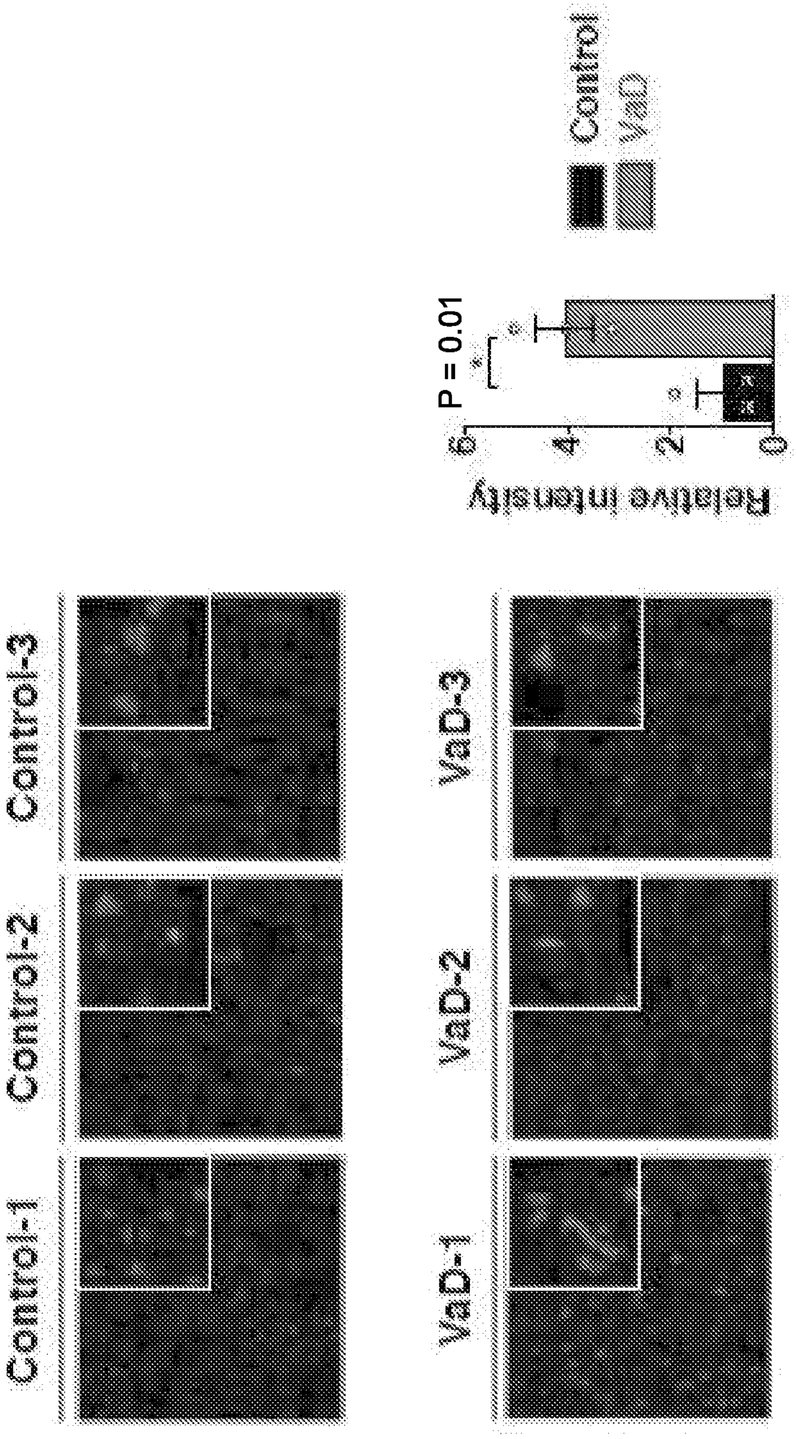

FIG. 116 is a group of immunofluorescence images showing DAPK1 is activated in human VaD patients and BCAS mice, whereas DAPK1 KO blocks VCID-like pathology and brain dysfunction in BCAS mice. Human (vascular dementia) VaD brain slices and aged-matched normal controls were immunostained using Pin1 P71 mAb and detected with bright-light microscopy. The relative intensity was quantified and shown as means±S.E.M.

Figure 117:
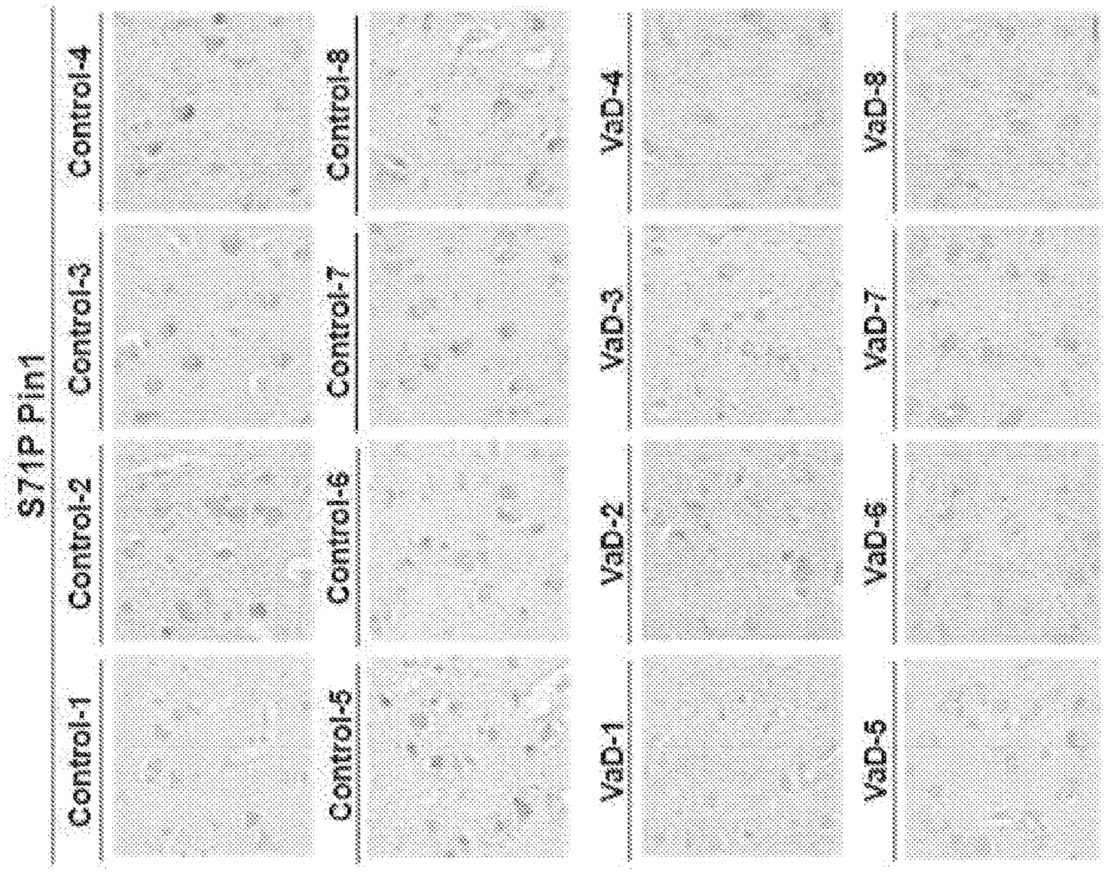

FIG. 117 is a group of microscopic images showing reduced Pin1 expression is correlated with increased S71P Pin1 expression in VaD human brains and correlated with increased DAPK1 in BCAS mouse brains. S71 P Pin1 levels are decreased in the cingulate cortex overlying the corpus callosum of human VaD brains compared with age-matched human brains. Human VaD brain slices and aged-matched normal controls were immunostained using Pin1 mAb detecting S71 P Pin1 (B). Scale bar, 20 μm.

Figure 118B:
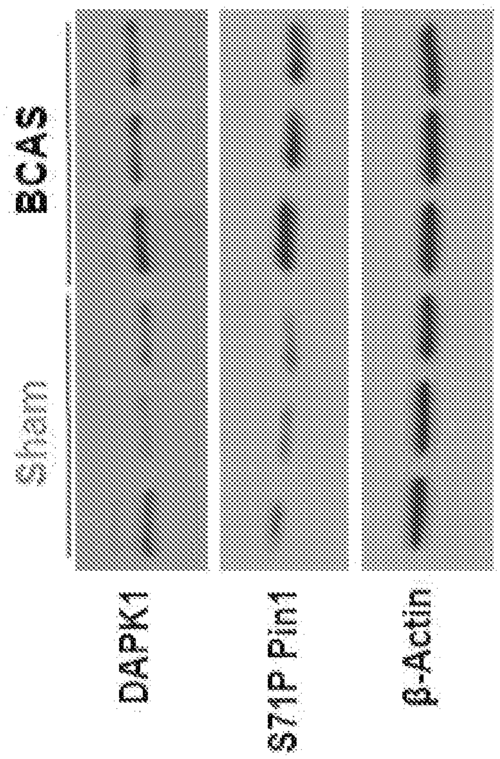
Figure 118A:
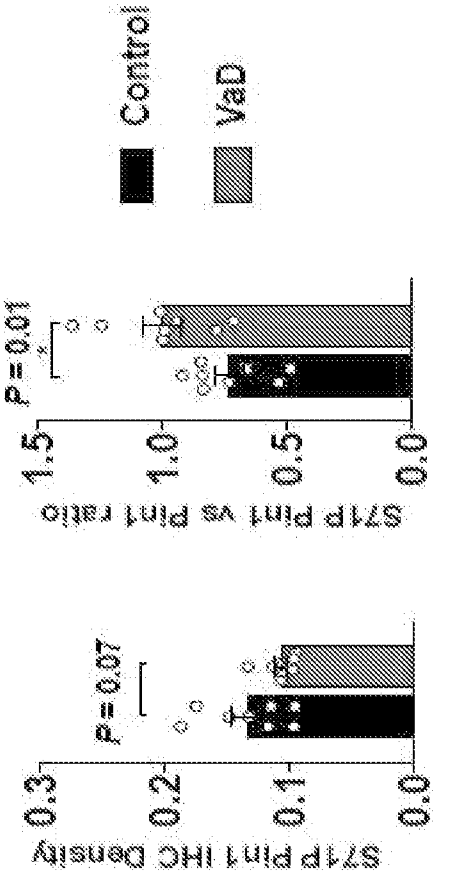

FIG. 118A is a graph showing reduced Pin1 expression is correlated with increased S71 P Pin1 expression in VaD human brains and correlated with increased DAPK1 in BCAS mouse brains. Images from (FIG. 117) were quantified and the ratio of S71 P and active Pin1 are calculated and shown as means±S.E.M. p values were calculated using unpaired two-tailed parametric Student's t-test.

FIG. 118B is a photographic immunoblot image showing S71 P Pin1 and DAPK1 levels are increased in the cortex overlying the corpus callosum of mice 28 days after BCAS, as compared to sham littermate controls.

Figure 119A:
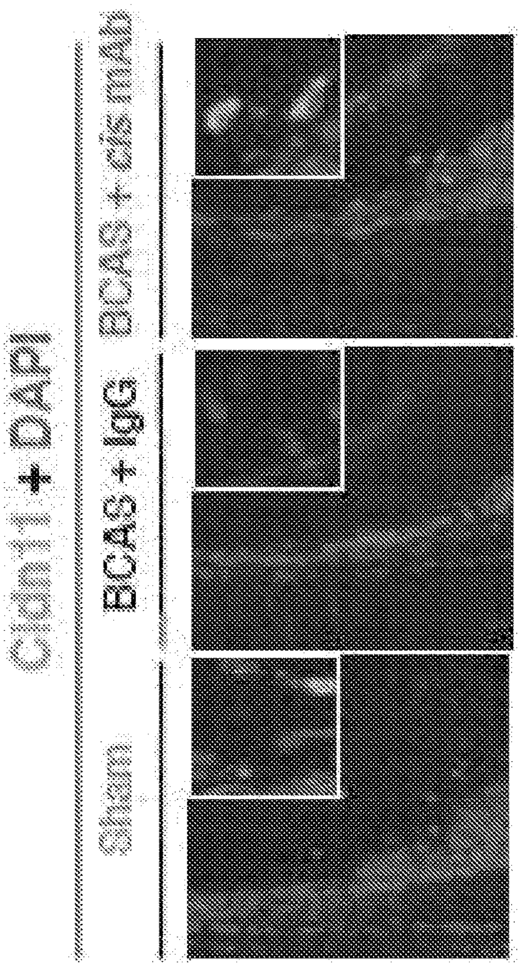

FIG. 119A is a group of immunofluorescence images validating BCAS-induced transcriptomic changes by immunofluorescence staining in BCAS mice and showing that the transcriptomic changes are highly induced after cis mAb treatment. Validation of selected scRNA-seq results by immunofluorescence staining is shown. Two-month-old WT mice were subjected to sham or BCAS operation and were continuously subjected to treatment of cis mAb, IgG isotype or vehicle controls over one month, followed by immunofluorescence staining of Cldn11.

Figure 119B:
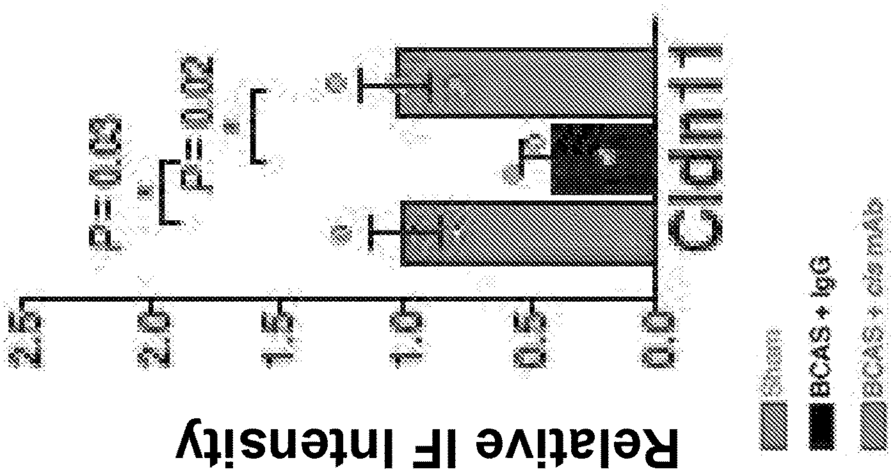

FIG. 119B is a graph showing the quantification of the relative immunofluorescence intensity of the validation of selected scRNA-seq results by immunofluorescence staining. Two-month-old WT mice were subjected to sham or BCAS operation and were continuously subjected to treatment of cis mAb, IgG isotype or vehicle controls over one month, followed by immunofluorescence staining of Cldn11,

DETAILED DESCRIPTION

The present disclosure provides conformation-specific antibodies or antigen-binding fragments that bind specifically to the cis conformation of phosphorylated-Threonine23-Proline (pThr231-Pro) of tau protein. The disclosure also provides methods for treating a subject with elevated levels of soluble cis P-tau by reducing the levels of cis P-tau with therapeutic antibodies. Some aspects of the present disclosure are based, at least in part, on the surprising discovery that levels of soluble cis P-tau are elevated in the brain in response to ischemia or hypoxia, and that elevated levels of soluble cis P-tau can occur in advance of the onset of symptoms associated with a neurological disorder. Also included in the disclosure are related pharmaceutical compositions, polynucleotides, vectors, host cells, methods of production, methods of treatment, diagnostic methods, and kits.

I. Conformation-Specific P-Tau Antibodies or Fragments Thereof

Proline is an amino acid residue unique in its ability to adopt either the cis or trans conformation. Due to the relatively large energy barrier of its isomerization (su=14 to 24 kcal mol-1), uncatalyzed isomerization is a slow process, but may be accelerated by enzymes, such as isomerases. Cis-trans isomerization of the peptidyl-prolyl bond can regulate the folding and therefore biological activity of a protein or polypeptides (e.g., tau), and therefore cis-trans isomerization may affect, for example, growth-signal responses, cell-cycle progression, cellular stress responses, neuronal function, and immune responses. Pin1, a phosphorylation-specific proline isomerase, inhibits neurodegeneration in Alzheimer's Disease by converting phosphorylated Thr231-Pro motif in tau (P-tau) from cis to trans conformation. Studies on the dysregulation of Pin1 have implicated cis P-tau as an early pathogenic conformation in Alzheimer's Disease.

Without wishing to be bound by theory, the present disclosure is based, at least in part, on the discovery that cis, not trans, P-tau is induced upon hypoxic neuronal stress and after traumatic brain injury in humans and in mouse models. Furthermore, levels of cis P-tau correlate with injury severity, frequency, and with axonal injury and clinical outcome. Cis P-tau fails to stabilize neuronal microtubules, it resists protein degradation and/or dephosphorylation, disrupts axonal microtubule networks resulting in axonopathy and neuron death. This process called "cistauosis" occurs long before tau oligomerization and tangle formation. cis P-tau antibodies for early detection and visualization of cis-trans conformational changes of P-tau in vivo and for the treatment of disorders associated with pathogenic tau protein are provided.

Described herein are methods and compositions for the generation and use of conformation-specific P-tau antibodies or fragments thereof. Conformation-specific antibodies or fragments thereof recognize and specifically bind to a particular conformation (e.g., a conformational isomer or conformer) of its complementary antigen. For example, as described herein, conformation-specific antibodies may specifically bind to the cis conformation of a pThr-Pro motif (e.g., binds preferentially to the cis conformation as compared to the trans conformation of the pThr-Pro motif). In particular, antibodies described herein bind specifically to an epitope including cis-pThr231-Pro of phosphorylated tau protein (e.g., relative to an epitope including trans-pThr231-Pro of phosphorylated tau). A conformation specific antibody may have at least 2-fold (e.g., at least 5-fold, 10-fold, 20-fold, 30-fold, 40-fold, 50-fold, 60-fold, 70-fold, 80-fold, 90-fold, 100-fold, 200-fold, or 500-fold) greater affinity for the cis conformation of pThr231-Pro of tau relative to the trans conformation of pThr231-Pro of tau.

Particularly, the disclosure features a conformation-specific tau antibody or antigen-binding fragment thereof that contains one or more, or all, of the CDR sequences of a cis-mAb, such as a human, humanized, or chimeric variant of a cis-mAb, to a human or a non-human mammal in order to treat a vascular-associated neural disease. The following cis-pThr231-tau mAbs were produced according to the methods described herein. Cis-mAbs HT1-HT12 and HT14-HT18 are humanized antibodies. Cis-mAb HT13 is a mouse-human chimeric antibody.

Cis-mAb HT1 (Humanized)

HT1 Heavy Chain

HT1 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSDSYTRYNQKFKG (SEQ ID NO: 11); and a CDR heavy chain 3 (CDR-H3) having the amino acid sequence of WEVDY (SEQ ID NO: 6).

HT1 includes a heavy chain variable domain having an amino acid sequence of

QVQLVQSGAELKKPGASVKMSCKASGYTFTSYWIHWVKQRPGQGLEWIG
VIDPSDSYTRYNQKFKGRATLTVDTSASTAYMQLSSLTSEDSAVYYCTT
WEVDYWGQGTTVTVSS (SEQ ID NO: 25; CDRs underlined).

HT1 Light Chain

HT1 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT1 includes a light chain variable domain having an amino acid sequence of

DVVMTQSPLSLPVTLGQPASISCRSSQSLVHSDGNTYLHWYLQKPGQSP
QLLIYKVSNRFSGVPDRFSGSGSGTDFTLKISRVEAEDVGVYFCSQSTH
VPWTFGGGTKVEIK (SEQ ID NO: 16; CDRs underlined).

Cis-mAb HT2 (Humanized)

HT2 Heavy Chain

HT2 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSDSYTRYNQKFKG (SEQ ID NO: 11); and a CDR heavy chain 3 (CDR-H3) having the amino acid sequence of WEVDY (SEQ ID NO: 6).

HT2 includes a heavy chain variable domain having an amino acid sequence of

QVQLVQSGAEVKKPGASVKMSCKASGYTFTSYWIHWVKQRPGQGLEWIG
VIDPSDSYTRYNQKFKGRATLTVDTSASTAYMELSSLRSEDTAVYYCTT
WEVDYWGQGTLVTVSS (SEQ ID NO: 26; CDRs underlined).

HT2 Light Chain

HT2 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT2 includes a light chain variable domain having an amino acid sequence of

DVVMTQSPLSLPVTLGQPASISCRSSQSLVHSDGNTYLHWYLQKPGQSP
QLLIYKVSNRFSGVPDRFSGSGSGTDFTLKISRVEAEDVGVYFCSQSTH
VPWTFGGGTKVEIK (SEQ ID NO: 16; CDRs underlined).

Cis-mAb HT3 (Humanized)

HT3 Heavy Chain

HT3 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSDSYTRYNQKFKG (SEQ ID NO: 11); and a CDR heavy chain 3 (CDR-H3) having the amino acid sequence of WEVDY (SEQ ID NO: 6).

HT3 includes a heavy chain variable domain having an amino acid sequence of

QVQLVQSGAEVKKPGASVKVSCKASGYTFTSYWIHWVRQRPGQGLEWIG
VIDPSDSYTRYNQKFKGRVTLTVDTSASTAYMELSSLRSEDTAVYYCTT
WEVDYWGQGTLVTVSS (SEQ ID NO: 27; CDRs underlined).

HT3 Light Chain

HT3 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT3 includes a light chain variable domain having an amino acid sequence of

DVVMTQSPLSLPVTLGQPASISCRSSQSLVHSDGNTYLHWYLQKPGQSP
QLLIYKVSNRFSGVPDRFSGSGSGTDFTLKISRVEAEDVGVYFCSQSTH
VPWTFGGGTKVEIK (SEQ ID NO: 16; CDRs underlined).

Cis-mAb HT4 (Humanized)

HT4 Heavy Chain

HT4 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSDSYTRYNQKFKG (SEQ ID NO: 11); and a CDR heavy chain 3 (CDR-H3) having the amino acid sequence of WEVDY (SEQ ID NO: 6).

HT4 includes a heavy chain variable domain having an amino acid sequence of

QVQLVQSGAEVKKPGASVKVSCKASGYTFTSYWIHWVRQRPGQGLEWIG
VIDPSDSYTRYNQKFKGRVTITRDTSASTAYMELSSLRSEDTAVYYCTT
WEVDYWGQGTLVTVSS (SEQ ID NO: 28; CDRs underlined).

HT4 Light Chain

HT4 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT4 includes a light chain variable domain having an amino acid sequence of

DVVMTQSPLSLPVTLGQPASISCRSSQSLVHSDGNTYLHWYLQKPGQSP
QLLIYKVSNRFSGVPDRFSGSGSGTDFTLKISRVEAEDVGVYFCSQSTH
VPWTFGGGTKVEIK (SEQ ID NO: 16; CDRs underlined).

Cis-mAb HT5 (Humanized)

HT5 Heavy Chain

HT5 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD- SYTRYNQKFKG (SEQ ID NO: 11); and a CDR heavy chain 3 (CDR-H3) having the amino acid sequence of WEVDY (SEQ ID NO: 6).

HT5 includes a heavy chain variable domain having an amino acid sequence of

```
QVQLVQSGAELKKPGASVKMSCKASGYTFTSYWIHWVKQRPGQGLEWIG
VIDPSDSYTRYNQKFKGRATLTVDTSASTAYMQLSSLTSEDSAVYYCTT
WEVDYWGQGTTVTVSS (SEQ ID NO: 25; CDRs underlined).
```

HT5 Light Chain

HT5 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRDS (SEQ ID NO: 10); and a CDR light chain 3 (CDR-L3) having the amino acid sequence of SQSTHVP (SEQ ID NO: 3).

HT5 includes a light chain variable domain having an amino acid sequence of

```
DVVMTQSPLSLPVTLGQPASISCRSSQSLVHSDGNTYLHWYLQKPGQSP
QLLIYKVSNRDSGVPDRFSGSGSGTDFTLKISRVEAEDVGVYFCSQSTH
VPWTFGGGTKVEIK (SEQ ID NO: 18; CDRs underlined).
```

Cis-mAb HT6 (Humanized)

HT6 Heavy Chain

HT6 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6)).

HT6 includes a heavy chain variable domain having an amino acid sequence of

```
QVQLVQSGAEVKKPGASVKMSCKASGYTFTSYWIHWVKQRPGQGLEWIG
VIDPSDSYTRYNQKFKGRATLTVDTSASTAYMELSSLRSEDTAVYYCTT
WEVDYWGQGTLVTVSS (SEQ ID NO: 26; CDRs underlined).
```

HT6 Light Chain

HT6 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRDS (SEQ ID NO: 10); and a CDR light chain 3 (CDR-L3) having the amino acid sequence of SQSTHVP (SEQ ID NO: 3).

HT6 includes a light chain variable domain having an amino acid sequence of

```
DVVMTQSPLSLPVTLGQPASISCRSSQSLVHSDGNTYLHWYLQKPGQSP
QLLIYKVSNRDSGVPDRFSGSGSGTDFTLKISRVEAEDVGVYFCSQSTH
VPWTFGGGTKVEIK (SEQ ID NO: 18; CDRs underlined).
```

Cis-mAb HT7 (Humanized)

HT7 Heavy Chain

HT7 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT7 includes a heavy chain variable domain having an amino acid sequence of

```
QVQLVQSGAEVKKPGASVKVSCKASGYTFTSYWIHWVRQRPGQGLEWIG
VIDPSDSYTRYNQKFKGRVTLTVDTSASTAYMELSSLRSEDTAVYYCTT
WEVDYWGQGTLVTVSS (SEQ ID NO: 27; CDRs underlined).
```

HT7 Light Chain

HT7 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRDS (SEQ ID NO: 10); and a CDR light chain 3 (CDR-L3) having the amino acid sequence of SQSTHVP (SEQ ID NO: 3).

HT7 includes a light chain variable domain having an amino acid sequence of

```
DVVMTQSPLSLPVTLGQPASISCRSSQSLVHSDGNTYLHWYLQKPGQSP
QLLIYKVSNRDSGVPDRFSGSGSGTDFTLKISRVEAEDVGVYFCSQSTH
VPWTFGGGTKVEIK (SEQ ID NO: 18; CDRs underlined).
```

Cis-mAb HT8 (Humanized)

HT8 Heavy Chain

HT8 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT8 includes a heavy chain variable domain having an amino acid sequence of

```
QVQLVQSGAEVKKPGASVKVSCKASGYTFTSYWIHWVRQRPGQGLEWIG
VIDPSDSYTRYNQKFKGRVTITRDTSASTAYMELSSLRSEDTAVYYCTT
WEVDYWGQGTLVTVSS (SEQ ID NO: 28; CDRs underlined).
```

HT8 Light Chain

HT8 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRDS (SEQ ID NO: 10); and a CDR light chain 3 (CDR-L3) having the amino acid sequence of SQSTHVP (SEQ ID NO: 3).

HT8 includes a light chain variable domain having an amino acid sequence of

```
DVVMTQSPLSLPVTLGQPASISCRSSQSLVHSDGNTYLHWYLQKPGQSP
QLLIYKVSNRDSGVPDRFSGSGSGTDFTLKISRVEAEDVGVYFCSQSTH
VPWTFGGGTKVEIK (SEQ ID NO: 18; CDRs underlined).
```

Cis-mAb HT9 (Humanized)

HT9 Heavy Chain

HT9 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT9 includes a heavy chain variable domain having an amino acid sequence of

```
QVQLVQSGAELKKPGASVKMSCKASGYTFTSYWIHWVKQRPGQGLEWIG
VIDPSDSYTRYNQKFKGRATLTVDTSASTAYMQLSSLTSEDSAVYYCTT
WEVDYWGQGTTVTVSS (SEQ ID NO: 25; CDRs underlined).
```

HT9 Light Chain

HT9 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT9 includes a light chain variable domain having an amino acid sequence of

DVVMTQSPLSLPVTLGQPASISCRSSQSLVHSDGNTYLHWYLQKPGQSP
QLLIYKVSNRFSGVPDRFSGSGSGTDFTLKISRVEAEDVGVYYCSQSTH
VPWTFGGGTKVEIK (SEQ ID NO: 19; CDRs underlined).

Cis-mAb HT10 (Humanized)

HT10 Heavy Chain

HT10 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT10 includes a heavy chain variable domain having an amino acid sequence of

QVQLVQSGAEVKKPGASVKMSCKASGYTFTSYWIHWVKQRPGQGLEWIG
VIDPSDSYTRYNQKFKGRATLTVDTSASTAYMELSSLRSEDTAVYYCTT
WEVDYWGQGTLVTVSS (SEQ ID NO: 26; CDRs underlined).

HT10 Light Chain

HT10 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT10 includes a light chain variable domain having an amino acid sequence, of

DVVMTQSPLSLPVTLGQPASISCRSSQSLVHSDGNTYLHWYLQKPGQSP
QLLIYKVSNRFSGVPDRFSGSGSGTDFTLKISRVEAEDVGVYYCSQSTH
VPWTFGGGTKVEIK (SEQ ID NO: 19; CDRs underlined).

Cis-mAb HT11 (Humanized)

HT11 Heavy Chain

HT11 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT11 includes a heavy chain variable domain having an amino acid sequence of

QVQLVQSGAEVKKPGASVKVSCKASGYTFTSYWIHWVRQRPGQGLEWIG
VIDPSDSYTRYNQKFKGRVTLTVDTSASTAYMELSSLRSEDTAVYYCTT
WEVDYWGQGTLVTVSS (SEQ ID NO: 27; CDRs underlined).

HT11 Light Chain

HT11 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT11 includes a light chain variable domain having an amino acid sequence of

DVVMTQSPLSLPVTLGQPASISCRSSQSLVHSDGNTYLHWYLQKPGQSP
QLLIYKVSNRFSGVPDRFSGSGSGTDFTLKISRVEAEDVGVYYCSQSTH
VPWTFGGGTKVEIK (SEQ ID NO: 19; CDRs underlined).

Cis-mAb HT12 (Humanized)

HT12 Heavy Chain

HT12 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT12 includes a heavy chain variable domain having an amino acid sequence of

QVQLVQSGAEVKKPGASVKVSCKASGYTFTSYWIHWVRQRPGQGLEWIG
VIDPSDSYTRYNQKFKGRVTITRDTSASTAYMELSSLRSEDTAVYYCTT
WEVDYWGQGTLVTVSS (SEQ ID NO: 28; CDRs underlined).

HT12 Light Chain

HT12 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT12 includes a light chain variable domain having an amino acid sequence of

DVVMTQSPLSLPVTLGQPASISCRSSQSLVHSDGNTYLHWYLQKPGQSP
QLLIYKVSNRFSGVPDRFSGSGSGTDFTLKISRVEAEDVGVYYCSQSTH
VPWTFGGGTKVEIK (SEQ ID NO: 19; CDRs underlined).

Cis-mAb HT 13 (Mouse-Human Chimera, Control)

HT13 Heavy Chain

HT13 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT13 includes a heavy chain variable domain having an amino acid sequence of

QVQLQQPGAELVKPGASVKMSCKASGYTFTSYWIHWVKQRPGQGLEWIG
VIDPSDSYTRYNQKFKGKATLTVDTSSSTAYMQLSSLTSEDSAVYYCTT
WEVDYWGQGTTLTVSS (SEQ ID NO: 24; CDRs underlined).

HT13 Light Chain

HT13 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT13 includes a light chain variable domain having an amino acid sequence of

DVVMTQTPLSLPVSLGDQASISCRSSQSLVHSDGNTYLHWYLQKPGQSP KLLIYKVSNRFSGVPDRFSGSGSGTDFTLKISRLEAEDLGVYFCSQSTH VPWTFGGGTKLEIK (SEQ ID NO: 15; CDRs underlined).

Cis-mAb HT14 (Humanized)

HT14 Heavy Chain

HT14 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT14 includes a heavy chain variable domain having an amino acid sequence of

QVQLVQSGAELKKPGASVKMSCKASGYTFTSYWIHWVKQRPGQGLEWIG VIDPSDSYTRYNQKFKGRATLTVDTSASTAYMQLSSLTSEDSAVYYCTT WEVDYWGQGTTVTVSS (SEQ ID NO: 25; CDRs underlined).

HT14 Light Chain

HT14 includes a complementarity-determining region (CDR) light chain 1 (CDR-L1) having the amino acid sequence of RSSQSLVHSDGNTYLN (SEQ ID NO: 8); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT14 includes a light chain variable domain having an amino acid sequence of

DVVMTQSPLSLPVTLGQPASISCRSSQSLVHSDGNTYLNWYLQKPGQSP QLLIYKVSNRFSGVPDRFSGSGSGTDFTLKISRVEAEDVGVYFCSQSTH VPWTFGGGTKVEIK (SEQ ID NO: 17; CDRs underlined).

Cis-mAb HT15 (Humanized)

HT15 Heavy Chain

HT15 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT15 includes a heavy chain variable domain having an amino acid sequence of

QVQLVQSGAEVKKPGASVKMSCKASGYTFTSYWIHWVKQRPGQGLEWIG VIDPSDSYTRYNQKFKGRATLTVDTSASTAYMELSSLRSEDTAVYYCTT WEVDYWGQGTLVTVSS (SEQ ID NO: 26; CDRs underlined).

HT15 Light Chain

HT15 includes a complementarity-determining region (CDR) light chain 1 (CDR-L1) having the amino acid sequence of RSSQSLVHSDGNTYLN (SEQ ID NO: 8); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT15 includes a light chain variable domain having an amino acid sequence of

DVVMTQSPLSLPVTLGQPASISCRSSQSLVHSDGNTYLNWYLQKPGQSP QLLIYKVSNRFSGVPDRFSGSGSGTDFTLKISRVEAEDVGVYFCSQSTH VPWTFGGGTKVEIK (SEQ ID NO: 17; CDRs underlined).

Cis-mAb HT16 (Humanized)

HT16 Heavy Chain

HT16 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6).

HT16 includes a heavy chain variable domain having an amino acid sequence of

QVQLVQSGAEVKKPGASVKVSCKASGYTFTSYWIHWVRQRPGQGLEWIG VIDPSDSYTRYNQKFKGRVTLTVDTSASTAYMELSSLRSEDTAVYYCTT WEVDYWGQGTLVTVSS (SEQ ID NO: 27; CDRs underlined).

HT16 Light Chain

HT16 includes a complementarity-determining region (CDR) light chain 1 (CDR-L1) having the amino acid sequence of RSSQSLVHSDGNTYLN (SEQ ID NO: 8); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT16 includes a light chain variable domain having an amino acid sequence of

DVVMTQSPLSLPVTLGQPASISCRSSQSLVHSDGNTYLNWYLQKPGQSP QLLIYKVSNRFSGVPDRFSGSGSGTDFTLKISRVEAEDVGVYFCSQSTH VPWTFGGGTKVEIK (SEQ ID NO: 17; CDRs underlined).

Cis-mAb HT17 (Humanized)

HT17 Heavy Chain

HT17 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD-SYTRYNQKFKG (SEQ ID NO: 11); and a CDR heavy chain 3 (CDR-H3) having the amino acid sequence of WEVDY (SEQ ID NO: 6). HT17 includes a heavy chain variable domain having an amino acid sequence of QVQLVQSGAEVKKPGASVKVSCKASGYTFTSYWIHWVRQRPGQGLEWIG VIDPSDSYTRYNQKFKGRVTITRDTSASTAYMELSSLRSEDTAVYYCTT WEVDYWGQGTLVTVSS (SEQ ID NO: 28; CDRs underlined).

HT17Light Chain

HT17 includes a complementarity-determining region (CDR) light chain 1 (CDR-L1) having the amino acid sequence of RSSQSLVHSDGNTYLN (SEQ ID NO: 8); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT17 includes a light chain variable domain having an amino acid sequence of

DVVMTQSPLSLPVTLGQPASISCRSSQSLVHSDGNTYLNWYLQKPGQSP QLLIYKVSNRFSGVPDRFSGSGSGTDFTLKISRVEAEDVGVYFCSQSTH VPWTFGGGTKVEIK (SEQ ID NO: 17; CDRs underlined).

Cis-mAb HT18 (Humanized)

HT18 Heavy Chain

HT18 includes a complementarity-determining region (CDR) heavy chain 1 (CDR-H1) having the amino acid sequence of SYWIH (SEQ ID NO: 4); a CDR heavy chain 2 (CDR-H2) having the amino acid sequence of VIDPSD- SYTRYNQKFKG (SEQ ID NO: 11); and a CDR heavy chain 3 (CDR-H3) having the amino acid sequence of WEVDY (SEQ ID NO: 6).

HT18 includes a heavy chain variable domain having an amino acid sequence of

QVQLVQSGAEVKKPGSSVKVSCKASGYTFTSYWIHWVRQAPGQGLEWMG VIDPSDSYTRYNQKFKGRVTITRDTSMSTAYTELSSLRSEDTAVYYCTT WEVDYWGQGTLVTVSS (SEQ ID NO: 29; CDRs underlined).

HT18 Light Chain

HT18 includes a complementarity-determining region (CDR) light chain 1 (CDR-L1) having the amino acid sequence of RSSQSLVHSDGNTYLH (SEQ ID NO: 7); a CDR light chain 2 (CDR-L2) having the amino acid sequence of KVSNRFS (SEQ ID NO: 9); and a CDR light chain 3 (CDR-L3) having the amino acid sequence of SQSTHVP (SEQ ID NO: 3).

HT18 includes a light chain variable domain having an amino acid sequence of

DIQMTQSPSTLSASVGDRVTITCRSSQSLVHSDGNTYLHWYQQKPGKAP KLLIYKVSNRFSGVPSRFSGS GSGTEFTLTISSLQPDDFATYYCSQST HVPWTFGQGTKLEIK (SEQ ID NO: 20; CDRs underlined).

Cis-mAb Light Chain Variable Domain Sequences

This disclosure provides an antibody or antigen-binding fragment thereof that includes a light chain variable domain including an amino acid sequence with at least 70%, 75%, 80%, 85%, 86%, 87%, 88%, 89%, 90%, 91%, 92%, 93%, 94%, 95%, 96%, 97%, 98%, 99% or 100% sequence identity to the amino acid sequence of any one of SEQ ID NOs: 16-23.

(Light chain sequence of cis-mAb HT13)

SEQ ID NO: 15

DVVMTQTPLSLPVSLGDQASISCRSSQSLVHSDGNTYLHWYLQKPGQSPKLLIYKVSNRFSGVPDRFSG
SGSGTDFTLKISRLEAEDLGVYFCSQSTHVPWTFGGGTKLEIK (Light chain sequence of cis-mAbs HT1, HT2, HT3, and HT4)

SEQ ID NO: 16

DVVMTQSPLSLPVTLGQPASISCRSSQSLVHSDGNTYLHWYLQKPGQSPQLLIYKVSNRFSGVPDRFSG
SGSGTDFTLKISRVEAEDVGVYFCSQSTHVPWTFGGGTKVEIK (Light chain sequence of cis-mAbs HT14, HT15, HT16, and HT17)

SEQ ID NO: 17

DVVMTQSPLSLPVTLGQPASISCRSSQSLVHSDGNTYLNWYLQKPGQSPQLLIYKVSNRFSGVPDRFSG
SGSGTDFTLKISRVEAEDVGVYFCSQSTHVPWTFGGGTKVEIK (Light chain sequence of cis-mAbs HT5, HT6, HT7, and HT8)

SEQ ID NO: 18

DVVMTQSPLSLPVTLGQPASISCRSSQSLVHSDGNTYLHWYLQKPGQSPQLLIYKVSNRDSGVPDRFSG
SGSGTDFTLKISRVEAEDVGVYFCSQSTHVPWTFGGGTKVEIK (Light chain sequence of cis-mAbs HT9, HT10, HT11, and HT12)

SEQ ID NO: 19

DVVMTQSPLSLPVTLGQPASISCRSSQSLVHSDGNTYLHWYLQKPGQSPQLLIYKVSNRFSGVPDRFSG
SGSGTDFTLKISRVEAEDVGVYYCSQSTHVPWTFGGGTKVEIK (Light chain sequence of cis-mAbs HT18)

SEQ ID NO: 20

DIQMTQSPSTLSASVGDRVTITCRSSQSLVHSDGNTYLHWYQQKPGKAPKLLIYKVSNRFSGVPSRFSG
S GSGTEFTLTISSLQPDDFATYYCSQSTHVPWTFGQGTKLEIK (Light chain sequence of cis-mAb)

SEQ ID NO: 21

DIVMTQSPLSLPVTPGEPASISCRSSQSLVHSDGNTYLHWYLQKPGQSPKLLIYKVSNRFSGVPDRFSGS
GSGTDFTLKISRLEAEDVGVYYCSQSTHVPWTFGQGTKLEIK (Light chain sequence of cis-mAb)

SEQ ID NO: 22

DIVMTQSPLSLPVTPGEPASISCRSSQSLVHSDGNTYLHWYLQKPGQSPKLLIYKVSNRFSGVPDRFSGS
GSGTDFTLKISRVEAEDVGVYYCSQSTHVPWTFGQGTKLEIK (Light chain sequence of cis-mAb)

SEQ ID NO: 23

DIQMTQSPSTLSASVGDRVTITCRSSQSLVHSDGNTYLHWYLQKPGKAPKLLIYKVSNRFSGVPSRFSGS
GSGTEFTLTISSLQPDDFATYYCSQSTHVPWTFGQGTKLEIK

Cis-mAb Heavy Chain Variable Domain Sequences

This disclosure provides an antibody or antigen-binding fragment thereof that includes a heavy chain variable domain including an amino acid sequence with at least 70%, 75%, 80%, 85%, 86%, 87%, 88%, 89%, 90%, 91%, 92%, 93%, 94%, 95%, 96%, 97%, 98%, 99% or 100% sequence identity to the amino acid sequence of any one of SEQ ID NOs: 25-35.

```
(Heavy chain sequence of cis-mAb HT13)
                                                  SEQ ID NO: 24
QVQLQQPGAELVKPGASVKMSCKASGYTFTSYWIHWVKQRPGQGLEWIGVIDPSDSYTRYNQKFKGKA
TLTVDTSSSTAYMQLSSLTSEDSAVYYCTTWEVDYWGQGTTLTVSS

(Heavy chain sequence of cis-mAbs HT1, HT5, HT9, and HT14)
                                                  SEQ ID NO: 25
QVQLVQSGAELKKPGASVKMSCKASGYTFTSYWIHWVKQRPGQGLEWIGVIDPSDSYTRYNQKFKGRA
TLTVDTSASTAYMQLSSLTSEDSAVYYCTTWEVDYWGQGTTVTVSS

(Heavy chain sequence of cis-mAbs HT2, HT6, HT10, and HT15)
                                                  SEQ ID NO: 26
QVQLVQSGAEVKKPGASVKMSCKASGYTFTSYWIHWVKQRPGQGLEWIGVIDPSDSYTRYNQKFKGRA
TLTVDTSASTAYMELSSLRSEDTAVYYCTTWEVDYWGQGTLVTVSS

(Heavy chain sequence of cis-mAbs HT3, HT7, HT11, and HT16)
                                                  SEQ ID NO: 27
QVQLVQSGAEVKKPGASVKVSCKASGYTFTSYWIHWVRQRPGQGLEWIGVIDPSDSYTRYNQKFKGRV
TLTVDTSASTAYMELSSLRSEDTAVYYCTTWEVDYWGQGTLVTVSS

(Heavy chain sequence of cis-mAbs HT4, HT8, HT12, and HT17)
                                                  SEQ ID NO: 28
QVQLVQSGAEVKKPGASVKVSCKASGYTFTSYWIHWVRQRPGQGLEWIGVIDPSDSYTRYNQKFKGRV
TITRDTSASTAYMELSSLRSEDTAVYYCTTWEVDYWGQGTLVTVSS

(Heavy chain sequence of cis-mAb HT18)
                                                  SEQ ID NO: 29
QVQLVQSGAEVKKPGSSVKVSCKASGYTFTSYWIHWVRQAPGQGLEWMGVIDPSDSYTRYNQKFKGR
VTITRDTSMSTAYTELSSLRSEDTAVYYCTTWEVDYWGQGTLVTVSS

(Heavy chain sequence of cis-mAb)
                                                  SEQ ID NO: 30
QVQLVQSGAEVKKPGSSVKVSCKASGYTFTSYWIHWVRQAPGQGLEWMGVIDPSDSYTRYNQKFKGR
VTITRDTSMSTAYTELSSLRSEDSAVYYCTTWEVDYWGQGTLVTVSS

(Heavy chain sequence of cis-mAb)
                                                  SEQ ID NO: 31
QVQLVQSGAEVKKPGSSVKVSCKASGYTFTSYWIHWVRQAPGQGLEWMGVIDPSDSYTRYNQKFKGR
VTITRDTSMSTAYTELSSLRSEDTAVYYCATWEVDYWGQGTLVTVSS

(Heavy chain sequence of cis-mAb)
                                                  SEQ ID NO: 32
QVQLVQSGAEVKKPGSSVKVSCKASGYTFTSYWIHWVRQAPGQGLEWMGVIDPSDSYTRYNQKFKGR
VTITRDTSMSTAYTELSSLRSEDSAVYYCTTWEVDYWGQGTLVTVSS

(Heavy chain sequence of cis-mAb)
                                                  SEQ ID NO: 33
QDQLVQSGAEVKKPGSSVKVSCKASGYTFTSYWIHWVRQAPGQGLEWMGVIDPSDSYTRYNQKFQGR
VTITRDTSMSTAYTELSSLRSEDTAVYYCARWEVDYWGQGTLVTVSS

(Heavy chain sequence of cis-mAb)
                                                  SEQ ID NO: 34
QVQLVQSGAEVKKPLSSVKVSCKASGYTFTSYWIHWVRQAPGQGLEWMGVIDPSDSYTRYNQKFQGR
VTITRDTSMSTAYTELSSLRSEDTAVYYCARWEVDYWGQGTLVTVSS

(Heavy chain sequence of cis-mAb)
                                                  SEQ ID NO: 35
QVQLVQSGAEVKKPGSSVKVSCKASGYTFTSYWIHWVRQAPGQGLEWMGVIDPSDSYTRYNQKFQGR
VTITRDTSMSTAYTELSSLRSEDTAVYYCARWEVDYWGQGTLVTVSS
```

Cis-mAb CDR Consensus Sequences

A consensus sequence for each of CDR-L1, CDR-L2, CDR-L3, CDR-H1, CDR-H2, and CDR-H3 may be generated in consideration of the above sequences. The disclosure provides an antibody or antigen binding fragment thereof including one or more of the following consensus CDR sequences or a variant thereof.

CDR-L1 consensus sequence (SEQ ID NO: 1)

RSSQSLVHSDGNTYLX$_1$, where $X_1$ is H or N

CDR-L2 consensus sequence (SEQ ID NO: 2)

KVSNRX$_1$S; where $X_1$ is F or D

-continued

CDR-L3 consensus sequence (SEQ ID NO: 3)

SQSTHVP

CDR-H1 consensus sequence (SEQ ID NO: 4)

SYWIH

CDR-H2 consensus sequence (SEQ ID NO: 5)

VIDPSDSYTRYNQKFX$_1$G, where X$_1$ is K or Q

CDR-H3 consensus sequence (SEQ ID NO: 6)

WEVDY

Cis-mAb Framework (FR) Region Sequences

This disclosure provides an antibody or antigen-binding fragment thereof that includes a framework region of the light chain or heavy variable domain including an amino acid sequence with at least 70%, 75%, 80%, 85%, 86%, 87%, 88%, 89%, 90%, 91%, 92%, 93%, 94%, 95%, 96%, 97%, 98%, 99% or 100% sequence identity to any one of SEQ ID NOs: 36-54. In some embodiments, the antibody or antigen-binding fragment thereof includes one or more of (e.g., one, two, three, four, five, six, seven or eight) of SEQ ID NOs: 36-54.

Consensus sequence of FR region of the light chain variable domain that is N-terminal to CDR-L1

(SEQ ID NO: 36)

SPX$_1$X$_2$LX$_3$X$_4$X$_5$X$_6$GX$_7$X$_8$X$_9$X$_{10}$IX$_{11}$C
where X$_1$ is S or L; X$_2$ is S or T; X$_3$ is S or P; X$_4$ is V or A; X$_5$ is S or T; X$_6$ is L or V; X$_7$ is D or Q; X$_8$ is R or P; X$_9$ is V or A; X$_{10}$ is S or T; X$_{11}$ is S or T Sequence of FR region of the light chain variable domain that is N-terminal to CDR-L1

(SEQ ID NO: 37)

SPLSLPVTLGQPASISC

Sequence of FR region of the light chain variable domain that is N-terminal to CDR-L1

(SEQ ID NO: 38)

SPSTLSASVGDRVTITC

Sequence of FR region of the light chain variable domain that is between CDR-L1 and CDR-L2

(SEQ ID NO: 39)

WYLQKPGQSPQLLIY

Sequence of FR region of the light chain variable domain that is between CDR-L1 and CDR-L2

(SEQ ID NO: 40)

WYQQKPGKAPKLLIY

Sequence of FR region of the light chain variable domain that is between CDR-L2 and CDR-L3

(SEQ ID NO: 41)

GVPDRFSGSGSGTDFTLKISRVEAEDVGVYYC

Sequence of FR region of the light chain variable domain that is between CDR-L2 and CDR-L3

(SEQ ID NO: 42)

GVPSRFSGSGSGTEFTLTISSLQPDDFATYYC

Sequence of FR region of the light chain variable domain that is C-terminal to CDR-L3

(SEQ ID NO: 43)

WYLQKPGQSPQLLIY

Sequence of FR region of the light chain variable domain that is C-terminal to CDR-L3

(SEQ ID NO: 44)

WYQQKPGKAPKLLIY

Consensus sequence of FR region of the heavy chain variable domain that is N-terminal to CDR-H1

(SEQ ID NO: 45)

VQSGAEX$_1$KKPGX$_2$SVKX$_3$SCKASGYTFT
where X$_1$ is V or L; X$_2$ is S or A; X$_3$ is V or M Sequence of FR region of the heavy chain variable domain that is N-terminal to CDR-H1

(SEQ ID NO: 46)

VQSGAEVKKPGASVKMSCKASGYTFT

Sequence of FR region of the heavy chain variable domain that is N-terminal to CDR-H1

(SEQ ID NO: 47)

VQSGAEVK KPGSSVKVSCKASGYTFT

Sequence of FR region of the heavy chain variable domain that is between CDR-H1 and CDR-H2

(SEQ ID NO: 48)

WVKQRPGQGLEWIG

Sequence of FR region of the heavy chain variable domain that is between CDR-H1 and CDR-H2

(SEQ ID NO: 49)

WVRQAPGQGLEWMG

-continued

Sequence of FR region of the heavy chain variable domain that is between CDR-H2 and CDR-H3
(SEQ ID NO: 50)

RATLTVDTSASTAYMELSSLRSEDTAVYYCTT

Sequence of FR region of the heavy chain variable domain that is between CDR-H2 and CDR-H3
(SEQ ID NO: 51)

RVTITRDTSMSTAYTELSSLRSEDTAVYYCTT

Consensus sequence of FR region of the heavy chain variable domain that is C-terminal to CDR-H3
(SEQ ID NO: 52)

WGQGTX$_1$VTVSS
where X$_1$ is L or T

Sequence of FR region of the heavy chain variable domain that is C-terminal to CDR-H3
(SEQ ID NO: 53)

WGQGTLVTVSS

Sequence of FR region of the heavy chain variable domain that is C-terminal to CDR-H3
(SEQ ID NO: 54)

WGQGTLVTVSS

Fully Human, Humanized, Primatized, and Chimeric Antibodies

Antibodies described herein include fully human, humanized, primatized, and chimeric antibodies. Additionally, antibodies described herein include fully human, humanized, primatized, and chimeric antibodies that contain one or more, or all, of the CDR-H1, CDR-H2, CDR-H3, CDR-L1, CDR-L2, and CDR-L3 sequences described herein in which one or more, or all, of the CDR sequences exhibits at least 70% sequence identity (e.g., 75%, 80%, 85%, 90%, 95%, 96%, 97%, 98%, 99%, or 100% sequence identity) to the corresponding CDR sequence of a cis-mAb described herein (e.g., any one of cis-mAb HT1, cis-mAb HT2, cis-mAb HT3, cis-mAb HT4, cis-mAb HT5, cis-mAb HT6, cis-mAb HT7, cis-mAb HT8, cis-mAb HT9, cis-mAb HT10, cis-mAb HT11, cis-mAb HT12, cis-mAb HT13, cis-mAb HT14, cis-mAb HT15, cis-mAb HT16, cis-mAb HT17, cis-mAb HT18, or a consensus sequence thereof).

In some embodiments, the antibody or antigen binding fragment is a humanized antibody or antigen-binding fragment that contains one or more, or all, of the CDR-H1, CDR-H2, CDR-H3, CDR-L1, CDR-L2, and CDR-L3 sequences described herein in which one or more, or all, of the CDR sequences have at least 70% sequence identity (e.g., 75%, 80%, 85%, 90%, 95%, 96%, 97%, 98%, 99%, or 100% sequence identity) to the corresponding CDR sequence of a humanized cis-mAb described herein (e.g., any one of cis-mAb HT1, cis-mAb HT2, cis-mAb HT3, cis-mAb HT4, cis-mAb HT5, cis-mAb HT6, cis-mAb HT7, cis-mAb HT8, cis-mAb HT9, cis-mAb HT10, cis-mAb HT11, cis-mAb HT12, cis-mAb HT14, cis-mAb HT15, cis-mAb HT16, cis-mAb HT17, cis-mAb HT18, or a consensus sequence thereof).

Conformation-specific P-tau antibodies described herein further include fully human, humanized, primatized, and chimeric antibodies that contain one or more, or all, of the CDR-H1, CDR-H2, CDR-H3, CDR-L1, CDR-L2, and CDR-L3 sequences in which one or more, or all, of the CDR sequences contains one or more (for instance, up to 3) amino acid substitutions (e.g., one or more conservative amino acid substitutions) relative to the corresponding CDR sequence of a cis-mAb described herein. For example, conformation-specific P-tau antibodies described herein can be generated by incorporating any one or more of the CDR sequences of a cis-mAb described herein into the framework regions (e.g., FW1, FW2, FW3, and FW4) of a human antibody.

As an example, one strategy that can be used to design humanized antibodies described herein is to align the sequences of the heavy chain variable region and light chain variable region of a cis-mAb described herein with the heavy chain variable region and light chain variable region of a consensus human antibody. Consensus human antibody heavy chain and light chain sequences are known in the art (see e.g., the "VBASE" human germline sequence database; see also Kabat, et al., Sequences of Proteins of Immunological Interest, Fifth Edition, U.S. Department of Health and Human Services, NIH Publication No. 91-3242, 1991; Tomlinson et al., J. Mol. Biol. 227:776-98, 1992; and Cox et al, Eur. J. Immunol. 24:827-836, 1994; the disclosure of which is incorporated herein by reference). In this way, the variable domain framework residues and CDRs can be identified by sequence alignment (see Kabat, supra). One can substitute, for example, one or more of the CDRs of the consensus human antibody with the corresponding CDR(s) of a cis-mAb described herein, in order to produce a humanized cis P-tau antagonist antibody. Exemplary variable domains of a consensus human antibody include the heavy chain variable domain are identified in U.S. Pat. No. 6,054,297; the disclosure of which is incorporated herein by reference. These amino acid substitutions can be made, for example, by recombinant expression of polynucleotides encoding the heavy and light chains of a humanized antibody in a host cell using methods known in the art or described herein.

Similarly, this strategy can also be used to produce primatized conformation-specific P-tau antibodies, as one can substitute, for example, one or more, or all, of the CDRs of a primate antibody consensus sequence with, for example, one or more, or all, of the CDRs of a cis-mAb described herein. Consensus primate antibody sequences known in the art (see e.g., U.S. Pat. Nos. 5,658,570; 5,681,722; and 5,693,780; the disclosures of each of which are incorporated herein by reference).

In some embodiments, it may be desirable to import particular framework residues in addition to CDR sequences from a conformation-specific P-tau antibody, such as a cis-mAb described herein, into the heavy and/or light chain variable domains of a human antibody. For instance, U.S. Pat. No. 6,054,297 identifies several instances when it may be advantageous to retain certain framework residues from a particular antibody heavy chain or light chain variable region in the resulting humanized antibody. In some embodiments, framework residues may engage in non-covalent interactions with the antigen and thus contribute to the affinity of the antibody for the target antigen. In some embodiments, individual framework residues may modulate the conformation of a CDR, and thus indirectly influence the interaction of the antibody with the antigen. Certain framework residues may form the interface between VH and VL domains and may therefore contribute to the global antibody structure. In some cases, framework residues may constitute functional glycosylation sites (e.g., Asn-X-Ser/Thr) which may dictate antibody structure and antigen affinity upon attachment to carbohydrate moieties. In cases such as those described above, it may be beneficial to retain certain framework residues of a conformation-specific P-tau antibody (e.g., a cis-mAb described herein in, e.g., a humanized or primatized antagonistic antibody or antigen-binding fragment thereof, as various framework residues may promote high epitope affinity and improved biochemical activity of the antibody or antigen-binding fragment thereof.

Antibodies described herein also include antibody fragments, Fab domains, F(ab') molecules, $F(ab')_2$ molecules, single-chain variable fragments (scFvs), tandem scFv fragments, diabodies, triabodies, dual variable domain immunoglobulins, multi-specific antibodies, bispecific antibodies, and heterospecific antibodies that contain one or more, or all, of the CDRs of a cis-mAb described herein, or one or more, or all, of the CDR-H1, CDR-H2, CDR-H3, CDR-L1, CDR-L2, and CDR-L3 sequences in which one or more, or all, of the CDR sequences exhibits at least 70% sequence identity (e.g., 75%, 80%, 85%, 90%, 95%, 96%, 97%, 98%, 99%, or 100% sequence identity) to the corresponding CDR sequence of a cis-mAb described herein. Conformation-specific P-tau antibodies described herein further include fully human, humanized, primatized, and chimeric antibodies that contain one or more, or all, of the CDR-H1, CDR-H2, CDR-H3, CDR-L1, CDR-L2, and CDR-L3 sequences in which one or more, or all, of the CDR sequences contains one or more (for instance, up to 3) amino acid substitutions (e.g., one or more conservative amino acid substitutions) relative to the corresponding CDR sequence of a cis-mAb described herein. These molecules can be expressed recombinantly, e.g., by incorporating polynucleotides encoding these proteins into expression vectors for transfection in a eukaryotic or prokaryotic cell using techniques described herein or known in the art, or synthesized chemically, e.g., by solid phase peptide synthesis methods described herein or known in the art.

Polypeptides described herein additionally include antibody-like scaffolds that contain, for example, one or more, or all, of the CDRs of a cis-mAb described herein, or one or more, or all, of the CDR-H1, CDR-H2, CDR-H3, CDR-L1, CDR-L2, and CDR-L3 sequences in which one or more, or all, of the CDR sequences exhibits at least 70% sequence identity (e.g., 75%, 80%, 85%, 90%, 95%, 96%, 97%, 98%, 99%, or 100% sequence identity) to the corresponding CDR sequence of a cis-mAb described herein or contains one or more (for instance, up to 3) amino acid substitutions (e.g., one or more conservative amino acid substitutions) relative to the corresponding CDR sequence of a cis-mAb described herein. Examples of antibody-like scaffolds include proteins that contain a tenth fibronectin type III domain ($^{10}$Fn3), which contains BC, DE, and FG structural loops analogous to canonical antibodies. The tertiary structure of the $^{10}$Fn3 domain resembles that of the variable region of the IgG heavy chain, and one of skill in the art can graft, e.g., one or more, or all, of the CDR sequences of a cis-mAb described herein or sequences having at least 70% sequence identity (e.g., 75%, 80%, 85%, 90%, 95%, 97%, 99%, or 100% sequence identity) to any one or more of these CDR sequences or sequences containing amino acid substitutions, such as conservative or nonconservative amino acid substitutions (e.g., up to 3 amino acid substitutions) relative to one or more of these CDR sequences onto the fibronectin scaffold by replacing residues of the BC, DE, and FG loops of $^{10}$Fn3 with residues of the corresponding CDR sequence of a cis-mAb described herein. This can be achieved by recombinant expression of a modified $^{10}$Fn3 domain in a prokaryotic or eukaryotic cell (e.g., using the vectors and techniques described herein). Examples of using the $^{10}$Fn3 domain as an antibody-like scaffold for the grafting of CDRs from antibodies onto the BC, DE, and FG structural loops are reported in WO 2000/034784, WO 2009/142773, WO 2012/088006, and U.S. Pat. No. 8,278,419; the disclosures of each of which are incorporated herein by reference.

II. Nucleic Acids and Expression Systems

Conformation-specific P-tau antibodies or antigen-binding fragments thereof described herein can be prepared by any of a variety of established techniques. For instance, a conformation-specific P-tau antibody or antigen-binding fragment thereof described herein can be prepared by recombinant expression of immunoglobulin light and heavy chain genes in a host cell. To express an antibody recombinantly, a host cell can be transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N. Y., 1989), Current Protocols in Molecular Biology (Ausubel et al., eds., Greene Publishing Associates, 1989), and in U.S. Pat. No. 4,816,397; the disclosures of each of which are incorporated herein by reference.

Vectors for Expression of Conformation-Specific P-Tau Antibodies

Viral genomes provide a rich source of vectors that can be used for the efficient delivery of exogenous genes into the genome of a cell (e.g., a eukaryotic or prokaryotic cell). Viral genomes are particularly useful vectors for gene delivery because the polynucleotides contained within such genomes are typically incorporated into the genome of a target cell by generalized or specialized transduction. These processes occur as part of the natural viral replication cycle, and do not require added proteins or reagents in order to induce gene integration. Examples of viral vectors include a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding antibody light and heavy chains or antibody fragments described herein include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., (U.S. Pat. No. 5,801,030); the disclosures of each of which are incorporated herein by reference.

Genome Editing Techniques

In addition to viral vectors, a variety of additional methods have been developed for the incorporation of genes, e.g., those encoding antibody light and heavy chains, single-chain polypeptides, single-chain variable fragments (scFvs), tandem scFvs, Fab domains, $F(ab')_2$ domains, diabodies, and triabodies, among others, such as those described herein, into the genomes of target cells for polypeptide expression. One such method that can be used for incorporating polynucleotides encoding conformation-specific P-tau antibodies or fragments thereof, such as those described herein, into prokaryotic or eukaryotic cells includes transposons. Transposons are polynucleotides that encode transposase enzymes and contain a polynucleotide sequence or gene of interest flanked by excision sites at the 5' and 3' positions. Once a transposon has been delivered into a cell, expression of the transposase gene commences and results in active enzymes that cleave the gene of interest from the transposon. This activity is mediated by the site-specific recognition of transposon excision sites by the transposase. In some embodiments, these excision sites may be terminal repeats or inverted terminal repeats. Once excised from the transposon, the gene of interest can be integrated into the genome of a prokaryotic or eukaryotic cell by transposase-catalyzed cleavage of similar excision sites that exist within nuclear genome of the cell. This allows the gene encoding a conformation-specific P-tau antibody or fragment or domain thereof to be inserted into the cleaved nuclear DNA at the excision sites, and subsequent ligation of the phosphodiester bonds that join the gene of interest to the DNA of the prokaryotic or eukaryotic cell genome completes the incorporation process. In some embodiments, the transposon may be a retrotransposon, such that the gene encoding the antibody is first transcribed to an RNA product and then reverse-transcribed to DNA before incorporation in the prokaryotic or eukaryotic cell genome. Exemplary transposon systems include the piggybac transposon (described in detail in WO 2010/085699) and the sleeping beauty transposon (described in detail in US20050112764); the disclosures of each of which are incorporated herein by reference.

Another useful method for the integration of nucleic acid molecules encoding conformation-specific P-tau antibodies or fragments thereof, such as those described herein, into the genome of a prokaryotic or eukaryotic cell is the clustered regularly interspaced short palindromic repeats (CRISPR)/Cas system, which is a system that originally evolved as an adaptive defense mechanism in bacteria and archaea against infection by viruses. The CRISPR/Cas system consists of palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can theoretically design a CRISPR/Cas system to cleave any target DNA molecule of interest. This technique has been exploited in order to edit eukaryotic genomes (Hwang et al., Nat. Biotech., 31:227-229, 2013) and can be used as an efficient means of site-specifically editing eukaryotic or prokaryotic genomes in order to cleave DNA prior to the incorporation of a polynucleotide encoding a conformation-specific P-tau antibody or fragment thereof described herein. The use of CRISPR/Cas to modulate gene expression has been described in U.S. Pat. No. 8,697,359, the disclosure of which is incorporated herein by reference.

Alternative methods for site-specifically cleaving genomic DNA prior to the incorporation of a polynucleotide encoding a conformation-specific P-tau antibody or fragment thereof, such as those described herein, include the use of zinc finger nucleases and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. Zinc finger nucleases and TALENs for use in genome editing applications are described in Urnov et al. (Nat. Rev. Genet., 11:636-646, 2010); and in Joung et al., (Nat. Rev. Mol. Cell. Bio. 14:49-55, 2013); incorporated herein by reference. Additional genome editing techniques that can be used to incorporate polynucleotides encoding antibodies described herein into the genome of a prokaryotic or eukaryotic cell include the use of ARCUS™ meganucleases that can be rationally designed so as to site-specifically cleave genomic DNA. The use of these enzymes for the incorporation of polynucleotides encoding conformation-specific P-tau antibodies or fragments thereof described herein into the genome of a prokaryotic or eukaryotic cell is particularly advantageous in view of the structure-activity relationships that have been established for such enzymes. Single-chain meganucleases can thus be modified at certain amino acid positions in order to create nucleases that selectively cleave DNA at desired locations. These single-chain nucleases have been described extensively, e.g., in U.S. Pat. Nos. 8,021,867 and 8,445,251; the disclosures of each of which are incorporated herein by reference.

Polynucleotide Sequence Elements

To express conformation-specific P-tau antibodies or fragments thereof, such as those described herein, polynucleotides encoding partial or full-length light and heavy chains, e.g., polynucleotides that encode a one or more, or all, of the CDR sequences of an antibody or antigen-binding fragment thereof described herein, can be inserted into expression vectors such that the genes are operatively linked to transcriptional and translational control sequences. The expression vector and expression control sequences are chosen to be compatible with the expression host cell used. Polynucleotides encoding the light chain gene and the heavy chain of a conformation-specific P-tau antibody or fragment thereof can be inserted into separate vectors, or, optionally, both polynucleotides can be incorporated into the same expression vector using established techniques described herein or known in the art.

In addition to polynucleotides encoding the heavy and light chains of an antibody (or a polynucleotide encoding a single-chain polypeptide, an antibody fragment, such as a scFv molecule, or a construct described herein), the recombinant expression vectors described herein may carry regulatory sequences that control the expression of the antibody chain genes in a host cell. The design of the expression vector, including the selection of regulatory sequences, may depend on such factors as the choice of the host cell to be transformed or the level of expression of protein desired. For instance, suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Viral regulatory elements, and sequences thereof, are described in detail, for instance, in U.S. Pat. Nos. 5,168,062, 4,510,245, and 4,968,615, the disclosures of each of which are incorporated herein by reference.

In addition to the antibody chain genes and regulatory sequences, the recombinant expression vectors described herein can carry additional sequences, such as sequences that regulate replication of the vector in host cells (e.g., origins of replication) and selectable marker genes. A selectable marker gene facilitates selection of host cells into which the vector has been introduced (see e.g., U.S. Pat. Nos. 4,399,216, 4,634,665 and 5,179,017). For example, typically the selectable marker gene confers resistance to cytotoxic drugs, such as G418, puromycin, blasticidin, hygromycin or methotrexate, to a host cell into which the vector has been introduced. Suitable selectable marker genes include the dihydrofolate reductase (DHFR) gene (for use in DHFR" host cells with methotrexate selection/amplification) and the neo gene (for G418 selection). In order to express the light and heavy chains of a conformation-specific P-tau antibody or fragment thereof, the expression vector(s) containing polynucleotides encoding the heavy and light chains can be transfected into a host cell by standard techniques.

Polynucleotides Encoding Modified Conformation-Specific P-Tau Antibodies

Conformation-specific P-tau antibodies or fragments thereof described herein may contain one or more, or all, of the CDRs of a cis-mAb described herein and variants thereof, or one or more, or all, of the CDR-H1, CDR-H2, CDR-H3, CDR-L1, CDR-L2, and CDR-L3 sequences in which one or more, or all, of the CDR sequences exhibits at least 70% sequence identity (e.g., 75%, 80%, 85%, 90%, 95%, 96%, 97%, 98%, 99%, or 100% sequence identity) to the corresponding CDR sequence of a cis-mAb described herein or contains, e.g., one or more (for instance, up to 3) amino acid substitutions (e.g., one or more conservative amino acid substitutions) relative to the corresponding CDR sequence of a cis-mAb described herein, but may feature differences in one or more framework regions of a cis-mAb described herein. For instance, one or more framework regions of a cis-mAb described herein may be substituted with the framework region of a human antibody. Exemplary framework regions include, for example, human framework regions described in U.S. Pat. No. 7,829,086, and primate framework regions as described in EP 1945668; the disclosures of each of which are incorporated herein by reference. To generate nucleic acids encoding such conformation-specific P-tau antibodies or fragments thereof, DNA fragments encoding, e.g., at least one, or both, of the light chain variable regions and the heavy chain variable regions can be produced by chemical synthesis (e.g., by solid phase polynucleotide synthesis techniques), in vitro gene amplification (e.g., by polymerase chain reaction techniques), or by replication of the polynucleotide in a host organism. For instance, nucleic acids encoding conformation-specific P-tau antibodies or fragments thereof described herein may be obtained by amplification and modification of germline DNA or cDNA encoding light and heavy chain variable sequences so as to incorporate one or more, or all, of the CDRs of a cis-mAb described herein into the framework residues of a consensus antibody.

In some embodiments, a humanized conformation-specific P-tau antibody or fragment thereof may include one or more, or all, of the CDR-H1, CDR-H2, CDR-H3, CDR-L1, CDR-L2, and CDR-L3 sequences in which one or more, or all, of the CDR sequences exhibits at least 70% sequence identity (e.g., 75%, 80%, 85%, 90%, 95%, 96%, 97%, 98%, 99%, or 100% sequence identity) to the corresponding CDR sequence of a cis-mAb described herein or contains one or more (for instance, up to 3) amino acid substitutions (e.g., one or more conservative amino acid substitutions) relative to the corresponding CDR sequence of a cis-mAb described herein. This can be achieved, for example, by performing site-directed mutagenesis of germline DNA or cDNA and amplifying the resulting polynucleotides using the polymerase chain reaction (PCR) according to established procedures. Germline DNA sequences for human heavy and light chain variable region genes are known in the art (see, e.g., the "VBASE" human germline sequence database; see also Kabat et al., Sequences of Proteins of Immunological Interest, Fifth Edition, U.S. Department of Health and Human Services, NIH Publication No. 91-3242, 1991; Tomlinson et al., J. Mol. Biol. 227:776-798, 1992; and Cox et al., Eur. J. Immunol. 24:827-836, 1994; incorporated herein by reference). Chimeric nucleic acid constructs encoding human heavy and light chain variable regions containing one or more, or all, of the CDRs of a cis-mAb described herein, or a similar sequence as described above, can be produced, e.g., using established cloning techniques known in the art. Additionally, a polynucleotide encoding a heavy chain variable region containing the one or more of the CDRs of a cis-mAb described herein, or a similar sequence as described above, can be synthesized and used as a template for mutagenesis to generate a variant as described herein using routine mutagenesis techniques. Alternatively, a DNA fragment encoding the variant can be directly synthesized (e.g., by established solid phase nucleic acid chemical synthesis procedures).

Once DNA fragments encoding VH segments containing one or more, or all, of the CDR-H1, CDR-H2, and CDR-H3 sequences of a cis-mAb described herein are obtained, these DNA fragments can be further manipulated by standard recombinant DNA techniques, e.g., to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The isolated DNA encoding the VH region of a conformation-specific P-tau antibody described herein can be converted to a full-length heavy chain gene (as well as a Fab heavy chain gene), e.g., by operatively linking the VH-encoding DNA to another DNA molecule encoding heavy chain constant region domains (CH1, CH2, CH3, and, optionally, CH4). The sequences of human heavy chain constant region genes are known in the art (see e.g., Kabat et al., Sequences of Proteins of Immunological Interest, Fifth Edition, U.S. Department of Health and Human Services, NIH Publication No. 91-3242, 1991) and DNA fragments encompassing these regions can be obtained by standard PCR amplification. The heavy chain constant region can be an IgG1, IgG2, IgG3, IgG4, IgA, IgE, IgM or IgD constant region, and in certain embodiments is an IgG1 constant region. For a Fab fragment heavy chain gene, the VH-encoding DNA can be operatively linked to another DNA molecule encoding only the heavy chain CH1 domain.

Isolated DNA encoding the VL region of a conformation-specific P-tau antibody can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al., Sequences of Proteins of Immunological Interest, Fifth Edition (U.S. Department of Health and Human Services, NIH Publication No. 91-3242, 1991)) and DNA fragments encompassing these regions can be obtained, e.g., by amplification in a prokaryotic or eukaryotic cell of a polynucleotide encoding these regions, by PCR amplification, or by chemical polynucleotide synthesis. The light chain constant region can be a kappa (κ) or lambda (λ) constant region, but in certain embodiments is a kappa constant region. To create a scFv gene, the VH and VL-encoding DNA fragments are operatively linked to another fragment encoding a flexible linker, e.g., a polynucleotide encoding a flexible, hydrophilic amino acid sequence, such as the amino acid sequence $(Gly_4Ser)_3$, such that the $V_H$ and $V_L$ sequences can be expressed as a contiguous single-chain protein, with the $V_L$ and $V_H$ regions joined by the linker (see e.g., Bird et al., Science 242:423-426, 1988; Huston et al., Proc. Natl. Acad. Sci. USA 85:5879-5883, 1988; McCafferty et al., Nature 348:552-554, 1990).

Recombinant DNA technology can also be used to remove some or all of the DNA encoding either or both of the light and heavy chains that is not necessary for binding to a particular epitope of P-tau. The molecules expressed from such truncated DNA molecules are also encompassed by the antibodies described herein. In addition, bifunctional antibodies can be produced in which one heavy contains one or more, or all, of the CDRs of a cis-mAb described herein, or a similar CDR sequence as described above, and the other heavy chain and/or the light chains are specific for an antigen other than P-tau. Such antibodies can be generated, e.g., by crosslinking a heavy chain and light chain containing one or more, or all, of the CDRs of a cis-mAb described herein, or a similar CDR sequence as described above, to a heavy chain and light chain of a second antibody specific for a different antigen, for instance, using standard chemical crosslinking methods (e.g., by disulfide bond formation). Bifunctional antibodies can also be made by expressing a nucleic acid molecule engineered to encode a bifunctional antibody in a prokaryotic or eukaryotic cell.

Dual specific antibodies, i.e., antibodies that bind a particular epitope of P-tau and a different antigen using the same binding site, can be produced by mutating amino acid residues in the light chain and/or heavy chain CDRs. In some embodiments, dual specific antibodies that bind two antigens, such as P-tau and a second cell-surface receptor, can be produced by mutating amino acid residues in the periphery of the antigen binding site (Bostrom et al., Science 323: 1610-1614, 2009). Dual functional antibodies can be made by expressing a polynucleotide engineered to encode a dual specific antibody.

Modified conformation-specific P-tau antibodies or fragments thereof described herein can also be produced by chemical synthesis (e.g., by the methods described in Solid Phase Peptide Synthesis, 2nd ed., 1984 The Pierce Chemical Co., Rockford, 111; incorporated herein by reference). Variant antibodies can also be generated using a cell-free synthetic platform (see, e.g., Chu et al., Biochemia No. 2, 2001 (Roche Molecular Biologicals); incorporated herein by reference).

Host Cells for Expression of a Conformation-Specific P-Tau Antibody or a Fragment Thereof It is possible to express the antibodies of fragments thereof described herein in either prokaryotic or eukaryotic host cells. In certain embodiments, expression of antibodies or fragments thereof is performed in eukaryotic cells, e.g., mammalian host cells, for optimal secretion of a properly folded and immunologically active antibody. Exemplary mammalian host cells for expressing the recombinant antibodies or antigen-binding fragments thereof described herein include Chinese Hamster Ovary (CHO cells) (including DHFR CHO cells, described in Urlaub and Chasin (1980, Proc. Natl. Acad. Sci. USA 77:4216-4220), used with a DHFR selectable marker, e.g., as described in Kaufman and Sharp (1982, Mol. Biol. 159:601-621), NSO myeloma cells, COS cells, 293 cells, and SP2/0 cells. Additional cell types that may be useful for the expression of antibodies and fragments thereof include bacterial cells, such as BL-21 (DE3) *E. coli* cells, which can be transformed with vectors containing foreign DNA according to established protocols. Additional eukaryotic cells that may be useful for expression of antibodies include yeast cells, such as auxotrophic strains of *S. cerevisiae*, which can be transformed and selectively grown in incomplete media according to established procedures known in the art. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown.

Antibodies or antigen-binding fragments thereof can be recovered from the culture medium using standard protein purification methods. Host cells can also be used to produce portions of intact antibodies, such as Fab fragments or scFv molecules. Also included herein are methods in which the above procedure is varied according to established protocols known in the art. For example, it can be desirable to transfect a host cell with DNA encoding either the light chain or the heavy chain (but not both) of a conformation-specific P-tau antibody or fragment thereof described herein in order to produce an antigen-binding fragment of the antibody.

Once a conformation-specific P-tau antibody or fragment thereof described herein has been produced by recombinant expression, it can be purified by any method known in the art, such as a method useful for purification of an immunoglobulin molecule, for example, by chromatography (e.g., ion exchange, affinity, and sizing column chromatography), centrifugation, differential solubility, or by any other standard technique for the purification of proteins. Further, the conformation-specific P-tau antibody or fragment thereof described herein or fragments thereof can be fused to heterologous polypeptide sequences described herein or otherwise known in the art to facilitate purification or to produce therapeutic conjugates.

Once isolated, a conformation-specific P-tau antibody or fragment thereof can, if desired, be further purified, e.g., by high performance liquid chromatography (see, e.g., Fisher, Laboratory Techniques in Biochemistry and Molecular Biology (Work and Burdon, eds., Elsevier, 1980); incorporated herein by reference), or by gel filtration chromatography, such as on a SUPERDEX™ 75 column (Pharmacia Biotech AB, Uppsala, Sweden).

III. Platforms for Generating Conformation-Specific Cis P-Tau Antibodies or Fragments Thereof Antigenic Peptides Conformation-specific antibodies may be generated using immunogenic antigens (e.g., antigenic peptides) containing, for example, a phosphorylated or non-phosphorylated Thr-Pro motif (e.g., a phosphorylated Thr-Pro motif), where the peptidyl prolyl bond is fixed in a particular conformation (e.g., the cis or trans conformation) or is mixed cis and trans conformations or any other motif or amino acid sequence that is capable of cis/trans isomerization. For example, the cis or trans content of a phosphorylated or non-phosphorylated Thr-Pro-containing antigenic peptide may be fixed by stereoselective synthesis of (Z)- and (E)-alkene mimics by Still-Wittig and Ireland-Claisen rearrangements (J. Org. Chem., 68: 2343-2349, 2003; hereby incorporated by reference). Alternatively, the cis or trans content of phosphorylated or nonphosphorylated Thr-Pro-containing antigenic peptides of the disclosure may be increased or fixed by substituting a proline amino acid residue with a proline analog. Proline analogs include, without limitation, homoproline, azetidine-2-carboxylic acid (Aze), tert-butyl-L-proline (TBP), trans-4-fluoro-L-proline (t-4F-Pro), and cis-4-fluoro-L-proline (c-4F-Pro). The cis or trans content of a given antigen may be analyzed by, for example, nuclear magnetic resonance (NMR) analysis.

Antigenic peptides of the disclosure may contain a phosphorylated or nonphosphorylated Thr-Pro motif (e.g., a pThr-Pro motif) which is capable of cis/trans isomerization. The antigenic peptide may contain an epitope from the tau protein including a pThr-Pro motif (e.g., pThr231-Pro). The antigenic peptide may further include additional residues surrounding the Thr-Pro motif of the full-length polypeptide. For example, the antigenic peptide may include the 3-10 amino acid residues N-terminal to the S residue of a full-length polypeptide and the 3-10 amino acid residues C-terminal to the proline of a full-length polypeptide.

An antigenic peptide may contain an epitope the tau protein including a pThr-Xaa motif (e.g., pThr231-Xaa). Xaa may be selected from Pro, a proline analog, or any natural or non-natural amino acid. Preferably, Xaa is any proline analog, or natural or non-natural amino acid wherein the peptide bond between pThr and Xaa in the pThr-Xaa motif is preferentially in the cis conformation. Most preferably, Xaa is an amino acid that share structural similarity to Pro, but which resides preferentially in the cis-peptide bond conformation. For example, the antigenic peptide may be a peptide containing the pThr231-Pro motif of the tau protein, wherein the Pro residue is replaced by a proline analog that favors the either the cis or the trans conformation, e.g., a proline analog selected from homoproline (i.e., pipecolic acid (PIP)), 5,5-dimethyl proline (DMP), azetidine-2-carboxylic acid (Aze), tert-butyl-L-proline (TBP), trans-4-fluoro-L-proline (t-4F-Pro), 2,2-dimethyl-thiazolidine (Thz), or cis-4-fluoro-L-proline (c-4F-Pro).

The antigenic peptide of the disclosure may be, for example, at least 4, 5, 6, 7, or 8 amino acid residues in length. The antigenic peptide may be between 8 and 20 amino acid residues in length (e.g., 8, 9, 10, 11, 12, 13, 14, 15, 16, 17, 18, 19, or 20 amino acids residues in length) or may be over 20 amino acid residues in length.

Such antigens may be produced and purified by any of a variety of methods known to one of skill in the art. Antigenic peptides may be produced and purified by, e.g., solid-phase chemical synthesis, in vitro transcription/translation, or by recombinant technology. The antigenic peptides may optionally be chemically coupled to a carrier protein or the peptides may be generated as fusion proteins to increase antigenicity. Antigenic peptides may be screened based upon their ability to induce the production of conformation-specific antibodies. In this respect, such screening techniques may include, but are not limited to, enzyme-linked immunosorbant assays (ELISA), immunoprecipitation, or other immunoassays.

Exemplary antigens useful in the production of conformation-specific antibodies include antigens containing a phosphorylated or nonphosphorylated Ser/Thr-homoproline, Ser/Thr-Aze, Ser/Thr-TBP, Ser/Thr-t-4F-Pro, Ser/Thr-c-4F-Pro motif. Such peptides may be used as antigens for generating, e.g., polyclonal or monoclonal antibodies (e.g., rabbit or mouse monoclonal antibodies).

Generation and Purification of Conformation-Specific Antibodies

The antigens of the present disclosure may be used to generate, for example, monoclonal, polyclonal, chimeric, humanized, or recombinant conformation-specific antibodies by any method known in the art. These methods include the immunological methods described by Kohler and Milstein (Nature 256: 495-497, 1975 and Eur. J. Immunol. 6: 511-519, 1976) and Campbell ("Monoclonal Antibody Technology, The Production and Characterization of Rodent and Human Hybridomas," in Burdon et al., Eds., Laboratory Techniques in Biochemistry and Molecular Biology, Volume 13, Elsevier Science Publishers, Amsterdam, 1985), as well as by the recombinant DNA method described by Huse et al. (Science 246: 1275-1281, 1989).

Briefly, the antigens of the present disclosure may, in combination with an adjuvant, be administered to a host animal (e.g., rabbits, mice, rats, goats, guinea pigs, hamsters, horses, and sheep, as well as non-human primates). The administration of such antigens may be accomplished by any of a variety of methods, including, but not limited to, subcutaneous or intramuscular injection. Once administered, the results of antibody titers produced in the host animal are monitored, which may be conducted by any of a variety of techniques well-known in the art (e.g., routine bleeds), with the antisera being isolated (e.g., via centrifugation) and thereafter screened for the presence of antibodies having a binding affinity for, e.g., the cis or trans conformation of a polypeptide or polypeptide fragment. Screening for the desired antibody may be accomplished by techniques including, e.g., radioimmunoassays, ELISA, sandwich immunoassays, immunoradiometric assays, gel diffusion precipitation reactions, in situ immunoassays (e.g., using colloidal gold, enzymatic, or radioisotope labels), Western blots, precipitation reactions, agglutination assays (e.g., gel agglutination assays or hemagglutination assays), complement fixation assays, immunofluorescence assays, protein A assays, and immunoelectrophoresis assays.

The resultant antisera derived from the host animal may be affinity purified to derive the antibodies for the present disclosure. The antisera may be purified via conventional techniques, such as the introduction of the antisera onto a separation column. The antigens of the present disclosure may be immobilized on the column to isolate and purify conformation-specific antibodies. For example, an antigenic peptide containing a Ser/Thr-Proline (e.g., pThr-Pro) motif that is used to generate a conformation-specific antibody (e.g., a cis-specific) may be immobilized on a column and used to purify the resulting conformation-specific antibody. The column may then be washed to remove antibodies not having specificity for the antigen immobilized on the column, with the remaining conformation-specific antibody ultimately being eluted from the column. The isolated conformation-specific antibody may then be stored per conventional practices known to those skilled in the art.

Established procedures for immunizing primates are known in the art (see, e.g., WO 1986/6004782; incorporated herein by reference). Immunization represents a robust method of producing monoclonal antibodies by exploiting the antigen specificity of B lymphocytes. For example, monoclonal antibodies can be prepared by the Kohler-Millstein procedure (described, e.g., in EP 0110716; incorporated herein by reference), wherein spleen cells from a non-human animal (e.g., a primate) administer peptide with an antigenic peptide. A clonally-expanded B lymphocyte produced by immunization can be isolated from the serum of the animal and subsequently fused with a myeloma cell in order to form a hybridoma. Hybridomas are particularly useful agents for antibody production, as these immortalized cells can provide a lasting supply of an antigen-specific antibody. Antibodies from such hybridomas can subsequently be isolated using techniques known in the art, e.g., by purifying the antibodies from the cell culture medium by affinity chromatography.

Alternatively, antibody libraries (e.g., naive antibody libraries, synthetic antibody libraries, semi-synthetic antibody libraries, or combinatorial libraries) may be screened for the identification of conformation-specific antibodies. Such libraries are commercially available from a number of sources (e.g., Cambridge Antibody, Cambridge, United Kingdom, Genetastix Corporation, Pacific Northwest Laboratory, Richland, Washington, and MorphoSys AG, Munich, Germany (e.g., HuCal GOLD)). See, e.g., U.S. Pat. Nos. 6,696,248; 6,706,484; 6,828,422; and 7,264,963, hereby incorporated by reference.

Screening of an antibody library may be performed by using one of the methods known to one of skill in the art including, e.g., phage-display, selectively infective phage, polysome technology, and assay systems for enzymatic activity or protein stability. Antibodies having the desired property can be identified, for example, by sequencing of the corresponding nucleic acid sequence, by amino acid sequencing, or by mass spectrometry. Optimization is performed by replacing sub-sequences with different sequences (e.g., random sequences) and then repeating the screening step one or more times. The antibodies may be screened for, e.g., optimized affinity or specificity for a target molecule (e.g., the cis or trans conformation of a target molecule), optimized expression yields, optimized stability, or optimized solubility.

Conformation-specific antibodies of the present disclosure recognize and specifically bind to, for example, a particular conformation (e.g., the cis or trans conformation) of its complementary antigen. For example, as described herein, the conformation-specific antibody may specifically bind to the cis conformation of a phosphorylated Thr-Pro motif of a polypeptide (e.g., pThr231-Pro of tau protein), relative to the trans conformation. In this case, the Kd between the conformation-specific antibody and its antigen is, for example, at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M or greater. In addition to the binding specificity, the conformation-specific antibody will have, for example, at least 10- to 500-fold greater affinity to one conformation (e.g., the cis conformation) than to another conformation (e.g., the trans conformation) of the pThr-Pro motif.

IV. Conformation-Specific Cis P-Tau Antibody Conjugates

It may be desirable to conjugate the antibody or fragment thereof to a second molecule, e g., to modulate the activity of the antibody in vivo or for diagnostic purposes. Conformation-specific P-tau antibodies or antigen-binding fragments thereof can be conjugated to other molecules at either the N-terminus or C-terminus of a light or heavy chain of the antibody using any one of a variety of established conjugation strategies that are well-known in the art. Examples of pairs of reactive functional groups that can be used to covalently tether a conformation-specific P-tau antibody or antigen-binding fragment thereof to another molecule include, without limitation, thiol pairs, carboxylic acids and amino groups, ketones and amino groups, aldehydes and amino groups, thiols and alpha, beta-unsaturated moieties (such as maleimides or dehydroalanine), thiols and alpha-halo amides, carboxylic acids and hydrazides, aldehydes and hydrazides, and ketones and hydrazides.

Conformation-specific P-tau antibodies or antigen-binding fragments thereof can be covalently appended directly to another molecule by chemical conjugation as described. Alternatively, fusion proteins containing a conformation-specific P-tau antibody or antigen-binding fragment thereof can be expressed recombinantly from a cell (e.g., a eukaryotic cell or prokaryotic cell). This can be accomplished, for example, by incorporating a polynucleotide encoding the fusion protein into the nuclear genome of a cell (e.g., using techniques described herein or known in the art). Optionally, antibodies and fragments thereof described herein can be joined to a second molecule by forming a covalent bond between the antibody and a linker. This linker can then be subsequently conjugated to another molecule, or the linker can be conjugated to another molecule prior to ligation to the conformation-specific P-tau antibody or antigen-binding fragment thereof. Examples of linkers that can be used for the formation of a conjugate include polypeptide linkers, such as those that contain naturally occurring or non-naturally occurring amino acids. In some embodiments, it may be desirable to include D-amino acids in the linker, as these residues are not present in naturally-occurring proteins and are thus more resistant to degradation by endogenous proteases. Fusion proteins containing polypeptide linkers can be made using chemical synthesis techniques, such as those described herein, or through recombinant expression of a polynucleotide encoding the fusion protein in a cell (e.g., a prokaryotic or eukaryotic cell). Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage (Leriche et al., Bioorg. Med. Chem., 20:571-582, 2012).

A conformation-specific P-tau antibody or antigen-binding fragment thereof described herein can be conjugated to, admixed with, or administered separately from a therapeutic agent.

Labeled Conformation-Specific P-Tau Antibodies or Antigen-Binding Fragments Thereof.

In some embodiments, conformation-specific P-tau antibodies or antigen-binding fragments thereof described herein are conjugated to another molecule (e.g., an epitope tag) for the purpose of purification or detection. Examples of such molecules that are useful in protein purification include those that present structural epitopes capable of being recognized by a second molecule. This is a common strategy that is employed in protein purification by affinity chromatography, in which a molecule is immobilized on a solid support and exposed to a heterogeneous mixture containing a target protein conjugated to a molecule capable of binding the immobilized compound. Examples of epitope tag molecules that can be conjugated to conformation-specific P-tau antibodies or antigen-binding fragments thereof for the purposes of molecular recognition include, without limitation, maltose-binding protein, glutathione-S-transferase, a poly-histidine tag, a FLAG-tag, a myc-tag, human influenza hemagglutinin (HA) tag, biotin, streptavidin. Conjugates containing the epitopes presented by these molecules are capable of being recognized by such complementary molecules as maltose, glutathione, a nickel-containing complex, an anti-FLAG antibody, an anti-myc antibody, an anti-HA antibody, streptavidin, or biotin, respectively. For example, one can purify an antibody or fragment thereof described herein that has been conjugated to an epitope tag from a complex mixture of other proteins and biomolecules (e.g., DNA, RNA, carbohydrates, phospholipids, etc.) by treating the mixture with a solid phase resin containing an complementary molecule that can selectively recognize and bind the epitope tag of the antibody or fragment thereof. Examples of solid phase resins include agarose beads, which are compatible with purifications in aqueous solution.

A conformation-specific P-tau antibody or antigen-binding fragment thereof described herein can also be covalently appended to a fluorescent molecule, e.g., to detect the antibody or antigen-binding fragment thereof by fluorimetry and/or by direct visualization using fluorescence microscopy. Exemplary fluorescent molecules that can be conjugated to antibodies described herein include green fluorescent protein, cyan fluorescent protein, yellow fluorescent protein, red fluorescent protein, phycoerythrin, allophycocyanin, hoescht, 4',6-diamidino-2-phenylindole (DAPI), propidium iodide, fluorescein, coumarin, rhodamine, tetramethylrhoadmine, and cyanine. Additional examples of fluorescent molecules suitable for conjugation to antibodies described herein are well-known in the art and have been described in detail in, e.g., U.S. Pat. Nos. 7,417,131 and 7,413,874, each of which is incorporated by reference herein.

Conformation-specific P-tau antibodies or antigen-binding fragments thereof containing a fluorescent molecule are particularly useful for monitoring the cell-surface localization properties of antibodies and fragments thereof described herein. For instance, one can expose cultured mammalian cells to conformation-specific P-tau antibodies or antigen-binding fragments thereof described herein that have been covalently conjugated to a fluorescent molecule and subsequently analyze these cells using conventional fluorescent microscopy techniques known in the art. Confocal fluorescent microscopy is a particularly powerful method for determining cell-surface localization of tagged antibodies, as individual planes of a cell can be analyzed in order to distinguish antibodies or fragments thereof that have been internalized into a cell's interior, e.g., by receptor-mediated endocytosis, from those that are bound to the external face of the cell membrane. Additionally, cells can be treated with an antibody conjugated to a fluorescent molecule that emits visible light of a particular wavelength (e.g., fluorescein, which fluoresces at about 535 nm) and an additional fluorescent molecule that is known to localize to a particular site on the cell surface and that fluoresces at a different wavelength (e.g., a molecule that localizes to CD25 and that fluoresces at about 599 nm). The resulting emission patterns can be visualized by confocal fluorescence microscopy and the images from these two wavelengths can be merged in order to reveal information regarding the location of the antibody or antigen-binding fragment thereof on the cell surface with respect to other receptors.

Bioluminescent proteins can also be incorporated into a fusion protein for the purposes of detection and visualization of antibodies or fragments thereof. Bioluminescent proteins, such as Luciferase and aequorin, emit light as part of a chemical reaction with a substrate (e.g., luciferin and coelenterazine). Exemplary bioluminescent proteins suitable for use as a diagnostic sequence and methods for their use are described in, e.g., U.S. Pat. Nos. 5,292,658, 5,670,356, 6,171,809, and 7,183,092, each of which is herein incorporated by reference. Conformation-specific P-tau antibodies or antigen-binding fragments thereof labeled with bioluminescent proteins are a useful tool for the detection of antibodies described herein following an in vitro assay. For instance, the presence of an antibody that has been conjugated to a bioluminescent protein can be detected among a complex mixture of additional proteins by separating the components of the mixture using gel electrophoresis methods known in the art (e.g., native gel analysis) and subsequently transferring the separated proteins to a membrane in order to perform a Western blot. Detection of the antibody among the mixture of other proteins can be achieved by treating the membrane with an appropriate Luciferase substrate and subsequently visualizing the mixture of proteins on film using established protocols.

A conformation-specific P-tau antibody or antigen-binding fragment thereof described herein can also be conjugated to a molecule including a radioactive nucleus, such that an antibody or fragment thereof described herein can be detected by analyzing the radioactive emission pattern of the nucleus. Alternatively, an antibody or fragment thereof can be modified directly by incorporating a radioactive nucleus within the antibody during the preparation of the protein. Radioactive isotopes of methionine ($^{35}S$), nitrogen ($^{15}N$), or carbon ($^{13}C$) can be incorporated into antibodies or fragments thereof described herein by, e.g., culturing bacteria in media that has been supplemented with nutrients containing these isotopes. Optionally, tyrosine derivatives containing a radioactive halogen can be incorporated into an antibody by, e.g., culturing bacterial cells in media supplemented with radiolabeled tyrosine. It has been shown that tyrosine functionalized with a radioactive halogen at the C2 position of the phenol system are rapidly incorporated into elongating polypeptide chains using the endogenous translation enzymes in vivo (U.S. Pat. No. 4,925,651; incorporated herein by reference). The halogens include fluorine, chlorine, bromine, iodine, and astatine. Additionally, an antibody can be modified following isolation and purification from cell culture by functionalizing polypeptides described herein with a radioactive isotope. The halogens represent a class of isotopes that can be readily incorporated into a purified protein by aromatic substitution at tyrosine or tryptophan, e.g., via reaction of one or more of these residues with an electrophilic halogen species. Examples of radioactive halogen isotopes include $^{18}F$, $^{75}Br$, $^{77}Br$, $^{122}I$, $^{123}I$, $^{124}I$, $^{125}I$, $^{129}I$, $^{131}I$, or $^{211}At$.

Another alternative strategy for the incorporation of a radioactive isotope is the covalent attachment of a chelating group to the antibody or fragment thereof, or construct. Chelating groups can be covalently appended to an antibody or fragment thereof by attachment to a reactive functional group, such as a thiol, amino group, alcohol, or carboxylic acid. The chelating groups can then be modified to contain any of a variety of metallic radioisotopes, including, without limitation, such radioactive nuclides as $^{125}I$, $^{67}Ga$, $^{111}In$, $^{99}Tc$, $^{169}Yb$, $^{186}Re$, $^{123}I$, $^{124}I$, $^{125}I$, $^{131}I$, $^{99m}Tc$, $^{111}In$, $^{64}Cu$, $^{67}Cu$, $^{186}Re$, $^{188}Re$, $^{177}Lu$ $^{90}Y$, $^{77}As$, $^{72}As$, $^{86}Y$, $^{89}Zr$, $^{211}At$, $^{212}Bi$, $^{213}Bi$, or $^{225}Ac$.

In some embodiments, it may be desirable to covalently conjugate the antibodies or fragments thereof described herein with a chelating group capable of binding a metal ion from heavy elements or rare earth ions, such as $Gd^{3+}$, $Fe^{3+}$, $Mn^{3+}$, or $Cr^{2+}$. Conjugates containing chelating groups that are coordinated to such paramagnetic metals are useful as in MRI imaging applications. Paramagnetic metals include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). In this way, antibodies can be detected by MRI spectroscopy. For instance, one can administer antibodies or fragments thereof conjugated to chelating groups bound to paramagnetic ions to a mammalian subject (e.g., a human patient) in order to monitor the distribution of the antibody following administration. This can be achieved by administration of the antibody to a patient by any of the administration routes described herein, such as intravenously, and subsequently analyzing the location of the administered antibody by recording an MRI of the patient according to established protocols. A conformation-specific P-tau antibody or antigen-binding fragment thereof can additionally be conjugated to other molecules for the purpose of improving the solubility and stability of the protein in aqueous solution. Examples of such molecules include PEG, PSA, bovine serum albumin (BSA), and human serum albumin (HSA), among others. For instance, one can conjugate an antibody to carbohydrate moieties in order to evade detection of the antibody or fragment thereof by the immune system of the patient receiving treatment. This process of hyperglycosylation reduces the immunogenicity of therapeutic proteins by sterically inhibiting the interaction of the protein with B cell receptors in circulation. Alternatively, antibodies or fragments thereof can be conjugated to molecules that prevent clearance from human serum and improve the pharmacokinetic profile of antibodies described herein. Exemplary molecules that can be conjugated to or inserted within conformation-specific P-tau antibody or antigen-binding fragment thereof described herein so as to attenuate clearance and improve the pharmacokinetic profile of these antibodies and fragments include salvage receptor binding epitopes. These epitopes are found within the Fc region of an IgG immunoglobulin and have been shown to bind Fc receptors and prolong antibody half-life in human serum. The insertion of salvage receptor binding epitopes into antibodies or fragments thereof can be achieved, e.g., as described in U.S. Pat. No. 5,739,277; incorporated herein by reference.

V. Methods of Treatment

Conformation-specific p-Tau antibodies or antigen-binding fragments thereof described herein can be used to treat a patient suffering from a disorder, for example a neurological disorder. In particular, the disclosure provides methods of treating neurological disorders that are associated with pathogenic accumulation of tau protein. Additionally, the disclosure provides methods for treating early-stage neurological disorders, e.g., prior to the detection of neurofibrillary tangles.

Methods of Treating Neurological Disorders

Conformation-specific p-Tau antibodies or antigen-binding fragments thereof described herein are useful therapeutics for the treatment of neurological disorders. Conformation-specific p-Tau antibodies or antigen-binding fragments thereof can be administered to a mammalian subject, such as a human, suffering from or at risk of developing a neurological disorder.

Exemplary compositions of the disclosure that can be used for these purposes include conformation-specific p-Tau antibodies or antigen-binding fragments thereof that bind specifically to an epitope including the pThr231-Pro motif of the phosphorylated tau protein (e.g., antibodies that bind specifically to the cis conformation of pThr231-Pro motif of the phosphorylated tau protein). Particularly, methods described herein include administering a conformation-specific p-Tau antibody or antigen-binding fragment thereof that contains one or more, or all, of the CDR sequences of a cis-mAb described herein, such as a human, humanized, or chimeric variant of a cis-mAb described herein, to a human or a non-human mammal in order to treat a neurological disorder.

A neurological disorder refers to a condition having as a component a disturbance in the structure or function of the nervous system. Neurological disorders may result from developmental abnormalities, disease, genetic defects, age, or injury. These disorders may affect the central nervous system (e.g., the brain, brainstem, cerebellum, and spinal cord), the peripheral nervous system (e.g., the cranial nerves, spinal nerves, and sympathetic and parasympathetic nervous systems), and/or the autonomic nervous system (e.g., the part of the nervous system that regulates involuntary to action and that is divided into the sympathetic and parasympathetic nervous systems). In particular, neurological disorders of the present disclosure may be associated with the pathogenic accumulation of tau protein (e.g., increased cis p-Tau and/or increased soluble cis p-Tau). Exemplary neurological disorders include traumatic brain injury (TBI), chronic traumatic encephalopathy (CTE), mild cognitive impairment, Alzheimer's disease, Parkinson's disease, multiple sclerosis, muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalitis, epilepsy, vascular dementia, age-related dementia, stroke, transient ischemic attacks (TIA), neurofibromatosis, Lewy body disease, amyotrophic lateral sclerosis (ALS), a peripheral neuropathy, diabetic neuropathy, macular degeneration, ischemia-related retinopathy, and diabetic retinopathy. Administration of a conformation-specific p-Tau antibody or antigen-binding fragment thereof described herein to a mammalian subject (e.g., a human) suffering from or at risk of developing a neurological disorder may prevent, reduce, or ameliorate one or more symptoms associated with sepsis or septic shock.

Methods of Treating Early-Stage Neurological Disorders

The disclosure provides methods for treating a subject with elevated levels of soluble cis P-tau by reducing the levels of cis P-tau with a cis-p-Tau specific antibody or antigen binding fragment thereof. This aspect of the disclosure is based, at least in part, on the surprising discovery that levels of soluble cis P-tau are elevated in the brain in response to ischemia or hypoxia, and that elevated levels of soluble cis P-tau can occur in advance of the onset of symptoms associated with a neurological disorder and/or before the presence of tau fibrils may be detected.

Accordingly, the disclosure provides a method of treating a subject having or at risk of developing a neurological disorder by administering to the subject an isolated conformation-specific antibody or an antigen-binding fragment thereof, such as one described herein and variants thereof, that binds specifically to a cis conformation of a phosphorylated-Threonine231-Proline (pThr231-Pro) motif of phosphorylated-Threonine231-tau protein (pThr231-tau), in which the subject is characterized as lacking any detectable neurofibrillary tangles (NFTs) and as having at least one of: (i) a detectable level of cis-pThr231-tau in the cerebrospinal fluid (CSF) and/or blood; and (ii) demyelination and/or neuroinflammation of neurons of the central nervous system.

The disclosure also provides a method of treating a subject having or at risk of developing a neurological disorder by administering to the subject an isolated conformation-specific antibody or an antigen-binding fragment thereof, such as one described herein and variants thereof, that binds specifically to a cis conformation of a phosphorylated-Threonine231-Proline (pThr231-Pro) motif of phosphorylated-Threonine231-tau protein (pThr231-tau), in which the subject has been determined to have: (i) increased expression of one or more genes selected from Meg3, Mme, Lrrc17, Hsd3b2, Phkg1, Grin 2a, Grin 2b, and EphA7 (e.g., an increase of 10%, 20%, 30%, 40%, 50%, 60%, 70%, 80%, 90%, 100% or more relative to a reference value); and/or (ii) decreased expression of one or more genes selected from GluI, Slc1 a2, Actb, Actg1, Atp6v1 b2, Mbp, Nsf, Ywhag, Kif5a, Actb, Actg1, Pafah1 b1 and Pak1 (e.g., a decrease of 10%, 20%, 30%, 40%, 50%, 60%, 70%, 80%, 90%, 100% or more relative to a reference value). Biomarkers, such as those described herein, can be measured according to methods known to those of skill in the art. For example, the expression level of one or more genes can be determined by extracting a nucleic acid from a biological sample and amplifying the biomarker in a quantitative method, such as RT-PCR. The detection and quantification of multiple nucleic acids, corresponding to multiple genes, can be performed in parallel by high-throughput gene profiling methods known in the art. Alternately, the resulting protein expression can be quantified, e.g., by an immunoassay such as ELISA or immunoblot. Alternately, protein expression may be quantified by quantitative mass spectrometry according to methods known to those of skill in the art.

The disclosure also provides a method of treating a subject having or at risk of developing a neurological disorder by administering to the subject an isolated conformation-specific antibody or an antigen-binding fragment thereof, such as one described herein and variants thereof, that binds specifically to a cis conformation of a phosphorylated-Threonine231-Proline (pThr231-Pro) motif of phosphorylated-Threonine231-tau protein (pThr231-tau), in which the subject has an increased risk of developing the neurological disorder based on the subject's genetic predisposition, medical history, or family history.

The antibody or an antigen-binding fragment thereof may be administered to the subject when the subject is presymptomatic or asymptomatic. In some embodiments, the subject has one or more relatives (e.g., a first, second, or third degree family member) that have been diagnosed with the neurological disorder. In some embodiments, the subject has previously experienced a head injury.

In some embodiments, the disorder is associated with pathogenic accumulation of tau protein. In some embodiments, the disorder is associated with an increased level of cis-pThr231-tau as compared to a reference value of cis-pThr231-tau (e.g., a reference value indicative of a subject not having or not at risk of developing the disorder). In some embodiments, the disorder is associated with an increased ratio of cis-pThr231-tau to trans-pThr231-tau as compared to a reference ratio of cis-pThr231-tau to trans-pThr231-tau (e.g., a reference ratio indicative of a subject not having or not at risk of developing the disorder). In some embodiments, the neurological disorder is a vascular disease of the central nervous system.

The disclosure also provides a method of treating a subject having or at risk of developing traumatic brain injury by administering to the subject an isolated conformation-specific antibody or an antigen-binding fragment thereof, such as one described herein and variants thereof, that binds specifically to the cis conformation of the phosphorylated-Threonine231-Proline (pThr231-Pro) motif of phosphorylated-Threonine231-tau protein (pThr231-tau), in which the antibody or an antigen-binding fragment thereof is administered to the subject within 2 weeks, within 1 week, within 48 hours, within 24 hours, or within 12 hours of a head injury.

Methods of Treating Vascular Diseases of the Central Nervous System

Conformation-specific p-Tau antibodies or antigen-binding fragments thereof described herein are useful therapeutics for the treatment of vascular diseases of the central nervous system (CNS). Vascular diseases of the central nervous system (CNS) are neurological disorders characterized by neuronal deficiencies involving a loss, damage, or inadequate or suboptimal function of neurons, astrocytes, endothelial cells, microglia, and any other cell-type of the central nervous system, where the neuronal deficiencies are associate with lack of supply of oxygen (e.g., hypoxia or ischemia) or lack of supply of nutrients to the affected CNS tissue. Exemplary vascular diseases of the CNS include vascular dementia, ischemia-related retinopathy, diabetic retinopathy, diabetic neuropathy, age-related macular degeneration, stroke, and transient ischemic attacks (TIA).

In particular, we have discovered that early-stage vascular disease of the CNS (e.g., early-stage vascular dementia or macular degeneration) can be detected by upregulated soluble cis-pTau, which is detectable in the blood or CSF of a subject. We have determined that soluble cis-p-Tau plays a pathogenic role in vascular diseases of the CNS, even before the presence of neurofibrillary tangles can be detected. Furthermore, we have shown that administering a cis-p-Tau specific antibody to the subject can treat vascular diseases of the CNS.

VI. Pharmaceutical Compositions

Pharmaceutical compositions containing a conformation-specific p-Tau antibody or antigen-binding fragment thereof described herein can be prepared using methods known in the art. The conformation-specific p-Tau antibodies or antigen-binding fragments thereof that can be incorporated into pharmaceutical compositions of the disclosure include conformation-specific p-Tau antibodies or antigen-binding fragments thereof that bind specifically to an epitope including the pThr231-Pro motif of the tau protein (e.g., antibodies that bind specifically to the cis conformation of the pThr231-Pro motif of the tau protein). Particularly, conformation-specific p-Tau antibodies or antigen-binding fragments thereof that can be incorporated into pharmaceutical compositions of the disclosure include a conformation-specific p-Tau antibody or antigen-binding fragment thereof that contains one or more, or all, of the CDR sequences of a cis-mAb described herein, such as a human, humanized, or chimeric variant of a cis-mAb described herein.

Pharmaceutical compositions described herein may contain a conformation-specific p-Tau antibody or antigen-binding fragment thereof described herein in combination with one or more pharmaceutically acceptable excipients. For instance, pharmaceutical compositions described herein can be prepared using, e.g., physiologically acceptable carriers, excipients or stabilizers (*Remington's Pharmaceutical Sciences* 16th edition, Osol, A. Ed. (1980); incorporated herein by reference), and in a desired form, e.g., in the form of lyophilized formulations or aqueous solutions. The compositions can also be prepared so as to contain the active agent at a desired concentration. For example, a pharmaceutical composition described herein may contain at least 10% (e.g., 10%, 20%, 30%, 40%, 50%, 60%, 70%, 80%, 90%, 95%, 97%, 98%, 99%, 99.5%, 99.9%, or 100%) active agent by weight (w/w).

Additionally, an active agent that can be incorporated into a pharmaceutical formulation can itself have a desired level of purity. For example, a conformation-specific p-Tau antibody or antigen-binding fragment thereof described herein may be characterized by a certain degree of purity after isolating the antibody from cell culture media or after chemical synthesis, e.g., of a single-chain antibody fragment (e.g., scFv) by established solid phase peptide synthesis methods or native chemical ligation as described herein. A conformation-specific p-Tau antibody or antigen-binding fragment thereof described herein may be at least 10% pure prior to incorporating the antibody into a pharmaceutical composition (e.g., 10%, 20%, 30%, 40%, 50%, 60%, 70%, 80%, 90%, 95%, 97%, 98%, 99%, 99.5%, 99.9%, 99.99%, or 100% pure).

Pharmaceutical compositions of conformation-specific p-Tau antibodies or antigen-binding fragments thereof described herein can be prepared for storage as lyophilized formulations or aqueous solutions by mixing the antibody having the desired degree of purity with optional pharmaceutically acceptable carriers, excipients or stabilizers typically employed in the art, e.g., buffering agents, stabilizing agents, preservatives, isotonifiers, non-ionic detergents, antioxidants, and other miscellaneous additives. See, e.g., Remington's Pharmaceutical Sciences, 16th edition (Osol, ed. 1980; incorporated herein by reference). Such additives must be nontoxic to the recipients at the dosages and concentrations employed.

Buffering Agents

Buffering agents help to maintain the pH in the range which approximates physiological conditions. They can be present at concentration ranging from about 2 mM to about 50 mM. Suitable buffering agents for use with conformation-specific p-Tau antibodies or antigen-binding fragments thereof described herein include both organic and inorganic acids and salts thereof such as citrate buffers {e.g., monosodium citrate-disodium citrate mixture, citric acid-trisodium citrate mixture, citric acid-monosodium citrate mixture, etc.), succinate buffers {e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers {e.g., fumaric acid-monosodium fumarate mixture, fumaric acid-disodium fumarate mixture, monosodium fumarate-disodium fumarate mixture, etc.), gluconate buffers (e.g., gluconic acid-sodium gluconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers {e.g., acetic acid-sodium acetate mixture, acetic acid-sodium hydroxide mixture, etc.). Additionally, phosphate buffers, histidine buffers and trimethylamine salts such as Tris can be used.

Preservatives

Preservatives can be added to a composition described herein to retard microbial growth and can be added in amounts ranging from 0.2%-1% (w/v). Suitable preservatives for use with conformation-specific p-Tau antibodies or antigen-binding fragments thereof described herein include phenol, benzyl alcohol, meta-cresol, methyl paraben, propyl paraben, octadecyldimethylbenzyl ammonium chloride, benzalconium halides {e.g., chloride, bromide, and iodide), hexamethonium chloride, and alkyl parabens such as methyl or propyl paraben, catechol, resorcinol, cyclohexanol, and 3-pentanol. Isotonifiers sometimes known as "stabilizers" can be added to ensure isotonicity of liquid compositions described herein and include polhydric sugar alcohols, for example trihydric or higher sugar alcohols, such as glycerin, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. Stabilizers can be present in the range from 0.1 to 10,000 weights per part of weight active protein.

Detergents

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

Other Pharmaceutical Carriers

Alternative pharmaceutically acceptable carriers that can be incorporated into a pharmaceutical composition described herein may include dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. A composition containing antibody described herein may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

VII. Routes of Administration and Dosing

A conformation-specific p-Tau antibody or antigen-binding fragment thereof described herein can be administered to a mammalian subject (e.g., a human) by a variety of routes, such as orally, transdermally, subcutaneously, intranasally, intravenously, intramuscularly, intraocularly, intratumorally, parenterally, topically, intrathecally and intracerebroventricularly, for the treatment of, e.g., the diseases and conditions described herein (e.g., a neurological disease). The most suitable route for administration in any given case will depend on the particular polypeptide administered, the patient, pharmaceutical formulation methods, administration methods (e.g., administration time and administration route), the patient's age, body weight, sex, severity of the diseases being treated, the patient's diet, and the patient's excretion rate.

A physician having ordinary skill in the art can readily determine an effective amount of a conformation-specific p-Tau antibody or antigen-binding fragment thereof for administration to a mammalian subject (e.g., a human) in need thereof. For example, a physician could start prescribing doses of an antibody described herein at levels lower than that required in order to achieve the desired therapeutic effect and gradually increase the dosage until the desired effect is achieved. Alternatively, a physician may begin a treatment regimen by administering a conformation-specific p-Tau antibody or antigen-binding fragment thereof at a high dose and subsequently administering progressively lower doses until a therapeutic effect is achieved. In general, a suitable daily dose of an antibody or antigen-binding fragment thereof will be an amount of the compound which is the lowest dose effective to produce a therapeutic effect. A conformation-specific p-Tau antibody or antigen-binding fragment thereof described herein may be administered, e.g., by injection, such as by intravenous, intramuscular, intraperitoneal, or subcutaneous injection, optionally proximal to the site of the target tissue. A daily dose of a therapeutic composition of an antibody described herein may be administered as a single dose or as two, three, four, five, six or more doses administered separately at appropriate intervals throughout the day, week, month, or year, or as needed, optionally, in unit dosage forms. While it is possible for an antibody described herein to be administered alone, it may also be administered as a pharmaceutical formulation in combination with excipients, carriers, and optionally, additional therapeutic agents.

The effective dose of a conformation-specific p-Tau antibody or antigen-binding fragment thereof described herein can range, for instance, from about 0.0001 to about 100 mg/kg of body weight per single (e.g., bolus) administration, multiple administrations or continuous administration (e.g., a continuous infusion), or to achieve a serum concentration of 0.0001-5000 μg/mL serum concentration per single (e.g., bolus) administration, multiple administrations or continuous administration (e.g., continuous infusion), or any effective range or value therein depending on the condition being treated, the route of administration and the age, weight, and condition of the subject. In certain embodiments, each dose can range from about 0.0001 mg to about 500 mg/kg of body weight. For instance, a pharmaceutical composition described herein may be administered in a daily dose in the range of 0.001-100 mg/kg (body weight). The dose may be administered one or more times (e.g., 2-10 times) per day, week, month, or year to a mammalian subject (e.g., a human) in need thereof.

Conformation-specific p-Tau antibodies or antigen-binding fragments thereof can be administered to a patient by way of a continuous intravenous infusion or as a single bolus administration. The conformation-specific p-Tau antibodies or antigen-binding fragments thereof may be administered to a patient in an amount of, for example, from 0.01 μg to about 5 g in a volume of, for example, from 10 μL to 10 mL. The conformation-specific p-Tau antibodies or antigen-binding fragments thereof may be administered to a patient over the course of several minutes to several hours. For example, the conformation-specific p-Tau antibodies or antigen-binding fragments thereof described herein may be administered to a patient over the course of from 5 minutes to 5 hours, such as over the course of 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 80 minutes, 90 minutes, 95 minutes, 100 minutes, 105 minutes, 110 minutes, 115 minutes, 120 minutes, 125 minutes, 130 minutes, 135 minutes, 140 minutes, 145 minutes, 150 minutes, 155 minutes, 160 minutes, 165 minutes, 170 minutes, 175 minutes, 180 minutes, 185 minutes, 190 minutes, 195 minutes, 200 minutes, 205 minutes, 210 minutes, 215 minutes, 220 minutes, 225 minutes, 230 minutes, 235 minutes, 240 minutes, 245 minutes, 250 minutes, 255 minutes, 260 minutes, 265 minutes, 270 minutes, 275 minutes, 280 minutes, 285 minutes, 290 minutes, 295 minutes, or 300 minutes, or more.

Antagonistic conformation-specific p-Tau antibodies or antigen-binding fragments thereof described herein may be administered in combination with one or more additional active agents. When an additional therapeutic agent is administered to a patient in combination with a conformation-specific p-Tau antibody or antigen-binding fragment thereof, the additional therapeutic agent may be administered to the patient by way of a single bolus administration or continuous intravenous infusion.

When conformation-specific p-Tau antibodies or antigen-binding fragments thereof are administered to a patient in combination with an additional therapeutic agent, the conformation-specific p-Tau antibody or antigen-binding fragment thereof and the additional therapeutic agent may be co-administered to the patient, for example, by way of a continuous intravenous infusion or bolus administration of the first agent, followed by a continuous intravenous infusion or bolus administration of the second agent. The administration of the two agents may occur concurrently. Alternatively, the administration of the conformation-specific p-Tau antibody or antigen-binding fragment thereof may precede or follow the administration of the additional therapeutic agent. In some embodiments, administration of the second agent (e.g., the conformation-specific p-Tau antibody or antigen-binding fragment thereof) commences within from about 5 minutes to about 4 weeks, or more, of the end of the administration of the first agent (e.g., the additional therapeutic agent). For example, administration of the second agent may commence within about 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, or more, of the end of the administration of the first agent.

Therapeutic compositions can be administered with medical devices known in the art. For example, in an embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in conjunction with the compositions and methods described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

VIII. Diagnostic Methods

The present disclosure features methods and compositions to treat, diagnose, and monitor the progression of a disorder described herein (e.g., a neurological disorder, such as a vascular disease of the CNS). The methods and compositions can include the detection and measurement of, for example, p-Tau or any fragments or derivatives thereof, containing a phosphorylated Thr-Pro motif in a cis or trans conformation (e.g., pThr231-Pro, specifically the cis conformation of pThr231-Pro or the ratio of cis:trans of pThr231-Pro). The methods can include measurement of absolute levels of p-Tau or any fragments or derivatives thereof in a cis or trans conformation as compared to a normal reference.

In particular, the inventors observed that a subject with an early-stage neurological disorder, including, e.g., a vascular disease of the CNS, exhibits an increased level of cis-pTau as compared to a healthy control (e.g., a control subject without the disorder). Accordingly, an antibody or antigen-binding fragment thereof described herein (e.g., an antibody or antigen-binding fragment thereof that specifically binds an epitope including the cis conformation of pThr231-Pro of the tau protein may be used (1) to diagnose a subject as having a neurological disorder; (2) to determine whether a subject is likely to be responsive to treatment for a disorder (e.g., a neurological disorder), and/or (3) to monitor the therapeutic response to treatment.

For diagnoses based on levels of substrate in a particular conformation (e.g., a cis-pTau substrate in the cis conformation), a subject with a disorder will show an alteration (e.g., an increase of 10%, 20%, 30%, 40%, 50%, 60%, 70%, 80%, 90%, or more) in the amount of the substrate in, for example, the cis conformation. A subject with a disorder may be diagnosed on the basis of an increased ratio of cis:trans of pThr231-Pro tau, for example as measured in PBMCs (e.g., an increase of 10%, 20%, 30%, 40%, 50%, 60%, 70%, 80%, 90%, or more). A normal reference sample can be, for example, a prior sample taken from the same subject prior to the development of the disorder or of symptoms suggestive of the disorder, a sample from a subject not having the disorder, a sample from a subject not having symptoms of the disorder, or a sample of a purified reference polypeptide in a given conformation at a known normal concentration (i.e., not indicative of the disorder).

Standard methods may be used to measure levels of the substrate in any bodily fluid, including, but not limited to, urine, blood, serum, plasma, saliva, amniotic fluid, or cerebrospinal fluid. Such methods include immunoassay, ELISA, Western blotting, and quantitative enzyme immunoassay techniques. In particular, the level of cis-pTau or trans-pTau in a sample (e.g., a blood sample of a CSF sample from a subject) may be determined by immunoprecipitation with a confirmation-specific antibody (e.g., a cis-mAb or a trans-mAb), followed by immunoblotting with a tau antibody (e.g., tau antibody E178). Alternately, the level of cis-pTau or trans-pTau in a sample (e.g., a blood sample of a CSF sample from a subject) may be determined by direct ELISA with confirmation-specific antibody (e.g., a cis-mAb or a trans-mAb). Such methods are known to those of skill in the art.

The disclosure specifically contemplates a method of determining the level of cis-phosphorylated-Threonine231-tau protein (cis-pThr231-tau) in a sample from a subject, the method including: (i) contacting the sample with an antibody or antigen-binding fragment thereof described herein; and (ii) detecting the level of cis-pThr231-tau in the sample (i) by determining the level of the antibody or antigen-binding fragment thereof bound to the cis-pThr231-tau. In some embodiments, the method further includes: (iii) comparing the level of cis-pThr231-tau detected in (ii) to a reference value of cis-pThr231-tau (e.g., a reference value that is the average level of cis-pThr231-tau in a population of subjects having a neurological disorder). In some embodiments, a level of cis-pThr231-tau in the sample that is greater than the reference value of cis-pThr231-tau indicates that the subject has or is at risk of developing a neurological disorder. In particular embodiments, the reference value for a subject not having or not at risk of developing the disorder is a level of cis-pThr231 tau that is below the threshold limit for detection (e.g., a subject not having or not at risk of developing the disorder has no detectable cis-pThr231-tau, for example, in a CSF or blood sample from the subject). Accordingly, a subject having or at risk of developing a disorder for treatment may have a detectable level of soluble cis-pThr231-tau, as determined from a sample (e.g., blood or CSF) from the subject. In some embodiments, the method further includes administering a therapeutically effective amount of an antibody or antigen-binding fragment thereof described herein, a polynucleotide described herein, a vector described herein, a host cell described herein, or a pharmaceutical composition described herein to the subject determined based on the level of cis-pThr231-tau in the sample to have or to be at risk of developing the neurological disorder.

The disclosure also specifically contemplates a method of determining the level of cis-phosphorylated-Threonine231-tau protein (cis-pThr231-tau) in a sample from a subject, the method including: (i) contacting the sample with an antibody or antigen-binding fragment thereof described herein; and (ii) detecting the level of cis-pThr231-tau in the sample (i) by determining the level of the antibody or antigen-binding fragment thereof bound to the cis-pThr231-tau. In some embodiments, the method further includes: (iii) determining the level of trans-pThr231-tau in the sample; and/or (iv) determining the ratio of cis-pThr231-tau to trans-pThr231-tau. In some embodiments., the method further includes: (v) comparing the ratio of cis-pThr231-tau to trans-pThr231-tau determined in (iv) to a reference value of the ratio of cis-pThr231-tau to trans-p231Thr-tau (e.g., a the reference value that is the average ratio of cis-pThr231-tau to trans-pThr231-tau in a population of subjects having a neurological disorder). In some embodiments, the ratio of cis-pThr231-tau to trans-pThr231-tau of greater than the reference ratio of cis-pThr231-tau to trans-pThr231-tau indicates that the subject has or is at risk of developing a neurological disorder. In some embodiments, the method further includes administering a therapeutically effective amount of an antibody or antigen-binding fragment thereof described herein, a polynucleotide described herein, a vector described herein, a host cell described herein, or a pharmaceutical composition described herein to the subject determined based on the ratio of cis-pThr231-tau to trans-pThr231-tau in the sample to have or to be at risk of developing the neurological disorder.

For diagnostic purposes, the conformation-specific antibodies may be labeled. Labeling of the antibody is intended to encompass direct labeling of the antibody by coupling (e.g., physically linking) a detectable substance to the antibody, as well as indirect labeling the antibody by reacting the antibody with another reagent that is directly labeled. For example, the antibody can be labeled with a radioactive or fluorescent marker whose presence and location in a subject can be detected by standard imaging techniques.

In another aspect, the disclosure provides a method of diagnosing a subject having or at risk of developing a neurological disorder. A subject may be diagnosed as having or at risk of developing a neurological disorder if the subject lacks any detectable neurofibrillary tangles (NFTs) and has at least one of: (i) a detectable level of cis-pThr231-tau in the cerebrospinal fluid (CSF) or blood; and (ii) demyelination and/or neuroinflammation of neurons of the central nervous system. A subject may be diagnosed as having or at risk of developing a neurological disorder if the subject has: (i) increased expression of one or more genes selected from Meg3, Mme, Lrrc17, Hsd3b2, Phkg1, Grin 2a, Grin 2b, and EphA7 (e.g., an increase of 10%, 20%, 30%, 40%, 50%, 60%, 70%, 80%, 90%, 100% or more relative to a reference value); and/or (ii) decreased expression of one or more genes selected from GluI, Slc1 a2, Actb, Actg1, Atp6v1 b2, Mbp, Nsf, Ywhag, Kif5a, Actb, Actg1, Pafah1 b1 and Pak1 (e.g., a decrease of 10%, 20%, 30%, 40%, 50%, 60%, 70%, 80%, 90%, 100% or more relative to a reference value). A subject may be diagnosed as having or at risk of developing a neurological disorder based on the subject's genetic predisposition or medical history (e.g., a family member of the subject has previously been diagnosed with the neurological disorder and/or the subject has experience head injury or trauma). In particular, the above-described diagnostic methods may be useful in detecting early-stage neurological disorders in asymptomatic or pre-symptomatic subjects. The above diagnostic criteria also indicated an increased likelihood of responsiveness to treatment with a cis-pTau specific antibody or antigen-binding fragment thereof.

The diagnostic methods described herein can be used individually or in combination with any other diagnostic method described herein for a more accurate diagnosis of the presence or severity of a disorder (e.g., a neurological disorder). Examples of additional methods for diagnosing such disorders include, e.g., examining a subject's health history, immunohistochemical staining of tissues, computed tomography (CT) scans, or culture growths.

Subject Monitoring

The diagnostic methods described herein can also be used to monitor the progression of a disorder (e.g., a neurological disorder such as a vascular disease of the CNS) during therapy or to determine the dosages of therapeutic compounds. In one embodiment, the levels of cis-pTau levels or the ratio of cis-pTau:trans-pTau are measured repeatedly as a method of diagnosing the disorder and monitoring the treatment or management of the disorder. In order to monitor the progression of the disorder in a subject, subject samples can be obtained at several time points and may then be compared. For example, the diagnostic methods can be used to monitor subjects during therapy. In this example, serum samples from a subject can be obtained before treatment with a therapeutic agent, again during treatment with a therapeutic agent, and again after treatment with a therapeutic agent. In this example, the level of cis-pTau levels or the ratio of cis-pTau:trans-pTau in a subject is closely monitored using the conformation-specific antibodies of the invention and, if the level of cis-pTau and/or the ratio of cis-pTau:trans-pTau begins to increase during therapy, the therapeutic regimen for treatment of the disorder can be modified as determined by the clinician (e.g., the dosage of the therapy may be changed or a different therapeutic may be administered). The monitoring methods of the invention may also be used, for example, in assessing the efficacy of a particular drug or therapy in a subject, determining dosages, or in assessing progression, status, or stage of a neurological disorder.

IX. Kits Containing Conformation-Specific pTau Antibodies or Antigen-Binding Fragments Thereof Also included herein are kits that contain conformation-specific pTau antibodies or antigen-binding fragments thereof. The kits provided herein may contain any of the conformation-specific pTau antibodies or antigen-binding fragments thereof described above, as well as any of the polynucleotides encoding these polypeptides, vectors containing these polynucleotides, or cells engineered to express and secrete antibodies described herein (e.g., prokaryotic or eukaryotic cells).

Exemplary compositions of the disclosure that can be incorporated into a kit described herein include conformation-specific pTau antibodies or antigen-binding fragments thereof that bind specifically to an epitope including the pThr231-Pro motif of the phosphorylated tau protein (e.g., antibodies that bind specifically to the cis conformation of pThr231-Pro motif of the phosphorylated tau protein). Particularly, methods described herein include administering a conformation-specific pThr231-Pro motif of the phosphorylated tau protein antibody or antigen-binding fragment thereof that contains one or more, or all, of the CDR sequences of a cis-mAb described herein, such as a human, humanized, or chimeric variant of a cis-mAb described herein, to a human or a non-human mammal in order to treat a neurological disorder.

A kit described herein may include reagents that can be used to produce the compositions described herein (e.g., a conformation-specific pTau antibody or antigen-binding fragment thereof). Optionally, kits described herein may include reagents that can induce the expression of a conformation-specific pTau antibody or antigen-binding fragment thereof within cells (e.g., mammalian cells), such as doxycycline or tetracycline. In other cases, a kit described herein may contain a compound capable of binding and detecting a fusion protein that contains a conformation-specific pTau antibody or antigen-binding fragment thereof and an epitope tag. For instance, in such cases a kit described herein may contain maltose, glutathione, a nickel-containing complex, an anti-FLAG antibody, an anti-myc antibody, an anti-HA antibody, biotin, or streptavidin.

Kits described herein may also include reagents that are capable of detecting a conformation-specific pTau antibody or antigen-binding fragment thereof directly. Examples of such reagents include secondary antibodies that selectively recognize and bind particular structural features within the Fc region of a conformation-specific pTau antibody or antigen-binding fragment thereof described herein. Kits described herein may contain secondary antibodies that recognize the Fc region of a conformation-specific pTau antibody or antigen-binding fragment thereof and that are conjugated to a fluorescent molecule. These antibody-fluorophore conjugates provide a tool for analyzing the localization of conformation-specific pTau antibodies or antigen-binding fragments thereof, e.g., in a particular tissue or cultured mammalian cell using established immunofluorescence techniques. In some embodiments, kits described herein may include additional fluorescent compounds that exhibit known sub-cellular localization patterns. These reagents can be used in combination with another antibody-fluorophore conjugate, e.g., one that specifically recognizes a different receptor on the cell surface in order to analyze the localization of a conformation-specific pTau antibody or antigen-binding fragment thereof relative to other cell-surface proteins.

Kits described herein may also contain a reagent that can be used for the analysis of a patient's response to treatment by administration of conformation-specific pTau antibodies or antigen-binding fragments thereof described herein. For instance, kits described herein may include a conformation-specific pTau antibody or antigen-binding fragment thereof and one or more reagents that can be used to determine the quantity of T-reg cells in a blood sample withdrawn from a subject (e.g., a human) that is undergoing treatment with an antibody described herein. Kits may contain, e.g., antibodies that selectively bind cell-surface antigens presented by T-reg cells, such as CD4 and CD25. Optionally, these antibodies may be labeled with a fluorescent dye, such as fluorescein or tetramethylrhodamine, in order to facilitate analysis of T-reg cells by fluorescence-activated cell sorting (FACS) methods known in the art. Kits described herein may optionally contain one or more reagents that can be used to quantify tumor-reactive T lymphocytes in order to determine the effectiveness of an antagonistic conformation-specific pTau antibodies or antigen-binding fragments thereof in restoring tumor-infiltrating lymphocyte proliferation. For instance, kits described herein may contain an antibody that selectively binds cell-surface markers on the surface of a cytotoxic T cell, such as CD8 or CD3. Optionally, these antibodies may be labeled with fluorescent molecules so as to enable quantitation by FACS analysis.

A kit described herein may also contain one or more reagents useful for determining the affinity and selectivity of a conformation-specific pTau antibody or antigen-binding fragment thereof described herein for one or more peptides derived from pTau. For instance, a kit may contain a conformation-specific pTau antibody or antigen-binding fragment thereof and one or more reagents that can be used in an ELISA assay to determine the $K_D$ of an antibody described herein for one or more peptides that present a pTau epitope in a conformation similar to that of the epitope in the native protein. A kit may contain, e.g., a microtiter plate containing wells that have been previously conjugated to avidin, and may contain a library of pTau-derived peptides, each of which conjugated to a biotin moiety. Such a kit may optionally contain a secondary antibody that specifically binds to the Fc region of a conformation-specific pTau antibody or antigen-binding fragment thereof described herein, and the secondary antibody may be conjugated to an enzyme (e.g., horseradish peroxidase) that catalyzes a chemical reaction that results in the emission of luminescent light.

Kits described herein may also contain a conformation-specific pTau antibody or antigen-binding fragment thereof described herein and a reagent that can be conjugated to such an antibody, including those previously described (e.g., a cytotoxic agent, a fluorescent molecule, a bioluminescent molecule, a molecule containing a radioactive isotope, a molecule containing a chelating group bound to a paramagnetic ion, etc.). These kits may additionally contain instructions for how the conjugation of a conformation-specific pTau antibody or antigen-binding fragment thereof described herein to a second molecule, such as those described above, can be achieved.

A kit described herein may also contain a vector containing a polynucleotide that encodes a conformation-specific pTau antibody or antigen-binding fragment thereof, such as any of the vectors described herein. Alternatively, a kit may include mammalian cells (e.g., CHO cells) that have been genetically altered to express and secrete conformation-specific pTau antibodies or antigen-binding fragments thereof or fragments thereof from the nuclear genome of the cell. Such a kit may also contain instructions describing how expression of the conformation-specific pTau antibody or antigen-binding fragment thereof from a polynucleotide can be induced, and may additionally include reagents (such as, e.g., doxycycline or tetracycline) that can be used to promote the transcription of these polynucleotides. Such kits may be useful for the manufacture of conformation-specific pTau antibodies or antigen-binding fragments thereof described herein.

Other kits described herein may include tools for engineering a prokaryotic or eukaryotic cell (e.g., a CHO cell or a BL21(DE3) *E. coli* cell) so as to express and secrete a conformation-specific pTau antibody or antigen-binding fragment thereof described herein from the nuclear genome of the cell. For example, a kit may contain CHO cells stored in an appropriate media and optionally frozen according to methods known in the art. The kit may also provide a vector containing a polynucleotide that encodes a nuclease (e.g., such as the CRISPER/Cas, zinc finger nuclease, TALEN, ARCUS™ nucleases described herein) as well as reagents for expressing the nuclease in the cell. The kit can additionally provide tools for modifying the polynucleotide that encodes the nuclease so as to enable one to alter the DNA sequence of the nuclease in order to direct the cleavage of a specific target DNA sequence of interest. Examples of such tools include primers for the amplification and site-directed mutagenesis of the polynucleotide encoding the nuclease of interest. The kit may also include restriction enzymes that can be used to selectively excise the nuclease-encoding polynucleotide from the vector and subsequently re-introduce the modified polynucleotide back into the vector once the user has modified the gene. Such a kit may also include a DNA ligase that can be used to catalyze the formation of covalent phosphodiester linkages between the modified nuclease-encoding polynucleotide and the target vector. A kit described herein may also provide a polynucleotide encoding a conformation-specific pTau antibody or antigen-binding fragment thereof, as well as a package insert describing the methods one can use to selectively cleave a particular DNA sequence in the genome of the cell in order to incorporate the polynucleotide encoding a conformation-specific pTau antibody or antigen-binding fragment thereof into the genome at this site. Optionally, the kit may provide a polynucleotide encoding a fusion protein that contains a conformation-specific pTau antibody or antigen-binding fragment thereof or fragment thereof and an additional polypeptide, such as, e.g., those described herein.

EXAMPLES

The following examples are put forth so as to provide those of ordinary skill in the art with a description of how the compositions and methods described herein may be used, made, and evaluated, and are intended to be purely exemplary of the disclosure and are not intended to limit the scope of what the inventors regard as their disclosure.

Figure 1A:
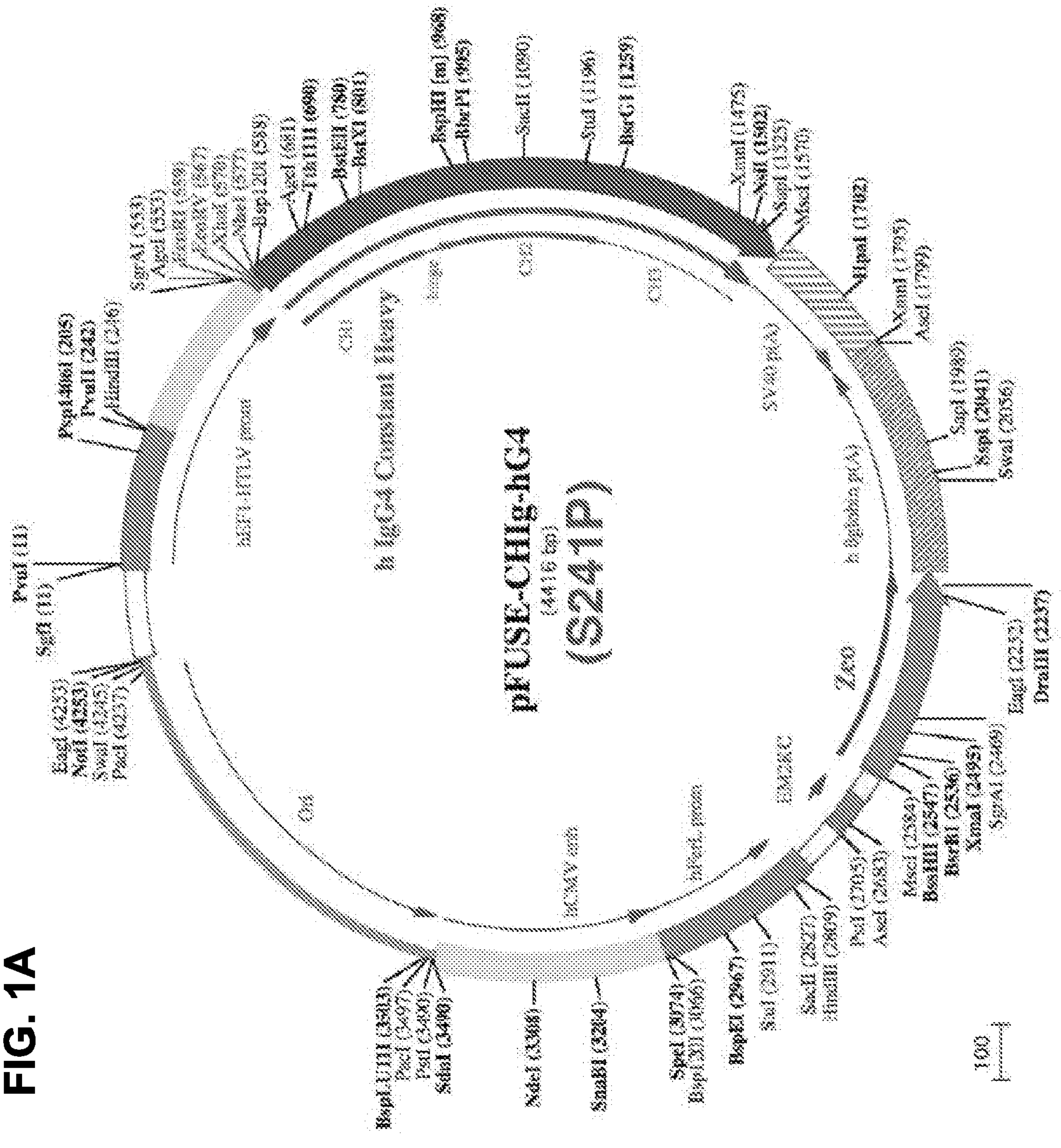
FIG. 1A is a schematic of a first genomic vector utilized for the expression and purification of humanized mAb variants.
Figure 1B:
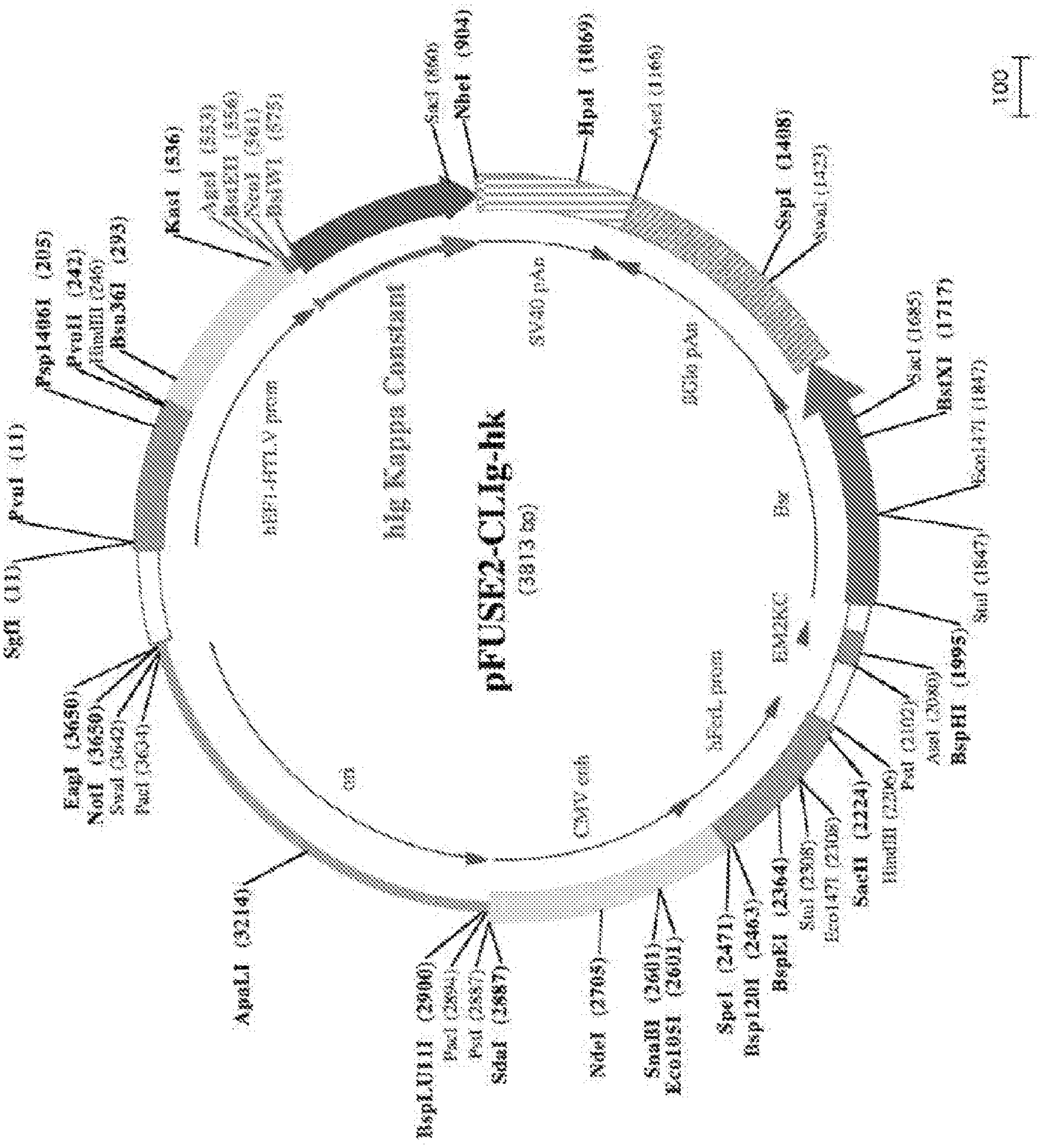
FIG. 1B is a schematic of a second genomic vector utilized for the expression and purification of humanized mAb variants.

Example 1. Generation of Humanized Cis pT231-Tau Monoclonal Antibodies (mAbs) and Determination of their Sequences New humanized cis-mAb antibodies were generated beginning with C113 (a previously described cis-pTau monoclonal antibody (see, e.g., U.S. Pat. No. 9,688,747)). We determined the heavy and light chain cDNA sequences of murine C113. Next, we constructed murine cis-mAb C113 into human IgG4 with an S241 P mutation due to its low potential to induce inflammation and reasonable half-life in humans (FIGS. 1A-1B). We next constructed a structural model of the parental cis-mAb variable region and selected an acceptor human framework by selecting each mouse framework individually with the most appropriate human germline framework for that framework for generating optimized humanized mAbs. We then expressed and produced the humanized candidate mAbs in CHO cells.

We next started to characterize and select lead humanized mAbs. We expressed and purified humanized mAb variants using a CHO expression system. We transfected over 45 plasmid DNA pairs of heavy and light chain cDNAs into CHO cells to express over 225 humanized cis mAb variants in various combinations. To evaluate the target binding specificity and affinity of our mouse mAbs, we established a simple and quantitative ELISA to screen the clones using a wild-type P-tau peptide and its pure cis or cis-locked, and pure trans counterparts and determined the binding affinity for selected clones using Biacore assays. We screened over 200 humanized cis mAb variants. Although most humanized cis mAb variants lost cis P-tau conformation specificity or also recognized the non-phosphorylated tau, about one quarter of variants showed specificity towards cis P-tau. Furthermore, one-tenth of humanized cis mAb variants were also able to recognize cis P-tau in human AD and TBI brains based on immunostaining analysis.

Figure 1C:
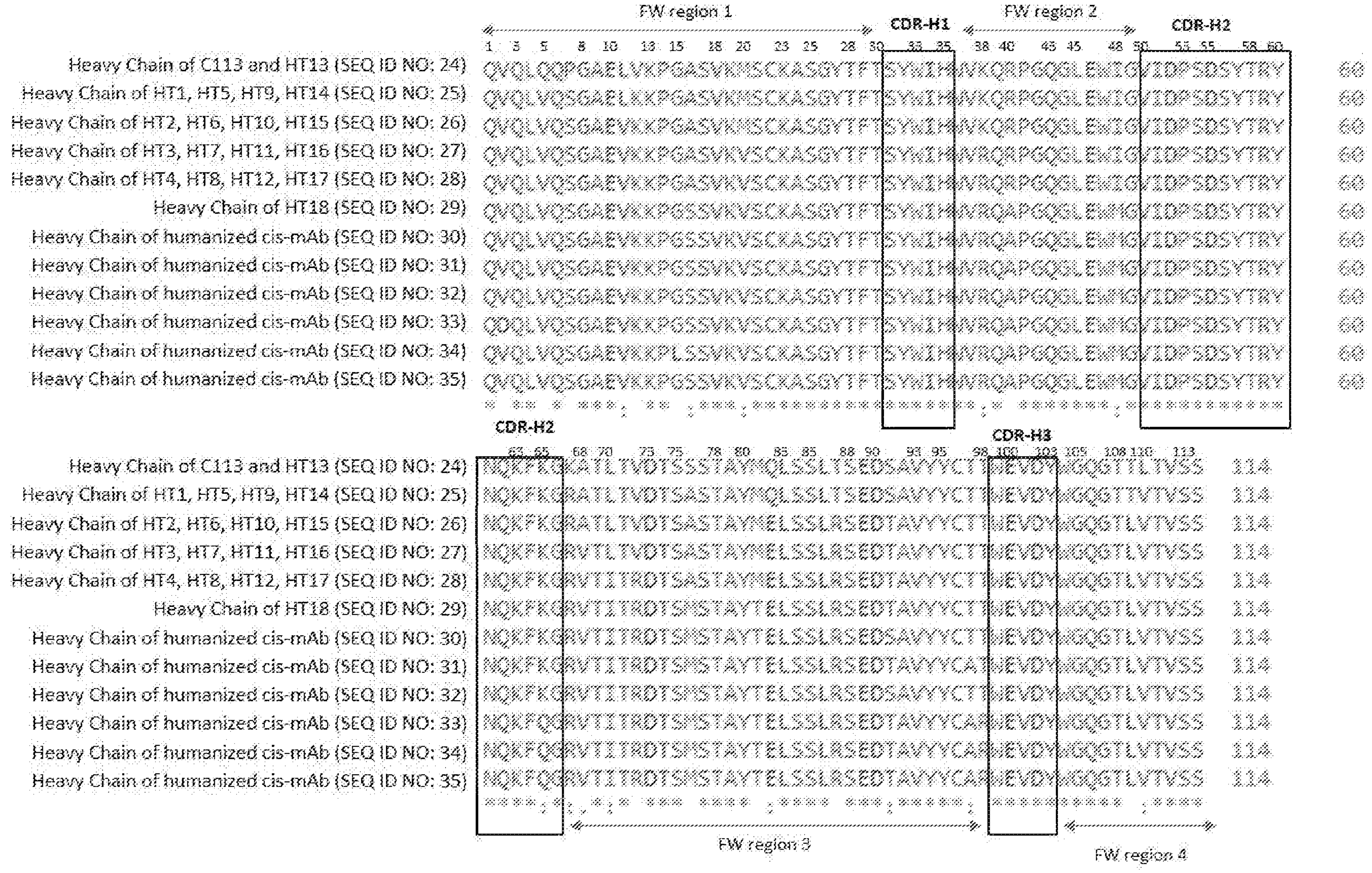
FIG. 1C is an image showing an alignment of the amino acid sequences of the heavy chain variable domains from C113 (a previously described murine cis-pTau monoclonal antibody (see, e.g., U.S. Pat. No. 9,688,747); SEQ ID NO:24); HT13 (a mouse-human chimera antibody; SEQ ID NO: 24) and humanized cis-mAbs described herein (SEQ ID NOs: 25-35). The alignment is annotated to show, in order, the framework region that is N-terminal to CDR-H1 (FW region 1); CDR-H1; the framework region that is between CDR-H1 and CDR-H2 (FW region 2); CDR-H2; the framework region that is between CDR-H2 and CDR-H3 (FW region 3); CDR-H3; and the framework region that is C-terminal to CDR-H3 (FW region 4).

An amino acid sequence alignment of the heavy chain variable domains of active humanized cis-mAbs is provide in FIG. 1C. The alignment shows that the following residues of the framework regions are conserved in the active humanized variants but are not present in the parent murine antibody C113: (i) the valine residue twenty-six amino acid residues N-terminal to the CDR-H1; (ii) the serine residue twenty-four amino acid residues N-terminal to the CDR-H1; (iii) the lysine residue nineteen amino acid residues N-terminal to the CDR-H1; (iv) the arginine residue at the amino acid residue directly C-terminal to CDR-H2; and (v) the valine residue seven amino residues C-terminal to CDR-H3.

An amino acid sequence alignment of the light chain variable domains of the active variants in provide in FIG. 1D. The alignment shows that the serine residue seventeen amino acid residues N-terminal to the CDR-L1, in the framework region, is conserved in the active humanized variants but is not present in the parent murine antibody C113.

Example 2. Characterization of Affinity of Humanized Cis pT231-Tau Monoclonal Antibodies The binding affinity of selected humanized antibody clones was determined by Biacore assay using a wild-type P-tau peptide and its pure cis or cis-locked, and pure trans counterparts. The binding affinity of the selected humanized cis mAb variants was determined by assessing their ability to eliminate cis P-tau in stressed neurons in cell cultures. Functional restoration of selected clones was determined by their ability to restore risk-taking behavior after 3-hit or 7-hit repetitive TBI in mice, as assayed by elevated plus maze. The results of these characterizations of humanized cis mAb variants are provided in Table 2.

TABLE 2

Characterization of humanized cis mAb variants

| Humanized Antibody (cis-mAb) | $K_D$ (M) | Relative $K_D$ | Cis P-tau elimination | Functional restoration 3-hit TBI | Functional restoration 7-hit TBI |
|---|---|---|---|---|---|
| HT13 (VH0/Vk0) Mouse-human chimera control | $1.26 \times 10^{-9}$ | 1.00 | 1.0 | 1.0 | 1.0 |
| HT1 (VH1/Vk1) | $1.83 \times 10^{-9}$ | 1.45 | 1.7 | 1.5 | — |
| HT2 (VH2/Vk1) | $1.62 \times 10^{-9}$ | 1.29 | 1.5 | 1.4 | 1.7 |
| HT3 (VH3/Vk1) | $3.51 \times 10^{-9}$ | 2.79 | 1.6 | 1.7 | 2.0 |
| HT4 (VH4/Vk1) | $2.42 \times 10^{-9}$ | 1.92 | — | — | — |
| HT5 (VH1/Vk3) | $6.91 \times 10^{-9}$ | 5.48 | — | — | — |
| HT6 (VH2/Vk3) | $6.48 \times 10^{-9}$ | 5.14 | — | — | — |
| HT7 (VH3/Vk3) | $1.08 \times 10^{-8}$ | 8.57 | — | — | — |
| HT8 (VH4/Vk3) | $7.68 \times 10^{-9}$ | 6.11 | 0.9 | 0.9 | 1.4 |
| HT9 (VH1/Vk4) | $1.89 \times 10^{-9}$ | 1.50 | — | — | — |
| HT10 (VH2/Vk4) | $1.77 \times 10^{-9}$ | 1.40 | 0.9 | 1.2 | 1.3 |
| HT11 (VH3/Vk4) | $3.99 \times 10^{-9}$ | 3.17 | — | — | — |
| HT12 (VH4/Vk4) | $3.55 \times 10^{-9}$ | 2.82 | — | — | — |
| HT14 (VH1/Vk2) | $3.02 \times 10^{-8}$ | 23.97 | — | — | — |
| HT15 (VH2/Vk2) | $3.34 \times 10^{-8}$ | 26.51 | — | — | — |
| HT16 (VH3/Vk2) | $3.26 \times 10^{-9}$ | 2.59 | — | — | — |
| HT17 (VH4/Vk2) | $4.94 \times 10^{-6}$ | 3920 | — | — | — |
| HT18 (VH5/Vk5) | $1.91 \times 10^{-9}$ | 1.52 | 0.8 | 1.0 | 1.1 |

Figure 2:
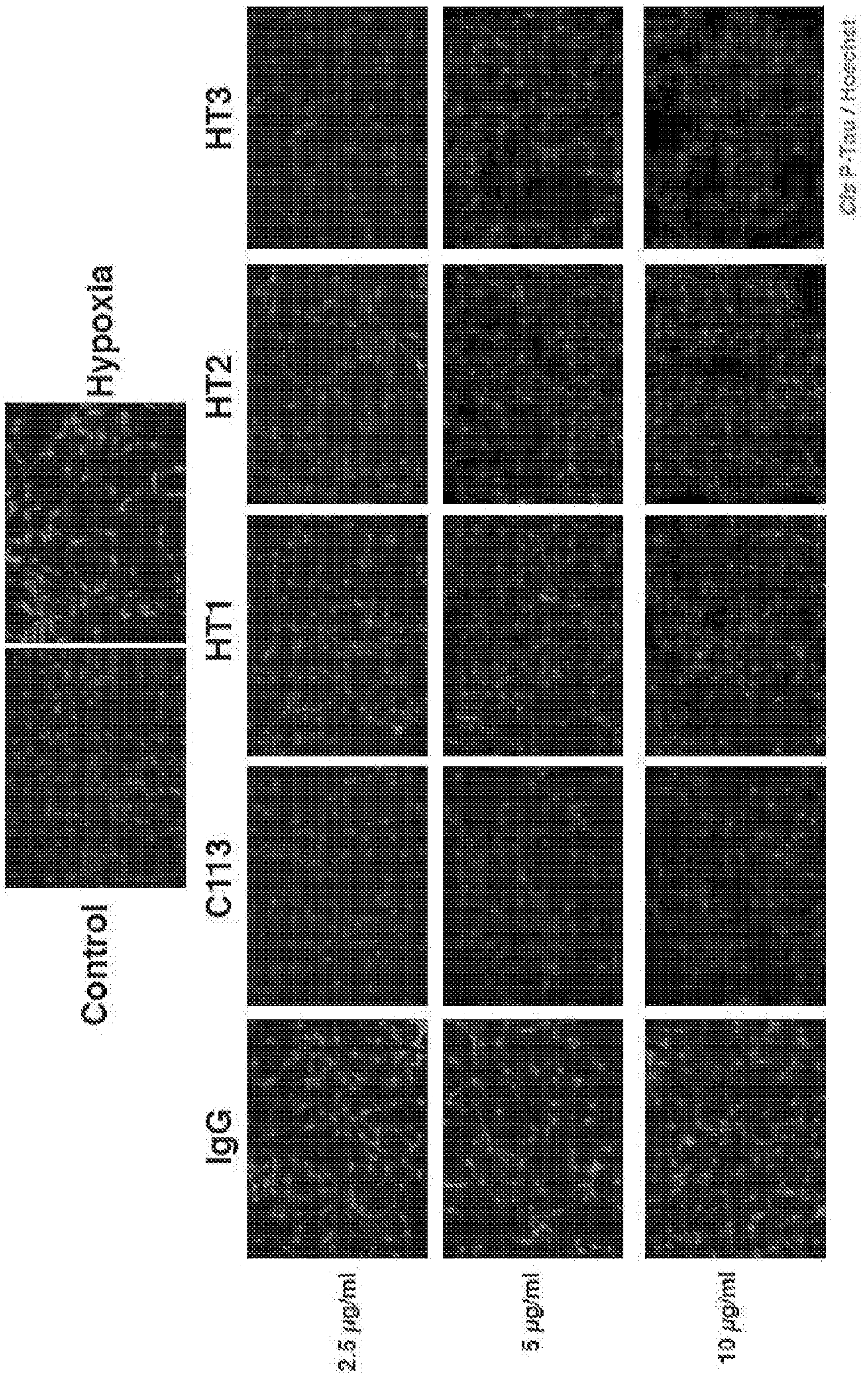
FIG. 2 is an immunostaining image showing the ability of humanized cis pT231-tau monoclonal antibody variants to eliminate cis P-tau in neurons under hypoxic conditions. Cis P-tau levels are reported in red and blue reports nuclear staining (Hoechst) to represent all neurons in the experiment. IgG control groups show no significant elimination of cis P-tau at three administered IgG concentrations, 2.5 pg/ml, 5 μg/ml and 10 μg/ml. Other images show the elimination of cis P-tau at the three administered concentrations of humanized cis pT231-tau monoclonal antibody variants C113, HT1, HT2 and HT3.
Figure 3:
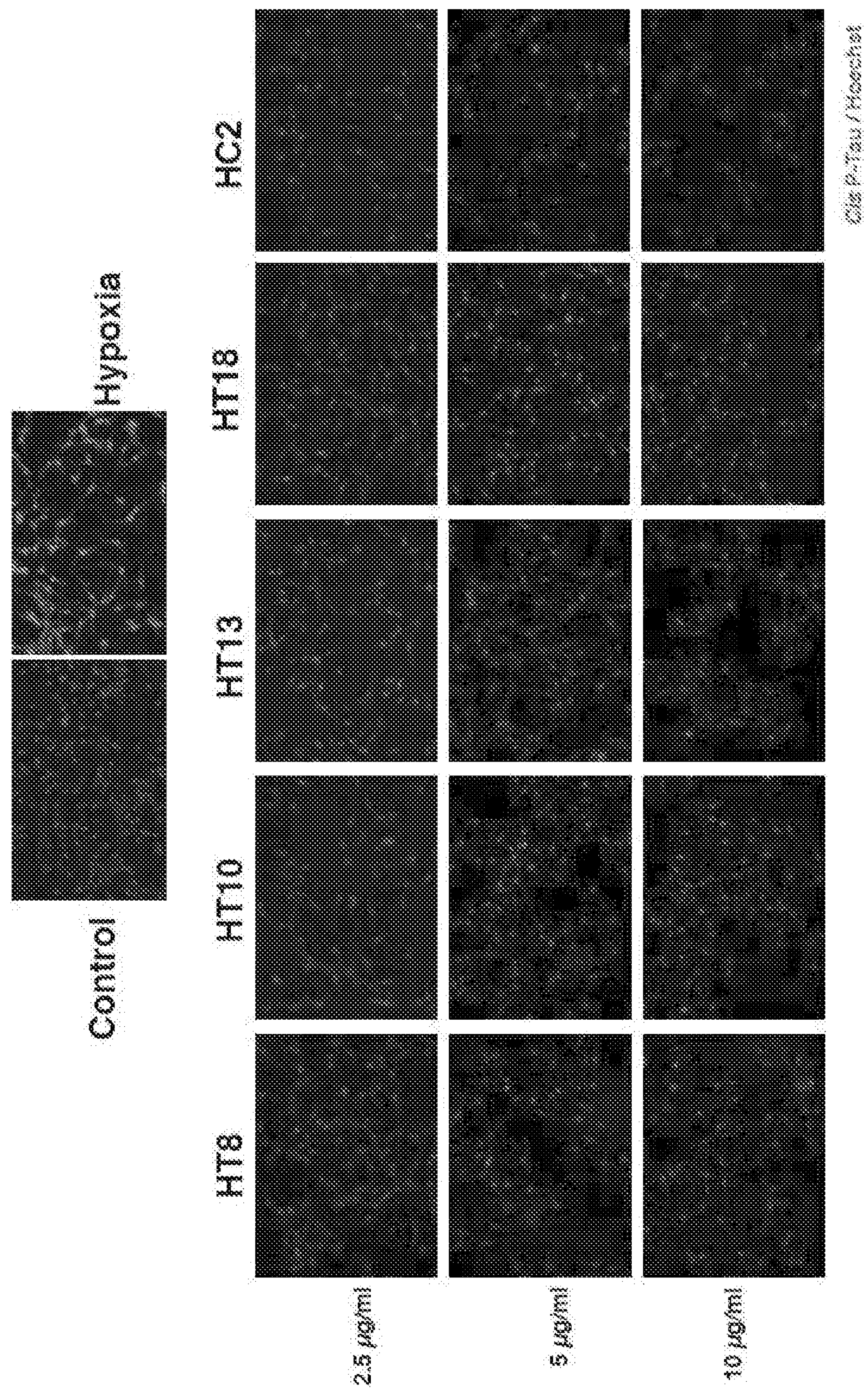
FIG. 3 shows immunostaining data of the ability of the humanized cis pT231-tau monoclonal antibody variants to eliminate cis P-tau in neurons under hypoxic conditions. Cis P-tau levels are reported in red and blue reports nuclear staining (Hoechst) to represent all neurons in the experiment. Images show the elimination of cis P-tau at the three administered concentrations, 2.5 μg/ml, 5 μg/ml and 10 μg/ml of humanized cis pT231-tau monoclonal antibody variants HT8, HT10, HT13, HT18 and HC2.
Figure 4:
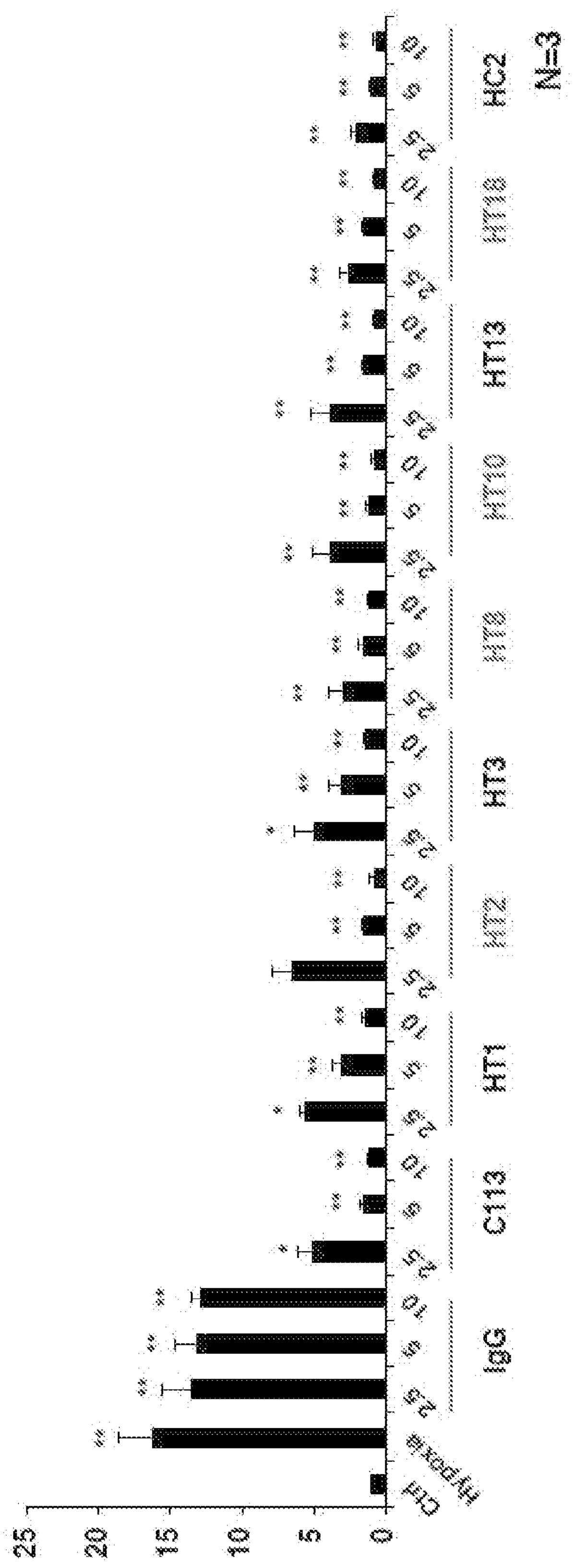
FIG. 4 is a graph showing the elimination of cis P-tau among three administered concentrations, 2.5 μg/ml, 5 μg/ml and 10 μg/ml, of either IgG control or humanized cis pT231-tau monoclonal antibody variants. Red text is used to highlight the top four performing variants from this assay: HT2, HT8, HT10, and HT18. IgG is a negative control. C113 is a previously described cis-pTau monoclonal antibody (see, e.g., U.S. Pat. No. 9,688,747), which serves as a positive control.

Example 3. Elimination of Cis P-Tau In Vitro with Humanized Cis pT231-Tau Monoclonal Antibody Variants Cultured neurons were subjected to neuron stress by hypoxia in the presence or absence of different concentration of humanized antibody variants, followed by immunoblotting analysis to analyze cis P-tau levels in the stressed neurons, the results of which are provided in FIGS. 2-4. FIG. 2 is an immunostaining image showing the ability of humanized cis pT231-tau monoclonal antibody variants to eliminate cis P-tau in neurons under hypoxic conditions. Cis P-tau levels are reported in red and blue reports nuclear staining (Hoechst) to represent all neurons in the experiment. IgG control groups show no significant elimination of cis P-tau at three administered IgG concentrations, 2.5 μg/ml, 5 μg/ml and 10 μg/ml. Other images show the elimination of cis P-tau at the three administered concentrations of humanized cis pT231-tau monoclonal antibody variants C113, HT1, HT2 and HT3. FIG. 3 shows immunostaining data of the ability of the humanized cis pT231-tau monoclonal antibody variants to eliminate cis P-tau in neurons under hypoxic conditions. Cis P-tau levels are reported in red and blue reports nuclear staining (Hoechst) to represent all neurons in the experiment. Images show the elimination of cis P-tau at the three administered concentrations, 2.5 μg/ml, 5 μg/ml and 10 μg/ml of humanized cis pT231-tau monoclonal antibody variants HT8, HT10, HT13, HT18 and HC2. FIG. 4 is a graph showing the elimination of cis P-tau among three administered concentrations, 2.5 μg/ml, 5 μg/ml and 10 μg/ml, of either IgG control or humanized cis pT231-tau monoclonal antibody variants. Red text is used to highlight the top four performing variants from this assay: HT2, HT8, HT10, and HT18. IgG is a negative control. The cis-pTau monoclonal antibody C113 serves as a positive control.

Figure 5:
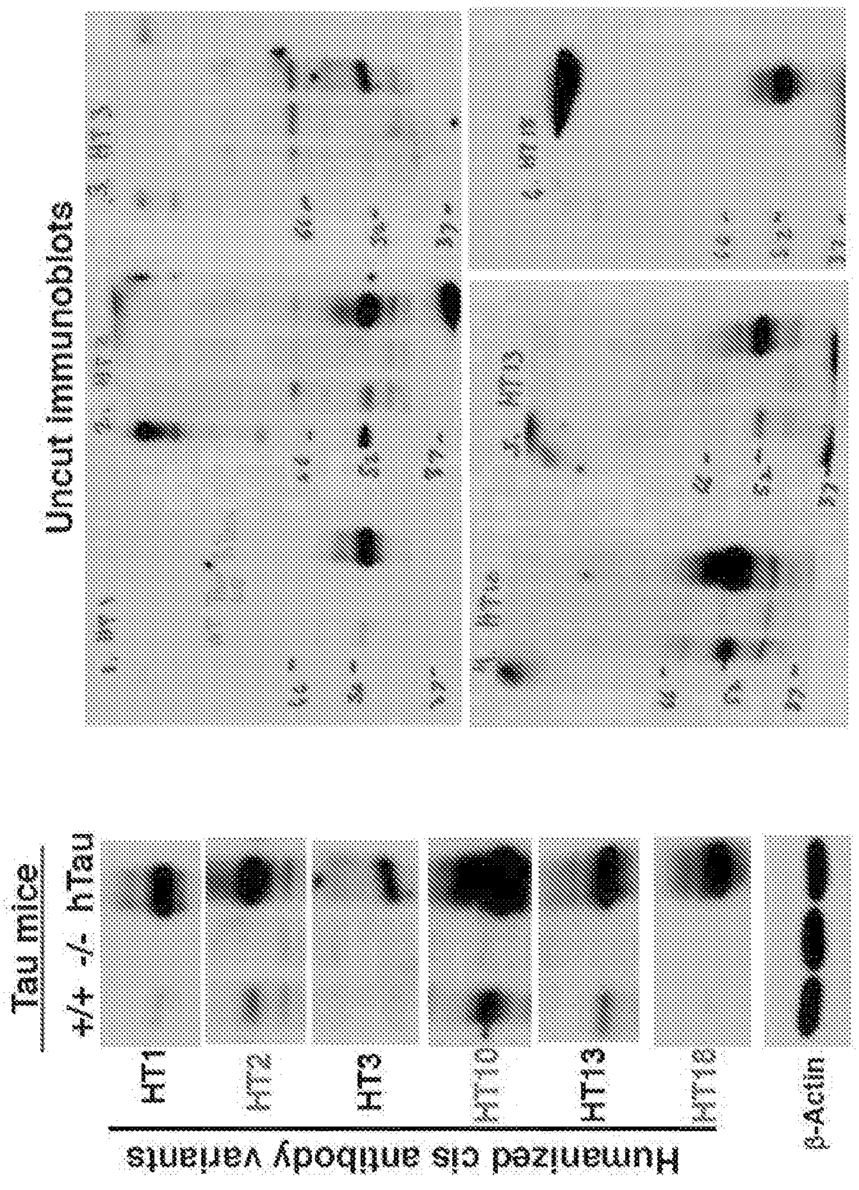
FIG. 5 is a series of images showing the ability of humanized cis mAb variants to specifically recognize cis P-tau in whole brain lysates of tau wild-type (+/+), tau knockout (−/−) and hTau transgenic mice.

Example 4. Evaluation of Specific Recognition of Mouse and Human Tau Protein by the Synthesized Humanized Cis pT231-Tau Monoclonal Antibody Variants Whole brain lysates from WT mice, tau KO mice and htau mice (overexpressing human tau) were subjected to immunoblotting analyses using different humanized antibody variants. FIG. 5 is a series of images showing the ability of humanized cis mAb variants to specifically recognize cis P-tau in whole brain lysates of tau wild-type (+/+), tau knockout (−/−) and hTau transgenic mice.

Figure 6:
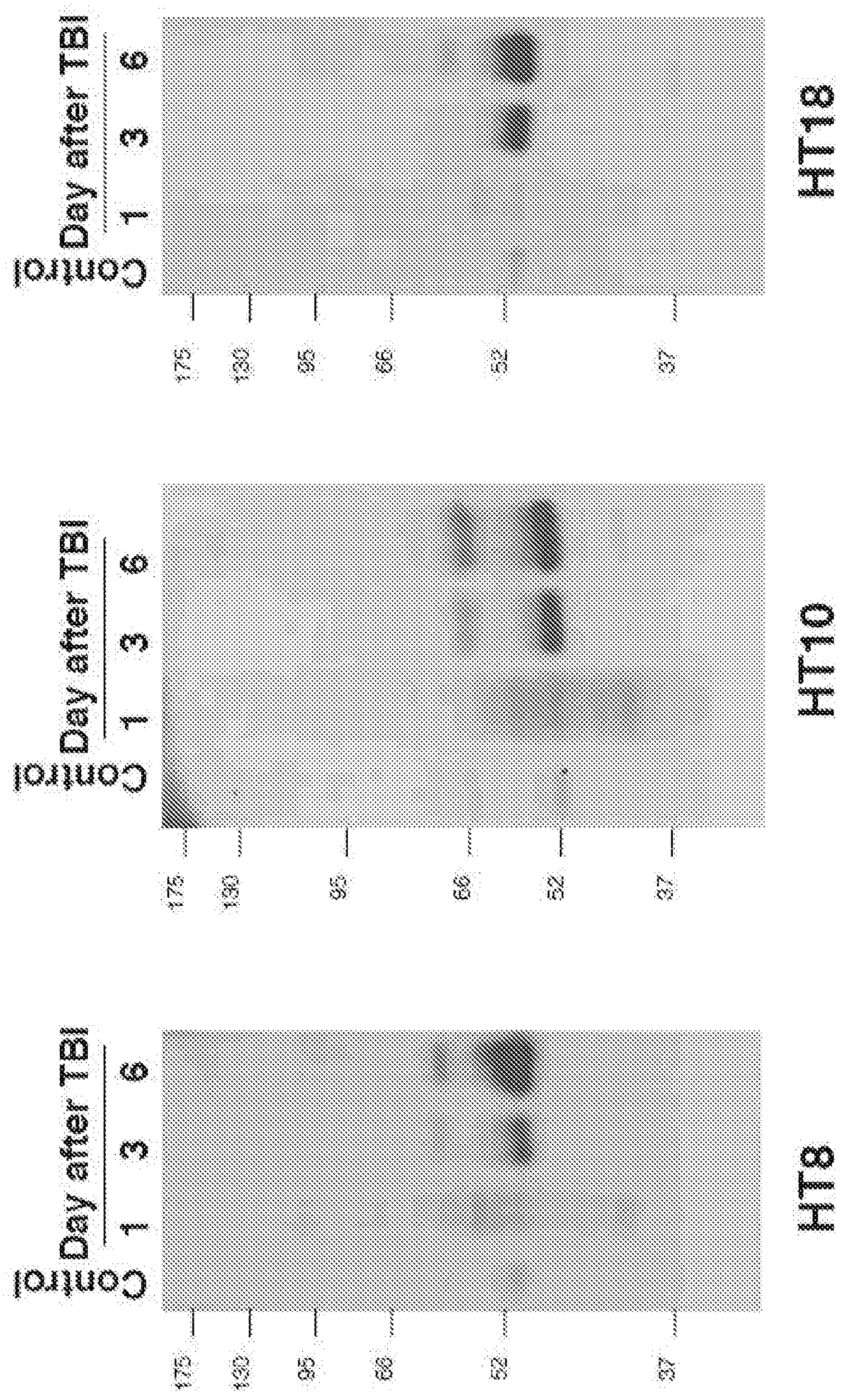
FIG. 6 is a series of images showing the ability of humanized cis pT231-tau monoclonal antibody variants HT8, HT10 and HT18 to recognize cis P-tau in live human traumatic brain injury patient cerebrospinal fluid.

Example 5. Cis pT231-Tau is Present in Cerebral Spinal Fluid (CSF) of Traumatic Brain Injury Patients and Recognized by the Synthesized Humanized Cis pT231-Tau Monoclonal Antibody Variants CSF pT231-tau is an early biomarker of traumatic brain injury (TBI). The recognition of cis P-tau in the CSF of live TBI patients by the humanized cis pT231-tau monoclonal antibody variants evaluated immunoblotting analyses using different humanized antibody variants. Strikingly, cis-mAbs HT8, HT10 and HT18 demonstrated robust detection of cis P-tau as early as three days after TBI relative to control CSF samples, with detectable levels of recognition observed as early as one day after TBI (FIG. 6).

Figure 7:
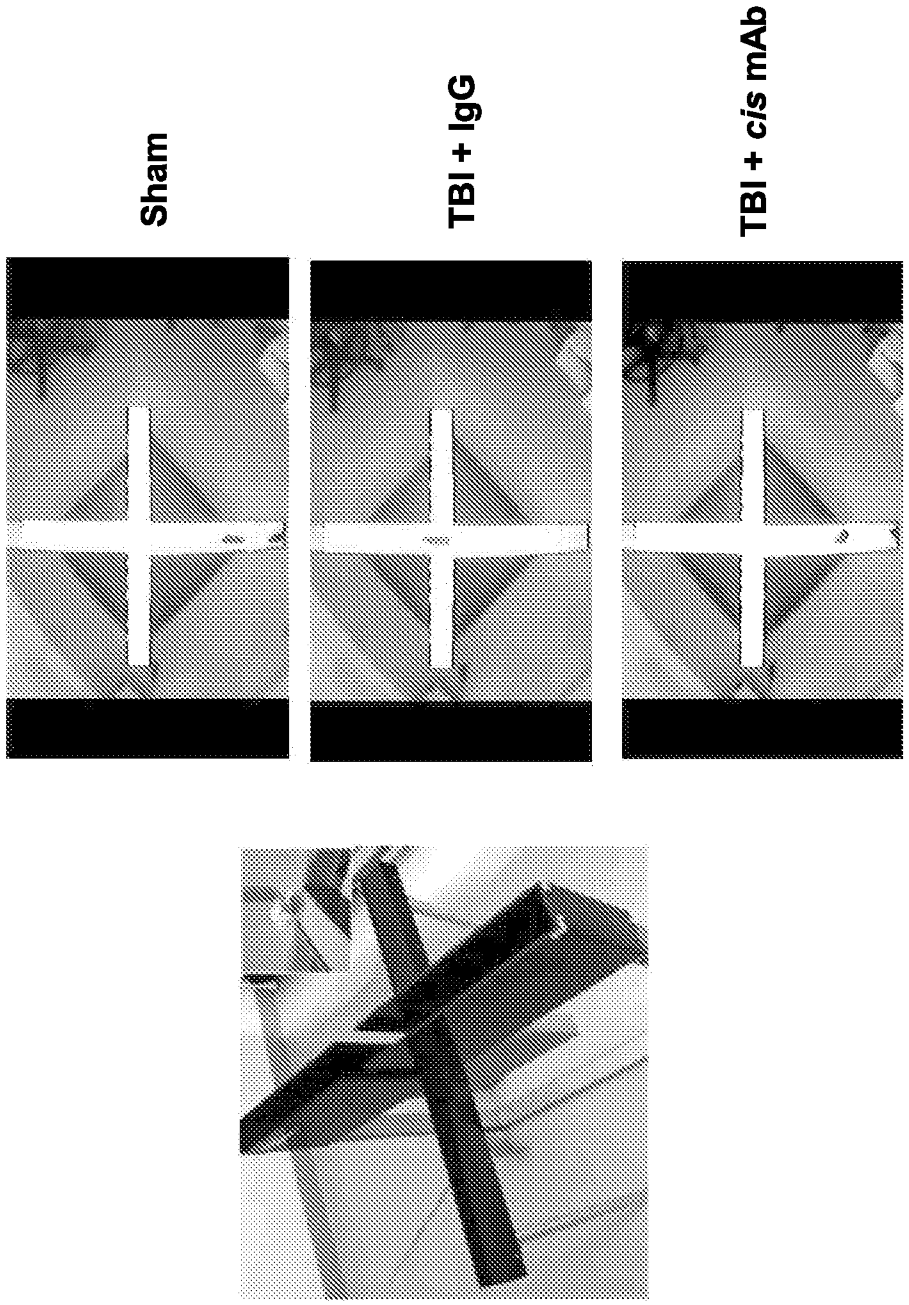
FIG. 7 is a series of photographic images showing the configuration of the elevated plus maze assay. On the right, the figure shows representative photographic top-view images of mice, Sham (no TBI), TBI+IgG and TBI+cis mAb, displaying measurable behavior within the arms of the elevated plus maze.
Figure 8A:
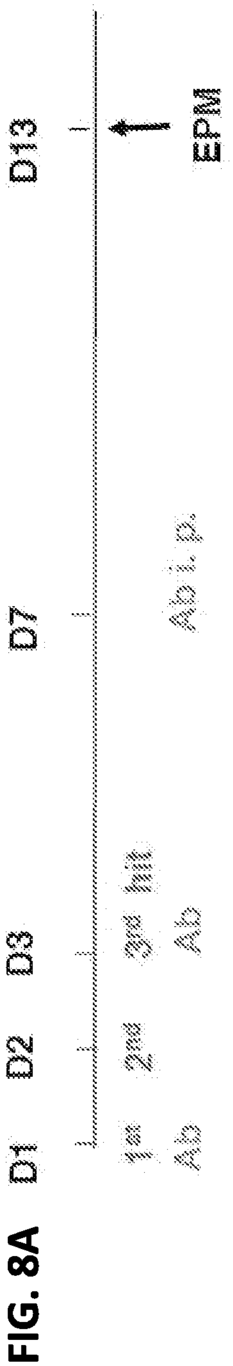
FIG. 8A is a schematic of the experimental timeline used to evaluate the ability of top humanized cis mAb variants to restore initial brain dysfunction after 3 hit traumatic brain injury. Elevated plus maze (EPM) assays were performed on day 13.
Figure 8B:
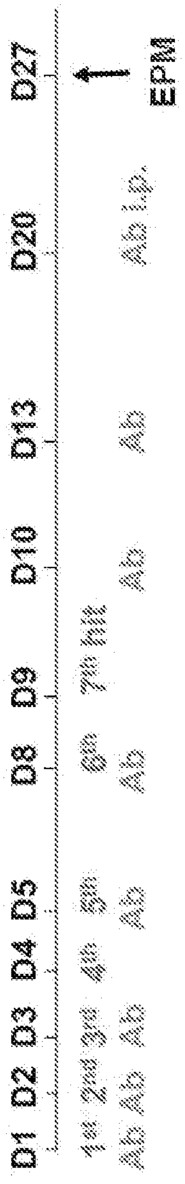
FIG. 8B is a schematic of the experimental timeline used to evaluate the ability of top humanized cis mAb variants to restore initial brain dysfunction after 7 hit traumatic brain injury. Elevated plus maze (EPM) assays were performed on day 13.
Figure 9:
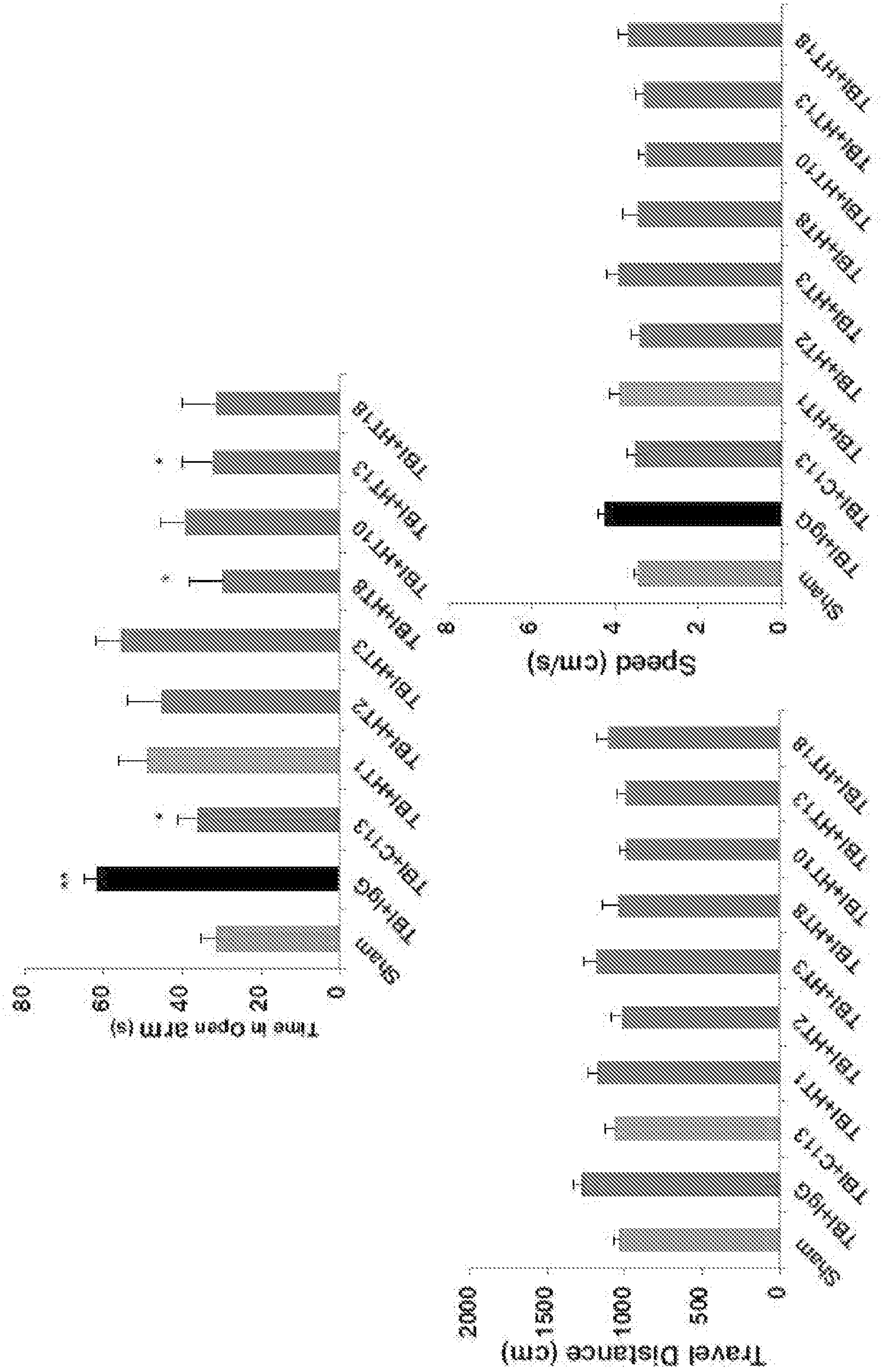
FIG. 9 shows graphs of the measurable behavioral parameters, Time in open arms in secs, Travel distance in cm and Speed in cm/s, of Sham or TBI test mice that were administered 250 μg of IgG or humanized cis mAb variant collected from the 3 hit TBI assay.
Figure 10:
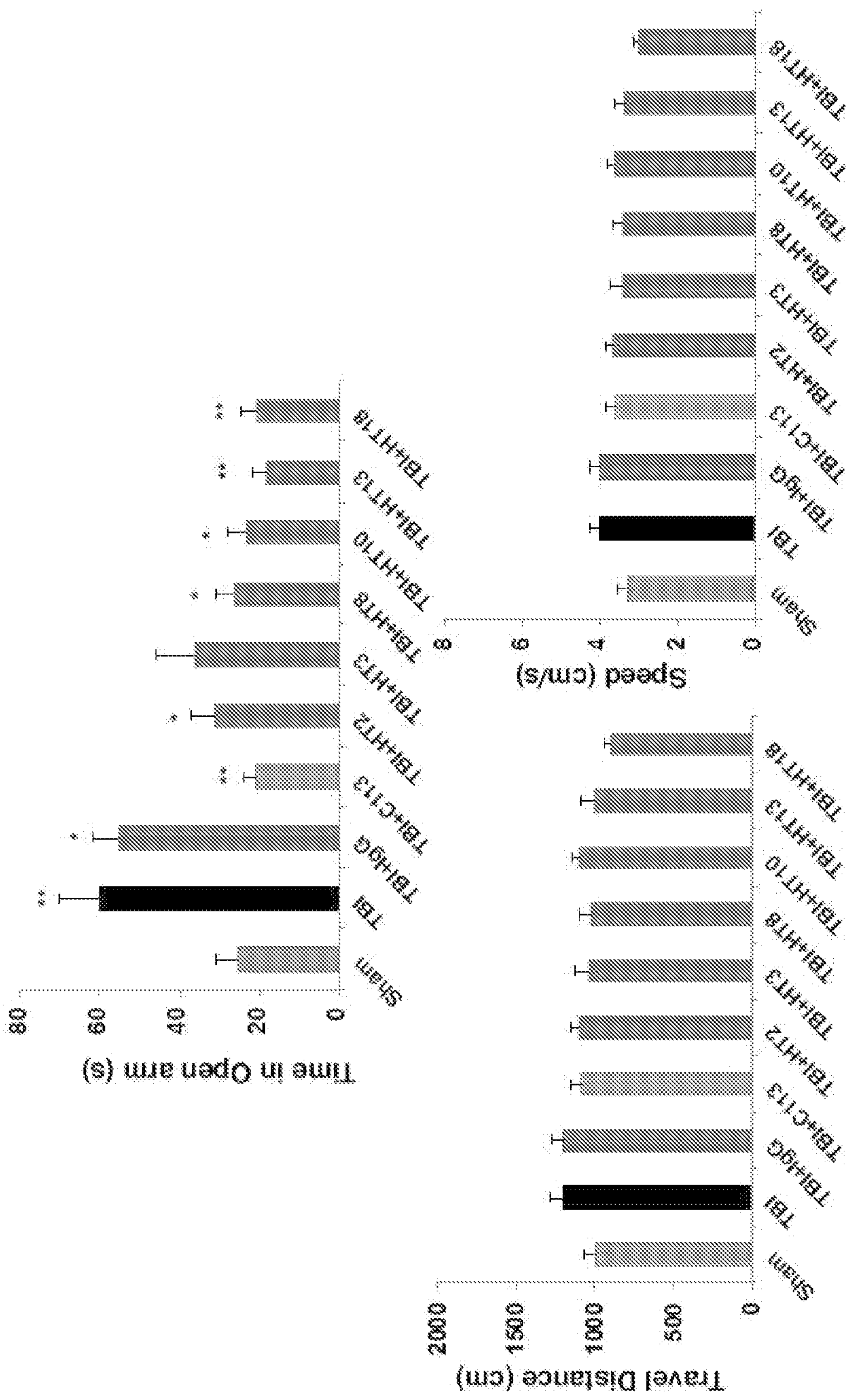
FIG. 10 shows graphs of the measurable behavioral parameters, Time in open arms in secs, Travel distance in cm and Speed in cm/s, of Sham or TBI test mice that were administered 250 μg of IgG or humanized cis mAb variant collected from the 7 hit TBI assay.

Example 6. Cis pT231-Tau Monoclonal Antibody Variants Restore Initial Brain Dysfunction Following Traumatic Brain Injury An initial sign of brain dysfunction following traumatic brain injury (TBI) is an increase in risk-taking behavior. To determine the therapeutic effect of the herein described cis pT231-tau monoclonal antibodies in restoring brain function 11-week old mice (C57/BL6) mice were subjected to elevated plus maze behavioral assays designed to evaluate risk-taking behavior following repetitive mild TBIs. The behavioral assays were performed as previously described in Walf, Nature Protocols 2(2): 322-328, 2007 (FIG. 7). 10 groups of mice were evaluated, with one Sham group (n=11 mice) that did not sustain TBI injury. All other mice sustained mild TBI (rmTB) either three times, once a day for three consecutive days, or seven times once a day for five consecutive days and two consecutive times on days 8 and 9. In the 3-hit TBI experiment (FIG. 8A), nine groups of mice received three doses (250 ug/mouse) via intraperitoneal injection of either IgG control (n=10 mice) or one of the following humanized cis pT231-tau monoclonal antibody variants C113 (n=5 mice), HT1 (n=10 mice), HT2 (n=10), HT3 (n=10), HT8 (n=5), HT10 (n=10), HT13 (n=15), HT18 (n=4). Treatment with IgG or humanized cis-pT231-tau monoclonal antibody was administered on Days 1, 2 and 7. Behavioral evaluation was performed on Day 13. In the 7-hit TBI experiment (FIG. 8B), one group sustained TBI only (n=10 mice). The other groups received 8 doses (250 ug/mouse) via intraperitoneal injection of either IgG control (n=10 mice) or one of the following humanized cis pT231-tau monoclonal antibody variants C113 (n=10 mice), HT2 (n=10), HT3 (n=10), HT8 (n=10), HT10 (n=10), HT13 (n=10), HT18/HC2 (n=10). Treatment with IgG or humanized cis-pT231-tau monoclonal antibody was administered on Days 1, 2, 3, 5, 8, 10, 13 and 20. Behavioral evaluation was performed on Day 27. The elevated plus maze was used to assess anxiety/risk-taking behavior and carried out as described in Kondo et al, Nature 523, 431-436, 2015. Briefly, the elevated plus maze consists of two white open arms (30×5 cm) and two white closed arms of the same size with 15-cm-high walls, extended out opposite from each other from a central platform (decision zone) to create a plus shape. The entire apparatus is raised 38 cm above the floor (Lafayette Instruments). Mice are placed on the center platform of the maze, facing a closed arm, and allowed to explore the apparatus for 5 min. The maze is cleaned between subjects with a weak ethanol solution and dried. A computer-assisted video tracking system (Noldus Ethovision) recorded the total time spent in the center platform (decision zone), and the two closed or 'safe' arms and the two open or 'aversive' arms. Mice with lower levels of anxiety/risk-taking behavior spend less time in the open arms. Surprisingly, in both experimental scenarios, 3-hit and 7-hit experiments (FIGS. 8A-8B, 9, and 10), treatment with humanized cis pT231-tau monoclonal antibody variants (FIGS. 9 and 10) robustly rescued the higher risk-taking behavior compared to control TBI-only and TBI-IgG mice evaluated using the parameters Time in Open arms and Travel Distance (FIGS. 9 and 10).

Example 7. Cis p-Tau Induced in Both VaD Patients and BCAS Mice Modeling Key Aspects of Clinical Vascular Contributions to Cognitive Impairment and Dementia (VCID)

Figure 11A:
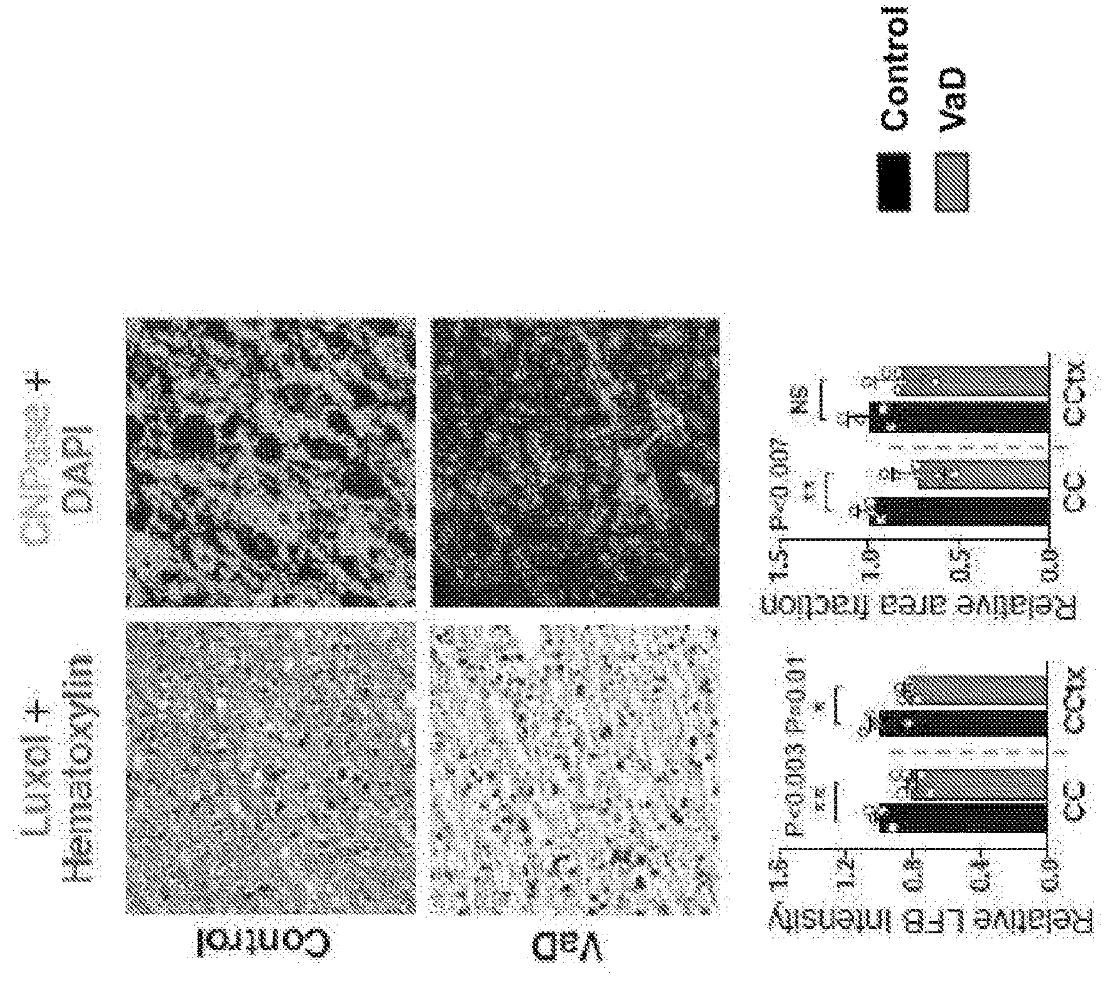
FIG. 11A shows histopathological and immunostaining results, and their accompanying quantification graphs, of brain sections of human vascular dementia (VaD) and healthy controls. Luxol fast blue and hematoxylin staining and immunostaining with the oligodendrocyte marker CNPase were performed to detect degeneration of myelin/myelinated axons.
Figure 11B:
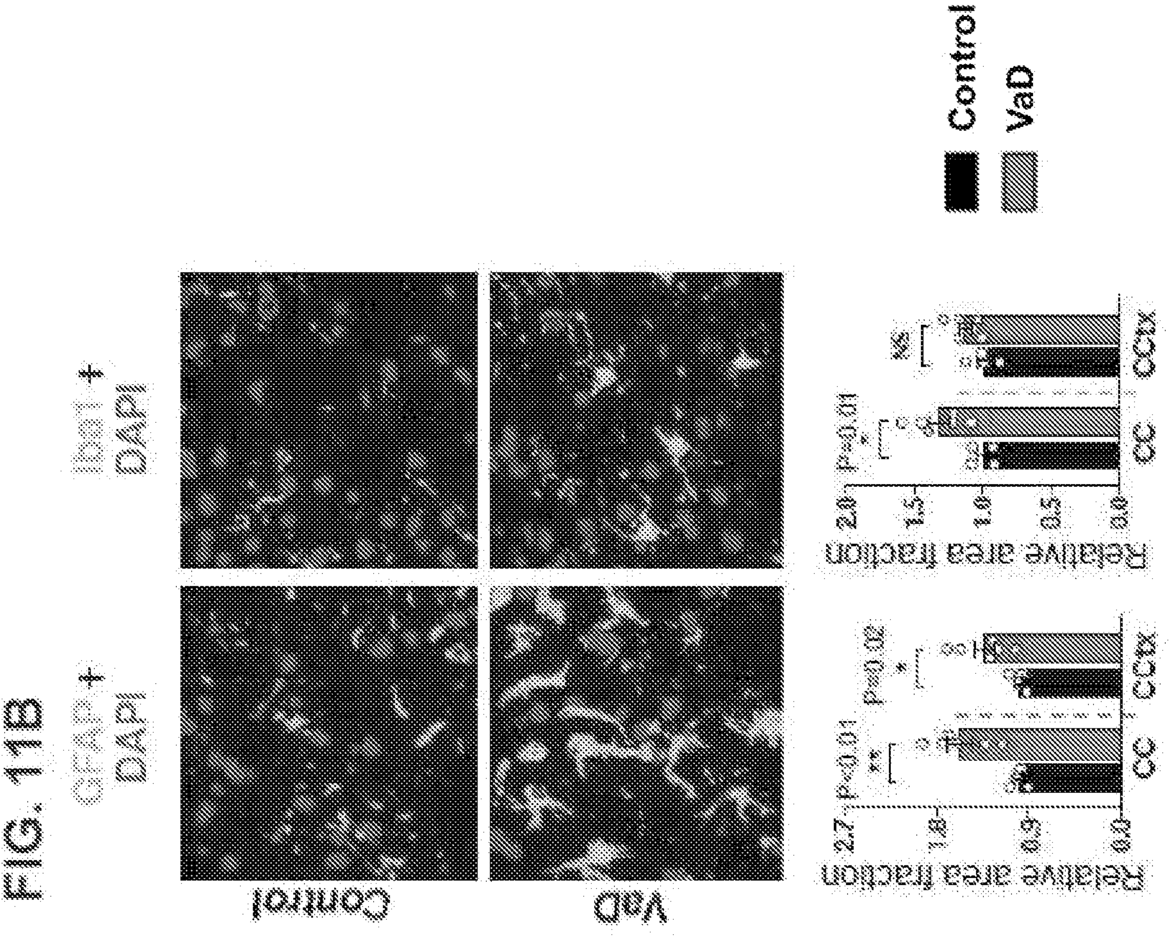
FIG. 11B shows immunostaining results, and their accompanying quantification graphs, of brain sections of human vascular dementia (VaD) and healthy controls. The tissue was subjected to immunostaining of GFAP and Iba1 markers of neuroinflammation.
Figure 12A:
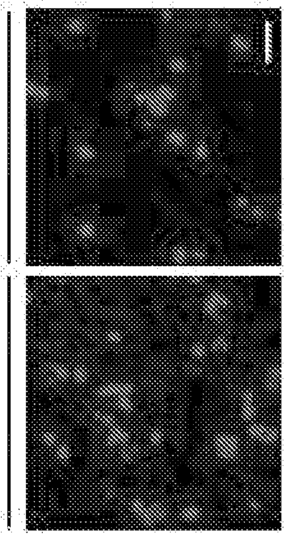
FIG. 12A is a representative immunofluorescence image of healthy and VaD brain sections that were subjected to phospho-tau monoclonal antibody AT8 immunostaining to detect early tangle-like structures.
Figure 12B:
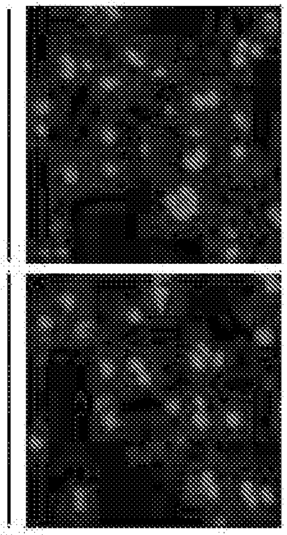
FIG. 12B is a representative immunofluorescence image of healthy and VaD brain sections that were subjected to phospho-tau monoclonal antibody AT100 immunostaining to detect late tangle-like structures.
Figure 12C:
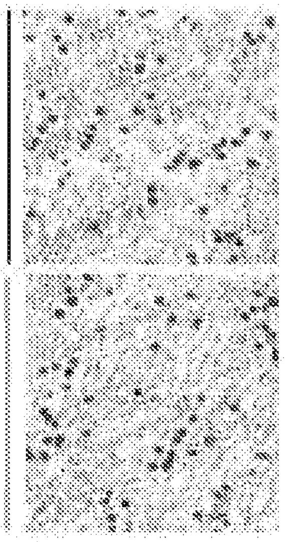
FIG. 12C is a representative immunostaining image of healthy and VaD brain sections that were subjected to thioflavin S staining to detect NFT-like structures.

To explore the role of cis P-tau in VCID, cis P-tau was first examined in human VaD brain. In verified pure VaD human brains (Table 3) significant demyelination (FIG. 11A), and neuroinflammation (FIG. 11B) was observed, but none of the 9 human VaD brains had indications of the presence of neurofibrillary tangles (NFTs) (FIGS. 12A-12C and FIG. 110).

TABLE 3

The clinical information of patients with VaD and healthy controls

| | ID | Gender | Age | Primary diagnosis | Secondary diagnosis | Evidence for vascular insults | Tangles | Plaques |
|---|---|---|---|---|---|---|---|---|
| Control | Control-1 | Male | 74 | No brain disease | — | No | No | No |
| | Control-2 | Male | 78 | No brain disease | — | No | No | No |
| | Control-3 | Female | 61 | No brain disease | — | No | No | No |
| | Control-4 | Male | 84 | No brain disease | — | No | No | No |
| | Control-5 | Male | 79 | No brain disease | — | No | No | No |
| | Control-6 | Male | 86 | No brain disease | — | No | No | No |
| | Control-7 | Female | 88 | No brain disease | — | No | No | No |
| | Control-8 | Male | 96 | No brain disease | — | No | No | No |
| Vascular Dementia | VaD-1 | Female | 77 | (Braak 0) | — | Lacunary and columnary infarctions; Moderate atherosclerosis of the large cerebral arteries. | No | No |
| | VaD-2 | Female | 71 | (Braak 1) | — | Severe atherosclerosis of the large basal cerebral vessels; Hyalino-fibrotic necrotisising vasculopathy with perivascular infiltrates | No | Slight |
| | VaD-3 | Male | 65 | (Braak 0) | — | Moderate subcortical infarction | No | No |
| | VaD-4 | Female | 61 | (Braak 1) | — | Severe atherosclerosis of the cerebral arteries; Vascular encephalopathy, diffuse. | No | No |
| | VaD-5 | Male | 64 | (Braak 0) | — | Severe atherosclerosis of the large cerebral arteries; severe agonal ischemic changes. | Few | No |
| | VaD-6 | Male | 50 | (Braak 0) | — | Many vessels with perivascular lymphatic infiltrate; Several vessels are densely fibrotic | No | No |
| | VaD-7 | Male | 60 | (Braak 2) | — | The ventricular system shows severe dilation; Vessels with perivascular lymphocytic infiltrate | No | Slight |
| | VaD-8 | Male | 57 | (Braak 0) | — | Large cerebral arteries with bilateral infarctions; Focally small ischemic defects. | No | No |
| | VaD-9 | Female | 65 | (Braak 1) | — | Lacunar infarction; some vascular deviances | No | No |

Figure 14B:
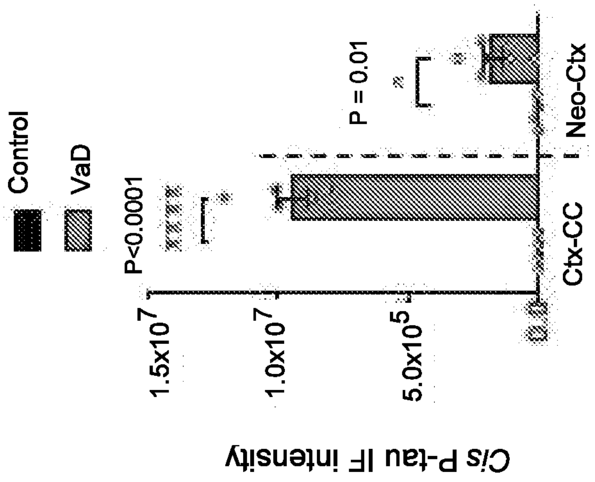
FIG. 14B is a graph of the quantified levels of cis P-tau the cortex overlying the corpus callosum (Ctx-CC) and the neo-cortex in aged-matched normal control human brains and in VaD human brains.
Figure 14A:
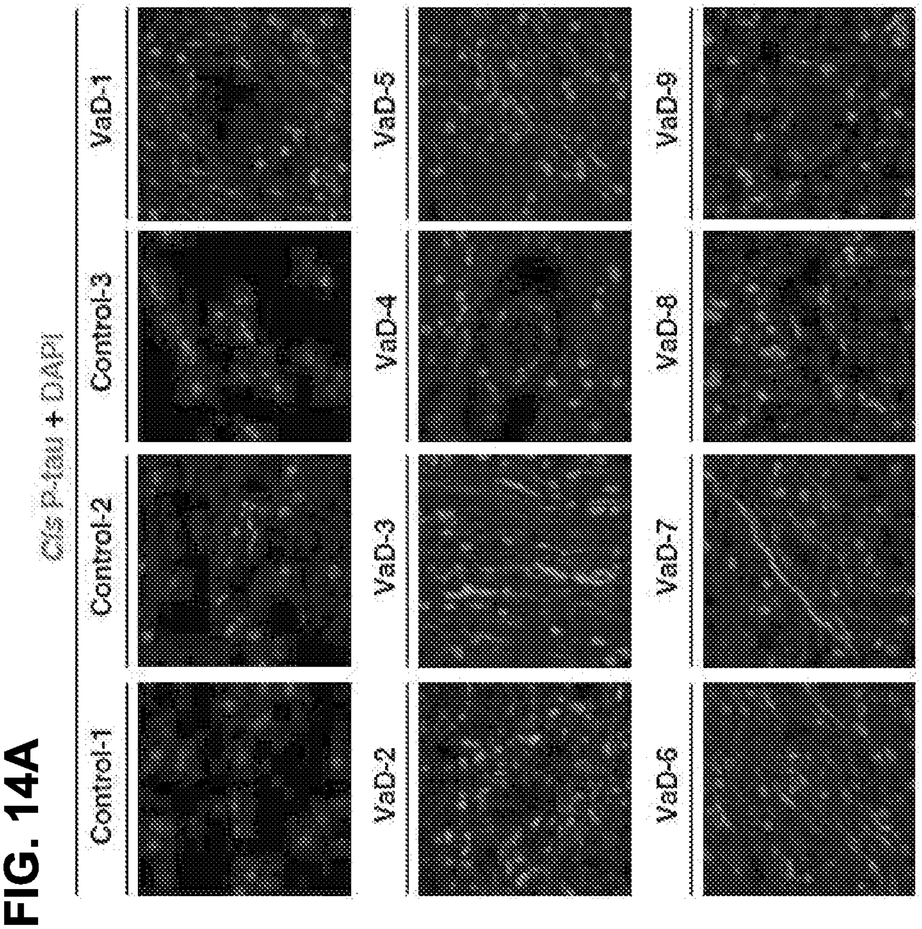
FIG. 14A shows immunofluorescence results of the elevated level of cis P-tau (red) in VaD human brains in the cortex overlying the corpus callosum compared to the cis P-tau levels in age-matched normal control human brains. Blue denotes DAPI nuclear staining to report all cells.
Figure 15A:
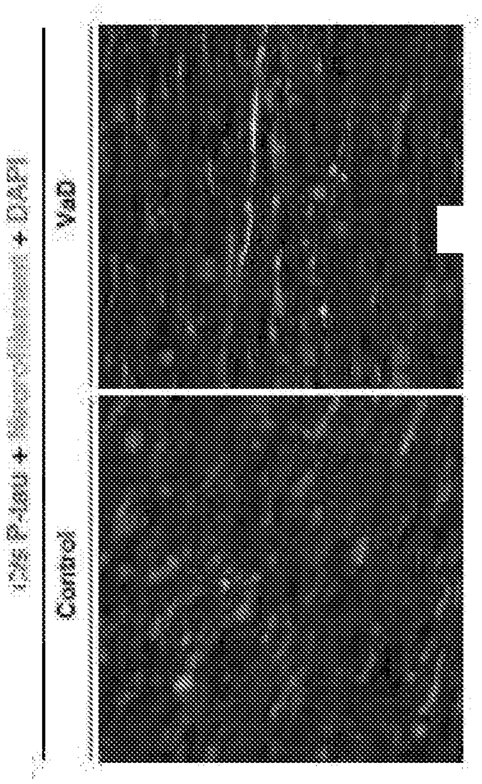
FIG. 15A shows immunofluorescence staining results marking the localization of cis P-tau notably to axons in human VaD brains. Human VaD brains and normal controls were subjected to double immunofluorescence with cis mAb (red) and neurofilament marker (green). Blue denotes DAPI nuclear staining to report all cells.
Figure 15B:
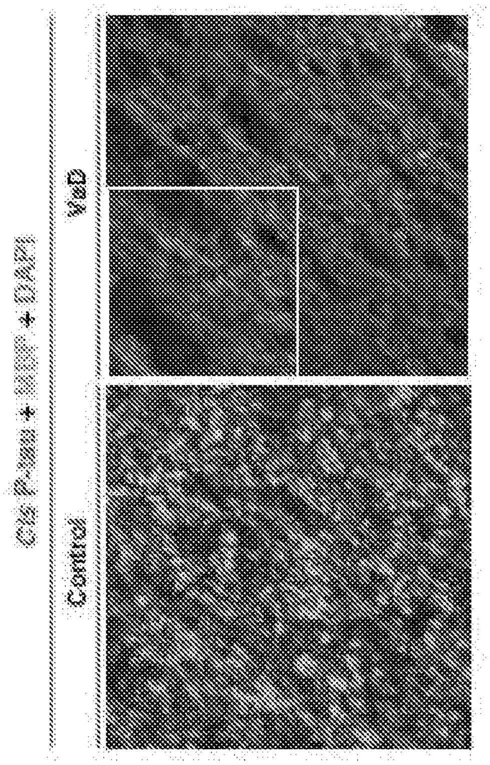
FIG. 15B shows immunofluorescence staining results marking the localization of cis P-tau to axons. Human VaD brains and normal controls were subjected to double immunofluorescence staining with cis mAb (red) and myelin basic protein (green). Blue denotes DAPI nuclear staining to report all cells. Inset shows higher magnification.
Figure 15C:
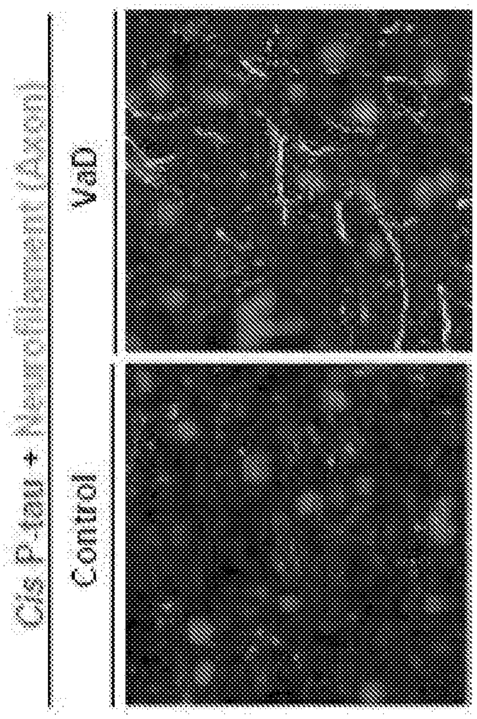
FIG. 15C shows immunofluorescence staining results marking the localization of cis P-tau notably to axons in human VaD brains. Human VaD brains and normal controls were subjected to double immunofluorescence with cis mAb (red) and neurofilament marker (green). Blue denotes DAPI nuclear staining to report all cells.
Figure 16B:
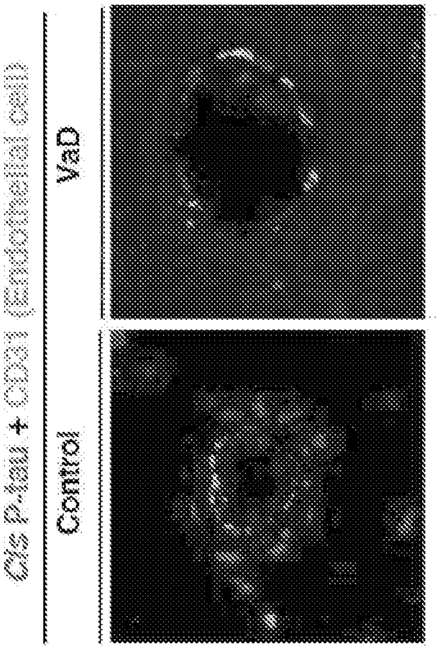
FIG. 16B shows immunofluorescence staining results of cis P-tau in microvascular endothelial cells in VaD. Brain sections of human VaD and healthy controls were subjected to double immunostaining with cis P-tau (red) and the endothelial cell marker, CD31, (green). Blue denotes DAPI nuclear staining to report all cells. Inset shows higher magnification.
Figure 16A:
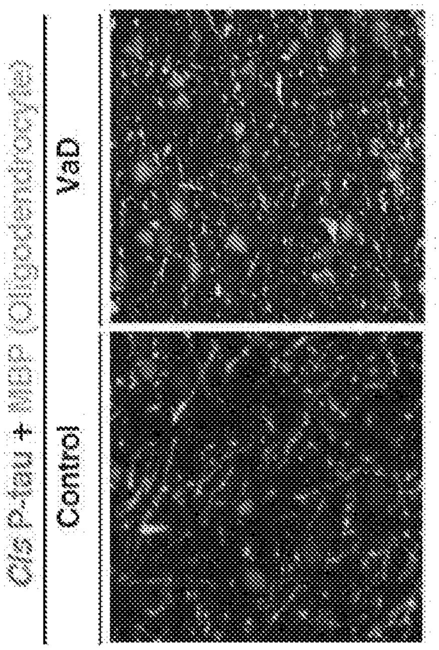
FIG. 16A shows immunofluorescence staining results of cis P-tau in oligodendrocytes. Brain sections of human VaD and healthy controls were subjected to double immunostaining with cis P-tau (red) and the oligodendrocyte marker, MBP, (green). Blue denotes DAPI nuclear staining to report all cells. Inset shows higher magnification.
Figure 17A:
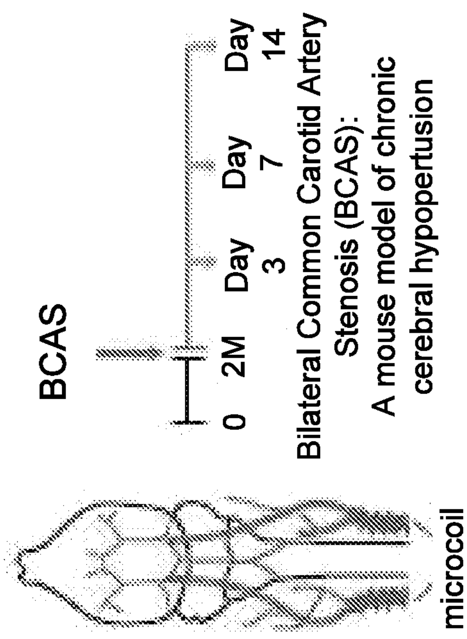
FIG. 17A is a schematic of the Bilateral Common Carotid Artery Stenosis (BCAS) mouse model of chronic hypoperfusion and the timeline used to evaluate cis P-tau levels post-surgery.
Figure 17B:
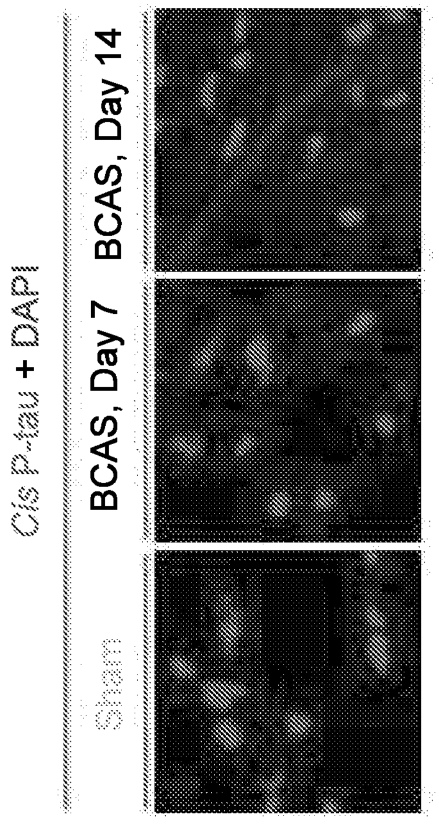
FIG. 17B shows immunofluorescence results of cis P-tau (red) in control (Sham) and BCAS brain slices at 7 days and 14 days pos-surgery. Blue denotes DAPI nuclear staining to report all cells.
Figure 17C:
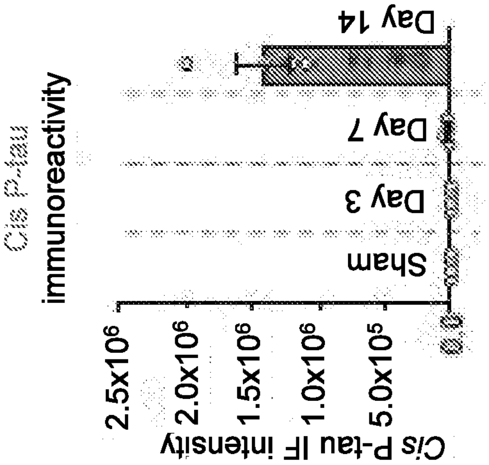
FIG. 17C is a graph of the quantified fluorescence intensity of cis P-tau in brain slices of Sham control mice and BCAS mice. The level of cis P-tau is robustly elevated by day 14 post BCAS surgery.

Surprisingly, robust cis P-tau signal notably in the cingulate cortex overlying the corpus callosum was observed in large sections of brains using immunostaining and near-infrared detection (FIG. 13). Confocal microscopy further confirmed robust cis P-tau signals in all 9 VaD patients, particularly in the same cortical regions, with little signals in all 8 healthy controls (FIG. 14). Cis P-tau was localized notably to axons (FIG. 15A and FIG. 15C) and within the surrounding myelin sheath (FIG. 151B) determined using immunostaining of Neurofilament and Myelin Basic Protein (MBP). In human VaD, cis P-tau was also detected in oligodendrocytes (FIG. 16A) and microvascular endothelial cells (FIG. 161B), consistent with the findings that phosphorylated tau has been detected in oligodendrocytes and lung vascular endothelial cells. Thus, robust cis P-tau is detected in human VaD brains. Since these human VaD brains are at late stages of VOID, critical questions are whether cis P-tau is induced after vascular insufficiency and even has any role in VOID. Since chronic cerebral hypoperfusion is a major vascular factor in VOID. cis P-tau levels were examined in the bilateral common carotid artery stenosis (BOAS) mouse model, where external microcoils (0.18 mm diameter) were permanently placed around both common carotid arteries (FIG. 17A) to chronically reduce parenchymal cerebral blood flow by ~50%, especially in the subcortical brain region. This model has been commonly used to mimic key aspects of clinical VOID. BOAS surgery induced time-dependent elevation of cis P-tau in the cortex overlying the corpus callosum, beginning at day 7 and becoming obvious at day 14 (FIGS. 17B and 17C). Thus, cis P-tau is induced in both VaD patients and BOAS mice modeling key aspects of clinical VOID.

Figures 18A, 18B, 18C:
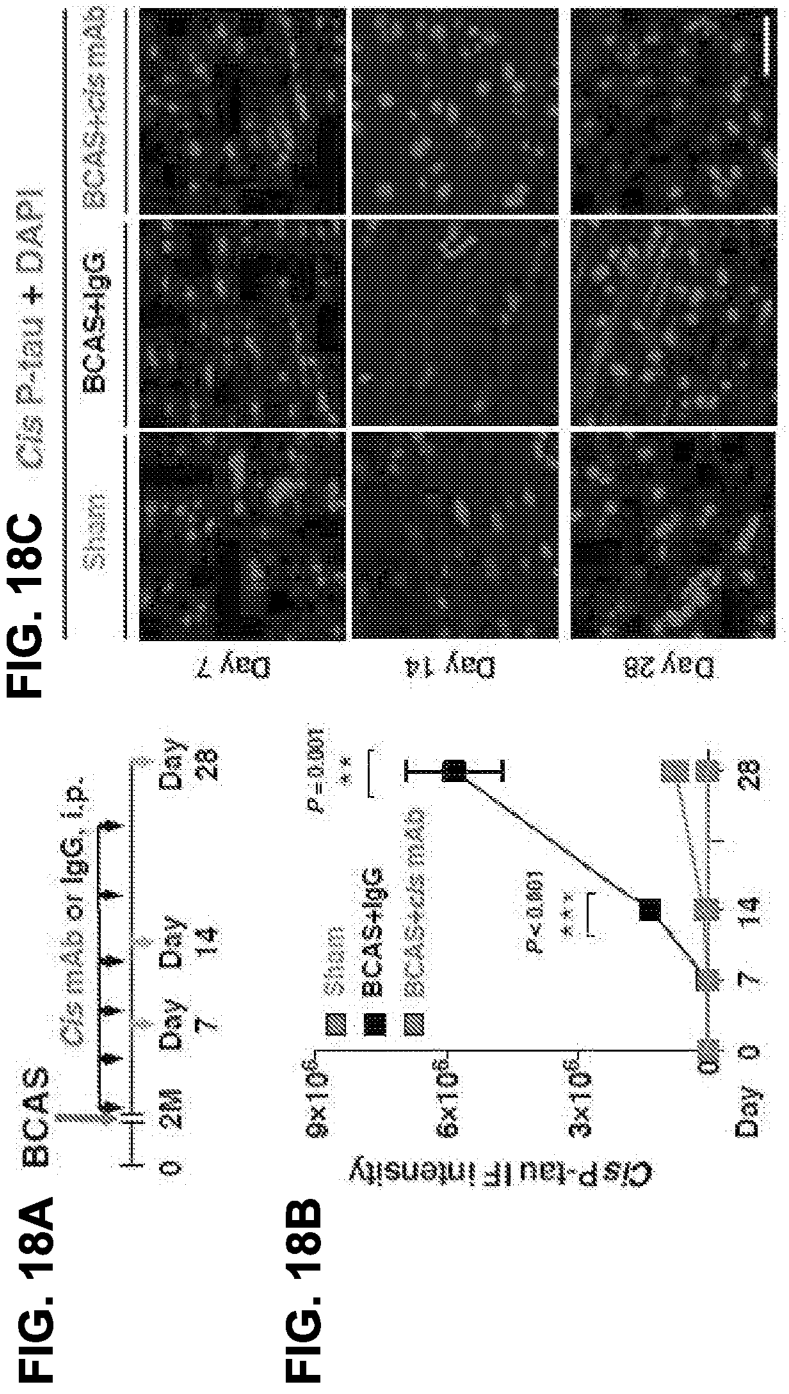
FIG. 18A is a schematic of the timeline used to assess the effect of treatment with cis mAb after BCAS surgery. Levels of cis P-tau were evaluated on day 7, day 14 and day 28 following BCAS surgery. Mice were administered, via intraperitoneal injection, cis mAb or control IgG at the timepoints represented by the black arrowheads. BCAS was performed at two months of age.
FIG. 18B is a graph of the level of cis P-tau at timepoints day 0, day 7, day 14 and day 28 after BCAS surgery. Sham control mice did not display an elevation of cis P-tau throughout the period of 28 days (data shown in green). BCAS mice treated with control IgG robustly displayed elevated levels of cis P-tau evident starting at day 14 post BCAS surgery (data shown in black). cis P-tau levels were rescued to levels near Sham levels in BCAS mice treated with cis mAb (data shown in red).
FIG. 18C shows immunofluorescence staining results describing the elimination of cis P-tau (red) induction in BCAS mice treated with cis mAb. Blue denotes DAPI nuclear staining to report all cells.
Figure 19A:
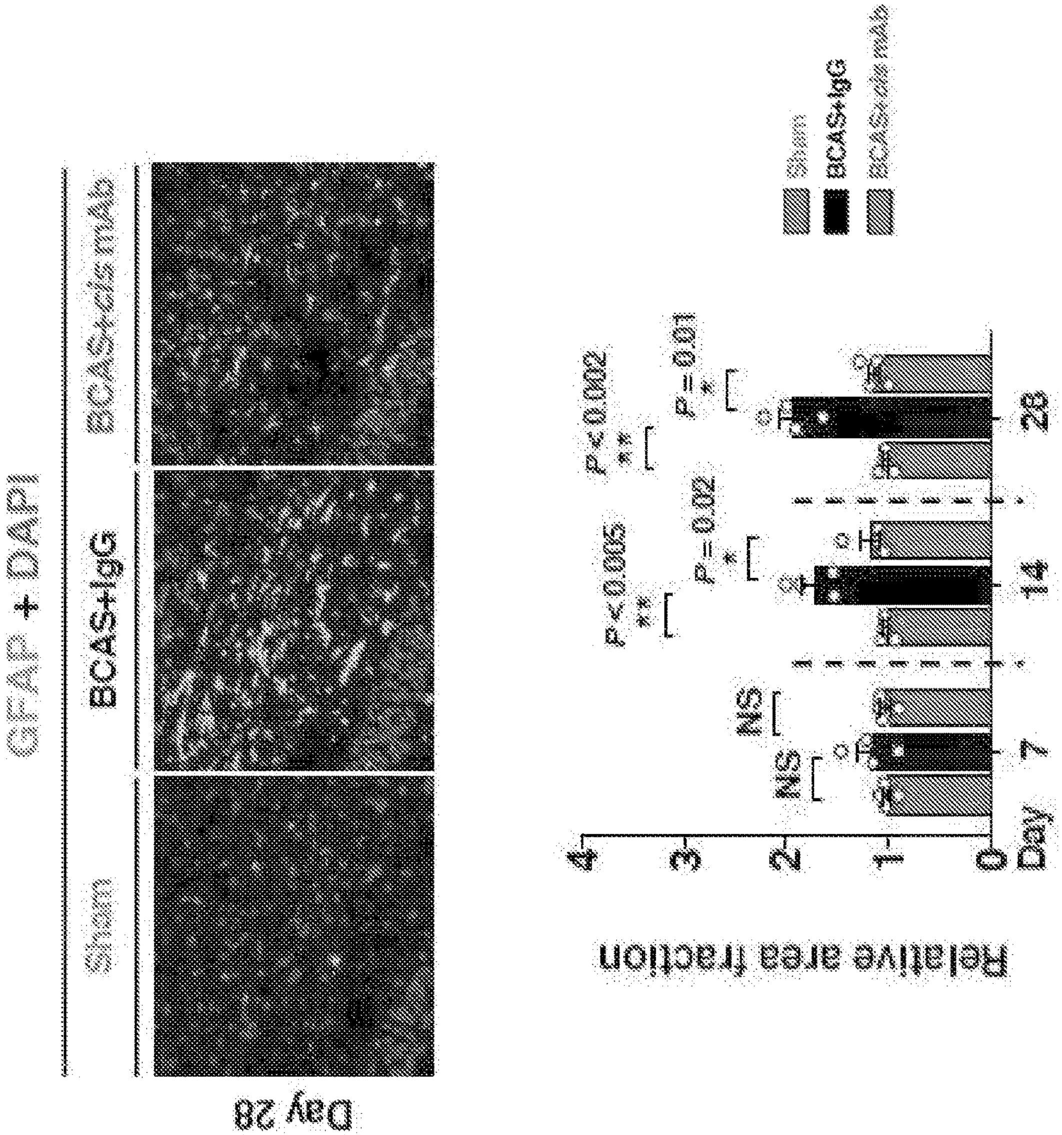
FIG. 19A shows immunofluorescence staining results, and their accompanying quantification graphs, describing the recovery of neuroinflammation in BCAS mice treated with cis mAb. Brain slices were subjected to immunofluorescence staining to evaluate levels of neuroinflammation marker GFAP (green) in Sham control and BCAS mice treated with control IgG and cis mAb. Blue denotes DAPI nuclear staining to report all cells.
Figure 19B:
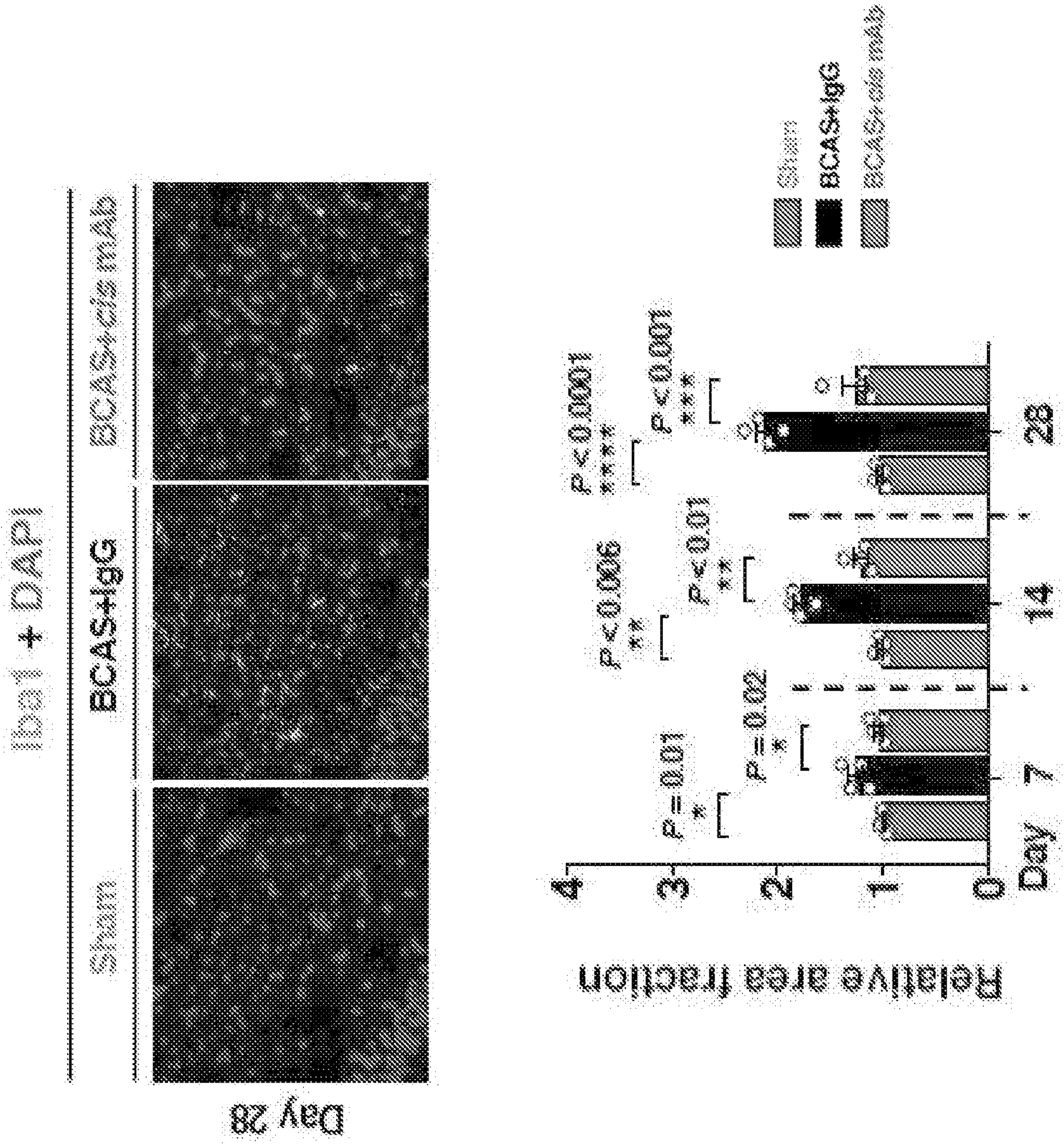
FIG. 19B shows immunofluorescence staining results, and their accompanying quantification graphs, describing the recovery of neuroinflammation in BCAS mice treated with cis mAb. Brain slices were subjected to immunofluorescence staining to evaluate levels of neuroinflammation marker Iba1 (green) in Sham control and BCAS mice treated with control IgG and cis mAb. Blue denotes DAPI nuclear staining to report all cells.
Figure 19C:
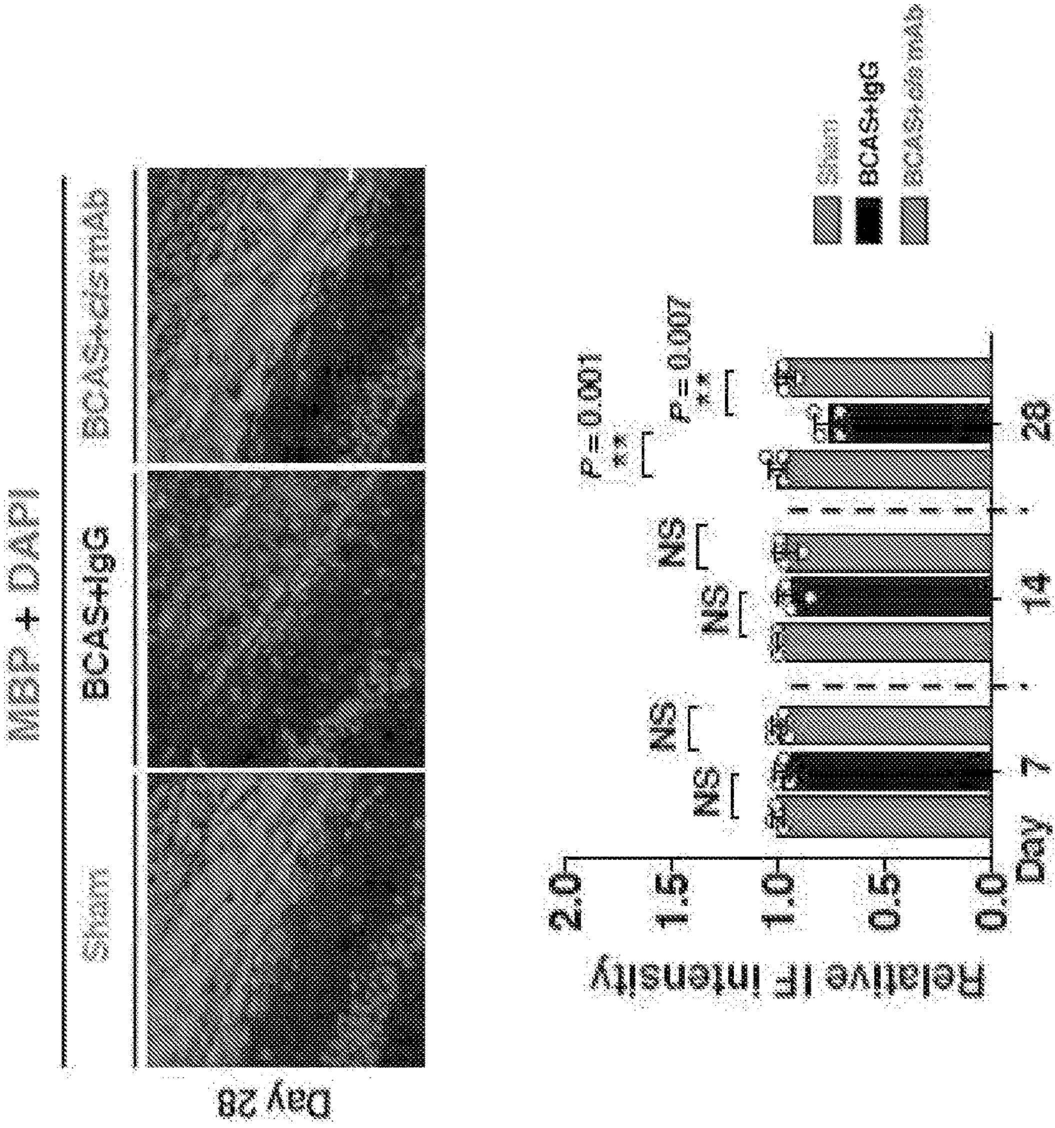
FIG. 19C shows immunofluorescence staining results, and their accompanying quantification graphs, describing the recovery of demyelination in BCAS mice treated with cis mAb. Brain slices were subjected to immunofluorescence staining to evaluate levels of demyelination using the myelin basic protein marker (green) in Sham control and BCAS mice treated with control IgG and cis mAb. Blue denotes DAPI nuclear staining to report all cells.
Figure 20A:
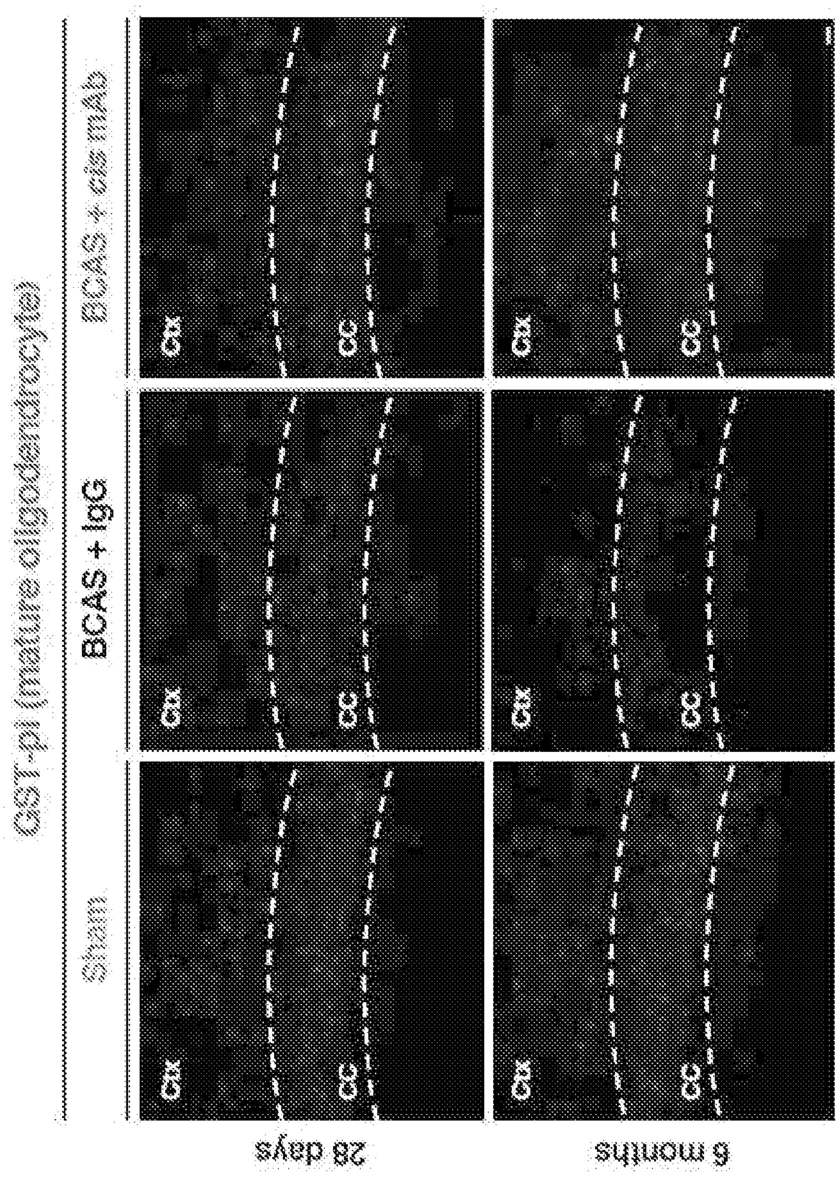
FIG. 20A shows immunofluorescence results describing the rescue of the loss of oligodendrocytes in cis mAb treated BCAS mice at 1 month and 6 months after BCAS surgery. Brain sections of BCAS mice and age-matched controls were subjected with GST-pi antibodies to detect mature oligodendrocytes (red) at 28 days and 6 months after BCAS surgery.
Figure 20B:
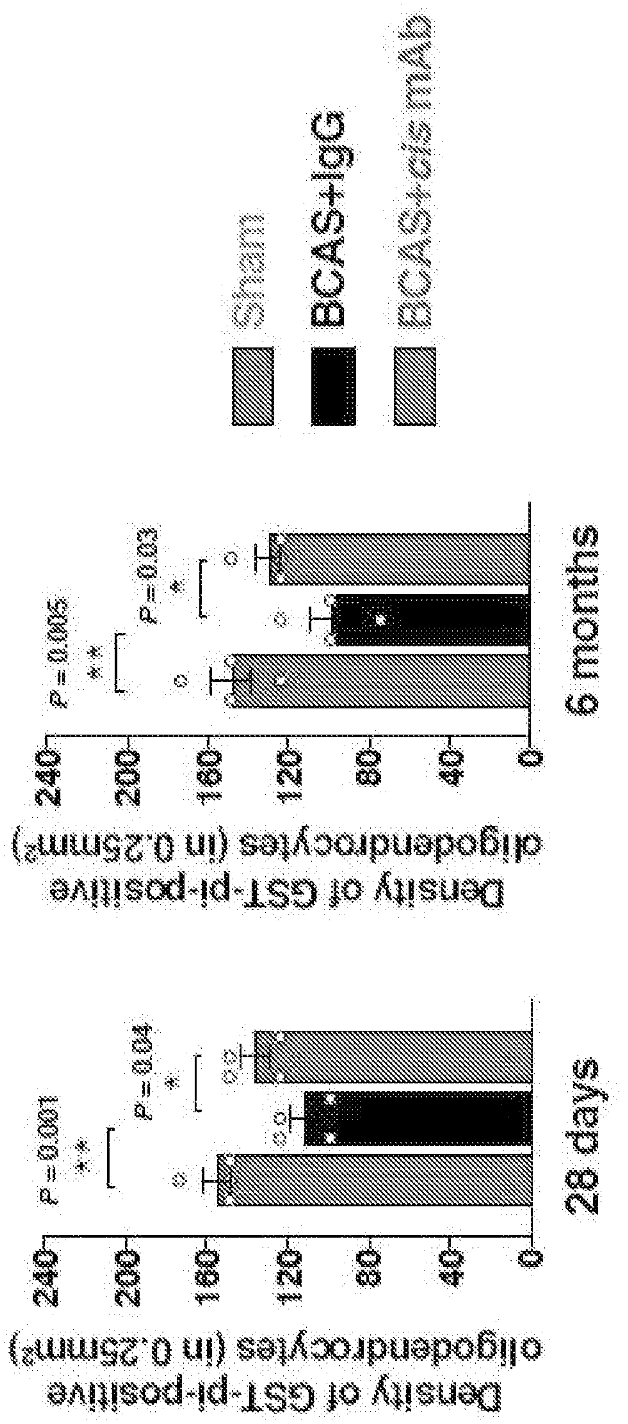
FIG. 20B are graphs of the quantified fluorescence intensity reporting the density of GST-pi positive mature oligodendrocytes in brain slices of cis mAb treated BCAS mice and age-matched controls at 1 month and 6 months after BCAS surgery.
Figures 21A, 21B:
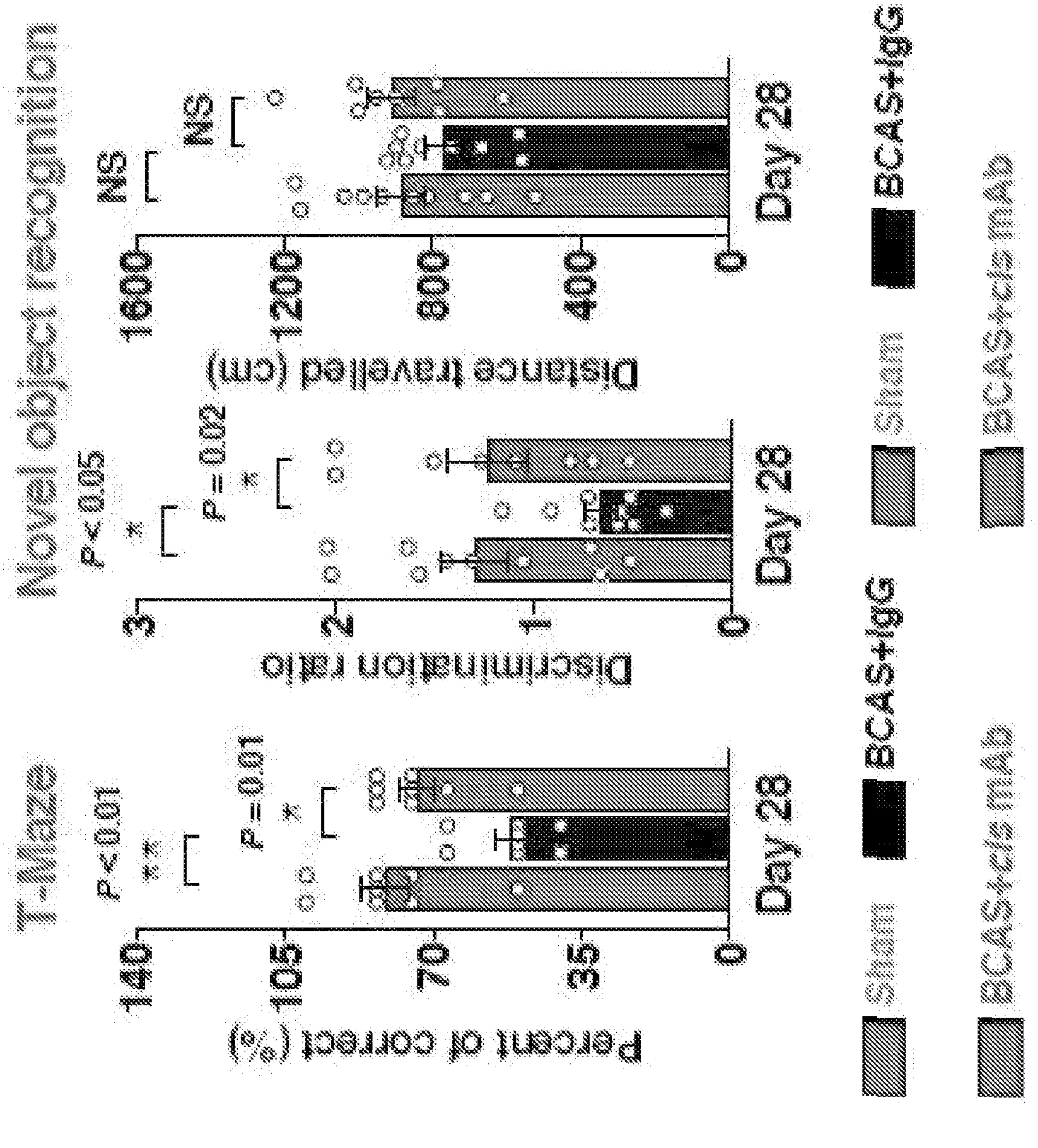
FIG. 21A is a graph describing the restoration of working memory deficits in cis mAb treated BCAS mice. Behavioral changes were analyzed using the T-maze test.
FIG. 21B is a graph describing the restoration of working memory deficits in cis mAb treated BCAS mice. Behavioral changes were analyzed using the Novel object recognition test.
Figure 21C:
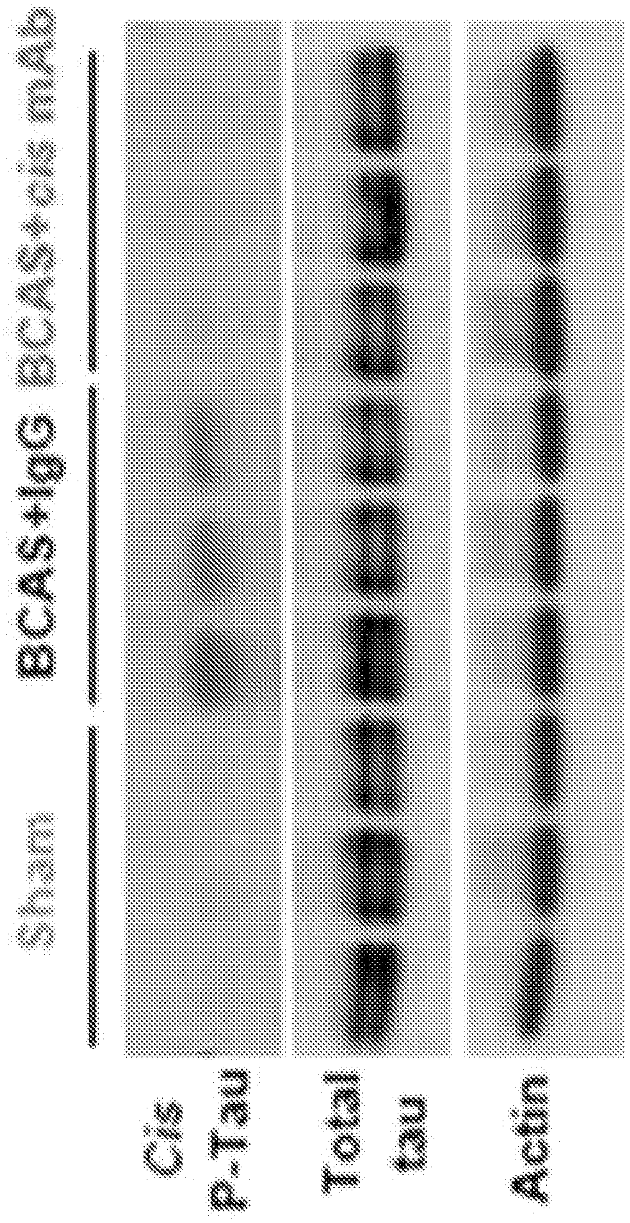
FIG. 21C is a photographic image showing that cis mAb treatment of BCAS mice does not affect total tau levels at 28 days. Brain lysates were examined by immunoblotting for total tau using Tau5 mAb, with an actin loading control.
Figure 21D:
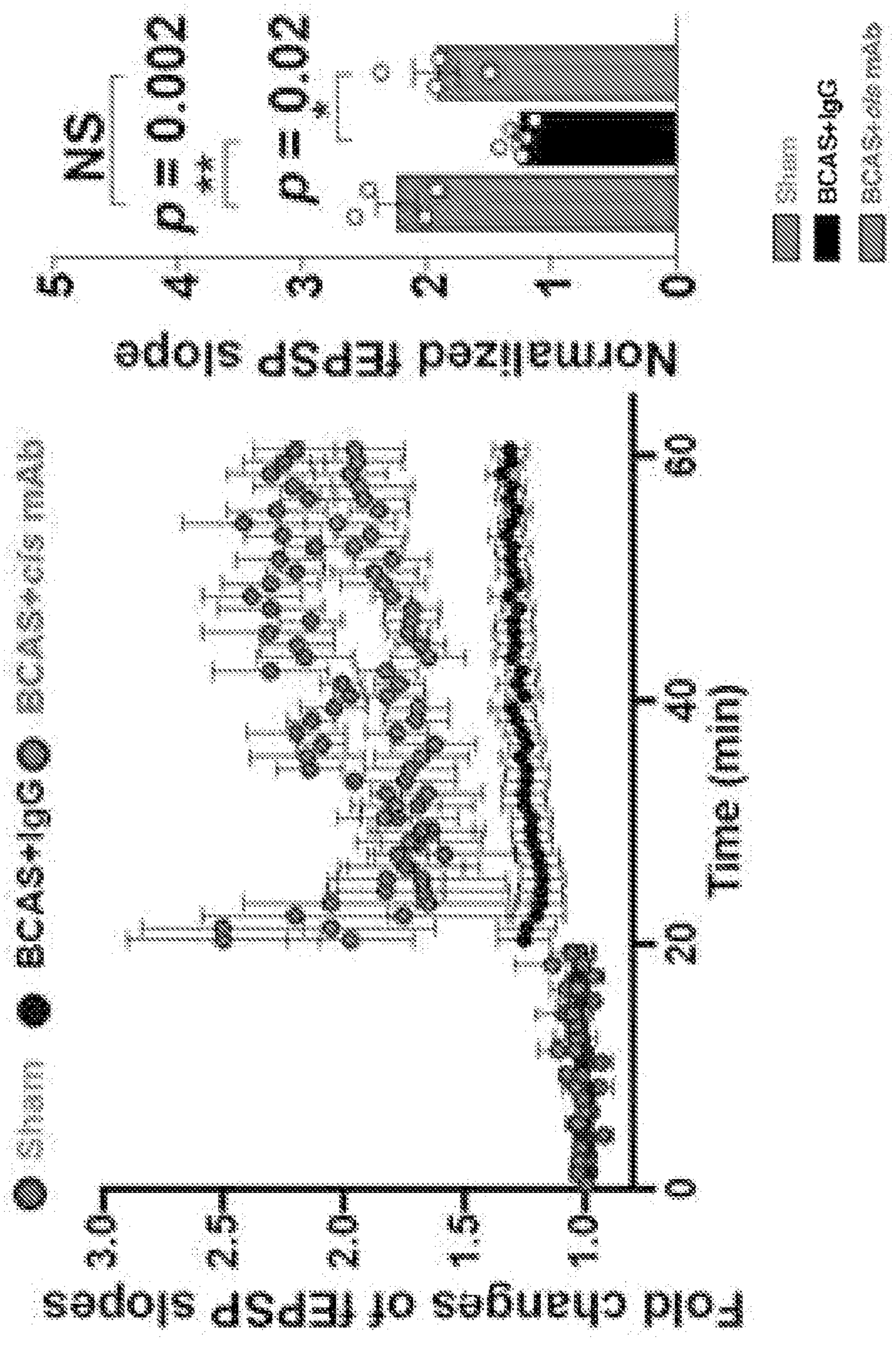
FIG. 21D is a pair of graphs showing the time course of hippocampal axonal long-term potentiation (LTP) that was determined 28 days after BCAS surgery and the quantification of the normalized field excitatory postsynaptic potentials (fEPSP) for Sham (green), BCAS+IgG (black), and BCAS+cis mAb (red) groups.
Figure 22:
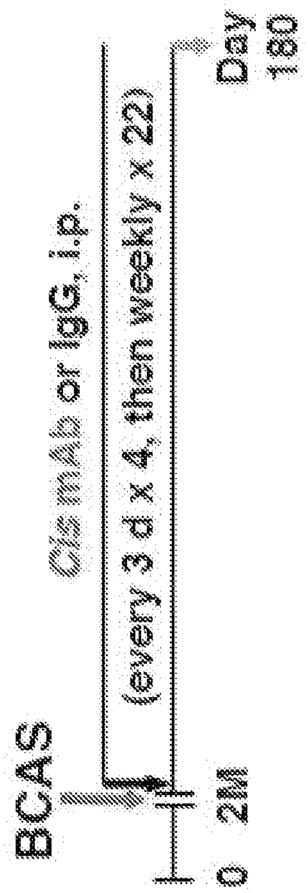
FIG. 22 is a schematic of the timeline used to assess the effect of treatment with cis mAb after BCAS surgery in the 6-month experiment. Two-month-old wild-type mice were subjected to either sham or BCAS surgery and treated with cis mAb or IgG isotype control for 6 months. IgG or cis mAb was administered via intraperitoneal injection every 3 days for 4 times (300 μg), then 200 μg every week afterwards.
Figure 23A:
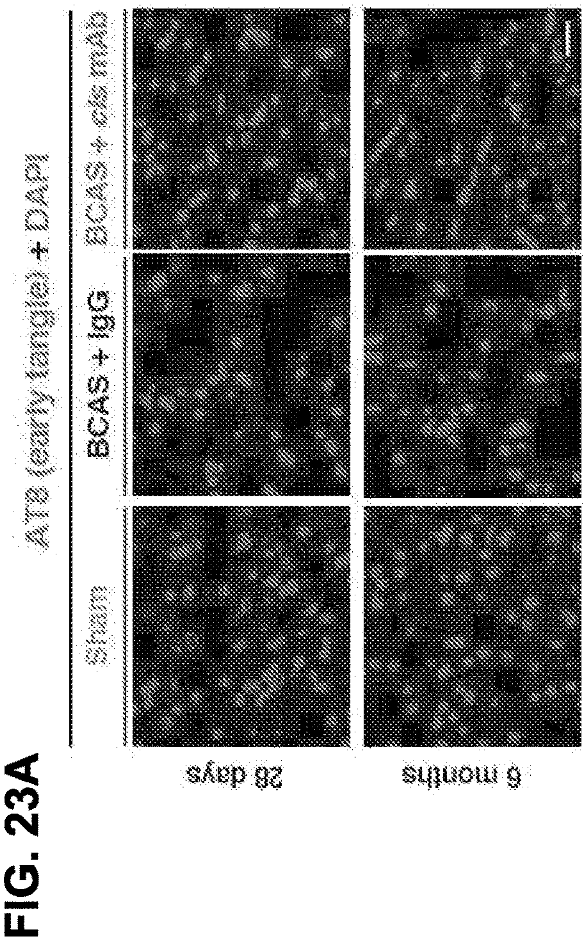
FIG. 23A shows immunofluorescence staining results indicating the paucity of early tangle like structures in BCAS mouse brains at 1 and 6 months after surgery. Brain sections of BCAS mice and age-matched sham controls were subjected with AT8 antibodies (red) to detect tangle-like structures at 28 days and 6 months after BCAS surgery.
Figure 23B:
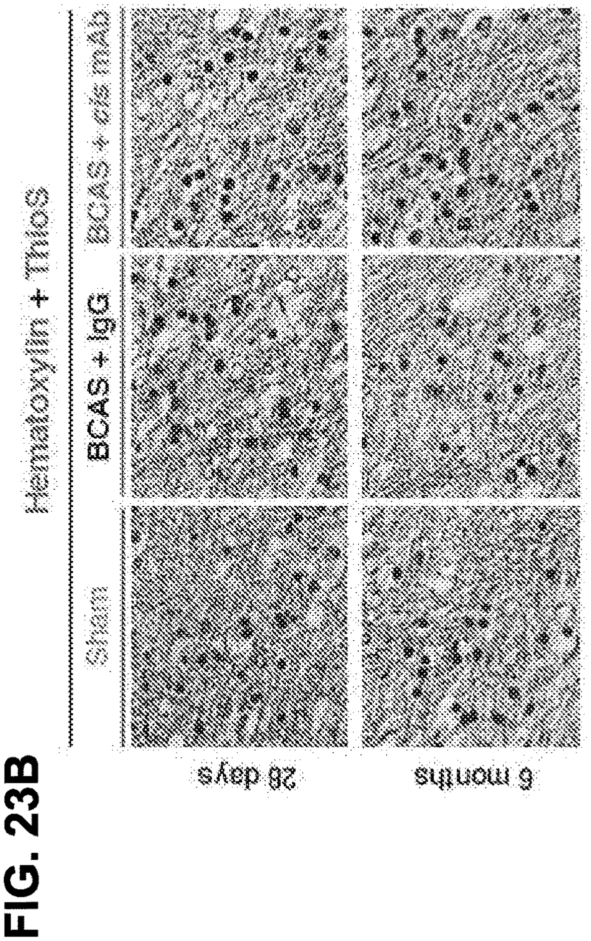
FIG. 23B shows immunostaining results indicating the paucity of early tangle like structures in BCAS mouse brains at 1 and 6 months after surgery. Brain sections of BCAS mice and age-matched sham controls were subjected with Hematoxylin and Thioflavin S to detect tangle-like structures at 28 days and 6 months after BCAS surgery.
Figure 24:
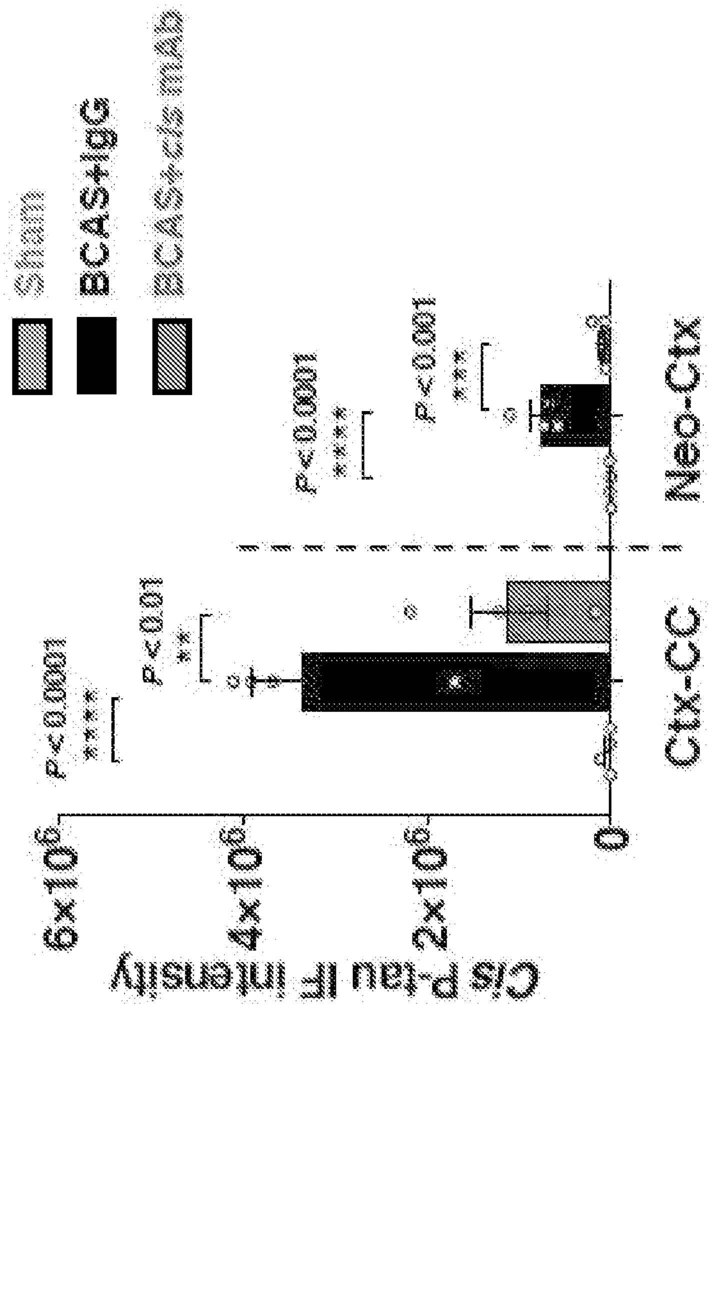
FIG. 24 is a graph showing the effect of treatment with cis mAbs in the elimination of cis P-tau induction in BCAS mice at 6 months post-surgery.
Figure 25A:
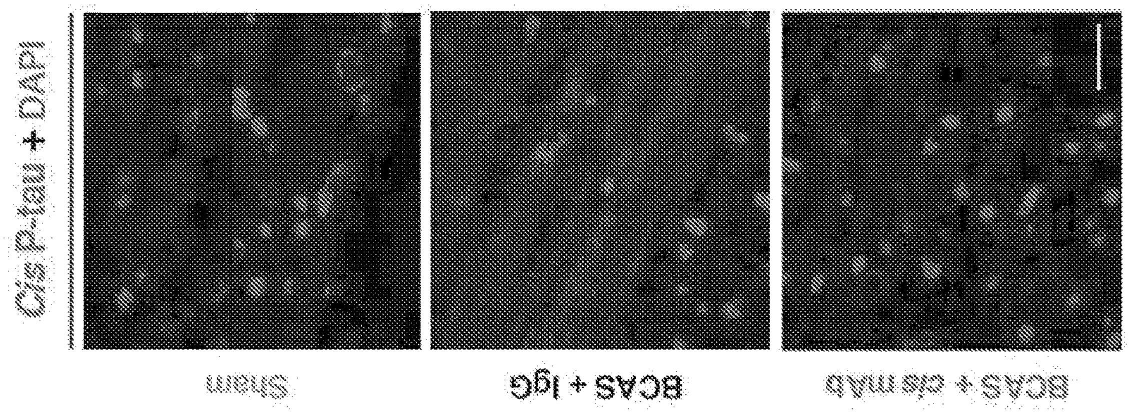
FIGS. 25A-25D are immunofluorescence results, and their accompanying quantification graphs, showing that cis mAb treatment of BCAS mice not only eliminates cis P-tau induction, but also inhibits neuroinflammation, and demyelination at 6 months. Brain sections were examined by immunostaining for cis P-tau (FIG. 25A), GFAP (FIG. 25B), Iba1 (FIG. 25C) and MBP (FIG. 25D), followed by quantifying signal intensity. Scale bar, 10 μm. CC: corpus callosum; Neo-Ctx: neocortex.
Figure 25B:
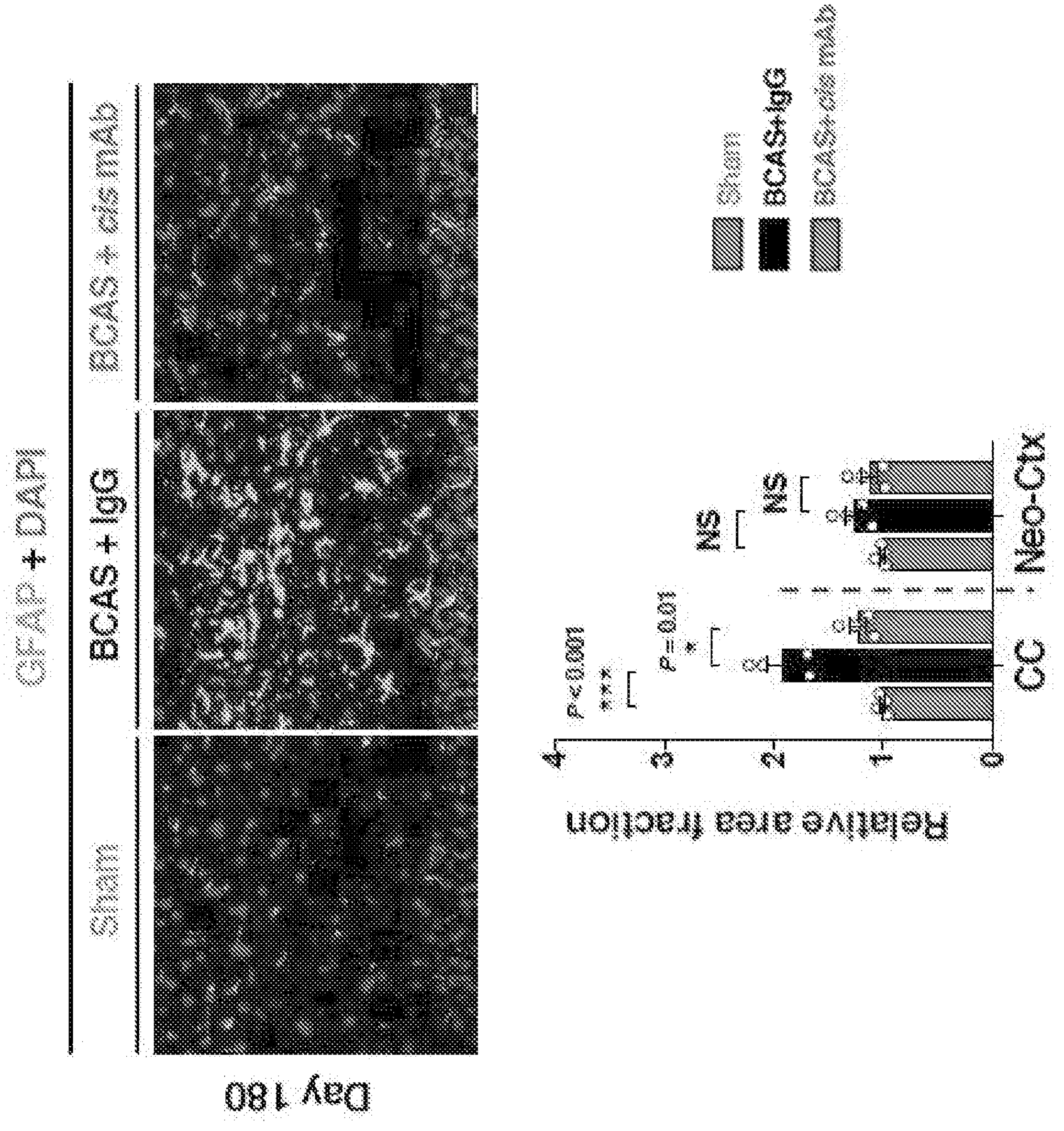
Figure 25C:
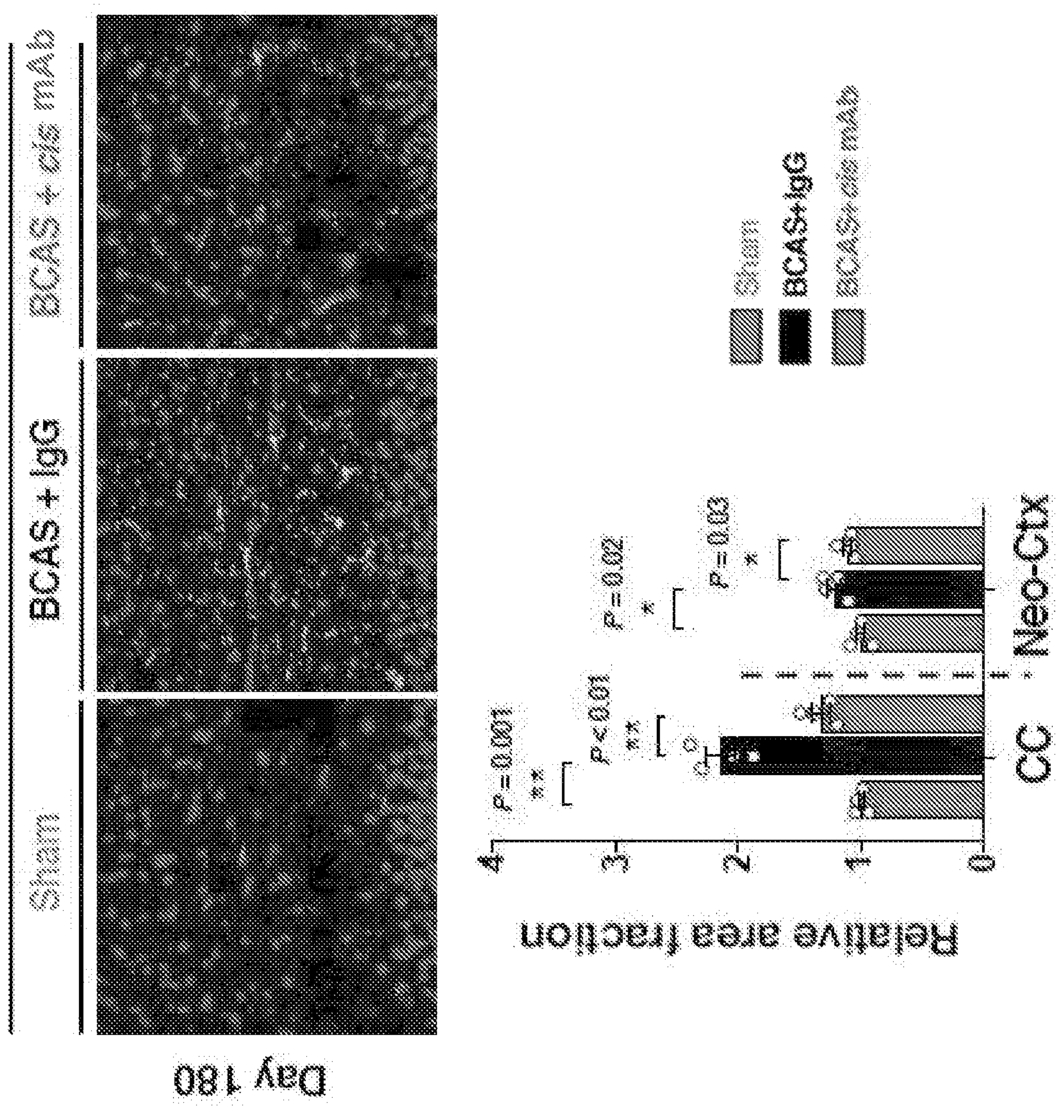
Figure 25D:
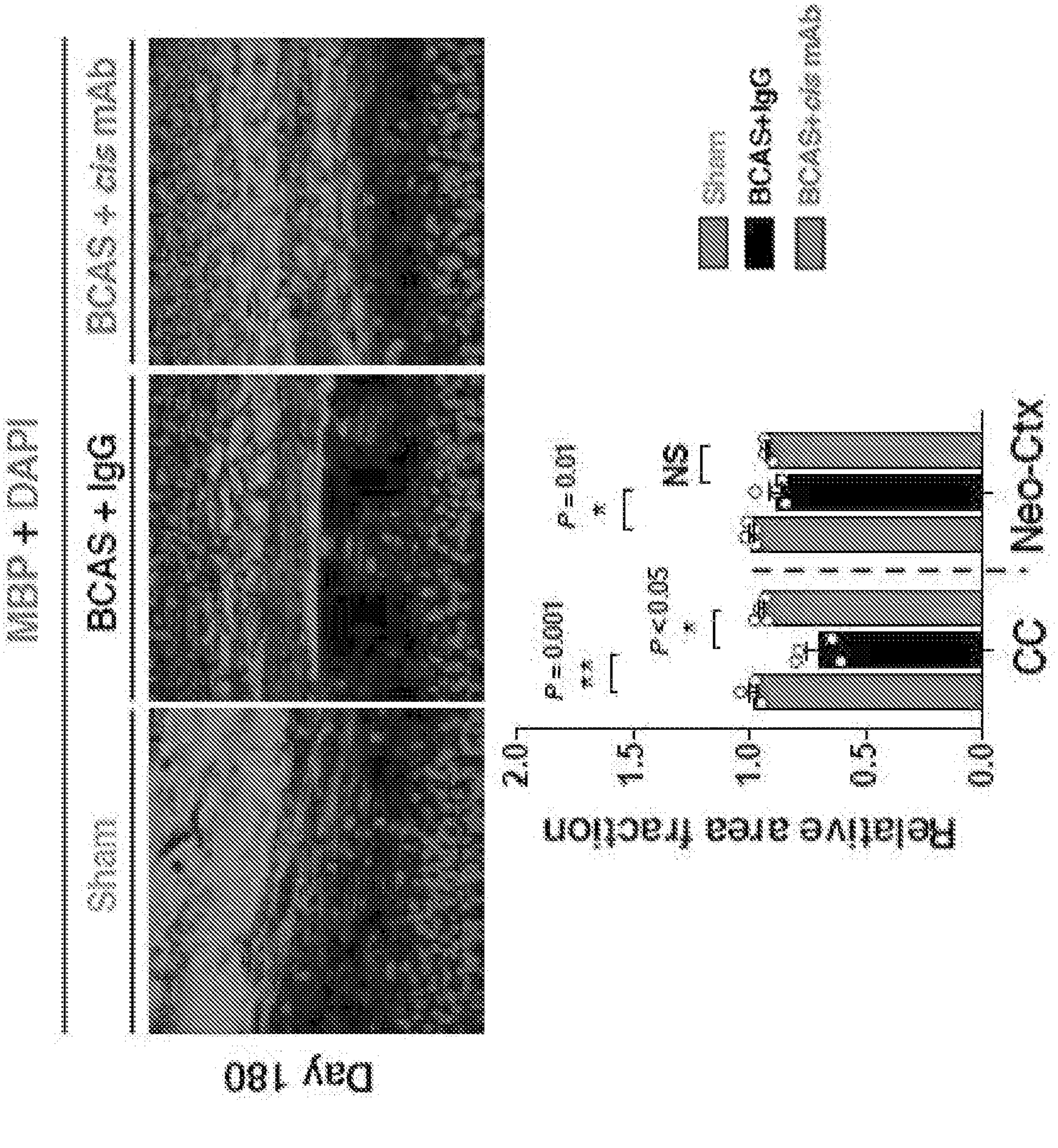
Figure 26A:
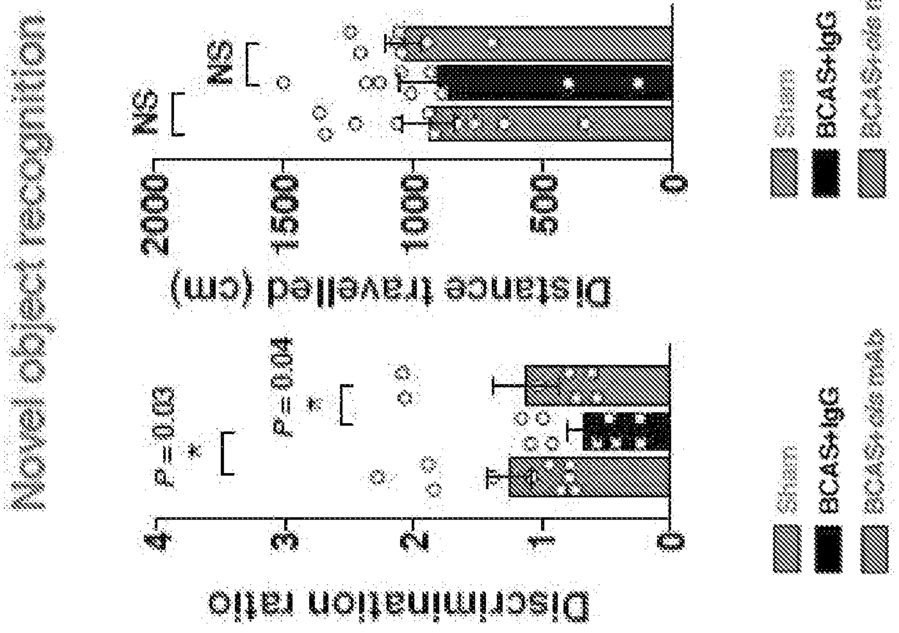
FIGS. 26A-26D are graphs describing the restoration of spatial and memory deficits and risk-taking behavior by cis mAb treatment of BCAS mice at 6 months post-surgery. Behavioral and functional changes were assessed by the novel object location recognition test (FIG. 26A), T maze test (FIG. 26B), accelerating rotarod test (FIG. 26C) and elevated plus maze test (FIG. 26D). 7-10 WT mice per group were included in each of the behavioral studies.
Figure 26B:
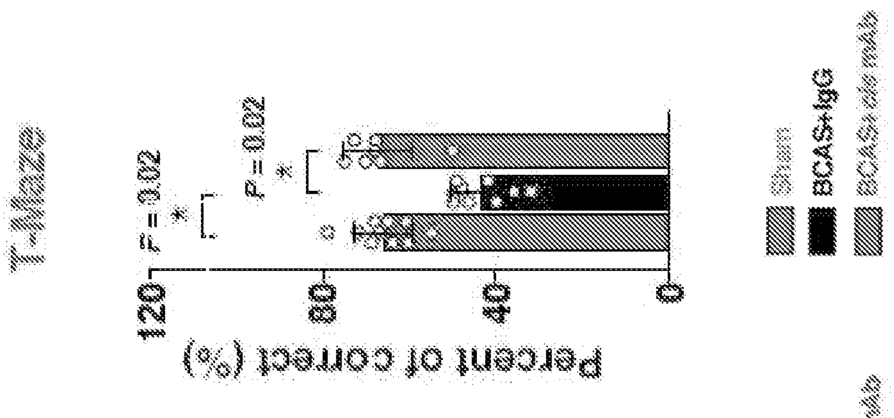
Figure 26D:
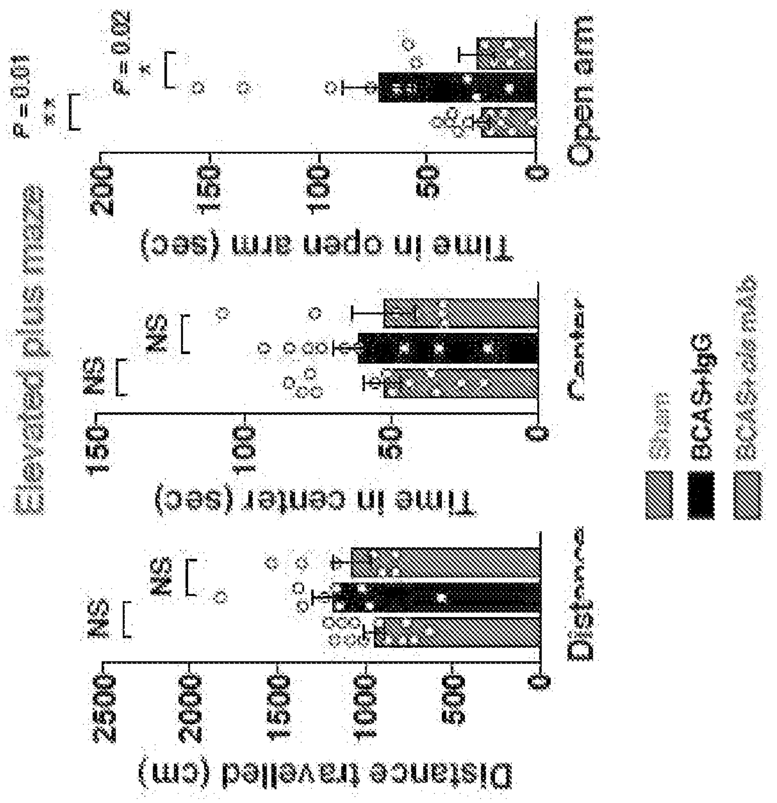
Figure 26C:
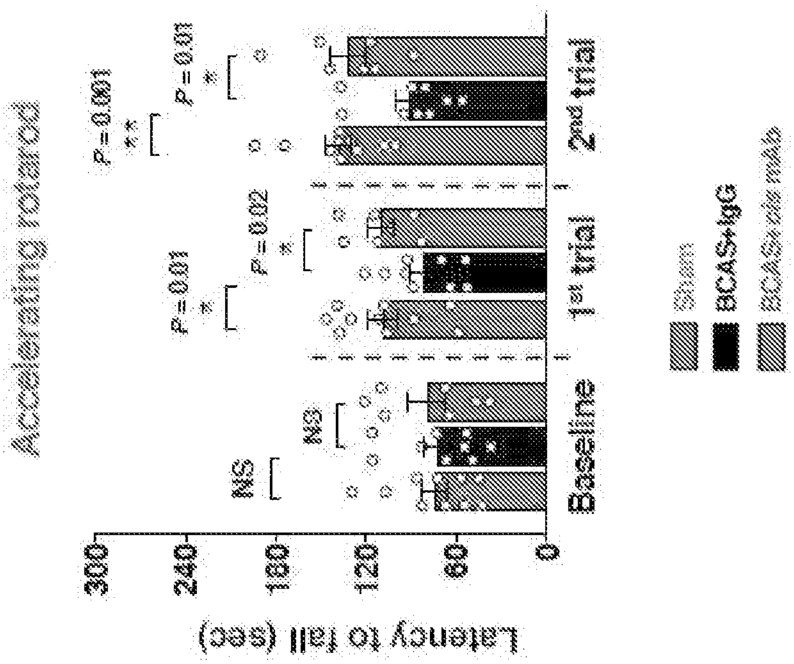
Figure 27B:
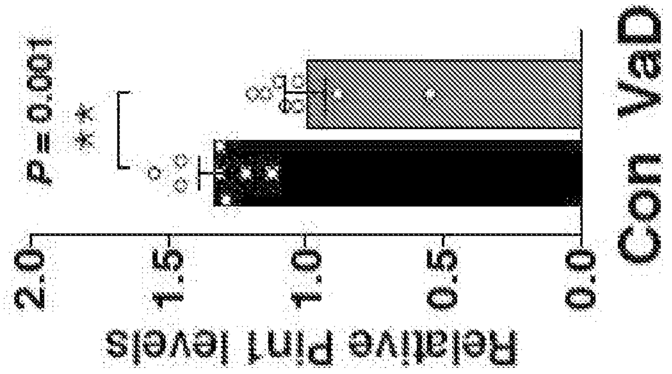
FIG. 27B is a graph of the quantified relative Pin levels in human VaD brain and normal control slices that were subjected to immunohistochemistry using mAb detecting active Pin1.
Figure 27A:
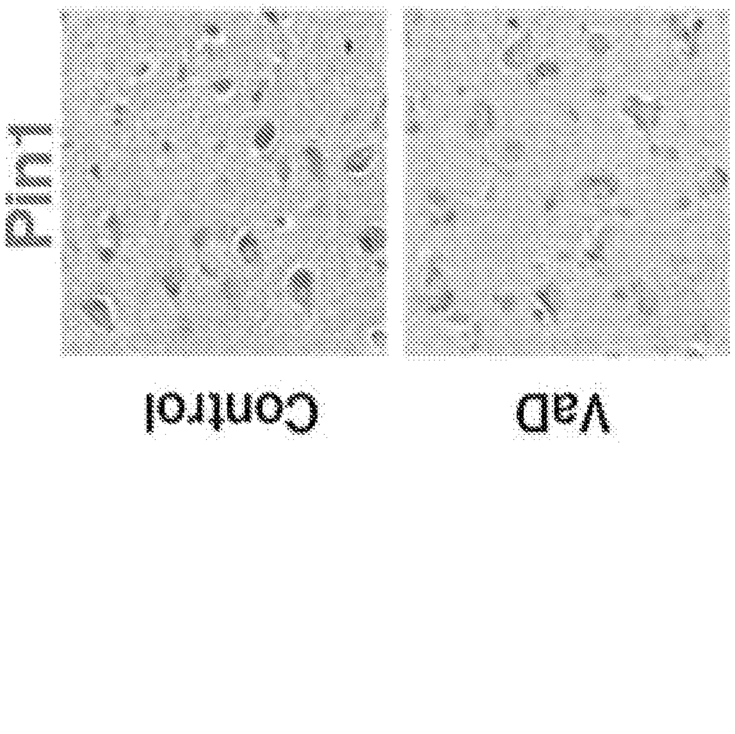
FIG. 27A shows immunohistochemistry results indicating the robust decrease in Pin 1 levels in the cingulate cortex overlying the corpus callosum of human VaD brains. Human VaD brain and normal control slices were subjected to immunohistochemistry using mAb detecting active Pin1, with representative data for immunostaining in the cingulate cortex overlying the corpus callosum (CCTx-CC).
Figure 28A:
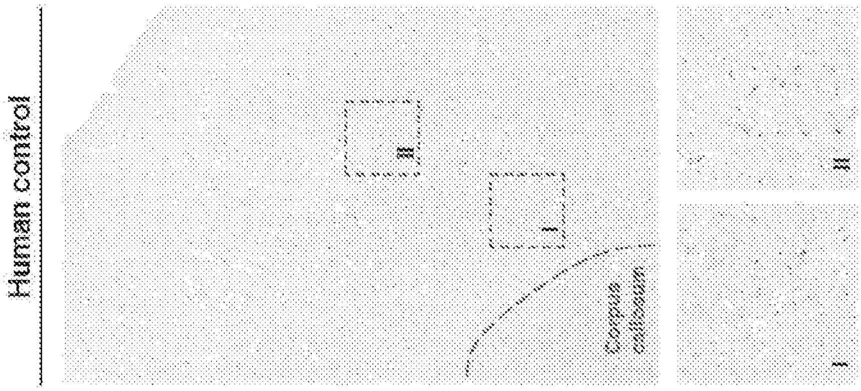
FIGS. 28A-28B show immunohistochemistry results indicating Pin1 staining in whole tissue slices of human VaD brain (FIG. 28A) and an age-matched control (FIG. 28B). Lower panels are higher magnification of the representative Pin1-labeled images comprised by the dashed rectangle with corresponding letters; Scale bar, 300 μm.
Figure 28B:
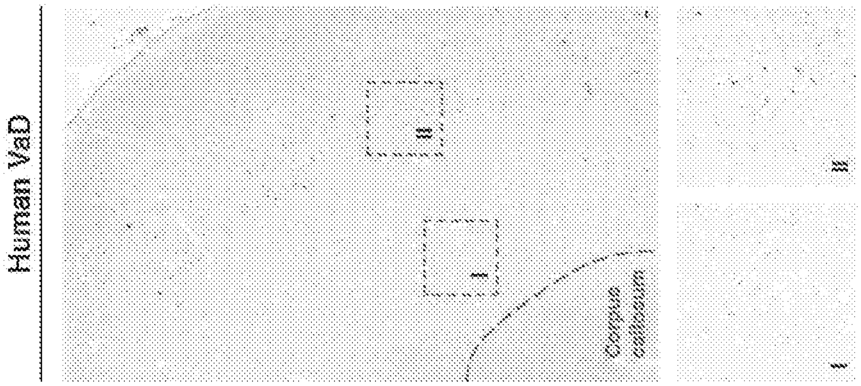
Figure 28C:
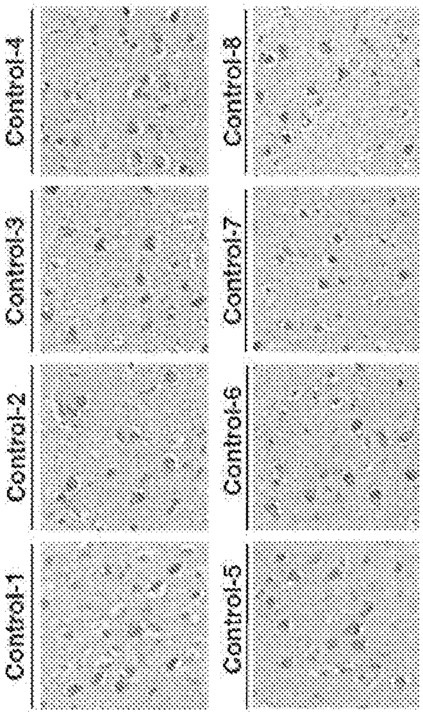
FIGS. 28C-28D show immunohistochemistry results indicating the decrease in active Pin1 levels in the cingulate cortex overlying the corpus callosum of human VaD brains (FIG. 28C) compared with age-matched human brains (FIG. 28D). Human VaD brain slices and aged-matched normal controls were immunostained using Pin1 mAb detecting active Pin1. Scale bar, 20 μm.
Figure 28D:
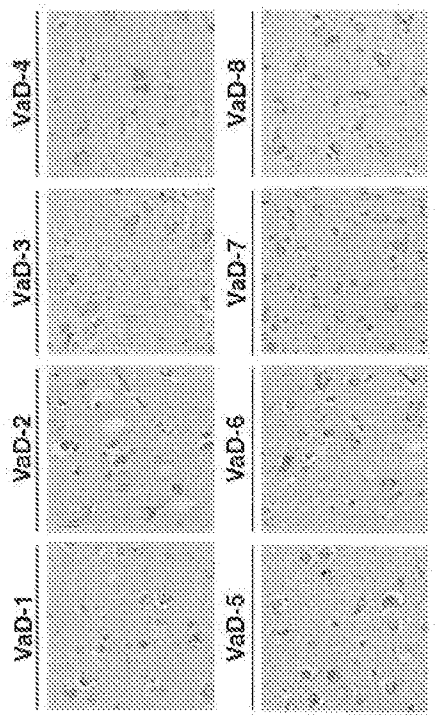

Example 8. Cis mAb Rescues VCID-Like Progressive Pathology and Memory Loss in BCAS Mice VCID-like pathology and brain dysfunction appear after 14 days and become obvious at 28 days after BCAS surgery, Such findings suggest that cis P-tau may affect the pathological and functional outcomes. To test this possibility, we eliminated cis P-tau in BCAS mice using a cis-mAb that binds specifically to pThr231-Pro of the phosphorylated tau protein. The cis-mAb targets non-degradable cis P-tau for TRIM21-mediated proteasome degradation, followed by assessment of VCID-related pathologies and executive function changes (FIG. 18A). Cis mAb treatment largely inhibited cis P-tau induction (FIGS. 18B and 18C), neuroinflammation (FIGS. 19A, 19B, 111, and 115), demyelination (FIG. 19C), as well as partially prevented loss of myelin-generating GST-pi positive mature oligodendrocytes (FIGS. 20A and 20B), which have been shown to occur in BCAS mice. These pathological changes were corroborated by impaired synaptic plasticity via recording field excitatory postsynaptic potentials (fEPSPs) and changes in executive function assessed using the T maze and novel object location recognition tests to quantify spatial working memory ability (FIGS. 21A, 21B, 21D), notably without affecting total endogenous tau levels (FIG. 21C). To characterize the longer-term effects of cis mAb treatment on VCID, BCAS surgery was performed followed by treatment with cis mAb or placebo for 6 months (FIG. 22). Compared with 28 days post BCAS, there was notable progression of degenerative pathologies and behavioral deficits at 6 months. None of the BCAS mice had detectable tau tangle epitopes (FIGS. 23A and 23B), which are consistent with no tangles in VaD. Cis mAb treatment of BCAS mice eliminated cis P-tau, and inhibited neuroinflammation and demyelination (FIGS. 24, 25A-25D, and 115), neurodegeneration (FIG. 112) and partially prevented loss of mature oligodendrocytes (FIGS. 20A and 20B) in the cortex overlaying corpus callosum or directly in the corpus callosum (FIGS. 113 and 114). These pathological effects were also supported by functional outcomes. Placebo-treated mice displayed impairment not only in spatial memory (FIGS. 26A and 26B), but also in motor memory, as assayed by the accelerating rotarod test (FIG. 26C). Of note in the accelerating rotarod test, all three groups of the mice had no difference during the day 1 training phase (baseline) (FIG. 26C), indicating comparable basal motor function. However, with repeated testing on days 2 (1st trial) and 3 (2nd trial), sham control mice remained on the accelerating rotarod much longer than on day 1 (baseline), but duration on the rotarod did not increase in placebo-treated BCAS mice (FIG. 26C), indicating impaired motor learning and memory. Finally, since cis P-tau was present in the neocortex at 6 months after BCAS (FIG. 24) and cortical cis P-tau contributes to risk-taking behavior after TBI, these BCAS mice were subjected to the elevated plus maze. All three groups of the mice had similar distances travelled and similar time spent at the center and most sham mice stayed in the two closed or “safe” arms (FIG. 26D). Strikingly, most BCAS mice treated with IgG placebo displayed “risk-taking” behavior, daring to explore the two open or “aversive” arms over significantly more time than sham mice (FIG. 26D). However, the behavior of cis mAb-treated BCAS mice was quite comparable to that of the sham mice in all the behavioral tests performed. Thus, eliminating cis P-tau using cis mAb restores most VCID-like neuropathology and brain dysfunction at 1 and 6 months after BCAS surgery.

Figure 29B:
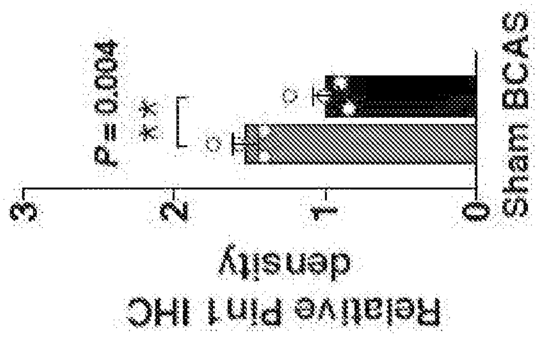
FIG. 29B is a graph of the quantified relative levels of active Pin1 the cortex overlying the corpus callosum in BCAS mouse brains. Images were quantified and results are shown as means±S.E.M. and p values calculated using unpaired two-tailed parametric Student's t-test. **, $p<0.01$.
Figure 29A:
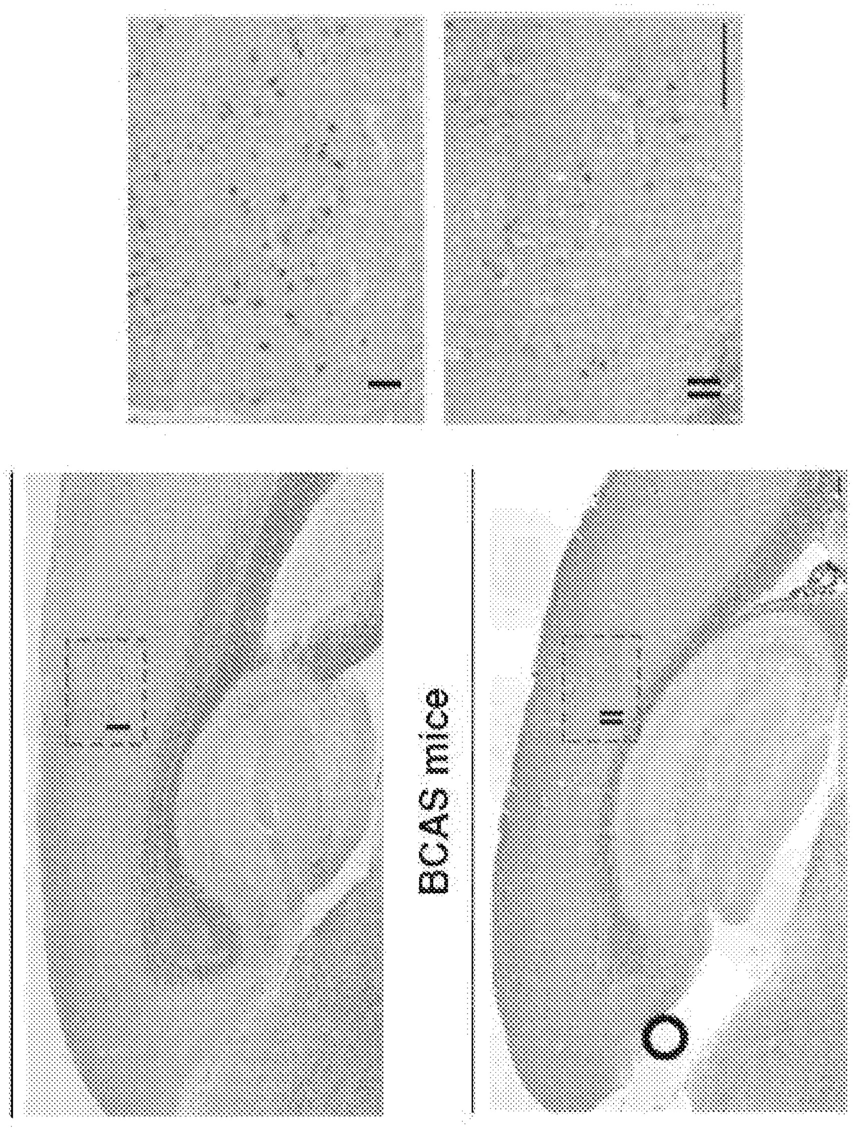
FIG. 29A shows immunohistochemistry results indicating the reduction of active Pin1 levels in the cortex overlying the corpus callosum in BCAS mouse brains. Brain sections of BCAS mice and sham controls were subjected with Pin1 antibody at 28 days after BCAS operation. Left images are higher magnification of the representative Pin1 labeled images comprised by the dashed rectangle with corresponding letters; Scale bar, 400 μm. Microscope images correspond to the statistical data for optical density signal of Pin1 immunoreactivity in the cortex. Boxes I and II provide a magnified view of sham and BCAS immunohistochemistry, respectively.
Figure 30B:
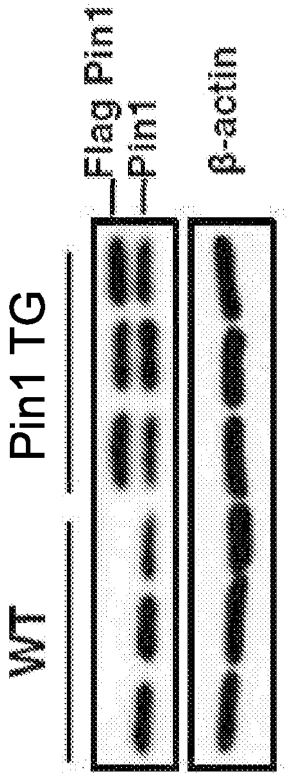
FIG. 30B shows immunoblotting results of the characterization of a brain-specific Pin1-transgenic (TG) mouse. Cortical lysate of 2-month old Pin1 transgenic mice (Pin1
Figure 30A:
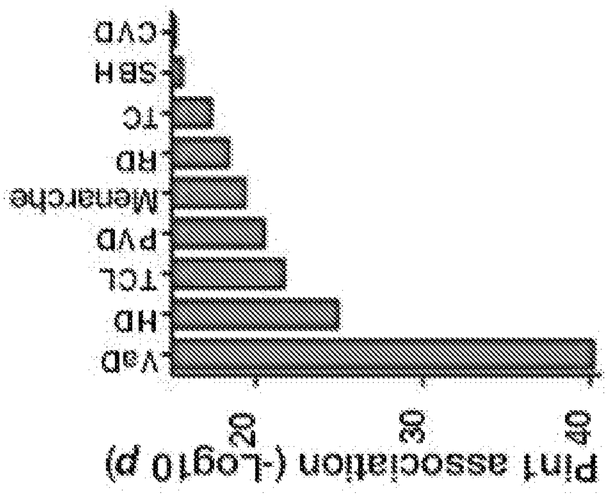
FIG. 30A is a graph describing a genome-wide genetic association study from UK biobank that identifies that a putative Pin1 enhancer SNP, E06-21879, is highly correlated with vascular dementia (P value=6×1042). VaD, vascular dementia; DD, Hodgkin's disease; TCL, T-cell lymphomas; PVD, peripheral vascular disease; RD, respiratory disorders; TC, thyroid cancer; SBH, subarachnoid hemorrhage; CVD, cerebrovascular disease and MSD, multisystem degeneration.

Example 9. Pin1 is Inhibited in VaD Patients and VCID Mice, Whereas Pin1 Overexpression Reduces Cis P-Tau Induction and Prevents VCID-Like Pathology and Dysfunction in BCAS Mice To investigate the mechanism of cis P-tau induction in VCID, Pin1 was examined given that it is the only enzyme known to reduce cis P-tau in vitro and in vivo and that the serum is widely known to induce Pin1 expression in other conditions. Active Pin1 was significantly reduced in the sub-regions with high cis P-tau, especially in the cingulate cortex overlying the corpus callosum in human VaD brains (FIGS. 27A-28B and 28A-28D) and in the cortex overlying the corpus callosum in mouse BCAS brains (FIGS. 29A and 29B), as detected by mAb recognizing active dephosphorylated Pin1. These are consistent with the reports that Pin1 expression is the highest in the anterior cingulate cortex among in the human 221 organs examined and that reduced blood flow to posterior cingulate cortex is often correlated with learning and memory loss in humans. Moreover, a putative Pin1 enhancer genetic change, E06-21879, which was predicted to affect Pin1 expression in other conditions, is most clearly associated with VaD in recent genome-wide association studies in the UK biobanks (p value=6.2×10-41) (FIG. 30A). These results collectively show that Pin1 is reduced in brains of both VaD patients and VCID model mice. To examine whether Pin1 functionally plays any role in VCID-related pathologies and brain dysfunction, brain-specific Pin1 transgenic (Pin1 TG) mice were examined. Pin1 TG mice overexpress Pin1 about 1-2 times over the endogenous levels in the postnatal brain under the Thy1.2 promoter, as validated by Western blot (FIG. 30B), and are resistant to cis P-tau induction and neurodegeneration induced by tau overexpression. Pin1 TG mice and wild-type littermates at 2 months of age, showed similar executive function assessed using the T maze (data not shown). BCAS surgery was performed in these mice, followed by assessment of VCID-related pathologies and executive function changes 28 days after the surgery. In contrast to wild-type littermates, Pin1 TG mice displayed much reduced cis P-tau induction (FIGS. 31A and 31B), neuroinflammation (FIGS. 32A and 32C), demyelination (FIGS. 33A and 33C) and loss of oligodendrocytes (FIGS. 33B and 33D) after BCAS, although Iba1 immunoreactivity was still mildly increased (FIGS. 32B and 32D). Moreover, BCAS-induced impairment in executive function was largely absent in the Pin1 TG mice, as assessed using the T maze and novel object location recognition tests (FIGS. 34A and 34B). Thus, Pin1 is reduced and correlated with cis P-tau in VCID patients and model mice, and Pin1 overexpression prevents VCID-like pathology and memory loss in model mice.

Example 10. Pin1 is Inhibited by DAPK1 in VCID Mice, Whereas DAPK1 KO Reduces Pin1 Inhibition and Cis P-Tau Induction, and Prevents VCID-Like Pathology and Dysfunction in BCAS Mice To further examine upstream regulators leading to Pin1 inhibition and cis P-tau induction after neurovascular insufficiency, DAPK1 was examined because this kinase is known to be activated after stroke and to phosphorylate Pin1 at the active site serine 71, thereby inhibiting Pin1 isomerase activity in cancer cells and neuronal cells. Indeed, both DAPK1 and Pin1 S71 phosphorylation were notably increased in the cortex overlaying the corpus callosum in BCAS mice 1 month after surgery (FIGS. 35A-35C) and human VaD patients despite decreases in active Pin1 (FIGS. 116, 117, and 118). To further test if DAPK1 activation has any functional significance in the development of cis P-tau and VCID-like pathology and brain dysfunction, DAPK1 KO mice and WT littermates were subjected to BCAS surgery. Strikingly, DAPK1 KO potently eliminated the induction of Pin1 S71 phosphorylation (FIGS. 35B and 35C), cis P-tau (FIGS. 36A-36B), neuroinflammation (FIGS. 37A-37D) and demyelination (FIGS. 38A-B) in BCAS mice. Moreover, DAPK1 KO mice did not have impaired executive functions 1 month after BCAS surgery, in contrast to the WT littermate controls, as assessed using the T maze and novel object location recognition tests (FIGS. 39A-39B). Thus, BCAS leads to cis P-tau induction likely due to Pin1 inhibition by activated DAPK1, whereas reducing cis P-tau by Pin1 overexpression or DAPK1 KO prevents VCID-like pathology and impairment in executive function in BCAS mice.

Example 11. BCAS in Young Mice Induces Diverse Cortical Cell-Type Specific Transcriptomic Changes and about 90% of the Global Alterations are Remarkably Recovered by Cis mAb The above pathological and functional evaluations mainly focus on a limited number of known factors and phenotypes. However, they are unlikely to reveal the complicated alterations and interactions among different cell types and within cell groups in the brain, which likely occur after chronic cerebral hypoperfusion. Published transcriptome profiling at the tissue level have largely focused on the acute response within 48 hrs after vascular insults, and do not correlate with chronic phenotypes relevant to dementia. Notably, single-cell transcriptomic analysis of human brains has solely been used to interrogate the molecular and cellular basis of AD in diverse cell types. Since VCID-like pathologies and behavioral changes are becoming detectable 1 month after BCAS surgery (FIG. 18), with neurodegeneration being progressive over 1 year, it was reasoned that cell-type specific transcriptomic profiling at this time with early pathology may be informative for understanding the impact of cis P-tau on the development of VCID and for evaluating the efficacy of cis mAb in treating VCID at the single cell levels. Thus, single-nucleus RNA-seq was used to profile the transcriptomic changes of total ~15,000 cortical cells from BCAS mice treated with cis mAb or IgG control for 1 month, referencing to sham littermates (FIG. 40A). Twenty-five distinct cell clusters were recovered based on their expression profiles using an unsupervised t-SNE approach. Similar clusters were collapsed into 5 major cell types (excitatory neurons, inhibitory neurons, astrocytes, oligodendrocytes, and endothelia) (FIGS. 40B-40C and 41A-41F) based on the expression of cell-type specific markers and independently validated by the expression correlation with the published profile from Mouse Cell Atlas. The results are robust to the inclusion of brain cells that are affected by VCID pathology, consistent with the previous studies. To investigate the transcriptomic changes after BCAS, unique differentially expressed genes (DEGs) were identified in the 5 major cell types by comparing BCAS mice with sham littermate controls (false discovery rate (fdr) adjusted p value <0.00001 for excitatory neurons and p value <0.01 for all other cell types). A number of top up-regulated (FIG. 42) and down-regulated (FIG. 43) DEGs have been implicated in stroke and/or neurodegeneration, which were effectively restored by cis mAb, both at the average expression and the number of DEG-expressing cells. The notable up-regulated DEGs included two MHC class I genes implicated in neuroinflammation, stress response and neurodegeneration, Meg3 in ischemic neuronal death and Mme in demyelinating neuropathy, and down-regulated DEGs included Glul implicated in VCI and Slc1a2 in AD. Importantly, our analyses also revealed many top DEGs that have not been linked to neurodegeneration (FIG. 44), including Lrrc17, a negative NFkB regulator, Hsd3b2, an enzyme in steroid biosynthesis and Phkg1, a kinase in glycogenolysis. Immunostaining confirmed differential expression for 8 out of total 8 top DEGs examined and their therapeutic response to cis mAb (FIGS. 45A-45D, 46A-46D, 47A-47D, 48A-48B, 49A-49B, and 119). These significant changes in top DEGs and their striking recovery after cis mAb treatment led to the systematic evaluation of the transcriptomic changes and cis mAb dependent recovery of DEGs in different cell types. Hundreds to thousands of unique DEGs were identified after BCAS (FIG. 50), with excitatory neurons being the most affected, as is in human AD. The number of DEGs was smaller in other cell types, which could potentially be due to reduced statistical power in the lower abundant cell types. Remarkably ~90% of BCAS-induced DEGs were recovered by cis mAb treatment (FIG. 50) and the extent of the recovery in different cell types was correlated with their cellular tau expression (FIG. 51), the source for cis P-tau, consistent with the presence of cis P-tau in different brain cells. These results indicate that BCAS induces diverse cell-type specific transcriptomic changes and the vast majority of these alterations are remarkably recovered by cis mAb, unbiasedly and comprehensively demonstrating the potency of cis-targeted immunotherapy in restoring the global transcriptomic changes in VCID at the single-cell resolution.

Example 12. BCAS in Young Mice Induces the Global Transcriptomic Changes Notably Related to Myelin and Axon Processes Resembling AD Patients and Largely Recoverable by Cis mAb To understand the biology underlying the transcriptomic changes in BCAS mice, gene ontology and gene set enrichment analyses were performed. Gene ontology analysis showed that the down-regulated DEGs in excitatory neurons, the most affected cell type, were most significantly associated with myelin sheath (FIG. 52, p value=10-65), which was also widely down-regulated in other cell types (FIGS. 53 and 54). Importantly, both the average expression and the number of excitatory neurons that expressed these DEGs were down-regulated, but 83.8% (83/99) of these down-regulated DEGs in excitatory neurons were significantly recovered by treatment with cis mAb (FIGS. 55 and 56). These results are consistent with the above findings that BCAS induced prominent demyelination but was recovered by cis mAb (FIGS. 19C and 25D), and with the previous findings that demyelination is probably the most prominent pathology in VaD and that widespread downregulation of myelination-related genes in different cell types is notable in human AD. The next prominently down-regulated DEGs in the excitatory neurons were associated with axon/synapse processes, microtubule/cytoskeleton, and GTP/nucleoside signaling (FIG. 52). Differential protein expression and therapeutic response to cis mAb was evaluated in 4 out of 4 microtubule-related DEGs (Tubb5, Tppp, ApoE, Fkbp4) (FIGS. 46A-46D, 47A-47D, and 57). These results are consistent with the findings that cis P-tau is notably localized to axons, but fails to promote microtubule assembly, disrupting axonal microtubule network and mitochondria leading to axonopathy, and that cis mAb targets cis P-tau for proteasome degradation and neutralizes its ability to induce axonopathy in TBI. Another notable finding in DEG analysis was that cis mAb treatment appeared to induce all the four hemoglobin genes in different cortical cell types both at the average expression and the number of hemoglobin-expressing cells (FIGS. 48A-48B and 58). Immunostaining showed that hemoglobin was slightly reduced notably in the cortex overlying the corpus callosum in BCAS mice and that cis mAb effectively restored hemoglobin to a level even higher than sham controls (FIGS. 48A-48B and 58). Of note, it has been shown that hemoglobin upregulation extends neuronal activity and reduces hypoxic zones in the brain under hypoxia, and is also associated with better recovery in stroke mice, whereas hemoglobin is reduced in hyperphosphorylated tau-bearing neurons in human AD. Thus, cis mAb treatment of BCAS mice may help cortical cells to function better under hypoxic conditions, consistent with its beneficial effects on VCID-like pathology and dysfunction. Gene set enrichment analysis, which determines whether a priori defined set of genes shows significant, concordant differences between two biological phenotypes, revealed that the only gene set from the curated MSigDb C2 database that was significantly and consistently down-regulated (negatively enriched) in all the five major cell types in our BCAS mouse brains was the transcriptomic changes in human AD brains identified using microarrays (FIGS. 59-63). Notably, the gene sets that are down-regulated in human incipient AD and AD patients were both highly enriched in our BCAS down-regulated DEGs in the excitatory neurons (p value <0.001) (FIGS. 64A-64B). We also observed a striking similarity in the direct comparison of enriched downregulated DEGs (FIGS. 65A-65B). Moreover, 84% (272/324) of the common DEGs in AD patients and BCAS mice were recovered by cis mAb in BCAS mice (FIG. 65B). Thus, BCAS induces the transcriptomic changes in young mice resembling those in AD patients, offering evidence for the transcriptomic similarity between VCID and AD, and the vast majority of the transcriptomic changes are recovered by cis mAb in BCAS mice, revealing the potency and potential clinical relevance of the immunotherapy.

Example 13. Purified Soluble Cis P-Tau is Sufficient to Induce Progressive Neurodegeneration and Brain Dysfunction by Causing and Spreading Cistauosis and Axonopathy The above results show that cis P-tau is induced relatively early in VCID, and its elimination using multiple independent approaches potently rescues VCID-like neurodegeneration and brain dysfunction. A major question is whether cis P-tau itself is sufficient to induce progressive neurodegeneration and brain dysfunction in wild-type animals. To address this question, cis mAb was used for affinity purification of soluble cis P-tau from TBI mice because severe TBI rapidly produces a large quantity of cis P-tau without tau oligomerization, aggregation or tangle epitopes, which could complicate assays of cis P-tau neurotoxicity. Purified cis P-tau, but not recombinant tau, caused neurotoxicity in SY5Y cells, which was blocked by cis mAb treatment (FIGS. 66A-66B). Purified cis P-tau also induced death in primary neurons, which was blocked by the pan-caspase inhibitor Z-VAD-FMK (FIG. 67). Thus, purified cis P-tau, but not recombinant tau, induces neuronal death and is blocked by cis mAb, as shown for cis P-tau after neuron stress. To investigate the ability of cis P-tau to induce progressive neurodegeneration, stereotactic administration of purified soluble cis P-tau or recombinant tau bilaterally into the upper and lower layers of the neocortex was performed in three-month-old WT mice, followed by behavioral testing at 1 and 10 months post-injection (FIG. 68A). At 1 month after injection, cis P-tau caused risk-taking behaviors assayed by elevated plus maze and bright light open field assays (FIGS. 68B and 68C), whereas recombinant tau even at four times higher doses, had not detectable effects (FIGS. 69A-69D), consistent with the previous findings that tau oligomers or pathogenic tau, but not normal tau, are neurotoxic. Notably, cis P-tau did not affect many other neurological tests, including accelerating rotarod and novel object location recognition tests to detect for sensorimotor and cognitive behavior, respectively (FIGS. 70A-70C). However, at 10 months post injection, we found not only the persistence of risk-taking behaviors, but also the appearance of many other neurological changes, including sensorimotor and cognitive behavioral changes revealed by accelerating rotarod and novel object location recognition tests, respectively (FIGS. 71A-71D), suggesting neurodegenerative progression. To confirm that the above phenotypes and their progression are indeed due to cis P-tau, new experiments using cis mAb to eliminate cis P-tau in cis P-tau injected mice were performed (FIG. 72). Indeed, treatment with a cis mAb almost fully prevented cis P-tau from inducing brain dysfunction at 1 month (FIGS. 73A-73B) and at 10 months (FIGS. 74A-74E), as assayed by various behavioral tests. Moreover, the progression of neurodegeneration was further supported by the presence of cis P-tau, cistauosis and axonopathy in a brain region distant from the injection site at 10 months after injection, which were fully restored by cis mAb (FIG. 75A). Evidence included cis P-tau in various brain subregions (FIG. 75B), impaired synaptic plasticity via recording field excitatory postsynaptic potentials (fEPSPs) (FIGS. 76A and 76B), ultrastructural pathologies of disrupted axonal microtubules and mitochondria (FIG. 76C), increased cleaved caspase-3 immunoreactivity (FIGS. 77A-77B), and demyelination (FIGS. 78A-78B) and early tangle-like AT8 epitope (FIGS. 79A-79B). In sharp contrast, no behavioral deficits were found when cis P-tau was injected to tau null mice at 1 or 10 months after the injection (FIGS. 80A-80C), indicating a requirement of endogenous tau. Thus, soluble cis P-tau is sufficient to induce progressive neurodegeneration by causing and spreading cistauosis and axonopathy dependent on endogenous tau resembling a prion.

Example 14. Injected Cis P-Tau Induces Conserved Transcriptomic Changes that are Highly Relevant to Cistauosis and Axonopathy, and are Also Found at VCID and AD with Early Pathologies Given the ability of cis P-tau to induce progressive neurodegeneration by causing and spreading cistauosis and axonopathy, it was assessed whether injected cis P-tau would also induce transcriptomic changes relevant to cistauosis and axonopathy and found at VCID and AD with early pathologies. To this end, 7,577 cortical cells away from the injection site were profiled for their transcriptomic changes at 10 months after cis P-tau injection, when the progression of pathological and behavioral changes was obvious. Distinct cell clusters were collapsed into the 5 major cell types (FIGS. 81A-81C and 82A-82F) and identified cell-type specific hundreds of unique DEGs from cis P-tau injected mice. This number was much smaller than that in BCAS mice, which might be expected from injecting a single cis P-tau protein vs reducing overall cerebral blood flow by ~50%, although we could not completely rule out the possibility of decreased statistical power due to different cell number. Despite a much smaller number of DEGs in cis injected mice, the top ontology terms associated with the transcriptomic changes in the excitatory neurons in cis injected mice were strikingly similar to those in the BCAS mice, again highly related to myelin, axon, synapses and microtubule function (FIG. 83 compared to FIG. 52), with a notable exception that GTP/nucleoside signaling was not reduced in cis injection, in contrast to BCAS (FIG. 52). This difference might be expected given that many serum-containing growth factors/regulators known to activate GTP/nucleoside signaling are reduced by BCAS, but not by cis injection. The striking similarity in DEG ontology terms between cis P-tau injection and BCAS led to a subsequent systematic comparison of their transcriptomic changes. A highly significant overlap in the DEGs was found in the excitatory neurons, the most affected cell type in both models, as is in human AD brains. About 70% ($^{209}/_{300}$) of the cis P-tau upregulated DEGs were also increased in the BCAS mice (overlap p value=4.7×10-222, Fisher's exact test) and ~98% ($^{46}/_{47}$) of the cis P-tau down-regulated DEGs were also decreased in the BCAS mice (overlap p value=9.7 ×10-62) (FIGS. 84A-84B). Immunostaining confirmed 4 out of 4 common DEGs examined (Caprin2, Hsd3b2, Ndrg2 and Mbp) in cis injected mice (FIGS. 85A-85D and 86A-86D), and BCAS mice. Notably, the commonly up-regulated DEGs were associated with synapse function (FIG. 87), including Grin2a and Grin2b, two N-methyl-D-aspartate (NMDA) receptors activated in stroke and implicated in neuronal death, and EphA7 implicated in neuron injury, inflammation and axon targeting. The commonly down-regulated DEGs (46 out of the 47 cis P-tau down-regulated genes) were associated with myelination, axon and microtubule function (FIGS. 52 and 83). 73% ($^{255}/_{347}$) of the total DEGs induced by cis P-tau injection were also differentially expressed after BCAS, and 98% of them ($^{250}/_{255}$) were remarkably recovered by cis mAb (FIGS. 88A-88B). Thus, we identify a specific set of "cistauosis" gene expression changes in both cis P-tau injected and BCAS mice. Given that the BCAS transcriptomic analysis was done in mice 1 month after the surgery, a relative early stage because neurodegeneration is slow and progressive after BCAS, as in humans, these cistauosis transcriptomic changes might reflect the conserved transcriptomic changes occurring in AD with early pathology. To examine this possibility, a search into recently published single-cell transcriptomic analysis of human brains with early and late AD pathology was performed. 42 out of the 46 down-regulated "cistauosis" DEGs shared between BCAS and cis P-tau injected mice have well defined human homologs, and 22 out of these 42 genes passed the human gene expression abundance filter for the gene set enrichment analysis. A significant negative enrichment of the cistauosis gene expression changes in human patients was observed only with early (FIG. 89, p values=0.01), but not late, AD pathology (no enrichment for the human AD with late pathology). 91% ($^{20}/_{22}$) of the commonly down-regulated DEGs in cis P-tau-injected mice and BCAS mice were also down-regulated in the cortical excitatory neurons of human patients only with early, but not late, AD pathology (FIG. 90), revealing the striking cistauosis gene expression change present at early, but not late, stage of AD and VCID. Again, half ($^{11}/_{22}$) of these early commonly down-regulated DEGs were related to myelination (Actb, Actg1, Atp6v1 b2, Mbp, Nsf and Ywhag) and axon process (Kif5a, Actb, Actg1, Pafah1 b1 and Pak1). Thus, in the most affected excitatory neurons, cis P-tau induces conserved gene expression changes that are not only relevant to cistauosis and axonopathy, but are also found at mouse VCID and human AD with early pathologies.

Example 15. Robust Cis P-Tau in Age-Related Macular Degeneration (AMD), Diabetic Retinopathy (DR) and Retinal Detachment in Human Patients and/or Mouse Models Although the importance of tau dysfunction in neuronal degeneration in the brain in dementia has been extensively studied, tau-related pathologies in retinal diseases have only recently been reported. So far nothing is known about the role of cis P-tau in retinal diseases. Since IRs share many clinical and pathological features with Alzheimer's Disease and hypoperfusion/Vascular Dementia, and furthermore since BCAS (bilateral common carotid artery stenosis) mice develop retinal degeneration, cis P-tau in human patients and/or animal models of IRs were examined. Strikingly robust cis P-tau accumulation was observed in the retina in age-related macular degeneration, diabetic retinopathy and retinal detachment in human patients (FIG. 91) and mouse models.

In summary, the histopathological, ultrastructural, electrophysiological, behavioral and single-cell genomic analyses all consistently support that cis P-tau underlies VCID by inducing the conserved transcriptomic changes and axonopathy, but is effectively targeted by immunotherapy, uncovering previously unrecognized pathogenic mechanisms and offering a promising new immunotherapy for VCID. Furthermore, the unprecedented observation of robust cis P-tau in human patients and mouse models of ischemia-induced retinopathies uncovers new disease targets for cis P-tau immunotherapy.

Example 16. Humanized Cis P-Tau mAb Variants have Potent Therapeutic Efficacy in VCID Model Mice As described above in Examples 1-4, we developed 225 humanized cis P-tau mAb variants and identified 10 top fully humanized cis mAb variants (HT1-4, HT6-10 and HT18) with the expected specificity and potency. We unexpectedly found that the affinity of humanized cis mAb variants is not the only determinant for their efficacy. In this experiment, we performed a 3 month treatment of BCAS (bilateral common carotid artery stenosis) mice with two humanized cis mAb variants, HT10 and HT18, along with murine cis mAb C113 (as described in, e.g., U.S. Pat. No. 9,688,747) and mouse-human chimeric HT13 as positive controls. Our results showed that humanized cis mAb variants (HT10 and HT18) were effective in preventing VCID-like behavioral changes both at 1 month (FIG. 92A) and 3 months (FIGS. 92B-92C) after BCAS surgery, assayed by Y maze, which measures the willingness to explore new environments, by novel object recognition (NOR), which measures the innate tendency to explore new objects within their environment, as well as by Barnes maze, which measures spatial and learning memory. These results further demonstrate the efficacy of our humanized cis mAbs to treat VCID.

Example 17. Cis mAb Prevents and Ameliorates Progression of AD-Like Pathology and Memory Loss in Mice Elimination of cis P-tau in a relevant mouse model for VCID using various approaches potently rescues most VCID-like pathological and functional outcomes. Given well-known vascular contributions to AD and cis P-tau as an early pathogenic tau species in human AD, we wondered whether eliminating cis P-tau would also inhibit progressive neurodegeneration and cognitive decline relevant to AD-like tauopathy. To this end, we used htau mice, which express the entire human tau gene in the place of the mouse one and develop age-dependent tau hyperphosphorylation, NFT-like pathologies, neuronal loss and cognitive deficits resembling AD. In 3-month-old htau mice, we found that cis P-tau was induced and localized notably to axons without tau tangles (FIG. 93). cis mAb treatment fully prevented learning and memory deficits, as assessed by the Morris water maze (FIGS. 94A-94C and 95A-95C), which was supported by almost full elimination of cis P-tau induction (FIGS. 96-98) and strong attenuation of NFT-like pathology (FIGS. 99A-99B and 100A-100D). Thus, cis mAb prevents the development of neurodegeneration and cognitive dysfunction in the AD-like tauopathy mouse model. To evaluate whether cis mAb treatment has any therapeutic effects in mice with existing tau pathologies and cognitive symptoms, we treated aged htau mice at 13 months old with cis mAb for 6 months (FIG. 101). At the start of treatment, htau mice had significant cognitive deficits (FIGS. 102A-102B). Longitudinal assessment showed that cognitive deficits in most placebo-treated mice further deteriorated over the 6 months of the treatment (FIGS. 103A-103B). In sharp contrast, cognitive deficits in cis mAb-treated mice were ameliorated in all mice, as assessed by the novel location recognition test ($p<0.01$) (FIG. 103A), which was confirmed using the T-maze, an independent spatial working memory test (FIG. 104). These functional outcomes also correlated well with brain pathology. Cis mAb treatment eliminated the accumulation of cis P-tau both in the cortex and hippocampus (FIGS. 105A-105C), and rescued neuronal loss in the neocortex and hippocampal CA1 subfield as well as atrophy of the hippocampal CA1 layer (FIGS. 106A-106B). Notably, cis mAb treatment did not significantly reduce NFT-like pathology (FIGS. 107A-107B and 108A-108D), consistent with the previous findings that NFTs may not be neurotoxic. Thus, cis P-tau is required for the development and progression of neurodegeneration and cognitive impairment in two independent mouse models relevant to VCID and AD-like tauopathy.

Example 18. Treatment of Vascular Dementia with a Cis-pTau Specific Antibody

A subject can be diagnosed as having or at risk of developing vascular dementia by satisfying any of the following criteria:

A. the subject lacks any detectable neurofibrillary tangles (NFTs) and has at least one of: (i) a detectable level of cis-pThr231-tau in the cerebrospinal fluid (CSF) or blood; and (ii) demyelination and/or neuroinflammation of neurons of the central nervous system;

B. the subject has: (i) increased expression of one or more genes selected from Meg3, Mme, Lrrc17, Hsd3b2, Phkg1, Grin 2a, Grin 2b, and EphA7 (e.g., an increase of 10%, 20%, 30%, 40%, 50%, 60%, 70%, 80%, 90%, 100% or more relative to a reference value); and/or (ii) decreased expression of one or more genes selected from GluI, Slc1 a2, Actb, Actg1, Atp6v1 b2, Mbp, Nsf, Ywhag, Kif5a, Actb, Actg1, Pafah1 b1 and Pak1 (e.g., a decrease of 10%, 20%, 30%, 40%, 50%, 60%, 70%, 80%, 90%, 100% or more relative to a reference value); and/or C. the subject has a genetic pre-disposition for vascular dementia or medical history associated with increased risk for vascular dementia (e.g., a family member of the subject has previously been diagnosed with vascular dementia and/or the subject has experienced head injury or trauma).

The subject may be asymptomatic or pre-symptomatic as to symptoms associated with vascular dementia. The subject diagnosed as having or at risk of developing vascular dementia is administered a cis-pTau specific antibody or antigen binding fragment thereof (e.g., a cis-pTau specific antibody or antigen binding fragment thereof described herein), thereby treating the vascular dementia. Treatment can be assessed by any of the methods described herein (e.g., diagnostic and subject monitoring methods), including monitoring levels of cis-pTau in the subject, monitoring the ratio of cis-pTau:trans-pTau in the subject, monitoring demyelination and/or neuroinflammation in the subject, monitoring the expression of biomarkers in the subject, and/or monitoring the onset or progression of symptoms associated with vascular dementia in the subject.

Example 19. Treatment of a Retinopathy with a Cis-pTau Specific Antibody

A subject can be diagnosed as having or at risk of developing a retinopathy, such as age-related macular degeneration (AMD), diabetic retinopathy (DR), ischemia-related retinopathy, or retinal detachment, by satisfying any of the following criteria:

A. the subject lacks any detectable neurofibrillary tangles (NFTs) and has at least one of: (i) a detectable level of cis-pThr231-tau in the cerebrospinal fluid (CSF) or blood; and (ii) demyelination and/or neuroinflammation of neurons of the central nervous system;

B. the subject has: (i) increased expression of one or more genes selected from Meg3, Mme, Lrrc17, Hsd3b2, Phkg1, Grin 2a, Grin 2b, and EphA7 (e.g., an increase of 10%, 20%, 30%, 40%, 50%, 60%, 70%, 80%, 90%, 100% or more relative to a reference value); and/or (ii) decreased expression of one or more genes selected from GluI, Slc1 a2, Actb, Actg1, Atp6v1 b2, Mbp, Nsf, Ywhag, Kif5a, Actb, Actg1, Pafah1 b1 and Pak1 (e.g., a decrease of 10%, 20%, 30%, 40%, 50%, 60%, 70%, 80%, 90%, 100% or more relative to a reference value); and/or C. the subject has a genetic pre-disposition for vascular dementia or medical history associated with increased risk for vascular dementia (e.g., a family member of the subject has previously been diagnosed with vascular dementia and/or the subject has experienced head injury or trauma).

The subject may be asymptomatic or pre-symptomatic as to symptoms associated with the retinopathy. The subject diagnosed as having or at risk of developing a retinopathy is administered a cis-pTau specific antibody or antigen binding fragment thereof (e.g., a cis-pTau specific antibody or antigen binding fragment thereof described herein), thereby treating the retinopathy. Treatment can be assessed by any of the methods described herein (e.g., diagnostic and subject monitoring methods), including monitoring levels of cis-pTau in the subject, monitoring the ratio of cis-pTau:trans-pTau in the subject, monitoring demyelination and/or neuroinflammation in the subject, monitoring the expression of biomarkers in the subject, and/or monitoring the onset or progression of symptoms associated with the retinopathy in the subject.

Other Embodiments

While the disclosure has been described in connection with specific embodiments thereof, it will be understood that it is capable of further modifications and this application is intended to cover any variations, uses, or adaptations of the disclosure following, in general, the principles of the disclosure and including such departures from the disclosure that come within known or customary practice within the art to which the disclosure pertains and may be applied to the essential features hereinbefore set forth, and follows in the scope of the claims. Other embodiments are within the claims.

The invention claimed is:

1. An isolated antibody or antigen-binding fragment thereof that binds specifically to a phosphorylated-Threonine231-Proline (pThr231-Pro) motif of phosphorylated-Threonine231-tau protein (pThr231-tau) comprising:

a CDR-L1 having the amino acid sequence of SEQ ID NO: 7 or SEQ ID NO: 8; a CDR-L2 having the amino acid sequence of SEQ ID NO: 10; and a CDR-L3 having the amino acid sequence of SEQ ID NO: 3; and a CDR-H1 having the amino acid sequence of SEQ ID NO: 4; a CDR-H2 having the amino acid sequence of SEQ ID NO: 11 or SEQ ID NO: 12; and a CDR-H3 having the amino acid sequence of SEQ ID NO: 6.

2. The antibody or antigen-binding fragment thereof of claim 1, wherein:

(a) the antibody or antigen-binding fragment thereof further comprises a threonine residue directly N-terminal to CDR-H3; or (b) the antibody or antigen-binding fragment thereof further comprises two threonine residues directly N-terminal to CDR-H3.

3. The antibody or antigen-binding fragment thereof of claim 1, wherein:

(a) the framework region of the light chain variable domain that is N-terminal to CDR-L1 comprises the sequence of SEQ ID NO: 36;

(b) the framework region that is between CDR-L1 and CDR-L2 of the light chain variable domain comprises the amino acid sequence of SEQ ID NO: 39 or SEQ ID NO: 40;

(c) the framework region that is between CDR-L2 and CDR-L3 of the light chain variable domain comprises the amino acid sequence of SEQ ID NO: 41 or SEQ ID NO: 42;

(d) the framework region that is C-terminal to CDR-L3 of the light chain variable domain comprises the amino acid sequence of SEQ ID NO: 43 or SEQ ID NO: 44;

(e) the framework region of the heavy chain variable domain that is N-terminal to CDR-H1 comprises the sequence of SEQ ID NO: 45;

(f) the framework region that is between CDR-H1 and CDR-H2 of the heavy chain variable domain comprises the amino acid sequence of SEQ ID NO: 48 or SEQ ID NO: 49;

(g) the framework region that is between CDR-H2 and CDR-H3 of the heavy chain variable domain comprises the amino acid sequence of SEQ ID NO: 50 or SEQ ID NO: 51; and/or (h) the framework region that is C-terminal to CDR-H3 of the heavy chain variable domain comprises the amino acid sequence of SEQ ID NO: 52.

4. A pharmaceutical composition comprising the antibody or antigen-binding fragment thereof of claim 1 and a pharmaceutically acceptable carrier or excipient.

5. A kit comprising the antibody or antigen-binding fragment thereof of claim 1 or a pharmaceutical composition comprising the antibody or antigen-binding fragment thereof.

6. The antibody or antigen-binding fragment thereof of claim 3, wherein:

(a) the framework region that is N-terminal to CDR-L1 of the light chain variable domain comprises the amino acid sequence of SEQ ID NO: 37 or SEQ ID NO: 38;

(b) the framework region that is N-terminal to CDR-H1 of the heavy chain variable domain comprises the amino acid sequence of SEQ ID NO: 46 or SEQ ID NO: 47; or (c) the framework region that is C-terminal to CDR-H3 of the heavy chain variable domain comprises the amino acid sequence of SEQ ID NO: 53 or SEQ ID NO: 54.

7. The antibody or antigen-binding fragment thereof of claim 1, wherein the light chain variable domain comprises an amino acid sequence having at least 97% sequence identity to SEQ ID NO: 18 and the heavy chain variable domain comprises an amino acid sequence having at least 96% sequence identity to SEQ ID NO: 28.

8. The antibody of claim 7, wherein the light chain variable domain comprises the amino acid sequence of SEQ ID NO: 18 and the heavy chain variable domain comprises the amino acid sequence of SEQ ID NO: 28.

9. An isolated antibody or antigen-binding fragment thereof that binds specifically to a phosphorylated-Threonine231-Proline (pThr231-Pro) motif of phosphorylated-Threonine231-tau protein (pThr231-tau) comprising a light chain variable domain comprising the amino acid sequence of SEQ ID NO: 19 and a heavy chain variable domain comprising the amino acid sequence of SEQ ID NO: 26.

10. An isolated antibody or antigen-binding fragment thereof that binds specifically to a phosphorylated-Threonine231-Proline (pThr231-Pro) motif of phosphorylated-Threonine231-tau protein (pThr231-tau) comprising a light chain variable domain comprising the amino acid sequence of SEQ ID NO: 20 and a heavy chain variable domain comprising the amino acid sequence of SEQ ID NO: 29.

11. The antibody or antigen-binding fragment thereof of claim 1, wherein:

(a) the light chain variable domain comprises a serine residue seventeen amino acid residues N-terminal to the CDR-L1; and/or (b) the heavy chain variable domain comprises:

(i) a valine residue twenty-six amino acid residues N-terminal to the CDR-H1;

(ii) a serine residue twenty-four amino acid residues N-terminal to the CDR-H1;

(iii) a lysine residue nineteen amino acid residues N-terminal to the CDR-H1;

(iv) an arginine residue at the amino acid residue directly C-terminal to CDR-H2; and/or (v) a valine residue seven amino residues C-terminal to CDR-H3.

12. The antibody or antigen-binding-fragment thereof of claim 1, wherein the antibody or antigen-binding fragment thereof further comprises a light chain variable domain comprising an amino acid sequence with at least 97% sequence identity to SEQ ID NO: 18.

13. The antibody or antigen-binding-fragment thereof of claim 1, wherein the antibody or antigen-binding fragment thereof further comprises a heavy chain variable domain comprising an amino acid sequence with at least 96% sequence identity to any one of SEQ ID NOs: 25-35.

* * * * *